(12) United States Patent
Johns et al.

(10) Patent No.: US 9,023,356 B2
(45) Date of Patent: May 5, 2015

(54) TREATMENT METHOD USING EGFR ANTIBODIES AND SRC INHIBITORS AND RELATED FORMULATIONS

(75) Inventors: Terrance Grant Johns, Heidelberg (AU); Webster Cavenee, La Jolla, CA (US); Frank Furnari, La Jolla, CA (US); Andrew Scott, Heidelberg (AU)

(73) Assignees: Ludwig Institute for Cancer Research Ltd, New York, NY (US); The Regents of the University of California, Oakland, CA (US)

( * ) Notice: Subject to any disclaimer, the term of this patent is extended or adjusted under 35 U.S.C. 154(b) by 457 days.

(21) Appl. No.: 12/450,196

(22) PCT Filed: Mar. 14, 2008

(86) PCT No.: PCT/US2008/003369
§ 371 (c)(1),
(2), (4) Date: Dec. 17, 2009

(87) PCT Pub. No.: WO2008/115404
PCT Pub. Date: Sep. 25, 2008

(65) Prior Publication Data
US 2010/0092475 A1    Apr. 15, 2010

Related U.S. Application Data

(60) Provisional application No. 60/918,084, filed on Mar. 15, 2007.

(51) Int. Cl.
| | |
|---|---|
| A61K 39/395 | (2006.01) |
| C07K 16/28 | (2006.01) |
| C07K 14/71 | (2006.01) |
| A61K 31/517 | (2006.01) |
| A61K 31/506 | (2006.01) |
| A61K 45/06 | (2006.01) |

(52) U.S. Cl.
CPC ........... *A61K 31/506* (2013.01); *A61K 31/517* (2013.01); *A61K 39/39541* (2013.01); *A61K 45/06* (2013.01); *C07K 2317/30* (2013.01)

(58) Field of Classification Search
None
See application file for complete search history.

(56) References Cited

U.S. PATENT DOCUMENTS

| | | | |
|---|---|---|---|
| 4,137,230 A | 1/1979 | Hashimoto et al. |
| 4,151,042 A | 4/1979 | Higashide et al. |
| 4,169,888 A | 10/1979 | Hanka et al. |
| 4,190,580 A | 2/1980 | Hashimoto et al. |
| 4,225,494 A | 9/1980 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,263,294 A | 4/1981 | Miyashita et al. |
| 4,264,596 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,317,821 A | 3/1982 | Miyashita et al. |
| 4,322,348 A | 3/1982 | Asai et al. |
| 4,331,598 A | 5/1982 | Hasegawa et al. |
| 4,342,566 A | 8/1982 | Theofilopoulos et al. |
| 4,360,462 A | 11/1982 | Higashide et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,413,132 A | 11/1983 | Wierenga |
| 4,418,064 A | 11/1983 | Powell et al. |
| 4,671,958 A | 6/1987 | Rodwell et al. |
| 4,762,707 A | 8/1988 | Jansen et al. |
| 4,816,567 A | 3/1989 | Cabilly et al. |
| 4,867,973 A | 9/1989 | Goers et al. |
| 4,933,294 A | 6/1990 | Waterfield et al. |
| 4,937,183 A | 6/1990 | Ultee et al. |
| 4,943,533 A | 7/1990 | Mendelsohn et al. |
| 4,952,394 A | 8/1990 | Senter |
| 4,997,913 A | 3/1991 | Hellstrom et al. |
| 5,013,547 A | 5/1991 | Sweet et al. |
| 5,028,697 A | 7/1991 | Johnson et al. |
| 5,034,223 A | 7/1991 | Abrams et al. |

(Continued)

FOREIGN PATENT DOCUMENTS

| | | |
|---|---|---|
| EP | 0120694 | 10/1984 |
| EP | 0125023 | 11/1984 |

(Continued)

OTHER PUBLICATIONS

Yang et al, Clin Cancer Res 10: 658-667, Jan. 15, 2004.*
Stancovski et al, Proceedings of the National Academy of Science USA 88: 8691-8695, 1991.*
Riemer et al, Mol. Immunol. 42: 1121-1124, 2005.*
Cochran et al. J. Immunol. Meth. 287: 147-158, 2004.*
Zhu et al, Investigational New Drugs 17: 195-212, 1999.*
Nam et al, Cancer Res 65(20): 9185-9189, Oct. 2005.*
Stancovski et al., Proceedings of the National Academy of Science USA 88: 8691-8695, 1991.*

(Continued)

*Primary Examiner* — Phuong Huynh

(57) ABSTRACT

The present invention relates to the treatment of EGFR-mediated disease, particularly cancer by inhibiting or blocking EGFR and src in combination or simultaneously. The invention relates to treatment, prevention, or modulation of cancer, particularly EGFR-mediated disease, with one or more EGFR modulator and src inhibitor in combination. The invention further relates to the treatment of cancer with anti-EGFR antibodies and src inhibitors. Methods and compositions for treatment of cancer with the antibody anti-EGFR mAb806 in combination or series with a src inhibitor or src inhibitors are described.

14 Claims, 14 Drawing Sheets

(56) References Cited

U.S. PATENT DOCUMENTS

| | | | |
|---|---|---|---|
| 5,047,324 A | 9/1991 | Fredrickson | |
| 5,087,616 A | 2/1992 | Myers et al. | |
| 5,106,951 A | 4/1992 | Morgan, Jr. et al. | |
| 5,122,368 A | 6/1992 | Greenfield et al. | |
| 5,130,116 A | 7/1992 | Woo et al. | |
| 5,141,736 A | 8/1992 | Iwasa et al. | |
| 5,164,311 A | 11/1992 | Gupta | |
| 5,171,563 A | 12/1992 | Abrams et al. | |
| 5,208,020 A | 5/1993 | Chari et al. | |
| 5,217,713 A | 6/1993 | Iwasa et al. | |
| 5,225,539 A | 7/1993 | Winter | |
| 5,306,809 A | 4/1994 | Boon et al. | |
| 5,332,837 A | 7/1994 | Kelly et al. | |
| 5,401,828 A | 3/1995 | Vogelstein et al. | |
| 5,416,064 A | 5/1995 | Chari et al. | |
| 5,457,105 A | 10/1995 | Barker | |
| 5,475,092 A | 12/1995 | Chari et al. | |
| 5,541,339 A | 7/1996 | Kelly et al. | |
| 5,556,623 A | 9/1996 | Barton et al. | |
| 5,558,864 A | 9/1996 | Bendig et al. | |
| 5,563,250 A | 10/1996 | Hylarides et al. | |
| 5,585,499 A | 12/1996 | Chari et al. | |
| 5,606,017 A | 2/1997 | Willner et al. | |
| 5,612,474 A | 3/1997 | Patel | |
| 5,622,929 A | 4/1997 | Willner et al. | |
| 5,635,483 A | 6/1997 | Pettit et al. | |
| 5,635,603 A | 6/1997 | Hansen et al. | |
| 5,639,641 A | 6/1997 | Pedersen et al. | |
| 5,643,573 A | 7/1997 | Barton et al. | |
| 5,665,358 A | 9/1997 | Barton et al. | |
| 5,674,977 A | 10/1997 | Gariepy | |
| 5,677,171 A | 10/1997 | Hudziak et al. | |
| 5,708,146 A | 1/1998 | Willner et al. | |
| 5,720,954 A | 2/1998 | Hudziak et al. | |
| 5,739,350 A | 4/1998 | Kelly et al. | |
| 5,760,041 A | 6/1998 | Wissner et al. | |
| 5,780,588 A | 7/1998 | Pettit et al. | |
| 5,807,715 A | 9/1998 | Morrison et al. | |
| 5,814,317 A | 9/1998 | Vogelstein et al. | |
| 5,824,805 A | 10/1998 | King et al. | |
| 5,844,093 A | 12/1998 | Kettleborough et al. | |
| 5,846,545 A | 12/1998 | Chari et al. | |
| 5,851,526 A | 12/1998 | Welt et al. | |
| 5,869,045 A | 2/1999 | Hellstrom et al. | |
| 5,869,619 A | 2/1999 | Studnicka | |
| 5,880,270 A | 3/1999 | Berninger et al. | |
| 5,891,996 A | 4/1999 | Mateo de Acosta del Rio et al. | |
| 5,911,995 A | 6/1999 | Uckun | |
| 5,980,896 A | 11/1999 | Hellstrom et al. | |
| 6,010,902 A | 1/2000 | Ledbetter et al. | |
| 6,060,608 A | 5/2000 | Boger | |
| 6,214,345 B1 | 4/2001 | Firestone et al. | |
| 6,224,868 B1 | 5/2001 | Wong et al. | |
| 6,235,883 B1 | 5/2001 | Jakobovits et al. | |
| 6,281,354 B1 | 8/2001 | Boger | |
| 6,306,393 B1 | 10/2001 | Goldenberg | |
| 6,331,175 B1 | 12/2001 | Goldenberg | |
| 6,331,415 B1 | 12/2001 | Cabilly et al. | |
| 6,333,410 B1 | 12/2001 | Chari et al. | |
| 6,340,701 B1 | 1/2002 | Chari et al. | |
| 6,372,738 B2 | 4/2002 | Chari et al. | |
| 6,395,272 B1 | 5/2002 | Deo et al. | |
| 6,436,931 B1 | 8/2002 | Chari et al. | |
| 6,441,163 B1 | 8/2002 | Chari et al. | |
| 6,506,883 B2 | 1/2003 | Meteo de Acosta del Rio et al. | |
| 6,512,101 B1 | 1/2003 | King et al. | |
| RE38,008 E | 2/2003 | Abrams et al. | |
| 6,534,660 B1 | 3/2003 | Yongxin et al. | |
| 6,548,530 B1 | 4/2003 | Boger | |
| 6,570,024 B2 | 5/2003 | Eldridge et al. | |
| 6,586,618 B1 | 7/2003 | Zhao et al. | |
| 6,596,757 B1 | 7/2003 | Chari et al. | |
| 6,630,579 B2 | 10/2003 | Chari et al. | |
| 6,660,742 B2 | 12/2003 | Lee | |
| 6,699,715 B1 | 3/2004 | Ledbetter et al. | |
| 6,706,708 B2 | 3/2004 | Chari et al. | |
| 6,716,821 B2 | 4/2004 | Zhao et al. | |
| 6,756,397 B2 | 6/2004 | Zhao et al. | |
| 6,759,509 B1 | 7/2004 | King et al. | |
| 6,790,954 B2 | 9/2004 | Chung et al. | |
| 6,797,492 B2 | 9/2004 | Daugherty et al. | |
| 6,849,625 B2 * | 2/2005 | Lambert et al. | 514/234.5 |
| 6,884,869 B2 | 4/2005 | Senter et al. | |
| 6,884,874 B2 | 4/2005 | Eldridge et al. | |
| 6,913,748 B2 | 7/2005 | Widdison | |
| 6,946,543 B2 | 9/2005 | Ward et al. | |
| 6,989,452 B2 | 1/2006 | Ng et al. | |
| 7,008,942 B2 | 3/2006 | Chari et al. | |
| 7,049,316 B2 | 5/2006 | Zhao et al. | |
| 7,060,808 B1 | 6/2006 | Goldstein et al. | |
| 7,091,186 B2 | 8/2006 | Senter et al. | |
| 7,097,840 B2 | 8/2006 | Erickson et al. | |
| 7,098,308 B2 | 8/2006 | Senter et al. | |
| 7,129,261 B2 | 10/2006 | Ng et al. | |
| 7,129,332 B2 | 10/2006 | Pastan et al. | |
| 7,132,511 B2 | 11/2006 | Carr et al. | |
| 7,132,554 B2 | 11/2006 | Rose | |
| 7,192,750 B2 | 3/2007 | Chung et al. | |
| 7,214,685 B2 | 5/2007 | Tietze et al. | |
| 7,217,819 B2 | 5/2007 | Chari et al. | |
| 7,223,837 B2 | 5/2007 | De Groot et al. | |
| 7,226,592 B2 | 6/2007 | Kreysch | |
| 7,247,301 B2 | 7/2007 | van de Winkel et al. | |
| 7,256,257 B2 | 8/2007 | Doronina et al. | |
| 7,276,497 B2 | 10/2007 | Chari et al. | |
| 7,276,499 B2 | 10/2007 | Chari et al. | |
| 7,276,585 B2 | 10/2007 | Lazar et al. | |
| 7,301,019 B2 | 11/2007 | Widdison et al. | |
| 7,303,749 B1 | 12/2007 | Chari | |
| 7,329,760 B2 | 2/2008 | Zhao et al. | |
| 7,368,565 B2 | 5/2008 | Chari et al. | |
| 7,374,762 B2 | 5/2008 | Amphlett et al. | |
| 7,375,078 B2 | 5/2008 | Feng | |
| 7,388,026 B2 | 6/2008 | Zhao et al. | |
| 7,390,898 B2 | 6/2008 | Baloglu et al. | |
| 7,411,063 B2 | 8/2008 | Widdison et al. | |
| 7,414,073 B2 | 8/2008 | Baloglu et al. | |
| 7,423,116 B2 | 9/2008 | Doronina et al. | |
| 7,432,088 B2 | 10/2008 | Kuo et al. | |
| 7,449,559 B2 | 11/2008 | Ward et al. | |
| 7,473,796 B2 | 1/2009 | Chari et al. | |
| 7,476,669 B2 | 1/2009 | Chari et al. | |
| 7,494,649 B2 | 2/2009 | Amphlett et al. | |
| 7,495,114 B2 | 2/2009 | Baloglu et al. | |
| 7,498,298 B2 | 3/2009 | Doronina et al. | |
| 7,498,302 B2 | 3/2009 | Ng et al. | |
| 7,501,120 B2 | 3/2009 | Amphlett et al. | |
| 7,514,080 B2 | 4/2009 | Amphlett et al. | |
| 7,517,903 B2 | 4/2009 | Chen et al. | |
| 7,521,541 B2 | 4/2009 | Eigenbrot et al. | |
| 7,528,130 B2 | 5/2009 | Chari et al. | |
| 7,550,609 B2 | 6/2009 | Chari et al. | |
| 7,553,816 B2 | 6/2009 | Senter et al. | |
| 7,575,748 B1 | 8/2009 | Erickson et al. | |
| 7,585,857 B2 | 9/2009 | Chari et al. | |
| 7,589,180 B2 * | 9/2009 | Old et al. | 530/387.3 |
| 7,595,378 B2 | 9/2009 | van de Winkel et al. | |
| 7,598,290 B2 | 10/2009 | Miller et al. | |
| 7,598,375 B2 | 10/2009 | Ho et al. | |
| 7,601,354 B2 | 10/2009 | Chari | |
| 7,628,986 B2 | 12/2009 | Weber et al. | |
| 7,635,570 B2 | 12/2009 | Siena et al. | |
| 7,651,687 B2 | 1/2010 | Buck et al. | |
| 7,655,660 B2 | 2/2010 | Zhao et al. | |
| 7,655,661 B2 | 2/2010 | Zhao et al. | |
| 7,659,241 B2 | 2/2010 | Senter et al. | |
| 7,667,054 B2 | 2/2010 | Miller et al. | |
| 7,691,962 B2 | 4/2010 | Boyd et al. | |
| 7,723,484 B2 | 5/2010 | Beidler et al. | |
| 7,736,644 B2 | 6/2010 | Weber et al. | |
| 7,745,394 B2 | 6/2010 | Doronina et al. | |
| 7,750,116 B1 | 7/2010 | Doronina et al. | |
| 7,754,681 B2 | 7/2010 | Feng | |
| 7,790,164 B2 | 9/2010 | Cao | |

(56) References Cited

U.S. PATENT DOCUMENTS

| | | |
|---|---|---|
| 7,807,798 B2 | 10/2010 | Jakobovits et al. |
| 2001/0005747 A1 | 6/2001 | Ball et al. |
| 2001/0036923 A1 | 11/2001 | Chari et al. |
| 2001/0046686 A1 | 11/2001 | Wong et al. |
| 2001/0048922 A1 | 12/2001 | Romet-Lemonne et al. |
| 2001/0055595 A1 | 12/2001 | Goldenberg |
| 2002/0001587 A1 | 1/2002 | Erickson et al. |
| 2002/0004587 A1 | 1/2002 | Miller et al. |
| 2002/0006379 A1 | 1/2002 | Hansen et al. |
| 2002/0012663 A1 | 1/2002 | Waksal |
| 2002/0013485 A1 | 1/2002 | Chari et al. |
| 2002/0049335 A1 | 4/2002 | Boger |
| 2002/0062009 A1 | 5/2002 | Taylor |
| 2002/0064785 A1 | 5/2002 | Mass |
| 2002/0082424 A1 | 6/2002 | Boger |
| 2002/0156274 A1 | 10/2002 | Terfloth |
| 2002/0173629 A1 | 11/2002 | Jakobovits et al. |
| 2003/0050331 A1 | 3/2003 | Ng et al. |
| 2003/0055226 A1 | 3/2003 | Chari et al. |
| 2003/0073731 A1 | 4/2003 | Lee |
| 2003/0073852 A1 | 4/2003 | Ng et al. |
| 2003/0083263 A1 | 5/2003 | Doronina et al. |
| 2003/0091561 A1 | 5/2003 | van de Winkel et al. |
| 2003/0096743 A1 | 5/2003 | Senter et al. |
| 2003/0109682 A1 | 6/2003 | Santi et al. |
| 2003/0130189 A1 | 7/2003 | Senter et al. |
| 2003/0194403 A1 | 10/2003 | van de Winkel et al. |
| 2003/0195365 A1 | 10/2003 | Zhao et al. |
| 2003/0199519 A1 | 10/2003 | Zhao et al. |
| 2003/0211097 A1 | 11/2003 | Pastan et al. |
| 2003/0211112 A1 | 11/2003 | Debinski |
| 2003/0215387 A1 | 11/2003 | Harrison |
| 2003/0224001 A1 | 12/2003 | Goldstein et al. |
| 2004/0006212 A1 | 1/2004 | Goldstein et al. |
| 2004/0033543 A1 | 2/2004 | Schwab et al. |
| 2004/0086943 A1 | 5/2004 | Andres et al. |
| 2004/0109867 A1 | 6/2004 | Yongxin et al. |
| 2004/0131611 A1 | 7/2004 | Oliver et al. |
| 2004/0147428 A1 | 7/2004 | Pluenneke |
| 2004/0157782 A1 | 8/2004 | Doronina et al. |
| 2004/0202666 A1 | 10/2004 | Griffiths |
| 2004/0235074 A1 | 11/2004 | Siegall et al. |
| 2004/0235840 A1 | 11/2004 | Chari et al. |
| 2004/0248196 A1 | 12/2004 | Adams et al. |
| 2004/0253645 A1 | 12/2004 | Daugherty et al. |
| 2005/0009751 A1 | 1/2005 | Senter et al. |
| 2005/0014700 A1 | 1/2005 | Boger |
| 2005/0026987 A1 | 2/2005 | Boger |
| 2005/0031627 A1 | 2/2005 | Mazzola et al. |
| 2005/0032860 A1 | 2/2005 | Boger |
| 2005/0053608 A1 | 3/2005 | Weber et al. |
| 2005/0059087 A1 | 3/2005 | Weber et al. |
| 2005/0064492 A1 | 3/2005 | DeSauvage et al. |
| 2005/0100546 A1 | 5/2005 | Jakobovits et al. |
| 2005/0106644 A1 | 5/2005 | Cairns et al. |
| 2005/0107595 A1 | 5/2005 | Cairns et al. |
| 2005/0113308 A1 | 5/2005 | Senter et al. |
| 2005/0113571 A1 | 5/2005 | Terfloth |
| 2005/0142133 A1 | 6/2005 | Lazar et al. |
| 2005/0152913 A1 | 7/2005 | Eldridge |
| 2005/0169933 A1 | 8/2005 | Steeves et al. |
| 2005/0214310 A1 | 9/2005 | Toki et al. |
| 2005/0227324 A1 | 10/2005 | Huang et al. |
| 2005/0238640 A1 | 10/2005 | Sliwkowski |
| 2005/0238649 A1 | 10/2005 | Doronina et al. |
| 2005/0255555 A1 | 11/2005 | Johns et al. |
| 2005/0271671 A1 | 12/2005 | Griffiths |
| 2005/0272798 A1 | 12/2005 | Ng et al. |
| 2005/0276812 A1 | 12/2005 | Ebens et al. |
| 2006/0004081 A1 | 1/2006 | Chen et al. |
| 2006/0009462 A1 | 1/2006 | Yongxin et al. |
| 2006/0024317 A1 | 2/2006 | Boyd et al. |
| 2006/0029574 A1* | 2/2006 | Albitar et al. ............... 424/93.1 |
| 2006/0074008 A1 | 4/2006 | Senter et al. |
| 2006/0084141 A1 | 4/2006 | Floss et al. |
| 2006/0088523 A1 | 4/2006 | Andya et al. |
| 2006/0116422 A1 | 6/2006 | De Groot et al. |
| 2006/0147959 A1 | 7/2006 | Bell et al. |
| 2006/0154334 A1 | 7/2006 | Tarnowski et al. |
| 2006/0165685 A1 | 7/2006 | Kreysch |
| 2006/0182750 A1 | 8/2006 | Chari et al. |
| 2006/0183887 A1 | 8/2006 | Jakobovits et al. |
| 2006/0229253 A1 | 10/2006 | Doronina et al. |
| 2006/0234343 A1 | 10/2006 | Ward et al. |
| 2006/0247295 A1 | 11/2006 | Gangwar et al. |
| 2007/0031402 A1 | 2/2007 | Zhang et al. |
| 2007/0037972 A1 | 2/2007 | Ho et al. |
| 2007/0048314 A1 | 3/2007 | Dai et al. |
| 2007/0071675 A1 | 3/2007 | Wu et al. |
| 2007/0092940 A1 | 4/2007 | Eigenbrot et al. |
| 2007/0112188 A1 | 5/2007 | Widdison et al. |
| 2007/0116707 A1 | 5/2007 | Goldstein et al. |
| 2007/0134243 A1 | 6/2007 | Gazzard et al. |
| 2007/0135346 A1 | 6/2007 | Zhao et al. |
| 2007/0202101 A1 | 8/2007 | Rosen et al. |
| 2007/0264266 A1 | 11/2007 | Chari et al. |
| 2007/0269447 A1 | 11/2007 | Chari et al. |
| 2007/0270585 A1 | 11/2007 | Chari et al. |
| 2008/0008704 A1 | 1/2008 | Rubin |
| 2008/0025983 A1 | 1/2008 | Adams et al. |
| 2008/0114153 A1 | 5/2008 | Steeves et al. |
| 2008/0145374 A1 | 6/2008 | Steeves et al. |
| 2008/0171040 A1 | 7/2008 | Ebens et al. |
| 2008/0171856 A1 | 7/2008 | Steeves et al. |
| 2008/0171865 A1 | 7/2008 | Steeves et al. |
| 2008/0226657 A1 | 9/2008 | Doronina et al. |
| 2008/0226659 A1 | 9/2008 | Erickson et al. |
| 2008/0241128 A1 | 10/2008 | Jeffrey |
| 2008/0248051 A1 | 10/2008 | Doronina et al. |
| 2008/0248053 A1 | 10/2008 | Doronina et al. |
| 2008/0249085 A1 | 10/2008 | Cassady et al. |
| 2008/0260685 A1 | 10/2008 | Zhao et al. |
| 2008/0267960 A1 | 10/2008 | Drachman et al. |
| 2008/0279868 A1 | 11/2008 | Boyd et al. |
| 2008/0281102 A1 | 11/2008 | Gangwar et al. |
| 2008/0293800 A1 | 11/2008 | Gangwar et al. |
| 2008/0300192 A1 | 12/2008 | Doronina et al. |
| 2008/0305044 A1 | 12/2008 | McDonagh et al. |
| 2008/0311136 A1 | 12/2008 | Beusker et al. |
| 2009/0010945 A1 | 1/2009 | Alley et al. |
| 2009/0018086 A1 | 1/2009 | Doronina et al. |
| 2009/0028821 A1 | 1/2009 | Zhao et al. |
| 2009/0031668 A1 | 2/2009 | Llorente Gonzalez et al. |
| 2009/0041791 A1 | 2/2009 | Feng |
| 2009/0047296 A1 | 2/2009 | Doronina et al. |
| 2009/0053240 A1 | 2/2009 | Lazar et al. |
| 2009/0111756 A1 | 4/2009 | Doronina et al. |
| 2009/0142361 A1 | 6/2009 | Amphlett et al. |
| 2009/0155282 A1 | 6/2009 | Weber et al. |
| 2009/0156790 A1 | 6/2009 | Weber et al. |
| 2009/0175865 A1 | 7/2009 | Eigenbrot et al. |
| 2009/0175887 A1 | 7/2009 | Weber et al. |
| 2009/0175888 A1 | 7/2009 | Ng et al. |
| 2009/0202536 A1 | 8/2009 | Ebens, Jr. et al. |
| 2009/0214541 A1 | 8/2009 | Gillies et al. |
| 2009/0220510 A1 | 9/2009 | Old et al. |
| 2009/0240038 A1 | 9/2009 | Weber et al. |
| 2009/0269343 A1 | 10/2009 | Bigner et al. |
| 2009/0274713 A1 | 11/2009 | Chari et al. |
| 2009/0281158 A1 | 11/2009 | Zhao et al. |
| 2009/0304693 A1 | 12/2009 | Ghayur et al. |
| 2009/0306101 A1 | 12/2009 | Solca et al. |
| 2009/0318668 A1 | 12/2009 | Beusker et al. |
| 2009/0324621 A1 | 12/2009 | Senter et al. |
| 2010/0008929 A1 | 1/2010 | van de Winkel et al. |
| 2010/0056762 A1 | 3/2010 | Old |
| 2010/0166744 A1 | 7/2010 | Wong |
| 2010/0196265 A1 | 8/2010 | Adams et al. |
| 2010/0203007 A1 | 8/2010 | Li et al. |
| 2011/0008766 A1 | 1/2011 | Ghayur et al. |
| 2011/0150759 A1 | 6/2011 | Johns et al. |
| 2011/0313230 A1 | 12/2011 | Johns et al. |

(56) References Cited

U.S. PATENT DOCUMENTS

| | | | |
|---|---|---|---|
| 2012/0183471 A1 | 7/2012 | Old et al. | |
| 2013/0266573 A1 | 10/2013 | Old et al. | |

FOREIGN PATENT DOCUMENTS

| | | |
|---|---|---|
| EP | 0519596 A1 | 12/1992 |
| EP | 0586002 A2 | 3/1994 |
| EP | 0699755 A2 | 3/1996 |
| WO | WO-8503357 | 8/1985 |
| WO | WO-9215683 | 9/1992 |
| WO | WO 9311161 | 6/1993 |
| WO | WO 9413804 | 6/1994 |
| WO | WO-9525167 | 9/1995 |
| WO | WO 9640210 | 12/1996 |
| WO | WO-9944645 | 9/1999 |
| WO | WO 02092771 | 11/2002 |
| WO | WO 03068920 | 8/2003 |
| WO | WO-2004003019 | 1/2004 |
| WO | WO-2004056847 | 7/2004 |
| WO | WO-2004085474 | 10/2004 |
| WO | WO 2005081854 | 9/2005 |
| WO | WO-2005094357 | 10/2005 |
| WO | WO-2007089149 | 8/2007 |
| WO | WO-2007103288 | 9/2007 |
| WO | WO-2008154927 | 12/2008 |
| WO | WO-2009017394 | 2/2009 |
| WO | WO-2010096434 | 8/2010 |

OTHER PUBLICATIONS

Cochran et al., J. Immunol. Meth. 287: 147-158, 2004.*
Riemer et al., Mol. Immunol. 42: 1121-1124, 2005.*
Park et al., Cancer Letters 320: 104-110, 2012.*
Tol et al., N Engl J Med. 5;360(6):563-72, Feb. 2009.*
Ishizawar et al., Cancer Cell 6: 209-214, 2004.*
Song et al., Cancer Research 66(11): 5542-5548, 2006.*
Arteaga, C. L., *Semin. Oncol.*, (2002) 3-9, 29.
Avital et al., *Cancer*, (2000) 1692-1698, 89(8).
Baselga, J, "Why the epidermal growth factor receptor? The rationale for cancer therapy." *Oncologist*, (2002) 2-8, 4.
Baselga, Pfister, Cooper, Cohen, Burtness, Bos, D'Andrea, Seidman, Norton, Gunnett, Falcey, Anderson, Waksal and Mendelsohn, "Phase I studies of anti-epidermal growth factor receptor chimeric antibody C225 alone and in combination with cisplatin." *J. Clin. Oncol.*, (2000) 904-914, 18.
Behr et al., *Cancer*, (2002) 1373-1381, 94(4 Suppl.).
Bianco et al., "Loss of PTEN/MMAC1/TEP in EGF receptor-expressing tumor cells counteracts the antitumor action of EGFR tyrosine kinase inhibitors." *Oncogene*, (2003) 2812-2822, 22.
Bird et al., *Science*, (1988) 423-426, 242.
Bishop et al., "Differential sensitivity of cancer cells to inhibitors of the epidermal growth factor receptor family." *Oncogene* (2002) 119-127, 21.
Bos, Mendelsohn, Kim, Albanell, Fry and Baselga, "PDI 53035, a tyrosine kinase inhibitor, prevents epidermal growth factor receptor activation and inhibits growth of cancer cells in a receptor number-dependent manner." *Clin. Cancer Res.* (1997) 2099-2106, 3.
Chakravarti, Loeffler and Dyson, "Insulin-like growth factor receptor I mediates resistance to anti-epidermal growth factor receptor therapy in primary human glioblastoma cells through continued activation of phosphoinositide 3-kinase signaling." *Cancer Res.* (2002) 200-207, 62.
Christensen et al., "High levels of HER-2 expression alter the ability of epidermal growth factor receptor (EGFR) family tyrosine kinase inhibitors to inhibit EGFR phosphorylation in vivo." *Clin. Cancer Res.* (2001) 4230-4238, 7.
Chung et al., "Cetuximab shows activity in colorectal cancer patients with tumors that do not express the epidermal growth factor receptor by immunohistochemistry." J. Clin. Oncol. (2005) 1803-1810, 23.
Dehm, S.M. and K. Bonham, *Biochem. Cell Biol.* (2004) 263-274, 82.
Foulon et al., *Cancer Res.* (2000) 4453-4460, 60(16).

Frame, M.C., *J. Cell Sci.* (2004) 989-998, 117.
Frederick, L., X. Y. Wang, G. Eley and C. D. James, *Cancer Res.* (2000) 1383-1387, 60.
Gold et al., Crit. Rev. *Oncol. Hematol.* (2001) 147-154, 39(1-2).
Goldenberg, D.M., *Crit. Rev. Oncol. Hematol.* (2001) 195-201, 39(1-2).
Halatsch et al., "Inverse correlation of epidermal growth factor receptor messenger RNA induction and suppression of anchorage-independent growth by OSI-774, an epidermal growth factor receptor tyrosine kinase inhibitor, in glioblastoma multiforme cell lines." *J. Neurosurg.* (2004) 523-533, 100.
Hambek et al., "Tumor necrosis factor alpha sensitizes low epidermal growth factor receptor (EGFR)-expressing carcinomas for anti-EGFR therapy." *Cancer Res.* (2001) 1045-1049, 61.
Heimberger et al., "Brain tumors in mice are susceptible to blockade of epidermal growth factor receptor (EGFR) with the oral, specific, EGFR-tyrosine kinase inhibitor ZD 1839 (iressa)." *Clin. Cancer Res.* (2002) 3496-3502, 8.
Hills, D., G. Rowlinson-Busza and W. J. Gullick, "Specific targeting of a mutant, activated EGF receptor found in glioblastoma using a monoclonal antibody." *Int. J. Cancer* (1995) 537-543, 63.
Holliger et al., *PNAS*, (1993) 6444-6448, 90.
Huang, Nagane and Klingbeil, "The enhanced tumorigenic activity of a mutant epidermal growth factor receptor common in human cancers is mediated by threshold levels of constitutive tyrosine phosphorylation and unattenuated signaling." *J. Biol. Chem.* (1997) 2927-2935, 272.
Huston et al., *PNAS*, (1988) 5879-5883, 85.
Ishizawar, R. and S.J. Parsons, "c-Src and cooperating partners in human cancer." *Cancer Cell* (2004) 209-214, 6.
Janmaat, M.L., F.A. Kruyt, J.A. Rodriguez and G. Giaccone, "Response to epidermal growth factor receptor inhibitors in non-small cell lung cancer cells: limited antiproliferative effects and absence of apoptosis associated with persistent activity of extracellular signal-regulated kinase or Akt kinase pathways." *Clin. Cancer Res.* (2003) 2316-2326, 9.
Ji et al., *Cell Cycle* (2006) 2072-2076, 5(18).
Johns, Mellman, Cartwright, Ritter, Old, Burgess and Scott, "The anti-tumor monoclonal antibody 806 recognizes a high-mannose form of the EGF receptor that reaches the cell surface when cells over-express the receptor." *FASEB J.* (2005) 780-782, 19(7).
Johns, T. G., E. Stockert, G. Ritter, A. A. Jungbluth, H. J. Huang, W. K. Cavenee, F. E. Smyth, C. M. Hall, N. Watson, E. C. Nice, W. J. Gullick, L. J. Old, A. W. Burgess and A. M. Scott, "Novel monoclonal antibody specific for the DE2-7 Epidermal Growth Factor Receptor (EGFR) that also recognizes the EGFR expressed in cells containing amplification of the EGFR gene." *Int. J. Cancer* (2002) 398-408, 98.
Johns, T. G., R. B. Luwor, C. Murone, F. Walker, J. Weinstock, A. A. Vitali, R. M. Perera, A. A. Jungbluth, E. Stockert, L. J. Old, E. C. Nice, A. W. Burgess and A. M. Scott, "Anti-tumor efficacy of cytotoxic drugs and the monoclonal antibody 806 is enhanced by the epidermal growth factor receptor (EGFR) inhibitor AG1478." *Proc. Natl. Acad. Sci. USA* (2003) 15871-15876, 100.
Johns, T.G., T.E. Adams, J.R. Cochran, N.E. Hall, P.A. Hoyne, M.J. Olsen, Y.S. Kim, J. Rothacker, E.C. Nice, F. Walker, G. Ritter, A.A. Jungbluth, L.J. Old, C.W. Ward, A.W. Burgess, K.D. Wittrup and A.M. Scott, "Identification of the Epitope for the EGFR-Specific Monoclonal Antibody 806 Reveals that it Preferentially Recognizes an Untethered Form of the Receptor." *J. Biol. Chem.* (2004) 30375-30384, 279(29).
Jungbluth, A. A., E. Stockert, H. J. Huang, V. P. Collins, K. Coplan, K. Iversen, D. Kolb, T. J. Johns, A. M. Scott, W. J. Gullick, G. Ritter, L. Cohen, M. J. Scanlan, W. K. Cavanee and L. J. Old, "A Monoclonal Antibody Recognizing Human Cancers with Amplification/Over-Expression of the Human Epidermal Growth Factor Receptor." *Proc. Natl. Acad. Sci. USA* (2003) 639-644, 100.
Kawamoto, T., J.D. Sato, A. Le, J. Polikoff, G.H. Sato and Mendelsohn. J., "Growth stimulation of A431 cells by epidermal growth factor: identification of high-affinity receptors for epidermal growth factor by an anti-receptor monoclonal antibody." PNAS, (1983) 1337-1341, 80.
Kim et al., Int. J. Cancer, (2002) 542-547, 97(4).

(56) References Cited

OTHER PUBLICATIONS

Kopetz, "Synergistic effects of combination therapy with anti-EGFR and anti-Src therapy in vitro in colon cancer." *GastroIntestinal Cancers Symposium* (2007) (Retrieved from Internet on Jun. 3, 2008) Abstract #406.
Kwok and Sutherland, "Differences in EGF related radiosensitisation of human squamous carcinoma cells with high and low numbers of EGF receptors." *Br. J. Cancer* (1991) 251-254, 64.
Learn et al., "Resistance to tyrosine kinase inhibition by mutant epidermal growth factor receptor variant III contributes to the neoplastic phenotype of glioblastoma multiforme." *Clin. Cancer Res.* (2004) 3216-3224, 10.
Li, B., C.M. Chang, M. Yuan, W.G. McKenna and H.K. Shu, "Resistance to small molecule inhibitors of epidermal growth factor receptor in malignant gliomas." *Cancer Res.* (2003) 7443-7450, 63.
Li, Schmitz, Jeffrey, Wiltzius, Kussie and Ferguson, *Cancer Cell* (2005) 301-311, 7.
Lichtner, Menrad, Sommer, Klar and Schneider, "Signaling-inactive Epidermal Growth Factor Receptor/Ligand Complexes in Intact Carcinoma Cells by Quinazoline Tyrosine Kinase Inhibitors." *Cancer Res.* (2001) 5790-5795, 61.
Luwor, R. B., T. G. Johns, C. Murone, H. J. Huang, W. K. Cavenee, G. Ritter, L. J. Old, A. W. Burgess and A. M. Scott, "Monoclonal Antibody 806 Inhibits the Growth of Tumor Xenografts Expressing Either the DE2-7 or Amplified Epidermal Growth Factor Receptor (EGFR) but not Wild-Type EGFR." *Cancer Res.* (2001) 5355-5361, 61.
Luwor, Zhu, Walker, Vitali, Perera, Burgess, Scott and Johns, "The Tumor Specific de2-7 Epidermal Growth Factor Receptor (EGFR) confers Increased survival in BaF/3 Cells via a PI-3 Kinase Dependent Mechanism." *Oncogene* (2004) 6095-6104, 23.
Lynch et al., "Activating mutations in the epidermal growth factor receptor underlying responsiveness of non-small-cell lung cancer to gefitinib." *N. Engl. J. Med.* (2004) 2129-2139, 350.
Lynch, D. H. and X. D. Yang, *Semin. Oncol.* (2002) 47-50, 29.
Magne et al., "Influence of epidermal growth factor receptor (EGFR), p53 and intrinsic MAP kinase pathway status of tumor cells on the antiproliferative effect of ZD1839 ("Iressa")." *Br. J. Cancer* (2002) 1518-1523, 86.
Masui, H., Moroyamam T. and J. Mendelsohn, "Mechanism of antitumor activity in mice for anti-epidermal growth factor receptor monoclonal antibodies with different isotypes." *Cancer Res.* (1986) 5592-5598, 46.
McIntosh et al., *Cancer Biother. Radiopharm.* (1997) 287-294, 12(4).
Mellinghoff et al., "Molecular determinants of the response of glioblastomas to EGFR kinase inhibitors." *N. Engl. J. Med.* (2005) 2012-2024, 353.
Mendelsohn, J., *J. Clin. Oncol.* (2002) 1S-13S, 20.
Mishima, K., T. G. Johns, R. B. Luwor, A. M. Scott, E. Stockert, A. A. Jungbluth, X. D. Ji, P. Suvarna, J. R. Voland, L. J. Old, H. J. Huang and W. K. Cavenee, "Growth Suppression of Intracranial Xenografted Glioblastomas Overexpressing Mutant Epidermal Growth Factor Receptors by Systemic Administration of Monoclonal Antibody (mAb) 806, a Novel Monoclonal Antibody Directed to the Receptor." *Cancer Res.* (2001) 5349-5354, 61.
Modjtahedi et al., *Cell Biophys.* (1993) 129-146, 22(1-3).
Motoyama, A.B., N.E. Hynes and Lane. H.A., "The efficacy of ErbB receptor-targeted anticancer therapeutics is influenced by the availability of epidermal growth factor-related peptides." *Cancer Res.* (2002) 3151-3158, 62.
Nishikawa, R., X. D. Ji, R. C. Harmon, C. S. Lazar, G. N. Gill, W. K. Cavenee and H. J. Huang, "A mutant epidermal growth factor receptor common in human glioma confers enhanced tumorigenicity." *Proc. Natl. Acad. Sci. USA* (1994) 7727-7731, 91.
Normanno et al., "Epidermal growth factor receptor (EGFR) signaling in cancer." *Gene*, (2006) 2-16, 366.
Okamoto, Yoshikawa, Obata, Shibuya, Aoki, Yoshida and Takahashi, "Monoclonal antibody against the fusion junction of a deletion-mutant epidermal growth factor receptor." *Br. J. Cancer* (1996) 1366-1372, 73.

Paez et al., "EGFR Mutations in Lung Cancer: Correlation with Clinical Response to Gefitinib Therapy." *Science* (2004) 1497-1500, 304.
Pao et al., "Acquired resistance of lung adenocarcinomas to gefitinib or erlotinib is associated with a second mutation in the EGFR kinase domain." *PLoS Med.* (2005) e73, 2(3).
Perera, A.D., E.V. Kleymenova and C.L. Walker, "Requirement for the von Hippel-Lindau tumor suppressor gene for functional epidermal growth factor receptor blockade by monoclonal antibody C225 in renal cell carcinoma." *Clin. Cancer Res.* (2000) 1518-1523, 6.
Perera, Narita, Furnari, Gan, Murone, Ahlkvist, Luwor, Burgess, Stockert and Jungbluth, "A novel EGFR antibody that displays synergistic anti-tumor activity when combined with conventional EGFR therapeutics." *Clin. Cancer Res.* (2005) 6390-6399, 11.
Power and Hudson, *J. Immunol. Methods* (2000) 193-204, 242.
Pruss, R.M. and H.R. Herschman, "Variants of 3T3 cells lacking mitogenic response to epidermal growth factor." *PNAS* (1977) 3918-3921, 74.
Reist, Archer, Kurpad, Wikstrand, Vaidyanathan, Willingham, Moscatello, Wong, Bigner and Zalutsky, "Tumor-specific anti-epidermal growth factor receptor variant in monoclonal antibodies: use of the tyramine-cellobiose radio iodination method enhances cellular retention and uptake in tumor xenografts." *Cancer Res.* (1995) 4375-4382, 55.
Reist, Archer, Wikstrand, Bigner and Zalutsky, "Improved targeting of an anti-epidermal growth factor receptor variant III monoclonal antibody in tumor xenografts after labeling using N-succinimidyl 5-iodo-3-pyridinecarboxylate." *Cancer Res.* (1997) 1510-1515, 57.
Schneebaum et al., *World J. Surg.* (2001) 1495-1498, 25(12).
Siegel-Lakhai, W.S., J.H. Beijnen and J.H. Schellens, "Current knowledge and future directions of the selective epidermal growth factor receptor inhibitors erlotinib (Tarceva) and gefitinib (Iressa)." *Oncologist* (2005) 579-589, 10.
Stein et al., *Cancer* (2002) 51-61, 94(1).
Stragliotto, G., F. Vega, P. Stasiecki, P. Gropp, M. Poisson and J. Y. Delattre, *Eur. J. Cancer* (1996) 636-640, 32A.
Sugawa, Ekstrand, James and Collins, "Identical splicing of aberrant epidermal growth factor receptor transcripts from amplified re-arranged genes in human glioblastomas." *Proc. Natl. Acad. Sci. USA* (1990) 8602-8606, 87.
Tang, C. K., X. Q. Gong, D. K. Moscatello, A. J. Wong and M. E. Lippman, "Epidermal growth factor receptor vin enhances tumorigenicity in human breast cancer." *Cancer Res.* (2000) 3081-3087, 60.
Viloria-Petit et al., "Acquired resistance to the antitumor effect of epidermal growth factor receptor-blocking antibodies in vivo: a role for altered tumor angiogenesis." *Cancer Res.* (2001) 5090-5101, 61.
Ward et al., *Nature* (1989) 544-546, 341.
Wikstrand, C. J., L. P. Hale, S. K. Batra, M. L. Hill, P. A. Humphrey, S. N. Kurpad, R. E. McLendon, D. Moscatello, C. N. Pegram and C. J. Reist, "Monoclonal antibodies against EGFRvin are tumor specific and react with breast and lung carcinomas and malignant gliomas." *Cancer Res.* (1995) 3140-3148, 55.
Wong, A. J., J. M. Ruppert, S. H. Bigner, C. H. Grzeschik, P. A. Humphrey, D. S. Bigner and B. Vogelstein, "Structural alterations of the epidermal growth factor receptor gene in human gliomas." *Proc. Natl. Acad. Sci. USA* (1992) 2965-2969, 89.
Yeatman, T.J., *Nat. Rev. Cancer* (2004) 470-480, 4(6).
"Clinical Trial Confirms Novel EGFR Antibody Targets Tumours But Not Normal Tissues," Ludwig Institute for Cancer Research, 2010.
Abbruzzese J.L., et al., "Phase II Study of Anti-Epidermal Growth Factor Receptor (EGFR) Antibody Cetuximab (IMC-C225) in Combination with Gemcitabine in Patients with Advanced Pancreatic Cancer," Proceedings of American Society of Clinical Oncology, 2001, vol. 20, pp. 130A.
Aboud-Pirak E., et al., "Inhibition of Human Tumor Growth in Nude Mice by a Conjugate of Doxorubicin with Monoclonal Antibodies to Epidermal Growth Factor Receptor," Proceedings of the National Academy of Sciences, 1989, vol. 86 (10), pp. 3778-3781.
Aboud-Pirak, et al., "Efficacy of Antibodies to Epidermal Growth Factor Receptor Against Kb Carcinoma In Vitro and in Nude Mice," Chemical Abstracts, 1989, vol. 110 (9), pp. 69068k.

(56) References Cited

OTHER PUBLICATIONS

Adams G.P., et al., "Monoclonal Antibody Therapy of Cancer," Nature Biotechnology, 2005, vol. 23 (9), pp. 1147-1157.
Aden D.P., et al., "Cell Surface Antigens Coded for by the Human Chromosome 7," Immunogenetics, 1976, vol. 3 (1), pp. 209-221.
Aghajanian, et al., "A Phase Ii Study of Cetuximab/Paclitaxellcarboplatin for the Initial Treatment of Advanced Stage Ovarian, Primary Peritoneal, and Fallopian Tube Cancer," Journal of Clinical Oncology, ASCO Annual Meeting Proceedings, 2005, Abstract 5047, pp. 16S.
Agosti R.M., et al., "Expression of the Epidermal Growth Factor Receptor in Astrocytic Tumours is Specifically Associated with Glioblastoma Multiforme," Virchows Archiv. A, Pathological Anatomy and Histopathology, 1992, vol. 420 (4), pp. 321-325.
Agulnik M., et al., "Predictive and Pharmacodynamic Biomarker Studies in Tumor and Skin Tissue Samples of Patients with Recurrent or Metastatic Squamous Cell Carcinoma of the Head and Neck Treated with Erlotinib," Journal of Clinical Oncology, 2007, vol. 25 (16), pp. 2184-2190.
Agus D.B., et al., "Phase I Clinical Study of Pertuzumab, a Novel Her Dimerization Inhibitor, in Patients with Advanced Cancer," Journal of Clinical Oncology, 2005, vol. 23 (11), pp. 2534-2543.
Agus D.B., et al., "Targeting Ligand-Activated ErbB2 Signaling Inhibits Breast; and Prostate Tumor Growth," Cancer Cell, 2002, vol. 2 (2), pp. 127-137.
Akiyama T., et al., "Genistein, a Specific Inhibitor of Tyrosine-specific Protein Kinases," Journal of Biological Chemistry, 1987, vol. 262 (12), pp. 5592-5595.
Albanell J., et al., "Activated Extracellular Signal-Regulated Kinases: Association with Epidermal Growth Factor Receptor/Transforming Growth Factor Alpha Expression in Head and Neck Squamous Carcinoma and Inhibition by Anti-Epidermal Growth Factor Receptor Treatments," Cancer Research, 2001, vol. 61 (17), pp. 6500-6510.
Albanell J., et al., "Pharmacodynamic Studies of the Epidermal Growth Factor Receptor Inhibitor Zd1839 in Skin from Cancer Patients: Histopathologic and Molecular Consequences of Receptor Inhibition," Journal of Clinical Oncology, 2002, vol. 20 (1), pp. 110-124.
Albanell J., et al., "Pharmacodynamic Studies With the Epidermal Growth Factor Receptor Tyrosine Kinase Inhibitor ZD1839," Seminars in Oncology, 2001, vol. 28 (5) (suppl. 16), pp. 56-66.
Aldape K.D., et al., "Immunohistochemical Detection of Egfrviii in High Malignancy Grade Astrocytomas and Evaluation of Prognostic Significance," Journal of Neuropathology & Experimental Neurology, 2004, vol. 63 (7), pp. 700-707.
Alimirah F., et al., "Du-145 and Pc-3 Human Prostate Cancer Cell Lines Express Androgen Receptor: Implications for the Androgen Receptor Functions and Regulation," FEBS Letters, 2006, vol. 580 (9), pp. 2294-2300.
Alroyl., et al., "The Erbb Signaling Network in Embryogenesis and Oncogenesis: Signal Diversification Through Combinatorial Ligand-Receptor Interactions," FEBS Letters, 1997, vol. 410 (1), pp. 83-36.
Anderson N.G., et al., "ZD1839 (Iressa), a Novel Epidermal Growth Factor Receptor (EGFR) Tyrosine Kinase Inhibitor, Potently Inhibits the Growth of EGFR-Positive Cancer Cell Lines with or without erbB2 Overexpression," International Journal of Cancer, 2001, vol. 94 (6), pp. 774-782.
Andrews P.A., et al., "Cellular Pharmacology of Cisplatin: Perspectives on Mechanisms of Acquired Resistance," Cancer Cells, 1990, vol. 2 (2), pp. 35-43.
Ang K.K., et al., "Epidermal Growth Factor Receptor and Response of Head-and-neck carcinoma to therapy," 2004, vol. 58 (3), pp. 959-965.
Ang K.K., et al., "Impact of epidermal growth factor receptor expression on survival and pattern of relapse in patients with advanced head and neck carcinoma," Cancer Research, 2002, vol. 62 (24), pp. 7350-7356.
Anido J., et al., "ZD1839, a Specific Epidermal Growth Factor Receptor (EGFR) Tyrosine Kinase Inhibitor, Induces the Formation of Inactive EGFR/HER2 and EGFR/HER3 Heterodimers and Prevents Heregulin Signaling in HER2-overexpressing Breast Cancer Cells," Clinical Cancer Research, 2003, vol. 9 (4), pp. 1274-1283.
Annual Research Highlights Report 2006, Ludwig Institute for Cancer Research, 2007, pp. 1-56.
Annual Research Report 2002-2003, Ludwig Institute for Cancer Research, 2003. pp. 1-7.
Archer G.E., et al., "Regional Treatment of Epidermal Growth Factor Receptor VIII-expressing Neoplastic Meningitis with a Single-Chain Immunotoxin, MR-1," Clinical Cancer Research, 1999, vol. 5 (9), pp. 2646-2652.
Arteaga C.L., "Epidermal Growth Factor Receptor Dependence in Human Tumors: More Than Just Expression," The Oncologist, 2002, vol. 7 (suppl. 4), pp. 31-39.
Arteaga C.L., "ErbB-Targeted Therapeutic Approaches in Human Cancer," Experimental Cell Research, 2003, vol. 284 (1), pp. 122-130.
Arteaga C.L., , "The Epidermal Growth Factor Receptor: From Mutant Oncogene in Nonhuman Cancers to Therapeutic Target in Human Neoplasia," Journal of Clinical Oncology, 2001, vol. 19 (suppl. 18), pp. 32S-42S.
Arteaga C.L., et al., "Overview of Rationale and Clinical Trials With Signal Transduction Inhibitors in Lung Cancer," Seminars in Oncology, 2002, vol. 29 (1) (suppl. 4), pp. 15-26.
Arteaga C.L., et al., "Tyrosine kinase inhibitors-ZD1839 (Iressa)," Current Opinion in Oncology, 2001, vol. 13 (6), pp. 491-498.
Arteaga C.L., et al., "Tyrosine Kinase Inhibitors:Why Does the Current Process of Clinical Development Not Apply to Them," Cancer Cell, 2004, vol. 5 (6), pp. 525-531.
Arteaga, et al., "Antibodies Against P185her2 Enhance Etoposide-Induced Cytotoxicity Against Human Breast Carcinoma Cells," Proceedings of the American Society of Clinical Oncology, 1993, vol. 75 (Abstract 101), pp. 12.
Atlas I., et al., "Growth Regulation of Human Renal Carcinoma Cells: Role of Transforming Growth Factor," Journal of Cancer Research, 1992, vol. 52 (12), pp. 3335-3339.
Aujame L., et al., "High Affinity Human Antibodies by Phage; Display," Human Antibodies, 1997, vol. 8 (4), pp. 155-168.
Austin C.D., et al., "Endocytosis and Sorting of Erbb2 and the Site of Action of Cancer Therapeutics Trastuzumab and Geldanamycin," Molecular Biology of the Cell, 2004, vol. 15 (12), pp. 5268-5282.
Azzazy H.M., et al., "Phage Display Technology: Clinical Applications and Recent Innovations," Clinical Biochemistry, 2002, vol. 35 (6), pp. 425-445.
Bailey, et al., "Evaluation of Epidermal Growth Factor Receptor (Egfr) as a Predictive Marker in Patients With Non-Small-Cell Lung Cancer (Nsclc) Receiving First-Line Gefitinib Combined With Platinum-Based Chemotherapy," Journal of Clinical Oncology, ASCO Annual Meeting Proceedings, Post-Meeting Edition, 2004, Abstract 7013, pp. 22 (14S).
Balaban N., et al., "The Effect of Ionizing Radiation on Signal Transduction: Antibodies to EGF Receptor Sensitize A431 Cells to Radiation," Biochimica Biophysica Acta. , 1996, vol. 1314 (1-2), pp. 147-156.
Baly, et al., "Development and Characterization of a Rhumab Her2 Antibody Adcc Assay for Clinical Evaluation of Cytotoxic Potency," Proceedings of the American Association for Cancer Research, 1997, vol. 27-28 (Abstract 181), pp. 38.
Bandyopadhyay D., et al., "Physical Interaction between Epidermal Growth Factor Receptor and DNA-dependent Protein Kinase in Mammalian Cells," Journal of Biological Chemistry, 1998, vol. 273 (3), pp. 1568-1573.
Barendswaard E.C., et al., "Rapid and Specific Targeting of Monoclonal Antibody A33 to a Colon Cancer Xenograft in Nude Mice," International Journal of Oncology, 1998, vol. 12 (1), pp. 45-53.
Barnette M.S., et al., "Association of the Anti-Inflammatory Activity of Phosphodiesterase 4 (PDE4) Inhibitors with either Inhibition of PDE4 Catalytic Activity or Competition for (3H)Rolipram Binding," Biochemical Pharmacology, 1996, vol. 51 (7), pp. 949-956.
Baselga J., "Clinical Trials of Herceptin(TrastuzumAb)," European Journal of Cancer, 2001, vol. 37 (Suppl. 1), pp. S18-S24.

(56) References Cited

OTHER PUBLICATIONS

Baselga J., "Combining the Anti-EGFR Agent Gefitinib With Chemotherapy in Non-Small-Cell Lung Cancer: How Do We Go From Intact to Impact," Journal of Clinical Oncology, 2004, vol. 22 (5), pp. 759-761.

Baselga J., "Herceptin Alone or in Combination with Chemotherapy in the Treatment of HER2-Positive Metastatic Breast Cancer: Pivotal Trials," Oncology, 2001, vol. 61 (suppl. 2), pp. 14-21.

Baselga J., "Targeting the Epidermal Growth Factor Receptor: A Clinical Reality," Journal of Clinical Oncology, 2001, vol. 19 (suppl. 18), pp. 41S-44S.

Baselga J., "Targeting Tyrosine Kinases in Cancer: The Second Wave," Science, 2006, vol. 312 (5777), pp. 1175-1178.

Baselga J., et al., "Continuous Administration of Z01839 (Iressa), a Novel Oral Epidermal Growth Factor Receptor Tyrosine Kinase Inhibitor (EGFR-TKI), in Patients with Five Selected Tumor Types: Evidence of Activity and Good Tolerability.," Proceedings of American Society of Clinical Oncology, 2000, vol. 19, pp. 177A.

Baselga J., et al., "Antitumor Effects of Doxorubicin in Combination with Anti-Epidermal Growth Factor Receptor Monoclonal Antibodies," Journal of the National Cancer Institute, 1993, vol. 85, pp. 1327-1333.

Baselga J., et al., "Critical Update and Emerging Trends in Epidermal Growth Factor Receptor Targeting in Cancer," Journal of Clinical Oncology, 2005, vol. 23 (11), pp. 2445-2459.

Baselga J., et al., "Mechanism of Action of Trastuzumab and Scientific Update," Seminars in Oncology, 2001, vol. 28 (5) (suppl. 16), pp. 4-11.

Baselga J., et al., "Phase I Safety, Pharmacokinetic, and Pharmacodynamic Trial of ZD1839, a Selective Oral Epidermal Growth Factor Receptor Tyrosine Kinase Inhibitor, in Patients With Five Selected Solid Tumor Types," Journal of Clinical Oncology, 2002, vol. 20 (21), pp. 4292-4302.

Baselga J., et al., "Phase II and Tumor Pharmacodynamic Study of Gefitinib in Patients With Advanced Breast Cancer," Journal of Clinical Oncology, 2005, vol. 23 (23), pp. 5323-5333.

Baselga J., et al., "Phase II Multicenter Study of the Antiepidermal Growth Factor Receptor Monoclonal Antibody Cetuximab in Combination With Platinum-Based Chemotherapy in Patients With Platinum-Refractory Metastatic and/or Recurrent Squamous Cell Carcinoma of the Head and Neck," Journal of Clinical Oncology, 2005, vol. 23 (24), pp. 5568-5577.

Baselga J., et al., "Phase II Study of Efficacy, Safety, and Pharmacokinetics of Trastuzumab Monotherapy Administered on a 3-Weekly Schedule," Journal of Clinical Oncology, 2005, vol. 23 (10), pp. 2162-2171.

Baselga J., et al., "Phase II Study of Weekly Intravenous Recombinant Humanized Anti-P185her2 Monoclonal Antibody in Patients with Her2/Neu-Overexpressing Metastatic Breast Cancer," Journal of Clinical Oncology, 1996, vol. 14 (3), pp. 737-744.

Baselga J., et al., "Receptor Blockade with Monoclonal Antibodies as Anti-Cancer Therapy," Pharmacology and Therapeutics, 1994, vol. 64 (1), pp. 127-154.

Baselga J., et al., "Recombinant Humanized Anti-HER2 Antibody (Herceptin) Enhances the Antitumor Activity of Paclitaxel and Doxorubicin Against HER2/neu Overexpressing Human Breast Cancer Xenografts," Journal of Cancer Research, 1998, vol. 58 (13), pp. 2825-2831.

Baselga J., et al., "ZD1839 (Iressa)1, 2 as an Anticancer Agent," Drugs, 2000, vol. 60 (1), pp. 33-42.

Baselga, et al., "Antitumor Activity of Paclitaxel in Combination With Anti-Growth Factor Receptor Monoclonal Antibodies in Breast Cancer Xenografts," Proceedings of the American Association for Cancer Research, 1994, vol. 380 (Abstract 2262), pp. 35.

Baselga, et al., "Cetuximab (C225) Plus Cisplatin/Carboplatin is Active in Patients (Pts) With Recurrent/Metastatic Squamous Cell Carcinoma of the Head and Neck (Scchn) Progressing on a Same Dose and Schedule Platinum-Based Regimen," Proceedings of the American Society of Clinical Oncology, 2002, Abstract 900, pp. 21.

Baselga, et al., "Mechanism of Action of Anti-Her2 Monoclonal Antibodies," Annals of Oncology, 2001, vol. 12 (Suppl. 1), pp. S35-S41.

Baselga, et al., "Phase I Study of Aee788, a Novel Multitargeted Inhibitor of Erbb and Vegf Receptor Family Tyrosine Kinases (A Pharmacokinetic (Pk)-Pharmacodynamic (Pd) Study to Identify the Optimal Therapeutic Dose Regimen)," Journal of Clinical Oncology, 2005, Abstract 3028, pp. 23.

Beckmann M.W., et al., "Expression Analyses of Epidermal Growth Factor Receptor and Her-2/Neu: No Advantage of Prediction of Recurrence or Survival in Breast Cancer Patients," Oncology, 1996, vol. 53 (6), pp. 441-447.

Beers R., et al., "Immunotoxins with Increased Activity against Epidermal Growth Factor Receptor vIII-expressing Cells Produced by Antibody Phage Display," Clinical Cancer Research, 2000, vol. 6 (7), pp. 2835-2843.

Behr T.M., et al., "Radioimmunotherapy of Small Volume Disease of Colorectal Cancer Metastatic to the Liver: Preclinical Evaluation in Comparison to Standard Chemotherapy and Initial Results of a Phase I Clinical Study," Clinical Cancer Research, 1999, vol. 5 (Suppl. 10), pp. 3232s-3242s.

Bell D.W., et al., "Epidermal Growth Factor Receptor Mutations and Gene Amplification in Non-Small-Cell Lung Cancer: Molecular Analysis of the Ideal/Intact Gefitinib Trials," Journal of Clinical Oncology, 2005, vol. 23 (31), pp. 8081-8092.

Bell D.W., et al., "Inherited Susceptibility to Lung Cancer may be Associated with the T790M Drug Resistance Mutation in EGFR," Nature Genetics, 2005, vol. 37 (12), pp. 1315-1316.

Bender H., et al., "Immunotherapy of Human Glioma Xenografts With Unlabeled, 131i-, or 125i-Labeled Monoclonal Antibody 425 to Epidermal Growth Factor Receptor," Cancer Research, 1992, vol. 52 (1), pp. 121-126.

Bequinot L et al. Down-regulation of the epidermal growth factor receptor in KB cells is due to receptor internalization and subsequent degradation in lysosomes. Proc Natl Acad Sci U S A. Apr. 1984;81(8):2384-8.

Bernier J., "Cetuximab in the Treatment of the Head and Neck Cancer," Expert Review of Anticancer Therapy, 2006, vol. 6 (11), pp. 1539-1552.

Bertics P.J., et al., "Alteration of Epidermal Growth Factor Receptor Activity by Mutation of Its Primary Carboxyl-Terminal Site of Tyrosine Self-Phosphorylation," Journal of Biological Chemistry, 1988, vol. 263 (8), pp. 3610-3617.

Bertics P.J., et al., "Self-Phosphorylation Enhances the Protein-Tyrosine Kinase Activity of the Epidermal Growth Factor Receptor," Journal of Biological Chemistry, 1985, vol. 260 (27), pp. 14642-14647.

Bhattacharya-Chatterjee M., et al., "The Anti-Idiotype Vaccines for Immunotherapy," Current Opinion in Molecular Therapeutics, 2001, vol. 3 (1), pp. 63-69.

Bianco C., et al., "Antitumor Activity of Combined Treatment of Human Cancer Cells with Ionizing Radiation and Anti-Epidermal Growth Factor Receptor Monoclonal Antibody C225 Plus Type I Protein Kinase A Antisense Oligonucleotide," Clinical Cancer Research, 2000, vol. 6 (11), pp. 4343-4350.

Bier H., et al., "Anti-(Epidermal Growth Factor) Receptor Monoclonal Antibodies for the Induction of Antibody-Dependent Cell-Mediated Cytotoxicity Against Squamous Cell Carcinoma Lines of the Head and Neck," Cancer Immunology, Immunotherapy, 1998, vol. 46 (3), pp. 167-173.

Bier H., et al., "Dose-Dependent Access of Murine Anti-Epidermal Growth Factor Receptor Monoclonal Antibody to Tumor Cells in Patients With Advanced Laryngeal and Hypopharyngeal Carcinoma," European archives of oto-rhino-laryngology, 1995, vol. 252 (7), pp. 433-439.

Biernat W., et al., "Predominant Expression of Mutant Egfr (Egfrviii) is Rare in Primary Glioblastomas," Brain Pathology, 2004, vol. 14 (2), pp. 131-136.

Bigner S.H., et al., "Characterization of the Epidermal Growth Factor Receptor in Human Glioma Cell Lines and Xenografts," Cancer Research, 1990, vol. 50 (24), pp. 8017-8022.

(56) References Cited

OTHER PUBLICATIONS

Bindon C.I., et al., "Importance of Antigen Specificity for Complement-Mediated Lysis by Monoclonal Antibodies," European Journal of Immunology, 1988, vol. 18 (10), pp. 1507-1514.
Biscardi J.S., et al., "C-Src, Receptor Tyrosine Kinases, and Human Cancer," Advanced Cancer Research, 1999, vol. 76, pp. 61-119.
Bishop J.M., "The Molecular Genetics of Cancer," Science, 1987, vol. 235 (4786), pp. 305-311.
Blagosklonny M.V., et al., "Why Iressa Failed: Toward Novel Use of Kinase Inhibitors (Outlook).," Cancer Biology and Therapy, 2003, vol. 2 (2), pp. 137-140.
Blume-Jensen P., et al., "Oncogenic Kinase Signalling," Nature, 2001, vol. 411 (6835), pp. 355-365.
Boger, "Design, Synthesis, and Evaluation of DNA Minor Groove Binding Agents: the Duocarmycins," Pure and Applied Chemistry, 1994, vol. 66 (4), pp. 837-844.
Boghaert E.R., et al., "Antibody-Targeted Chemotherapy with the Calicheamicin Conjugate hu3S193-N-Acetyl Calicheamicin Dimethyl Hydrazide Targets Lewisy and Eliminates Lewisy-Positive Human Carcinoma Cells and Xenografts ," Clinical Cancer Research , 2004, vol. 10 (13), pp. 4538-4549.
Bonner et al., "Enhanced Apoptosis with Combination C225/radiation Treatment Serves as the Impetus for Clinical Investigation in Head and Neck Cancers," Proceedings of the Annual Meeting of the American Society of Clinical Oncology, 2000, vol. 10 (Abstract 5F), pp. 4a.
Bonner J.A., et al., "Enhanced Apoptosis With Combination C225/ Radiation Treatment Serves as the Impetus for Clinical Investigation in Head and Neck Cancers," Journal of Clinical Oncology, 2000, vol. 18 (suppl. 21), pp. 47S-53S.
Bonner J.A., et al., "Radiotherapy Plus Cetuximab for Squamous-Cell Carcinoma of the Head and Neck," The New England Journal of Medicine, 2006, vol. 354 (6), pp. 567-578.
Bonner, et al., "Cetuximab Improves Locoregional Control and Survival of Locoregionally Advanced Head and Neck Cancer: Independent Review of Mature Data With a Median Follow-Up of 45 Months," Presented at the Annual Aacr-Nci-Eortc International Conference on Molecular Targets and Cancer Therapeutics: Discovery, Biology, and Clinical Applications; Nov. 2005, philadelphia; pa. (2011), Abstract B106.
Bonner, et al., "Cetuximab Prolongs Survival in Patients With Locoregionally Advanced Squamous Cell Carcinoma of Head and Neck (A Phase Iii Study of High Dose Radiation Therapy With or Without Cetuximab)," Journal of Clinical Oncology, 2004 ASCO Annual Meeting Proceedings (Post-Meeting Edition), 2004, Abstract 5507, pp. 22 (14S).
Boonstra J., et al., "The Epidermal Growth Factor," Cell Biology International, 1995, vol. 19 (5), pp. 413-430.
Bos, et al., "Phase I Studies of Anti-Epidermal Growth Factor Receptor Chimeric Monoclonal Antibody C225 in Patients With Egfr Overexpressing Tumors," American Society of Clinical Oncolog, 1996, vol. 443 (Abstract 1381), pp. 15.
Boschelli, "Small Molecule Inhibitors of Receptor Tyrosine Kinases," Drugs of the Future, 1999, vol. 24 (5), pp. 515-537.
Bouyain S., et al., "The Extracellular Region of ErbB4 Adopts a Tethered Conformation in the Absence of Ligand," Proceedings of the National Academy of Sciences, 2005, vol. 102 (42), pp. 15024-15029.
Boyer C.M., et al., "Relative Cytotoxic Activity of Immunotoxins Reactive with Different Epitopes on the Extracellular Domain of the c-ErbB-2 (HER-2/neu) Gene Product p185," International Journal of Cancer, 1999, vol. 82, pp. 525-531.
Brock C.S., et al., "Review Current Perspectives in Gliomas," Medical Oncology, 1997, vol. 14 (2), pp. 103-120.
Brown D., et al., "Antiepidermal Growth Factor Receptor Antibodies Augment Cytotoxicity of Chemotherapeutic Agents on Squamous Cell Carcinoma Cell Lines," Otolaryngology Head and Neck Surgery, 2000, vol. 122 (1), pp. 75-83.

Bruggemann M., et al., "The Immunogenicity of Chimeric Antibodies," The Journal of Experimental Medicine, 1989, vol. 170 (6), pp. 2153-2157.
Bruns C.J., et al., "Blockade of the Epidermal Growth Factor Receptor Signaling by a Novel Tyrosine Kinase Inhibitor Leads to Apoptosis of Endothelial Cells and Therapy of Human Pancreatic Cells and Therapy of Human Pancreatic," Clinical Cancer Research , 2000, vol. 60 (11), pp. 2926-2935.
Bruns C.J., et al., "Epidermal Growth Factor Receptor Blockade with C225 Plus Gemcitabine Results in Regression of Human Pancreatic Carcinoma Growing Orthotopically in Nude Mice by Antiangiogenic Mechanisms," Clinical Cancer Research , 2000, vol. 6 (5), pp. 1936-1948.
Bucci B., et al., "Egf-R Expression in Ductal Breast Cancer: Proliferation and Prognostic Implications," Anticancer Research, 1997, vol. 17 (1B), pp. 769-774.
Bucholtz J.D., "Radiolabeled Antibody Therapy," Seminars in Oncology Nursing, 1987, vol. 3 (1), pp. 67-73.
Buchsbaum D.J., et al., "Experimental Radioimmunotherapy," Medical Physics, 1993, vol. 20 (2 Pt 2), pp. 551-567.
Budillon, et al., "Zd1839, an Epidermal Growth Factor Receptor Tyrosine Kinase Inhibitor, Upgregulates P27kip1 Inducing Gi Arrest and Enhancing the Antitumor Effect of Interferon," Proceedings of the Annual Meeting of the American Association for Cancer Research, 2000, vol. 773 (Abstract 4910).
Burris H.A. 3rd., et al., "Phase I Safety, Pharmacokinetics, and Clinical Activity Study of Lapatinib (Gw572016), a Reversible Dual Inhibitor of Epidermal Growth Factor Receptor Tyrosine Kinases, in Heavily Pretreated Patients with Metastatic Carcinomas," Journal of Clinical Oncology, 2005, vol. 23 (23), pp. 5305-5313.
Burstein H.J., et al., "Trastuzumab and Vinorelbine as First-Line Therapy for Her2-Overexpressing Metastatic Breast Cancer: Multicenter Phase II Trial with Clinical Outcomes, Analysis of Serum Tumor Markers as Predictive Factors, and Cardiac Surveillance Algorithm," Journal of Clinical Oncology, 2003, vol. 21 (15), pp. 2889-2895.
Burstein, et al., "A Phase II, Open-Label, Multicenter Study of Lapatinib in Two Cohorts of Patients with Advanced or Metastatic Breast Cancer Who have Progressed While Receiving Trastuzumab-Containing Regimens," Annals of Oncology, 2004, vol. 27 (Abstract 1040), 15 (Suppl. 3).
Burtness B., et al., "Phase III Randomized Trial of Cisplatin Plus Placebo Compared with Cisplatin Plus Cetuximab in Metastatic/Recurrent Head and Neck Cancer: an Eastern Cooperative Oncology Group Study," Journal of Clinical Oncology, 2005, vol. 23 (34), pp. 8646-8654.
Burtness B.A., et al., "Phase III Trial Comparing Cisplatin (C) + Placebo (P) to C + Anti-Epidermal Growth Factor Antibody (EGF-R) C225 in Patients (pts) with Metastatic/Recurrent Head & Neck Cancer (HNC)," Proceedings of American Society of Clinical Oncology, 2002, vol. 21, pp. 226A.
Busam K.J., et al., "Cutaneous Side-Effects in Cancer Patients Treated with the Antiepidermal Growth Factor Receptor Antibody C225," British Journal of Dermatology, 2001, vol. 144 (6), pp. 1169-1176.
Cadena D.L., et al., "The Intracellular Tyrosine Kinase Domain of the Epidermal Growth Factor Receptor Undergoes a Conformational Change Upon Autophosphorylation," Journal of Biological Chemistry, 1994, vol. 269 (1), pp. 260-265.
Cai W., et al., "Quantitative Pet of EGFR Expression in Xenograft-Bearing Mice Using 64cu-Labeled Cetuximab, a Chimeric Anti-EGFR Monoclonal Antibody," European Journal of Nuclear Medicine and Molecular Imaging, 2007, vol. 34 (6), pp. 850-858.
Caldas C., et al., "Humanization of the Anti-CD18 Antibody 6.7: an Unexpected Effect of a Framework Residue in Binding to Antigen," Molecular Immunology, 2003, vol. 39 (15), pp. 941-952.
Callaghan T., et al., "A Complete Description of the Egf-Receptor Exon Structure: Implication in Oncogenic Activation and Domain Evolution," Oncogene, 1993, vol. 8 (11), pp. 2939-2948.
Campos-Gonzalez R., et al., "Immunodetection of the Ligand-Activated Receptor for Epidermal Growth Factor," Growth Factors, 1991, vol. 4 (4), pp. 305-316.

(56) References Cited

OTHER PUBLICATIONS

Cappuzzo F., et al., "Epidermal Growth Factor Receptor Gene and Protein and Gefitinib Sensitivity in Non-Small-Cell Lung Cancer," Journal of the National Cancer Institute, 2005, vol. 97 (9), pp. 643-655.

Cappuzzo, F., et al., "Increased Her2 Gene Copy Number Is Associated with Response to Gefitinib Therapy in Epidermal Growth Factor Receptor-Positive Non-Small-Cell Lung Cancer Patients," Journal of Clinical Oncology, 2005, vol. 23 (22), pp. 5007-5018.

Carlin C.R., et al., "Identity of Human Epidermal Growth Factor (EGF) Receptor with Glycoprotein SA-7: Evidence for Differential Phosphorylation of the Two Components of the EGF Receptor from A431 Cells," Proceedings of the National Academy of Sciences, 1982, vol. 79 (16), pp. 5026-5030.

Carlin C.R., et al., "S6 is theHhuman Receptor for Epidermal Growth Factor (EGF). (Abstract) Cytogenet," Cell Genet, 1982, vol. 32, pp. 256.

Carpenter G., "Properties of the Receptor for Epidermal Growth Factor," Cell, 1984, vol. 37, pp. 357-358.

Carpenter G., "Receptors for Epidermal Growth Factor and Other Polypeptide Mitogens," Annual Review of Biochemistry, 1987, vol. 56, pp. 881-914.

Carteni G., et al., "Panitumumab a Novel Drug in Cancer Treatment," Annals of Oncology, 2007, vol. 18 Suppl. 6, pp. vi16-vi21.

Carter P., "Improving the Efficacy of Antibody-based Cancer Therapies," Nature Reviews, 2001, vol. 1 (2), pp. 118-129.

Carter P., et al., "Humanization of an Anti-p185 HER2 Antibody for Human Cancer Therapy," Proceedings of the National Academy of Sciences, 1992, vol. 89 (10), pp. 4285-4289.

Carter P., et al., "Identification and Validation of Cell Surface Antigens for Antibody Targeting in Oncology," Endocrine-related Cancer, 2004, vol. 11 (4), pp. 659-687.

Carter T.H., et al., "Tissue-Specific Transformation by Oncogenic Mutants of Epidermal Growth Factor Receptor," Critical Reviews in Oncogenesis, 1994, vol. 5 (4), pp. 389-428.

Cartron G., et al., "Therapeutic Activity of Humanized Anti-CD20 Monoclonal Antibody and Polymorphism in IgG Fc Receptor Fc gRIIIa Gene," Blood, 2002, vol. 99 (3), pp. 754-758.

Casado, et al., "A Phase I/11a Pharmacokinetic (Pk) and Serial Skin and Tumor Pharmacodynamic (Pd) Study of the EGFR Irreversible Tyrosine Kinase Inhibitor Ekb-569 in Combination with 5-Fluorouracil (5fu), Leucovorin (Lv) and Irinotecan (Cpt-11) (Folfiri Regimen) in Patients (Pts) with Advanced Colorectal Cancer (Acc)," Journal of Clinical Oncology, 2004, vol. 255s (Abstract 3543), pp. 22.

Casset, F., et al., "A Peptie Mimetic of an Anti-CD4 Monoclonal Antibody by Rational Design," Biochemical and Biophysical Research Communications, 2003, vol. 307 (1), pp. 198-205.

Catimel B., et al., "Purification and Characterization of a Novel Restricted Antigen Expressed by Normal and Transformed Human Colonic Epithelium," Journal of Biological Chemistry, 1996, vol. 271 (41), pp. 25664-25670.

Chaffanet M., et al., "EGF Receptor Amplification and Expression in Human Brain Tumours," European Journal of Cancer, 1992, vol. 28 (1), pp. 11-17.

Chan, et al., "EGFR Tyrosine Kinase Inhibition Decreases Epithelial Proliferation in Dcis of the Breast, Whereas C-Erbb2 Blockade Does Not," Proceedings of the Annual Meeting of the American Association for Cancer Research, 2000, vol. 482 (Abstract 3074), pp. 41.

Chang C.P., et al., "Ligand-induced Internalization of the Epidermal Growth Factor Receptor Is Mediated by Multiple Endocytic Codes Analogous to the Tyrosine Motif Found in Constitutively Internalized Receptors," The Journal of Biological Chemistry, 1993, vol. 268 (26), pp. 19312-19320.

Chau N.G., et al., "The Association between EGFR variant III, HPV, p16, c-MET, EGFR Gene Copy Number and Response to EGFR Inhibitors in Patients with Recurrent or Metastatic Squamous Cell Carcinoma of the Head and Neck," Head and Neck Oncology, 2011, vol. 3, pp. 11.

Chen B., et al., "Mice Mutant for Egfr and Shp2 have Defective Cardiac Semilunar Valvulogenesis," Nature Genetics, 2000, vol. 24 (3), pp. 296-299.

Cherk M.H., et al., "Lack of Correlation of Hypoxic Cell Fraction and Angiogenesis with Glucose Metabolic Rate in Non-Small Cell Lung Cancer Assessed by 18 F-Fluoromisonidazole and 18 F-FDG PET," Journal of Nuclear Medicine, 2006, vol. 47 (12), pp. 1921-1926.

Chien N.C., et al., "Significant Structural and Functional Change of an Antigen-Binding Site by a Distant Amino Acid Substitution: Proposal of a Structural Mechanism," The Proceedings of the National Academy of Sciences, 1989, vol. 86 (14), pp. 5532-5534.

Ching K.Z., et al., "Expression of mRNA for Epidermal Growth Factor, Transforming Growth Factor-Alpha and their Receptor in Human Prostate Tissue and Cell Lines," Molecular and Cellular Biochemistry, 1993, vol. 126 (2), pp. 151-158.

Chinkers M., et al., "Rapid Induction of Morphological changes in Human Carcinoma Cells A-431 by Epidermal Growth Factor," 1979, vol. 83 (1), pp. 260-265.

Chong G., et al., "Phase I Trial of 131 I-huA33 in Patients with Advanced Colorectal Carcinoma," Clinical Cancer Research, 2005, vol. 11 (13), pp. 4818-4826.

Christensen, et al., "Immunohistochemical Detection of Epidermal Growth Factor Receptor in Laryngeal Squamous Cell Carcinomas," Acta Otolarvngol, 1992, vol. 112 (4), pp. 734-738.

Chung C.H., et al., "Increased Epidermal Growth Factor Receptor Gene Copy Number Is Associated with Poor Prognosis in Head and Neck Squamous Cell Carcinomas," Journal of Clinical Oncology, 2006, vol. 24 (25), pp. 4170-4176.

Ciardiello F., et al., "A Novel Approach in the Treatment of Cancer: Targeting the Epidermal Growth Factor Receptor," Clinical Cancer Research, 2001, vol. 7 (10), pp. 2958-2970.

Ciardiello F., et al., "Antiangiogenic and Antitumor Activity of Anti-Epidermal Growth Factor Receptor C225 Monoclonal Antibody in Combination with Vascular Endothelial Growth Factor Antisense Oligonucleotide in Human GEO Colon Cancer Cells," Clinical Cancer Research, 2000, vol. 6 (9), pp. 3739-3747.

Ciardiello F., et al., "Antitumor Activity of Combined Blockade of Epidermal Growth Factor Receptor and Protein Kinase A," Journal of National Cancer Institute, 1996, vol. 88 (23), pp. 1770-1776.

Ciardiello F., et al., "Antitumor Activity of Sequential Treatment with Topotecan and Anti-Epidermal Growth Factor Receptor Monoclonal Antibody C225," Clinical Cancer Research, 1999, vol. 5 (4), pp. 909-916.

Ciardiello F., et al., "Antitumor Effect and Potentiation of Cytotoxic Drugs Activity in Human Cancer Cells by ZD-1839 (Iressa), an Epidermal Growth Factor Receptor-selective Tyrosine Kinase Inhibitor," Clinical Cancer Research, 2000, vol. 6 (5), pp. 2053-2063.

Ciardiello F., et al., "Cooperative Antiproliferative Effects of 8-Chloro-Cyclic AMP and 528 Anti-Epidermal Growth Factor Receptor Monoclonal Antibody on Human Cancer Cells," Clinical Cancer Research, 1995, vol. 1 (2), pp. 161-167.

Ciardiello F., et al., "Cooperative Inhibition of Renal Cancer Growth by Anti-Epidermal Growth Factor Receptor Antibody and Protein Kinase a Antisense Oligonucleotide," Journal of National Cancer Institute, 1998, vol. 90 (14), pp. 1087-1094.

Ciardiello F., et al., "Epidermal Growth Factor Receptor (EGFR) as a Target in Cancer Therapy: Understanding the Role of Receptor Expression and Other Molecular Determinants That Could Influence the Response to Anti-EGFR Drugs," European Journal of Cancer, 2003, vol. 39 (10), pp. 1348-1354.

Ciardiello F., et al., "Epidermal Growth Factor Receptor Tyrosine Kinase Inhibitors as Anticancer Agents," Drugs, 2000, vol. 60 (1), pp. 25-32.

Ciardiello F., et al., "Inhibition of Growth Factor Production and Angiogenesis in Human Cancer Cells by ZD1839 (Iressa), a Selective Epidermal Growth Factor Receptor Tyrosine Kinase Inhibitor," Clinical Cancer Research, 2001, vol. 7 (5), pp. 1459-1465.

Ciardiello, et al., "Potentiation of Cytotoxic Drug Activity in Human Cancer Cells by Zd-1839 (Iressa), and EGFR-Selective Tyrosine Kinase Inhibitor," Proceedings of the American Association for Cancer Research, 2000, vol. 482 (Abstract 3075), pp. 41.

(56) References Cited

OTHER PUBLICATIONS

Ciesielski M.J., et al., "Oncogenic Epidermal Growth Factor Receptor Mutants with Tandem Duplication: Gene Structure and Effects on Receptor Function," Oncogene, 2000, vol. 19 (6), pp. 810-820.
Clark M., "Antibody Humanization: A Case of the 'Emperor's New Clothes'," Immunology Today, 2000, vol. 21 (8), pp. 397-402.
Clarke K., et al., "In Vivo Biodistribution of a Humanized Anti-Lewis Y Monoclonal Antibody (hu3S193) in MCF-7 xenografted BALB/c Nude Mice," Cancer Research, 2000, vol. 60 (17), pp. 4804-4811.
Clarke K., et al., "Mutant Epidermal Growth Factor Receptor Enhances Induction of Vascular Endothelial Growth Factor by Hypoxia and Insulin-Like Growth Factor-1 via a PI3 Kinase Dependent Pathway," British Journal of Cancer, 2001, vol. 84 (10), pp. 1322-1329.
Clarke K., et al., "Therapeutic Efficacy of Anti-Lewis (Y) Humanized 3S 193 Radioimmunotherapy in a Breast Cancer Model: Enhanced Activity When Combined with Taxol Chemotherapy," Clinical Cancer Research, 2000, vol. 6 (9), pp. 3621-3628.
Clayton A.H., et al., "Ligand-Induced Dimer-Tetramer Transition During the Activation of the Cell Surface Epidermal Growth Factor Receptor—A Multidimensional Microscopy Analysis," Journal of Biological Chemistry, 2005, vol. 280 (34), pp. 30392-30399.
Clayton A.H., et al., "Unligated Epidermal Growth Factor Receptor Forms Higher Order Oligomers within Microclusters on A431 Cells That Are Sensitive to Tyrosine Kinase Inhibitor Binding," Biochemistry, 2007, vol. 46 (15), pp. 4589-4597.
Clynes R.A., et al., "Inhibitory Fc Receptors Modulate in Vivo Cytoxicity Against Tumor Targets," Nature Medicine, 2000, vol. 6 (4), pp. 443-446.
Co M.S., et al., "Humanized Antibodies for Therapy," Nature, 1991, vol. 351, pp. 501-502.
Cobleigh M.A., et al., "Multinational Study of the Efficacy and Safety of Humanized Anti-HER2 Monoclonal Antibody in Women Who Have HER2-Overexpressing Metastatic Breast Cancer That Has Progressed After Chemotherapy for Metastatic Disease," Journal of Clincal Oncology, 1999, vol. 17 (9), pp. 2639-2648.
Cohen E.E.W., et al., "Phase II Study of Z01839 (Iressa) in Recurrent or Metastatic Squamous Cell Carcinoma of the Head and Neck," Proceedings of American Society of Clinical Oncology, 2002, vol. 21, pp. 225A.
Cohen M.H., et al., "United States Food and Drug Administration Drug Approval Summary: Gefitinib (ZD1839; Iressa) Tablets," Clinical Cancer Research, 2004, vol. 10, pp. 1212-1218.
Cohen S., et al., "Epidermal Growth Factor-Receptor-Protein Kinase Interactions," Journal of Biological Chemistry, 1980, vol. 225 (10), pp. 4834-4842.
Cohen, et al., "Safety Profile of the Monoclonal Antibody (Moab) Imc-C255, an Anti-Epidermal Growth Factor Receptor (EGFR) Used in the Treatment of EGFR-Positive Tumors," Proceedings of the American Society of Clinical Oncology, 2000, vol. 474a (Abstract 1862), pp. 19.
Cokgor I., et al., "Phase I Trial Results of Iodine-131-Labeled Antitenascin Monoclonal Antibody 81C6 Treatment of Patients With Newly Diagnosed Malignant Gliomas," Journal of Clinical Oncology, 2000, vol. 18 (22), pp. 3862-3872.
Colapinto E.V., et al., "Comparative Localization of Murine Monoclonal Antibody Me1-14 F(Ab')2 Fragment and Whole Igg2a in Human Glioma Xenografts," Cancer Research, 1988, vol. 48 (20), pp. 5701-5707.
Collins V.P., "Gene Amplification in Human Gliomas," Glia, 1995, vol. 15 (3), pp. 289-296.
Collins V.P., et al., "Amplified Genes in Human Gliomas," Cancer Biology, 1993, vol. 4 (1), pp. 27-32.
Cortez C., et al., "Influence of Size, Surface, Cell Line, and Kinetic Properties on the Specific Binding of A33 Antigen-Targeted Multilayered Particles and Capsules to Colorectal Cancer Cells," ACS Nano, 2007, vol. 1 (2), pp. 93-102.
Cortez C., et al., "Targeting and Uptake of Multilayered Particles to Colorectal Cancer Cells," Advanced Materials, 2006, vol. 18 (15), pp. 1998-2003.
Corti A., et al., "Idiotope Determining Regions of a Mouse Monoclonal Antibody and its Humanized Versions. Identification of Framework Residues that Affect Idiotype Expression," Journal of Molecular Biology, 1994, vol. 235 (1), pp. 53-60.
Cowley G.P., et al., "Increased EGF Receptors on Human Squamous Carcinoma Cell Lines," British Journal of Cancer, 1986, vol. 53 (2), pp. 223-229.
Cragg M.S., et al., "Signaling Antibodies in Cancer Therapy," Current Opinion in Immunology, 1999, vol. 11 (5), pp. 541-547.
Crawford, et al., "Abx-EGF in Combination with Paclitaxel and Carboplatin for Advanced Non-Small Cell Lung Cancer (Nsclc)," Journal of Clinical Oncology, ASCO Annual Meeting Proceedings (Post-Meeting Edition), 2004, vol. 22 (14S), pp. 7083.
Crombet T., et al., "Phase I Clinical Evaluation of a Neutralizing Monoclonal Antibody Against Epidermal Growth Factor Receptor in Advanced Brain Tumor Patients: Preliminary Study," Hybridoma, 2001, vol. 20 (2), pp. 131-136.
Crombet T., et al., "Use of the Anti-EGFR Antibody h-R3 in Combination with Radiotherapy in the Treatment of Advanced Head and Neck Cancer," Proceedings of American Society of Clinical Oncology, 2002, vol. 21, pp. 14A.
Crombet T., et al., "Use of the Humanized Anti-Epidermal Growth Factor Receptor Monoclonal Antibody H-R3 in Combination with Radiotherapy in the Treatment of Locally Advanced Head and Neck Cancer Patients," Journal of Clinical Oncology, 2004, vol. 22 (9), pp. 1646-1654.
Cunningham D., et al., "Cetuximab Monotherapy and Cetuximab Plus Irinotecan in Irinotecan-Refractory Metastatic Colorectal Cancer," New England Journal of Medicine, 2004, vol. 351 (4), pp. 337-345.
Cvrljevic A.N., et al., "Activation of Src Induces Mitochondrial Localisation of De2-7EGFR (EGFRviii) in Glioma Cells: Implications for Glucose Metabolism," Journal of Cell Science, 2011, vol. 124 (Pt 17), pp. 2938-2950.
Dadparvar S., et al., "Indium-111-Labeled Anti-Egfr-425 Scintigraphy in the Detection of Malignant Gliomas," Cancer, 1994, vol. 73 (Suppl. 3), pp. 884-889.
Damjanov I., et al., "Immunohistochemical Localization of the Epidermal Growth Factor Receptor in Normal Human Tissues," Laboratory Investigation, 1986, vol. 55 (5), pp. 588-592.
Damle N.K., "Antibody-Drug Conjugates Ace the Tolerability Test," Nature Biotechnology, 2008, vol. 26 (8), pp. 884-885.
Damstrup L., et al., "Epidermal Growth Factor Receptor Mutation Type III Transfected into a Small Cell Lung Cancer Cell Line is Predominantly Localized at the Cell Surface and Enhances the Malignant Phenotype," International Journal of Cancer, 2002, vol. 97 (1), pp. 7-14.
Daugherty B.L., et al., "Polymerase Chain Reaction Facilitates the Cloning, CDR-Grafting, and Rapid Expression of a Murine Monoclonal Antibody Directed Against the CD18 Component of Leukocyte Integrins," Nucleic Acids Research, 1991, vol. 19 (9), pp. 2471-2476.
Davies J., et al., "Affinity Improvement of Single Antibody VH Domains: Residues in all Three Hypervariable Regions Affect Antigen Binding," Immunotechnology, 1996, vol. 2 (3), pp. 169-179.
Davies R.L., et al., "Genetic Analysis of Epidermal Growth Factor Action: Assignment of Human Epidermal Growth Factor Receptor Gene to Chromosome 7," Proceedings of the National Academy of Sciences, 1980, vol. 77 (7), pp. 4188-4192.
Davies SP., et al., "Specificity and Mechanism of Action of Some Commonly used Protein Kinase Inhibitors," Biochemical Journal, 2000, vol. 351 (Pt 1), pp. 95-105.
Davis C.G., et al., "Transgenic Mice as a Source of Fully Human Antibodies for the Treatment of Cancer ," Cancer and Metastasis Reviews, 1999, vol. 18 (4), pp. 421-425.
Dawson N.A., et al., "A Phase II Trial of Gefitinib (Iressa, Zd1839) in Stage IV and Recurrent Renal Cell Carcinoma," Clinical Cancer Research, 2004, vol. 10 (23), pp. 7812-7819.
Dazzi H., et al., "Expression of Epidermal Growth Factor Receptor (Egf-R) in Non-Small Cell Lung Cancer use of Archival Tissue and Correlation of Egf-R with Histology, Tumour Size, Node Status and Survival," British Journal of Cancer, 1989, vol. 59 (5), pp. 746-749.

(56) References Cited

OTHER PUBLICATIONS

De Bono J.S., et al., "The ErbB Receptor Family: A Therapeutic Target for Cancer," Trends in Molecular Medicine, 2002, vol. 8 (4), pp. S19-S26.
De Jong J.S., et al., "Expression of Growth Factors, Growth-Inhibiting Factors, and their Receptors in Invasive Breast Cancer. II: Correlations with Proliferation and Angiogenesis," The Journal of pathology, 1998, vol. 184 (1), pp. 53-57.
De Larco J.E., et al., "Epithelioid and Fibroblastic Rat Kidney Cell Clones: Epidermal Growth Factor (EGF) Receptors and the Effect of Mouse Sarcoma Virus Transformation," Journal of Cellular Physiology, 1978, vol. 94 (3), pp. 335-342.
De Larco J.E., et al., "Sarcoma Growth Factor from Mouse Sarcoma Virus-Transformed Cells. Purification by Binding and Elution from Epidermal Growth Factor Receptor-Rich Cells," Journal of Biological Chemistry, 1980, vol. 225 (8), pp. 3685-3690.
De Nardo J., et al., "A New Era for Radiolabeled Antibodies in Cancer," Current Opinion Immunol, 1999, vol. 11 (5), pp. 563-569.
De Pascalis R., et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunological Methods, 2002, vol. 169 (6), pp. 3076-3084.
De Santes K., et al., "Radiolabeled Antibody Targeting of the Her-2/Neu Oncoprotein," Cancer Research, 1992, vol. 52 (7), pp. 1916-1923.
Dechant, et al., "Effect of combinations of EGFR-R antibodies on complement-dependent tumor cell lysis," Journal of Clinical Oncology, 2008, vol. 26 (15S), pp. 14005.
Decker S.J., "Aspects of the Metabolism of the Epidermal Growth Factor Receptor in A431 Human Epidermoid Carcinoma Cells," Molecular and Cellular Biology, 1984, vol. 4 (4), pp. 571-575.
Decker S.J., "Transmembrane Signaling by Epidermal Growth Factor Receptors Lacking Autophosphorylation Sites," Journal of Biological Chemistry, 1993, vol. 268 (13), pp. 9176-9179.
Deen D.F., "Brain Tumor Working Group Report on the 9th International Conference on Brain Tumor Research and Therapy. Organ System Program, National Cancer Institute," Journal of Neurooncolog, 1993, vol. 16 (3), pp. 243-272.
Denardo G.L., et al., "Strategies for Developing Effective Radioimmunotherapy for Solid Tumors," Clinical Cancer Research, 1999, vol. 5 (Suppl. 10), pp. 3219s-3223s.
Dewitt A.E., et al., "Quantitative Analysis of the EGF Receptor Autocrine System Reveals Cryptic Regulation of Cell Response by Ligand Capture," Journal of Cell Science, 2001, vol. 114 (Pt 12), pp. 2301-2313.
Di Fiore P.P., et al., "Overexpression of the Human EGF Receptor Confers an Egf-Dependent Transformed Phenotype to Nih 3t3 Cells," Cell, 1987, vol. 51 (6), pp. 1063-1070.
Di Lorenzo G., et al., "Expression of Epidermal Growth Factor Receptor Correlates With Disease Relapse and Progression to Androgen-Independence in Human Prostate Cancer," Clinical Cancer Research, 2002, vol. 8 (11), pp. 3438-3444.
Dicosimo, et al., "Schedule-Dependent Effects of the Epidermal Growth Factor Receptor (EGFR) Tyrosine Kinase Inhibitor Gefitinib in Combination with the Mammalian Target of Rapamycin (Mtor) Inhibitor Everolimus (Rad001)," Proceedings of the American Society of Clinical Oncology, 2004, vol. 213s (Abstract 3074).
Diedrich U., et al., "Distribution of Epidermal Growth Factor Receptor Gene Amplification in Brain Tumours and Correlation to Prognosis," Journal of Neurology, 1995, vol. 242 (10), pp. 683-688.
Discafani C.M., et al., "Irreversible Inhibition of Epidermal Growth Factor Receptor Tyrosine Kinase with in Vivo Activity by N-[4-[(3-Bromophenyl)Amino]-6-Quinazolinyl]-2-Butynamide (Cl-387,785)," Biochemical Pharmacology, 1999, vol. 57 (8), pp. 917-925.
Dittadi R., et al., "Epidermal Growth Factor Receptor in Lung Malignancies Comparison Between Cancer and Normal Tissue," British Journal of Cancer, 1991, vol. 64 (4), pp. 741-744.

Divgi C.R., et al., "Phase I and Imaging Trial of Indium 111-Labeled Anti-Epidermal Growth Factor Receptor Monoclonal Antibody 225 in Patients with Squamous Cell Lung Carcinoma," Journal of the National Cancer Institute, 1991, vol. 83 (2), pp. 97-104.
Domagala T., et al., "Stoichiometry, Kinetic and Binding Analysis of the Interaction Between Epidermal Growth Factor (EGF) and the Extracellular Domain of the EGF Receptor," Growth Factors, 2000, vol. 18 (1), pp. 11-29.
Doronina S.O., et al., "Enhanced Activity of Monomethylauristatin F Through Monoclonal Antibody Delivery: Effects of Linker Technology on Efficacy and Toxicity," Bioconjugate chemistry, 2006, vol. 17 (1), pp. 114-124.
Downward J., et al., "Close Similarity of Epidermal Growth Factor Receptor and V-Erb-B Oncogene Protein Sequences," Nature, 1984, vol. 307 (5951), pp. 521-527.
Eberhard D.A., et al., "Mutations in the Epidermal Growth Factor Receptor and in Kras Are Predictive and Prognostic Indicators in Patients with Non-Small-Cell Lung Cancer Treated with Chemotherapy Alone and in Combination with Erlotinib," Journal of Clinical Oncology, 2005, vol. 23 (25), pp. 5900-5909.
Egloff A.M., et al., "Targeting Epidermal Growth Factor Receptor and Src Pathways in Head and Neck Cancer," Seminars in Oncology, 2008, vol. 35 (3), pp. 286-297.
Ekstrand A.J., et al., "Altered Subcellular Location of an Activated and Tumour-Associated Epidermal Growth Factor Receptor," Oncogene, 1995, vol. 10 (7), pp. 1455-1460.
Ekstrand A.J., et al., "Amplified and Rearranged Epidermal Growth Factor Receptor Genes in Human Glioblastomas Reveal Deletions of Sequences Encoding Portions of the N- and/or C-terminal Tails," Proceedings of the National Academy of Sciences, 1992, vol. 89 (10), pp. 4309-4313.
Ekstrand A.J., et al., "Functional Characterization of an Egf Receptor with a Truncated Extracellular Domain Expressed in Glioblastomas with Egfr Gene Amplification," Oncogene, 1994, vol. 9 (8), pp. 2313-2320.
Ekstrand A.J., et al., "Genes for Epidermal Growth Factor Receptor, Transforming Growth Factor Alpha, and Epidermal Growth Factor and Their Expression in Human Gliomas in Vivo," Cancer Research, 1991, vol. 51 (8), pp. 2164-2172.
Eller J.L., et al., "Activity of Anti-Epidermal Growth Factor Receptor Monoclonal Antibody C225 Against Glioblastoma Multiforme, Discussion: 1013-1014," Neurosurgery, 2002, vol. 51 (4), pp. 1005-1013.
Ellis A.G., et al., "Preclinical Analysis of the Analinoquinazoline Ag1478, A Specific Small Molecule Inhibitor of EGF Receptor Tyrosine Kinase," Biochemical Pharmacology, 2006, vol. 71, pp. 1442-1434.
Emsley P., et al., "Coot: Model-Building Tools for Molecular Graphics," Acta Crystallographica, 2004, vol. D60, pp. 2126-2132.
Ennis B.W., et al., "Anti-Epidermal Growth Factor Receptor Antibodies Inhibit the Autocrine-Stimulated Growth of Mda-468 Human Breast Cancer Cells," Molecular Endocrinology, 1989, vol. 3 (11), pp. 1830-1838.
Ennis B.W., et al., "The EGF Receptor System as a Target for Antitumor Therapy," Cancer Investigation, 1991, vol. 9 (5), pp. 553-562.
Ennis, "Monoclonal Anti-EGF Receptor Antibodies Inhibit the Growth of Malignant and Nonmalignant Human Mammary Epithelial Cells," Journal of Cellular Biochemistry, 1989, vol. 104 (Abstract E207) (Suppl. 13B).
Epenetos A.A., et al., "Long Term Survival of Patients with Advanced Ovarian Cancer Treated with Intraperitoneal Radioimmunotherapy," International Journal of Gynecological Cancer, 2000, vol. 10 (S1), pp. 44-46.
Erickson H.K., et al., "Antibody-Maytansinoid Conjugates Are Activated in Targeted Cancer Cells by Lysosomal Degradation and Linker-Dependent Intracellular Processing," Cancer Research, 2006, vol. 66 (8), pp. 4426-4433.
Eriksen, et al., "The EGFR VIII Variant in Squamous Cell Carcinomas of the Head and Neck: Expression and Correlation with Clinico-Pathological Parameters in 675 Patients From the Randomised Dahanca 6/7 Study," ECCO 15—34th ESMO Multidisciplinary Congress (Berlin), 2009, vol. 472 (Abstract P-8507).

(56) References Cited

OTHER PUBLICATIONS

Extended European Search Report for Application No. EP10186053, mailed on May 11, 2011.
Ezekiel, et al., "Phase I Trial of Chimerized Anti-Epidermal Growth Factor Receptor (Anti-EGFR) Antibody in Combination with Either Once-Daily or Twice-Daily Irradiation for Locally Advanced Head and Neck Malignancies," Proceedings of the American Society of Clinical Oncology, 1999, vol. 388a (Abstract 1501), pp. 18.
Fairlie W.D., et al., "A Fusion Protein System for the Recombinant Production of Short Disulfide-Containing Peptides," Protein expression and purification, 2002, vol. 26 (1), pp. 171-178.
Fan Z., et al., "Antibody-Induced Epidermal Growth Factor Receptor Dimerization Mediates Inhibition of Autocrine Proliferation of A431 Squamous Carcinoma Cells," Journal of Biological Chemistry, 1994, vol. 269 (44), pp. 27595-27602.
Fan Z., et al., "Antitumor Effect of Anti-Epidermal Growth Factor Receptor Monoclonal Antibodies Plus cis-Diamminedichloroplatinum on well Established A431 Cell Xenografts," Cancer Research, 1993, vol. 53, pp. 4637-4642.
Fan Z., et al., "Blockade of Epidermal Growth Factor Receptor Function by Bivalent and Monovalent Fragments Of225 Anti-Epidermal Growth Factor Receptor Monoclonal Antibodies," Journal of Cancer Research, 1993, vol. 53 (18), pp. 4322-4328.
Fan, et al., "Blockade of Epidermal Growth Factor Receptor by Anti-EGFR Monoclonal Antibody 225 Causes Gi Arrest of A431 Cells with Induction of P27KIPI," Proceedings of the American Association for Cancer Research, 1999, vol. 10 (Abstract 69), pp. 37.
Fantl W.J., et al., "Signalling by Receptor Tyrosine Kinases," Annual Review of Biochemistry, 1993, vol. 62, pp. 453-481.
Farrugia W., et al., "A Possible Role for Metallic Ions in the Carbohydrate Cluster Recognition Displayed by a Lewis Y Specific Antibody," Plos One, 2009, vol. 4 (11), pp. e7777.
Feldkamp M.M., et al., "Expression of Activated-Epidermal Growth Factor Receptors, Ras-Guanosine Triphosphate, and Mitogenactivated Protein Kinase in Human Glioblastoma Multiforme Specimens," Neurosurgery, 1999, vol. 45 (6), pp. 1442-1453.
Fendly B.M., et al., "Characterization of Murine Monoclonal Antibodies Reactive to Either the Human Epidermal Growth Factor Receptor or Her2/Neu Gene Product," Cancer Research, 1990, vol. 50 (5), pp. 1550-1558.
Fenstermaker R.A., et al., "Deletion and Tandem Duplication of Exons 2-7 in the Epidermal Growth Factor Receptor Gene of a Human Malignant Glioma," Oncogene, 2000, vol. 19 (39), pp. 4542-4548.
Ferguson K.M., "Structure-Based View of Epidermal Growth Factor Receptor Regulation," Annual Review of Biophysics, 2008, vol. 37, pp. 353-373.
Ferrara N., et al., "Discovery and Development of Bevacizumab, an Anti-VEGF Antibody for Treating Cancer," Nature Reviews Drug Discovery, 2004, vol. 3 (5), pp. 391-400.
Ferry D., et al., "Intermittent Oral Zd1839 (Iressa), a Novel Epidermal Growth Factor Receptor Tyrosine Kinase Inhibitor (Egfr-Tki), Shows Evidence of Good Tolerability and Activity: Final Results from a Phase I Study," Proceedings of American Society of Clinical Oncology, 2000, vol. 19, pp. 3A.
Figlin R.A., et al., "ABX-EGF, a fully human anti-epidermal growth factor receptor (EGFR) monoclonal antibody (mAb) in patients with advanced cancer: phase 1 clinical results," Proceedings of American Society of Clinical Oncology, 2002, vol. 21, pp. 10A.
Filmus J., et al., "Amplified, Overexpressed and Rearranged Epidermal Growth Factor Receptor Gene in a Human Astrocytoma Cell Line," Biochemical and Biophysical Research Communications, 1985, vol. 131 (1), pp. 207-215.
Filmus J., et al., "Epidermal Growth Factor Receptor Gene-Amplified MDA-468 Breast Cancer Cell Line and Its Nonamplified Variants," Molecular and Cellular Biology, 1987, vol. 7 (1), pp. 251-257.
Filmus J., et al., "MDA-468, A Human Breast Cancer Cell Line with a High Number of Epidermal Growth Factor (EGF) Receptors, Has an Amplified EGF Receptor Gene and is Growth Inhibited by EGF," Biochemical and Biophysical Research Communications, 1985, vol. 128 (2), pp. 898-905.
Finkler N., et al., "Phase 2 Evaluation of OSI-774, a Potent Oral Antagonist of the EGFR-TK in Patients with Advanced Ovarian Carcinoma," Proceedings of American Society of Clinical Oncology, 2001, vol. 20, pp. 208A.
Fischer-Colbrie J., et al., "EGFR and Steroid Receptors in Ovarian Carcinoma: Comparison with Prognostic Parameters and Outcome of Patients," Anticancer Research, 1997, vol. 17 (1B), pp. 613-619.
Fisher G.H., et al., "Induction and Apoptotic Regression of Lung Adenocarcinomas by Regulation of a K-Ras Transgene in the Presence and Absence of Tumor Suppressor Genes," Genes & Development, 2001, vol. 15 (24), pp. 3249-3262.
Flynn J.M., et al., "Campath-1h Monoclonal Antibody Therapy," Current Opinion in Oncology, 2000, vol. 12 (6), pp. 574-581.
Fong C.J., et al., "Epidermal Growth Factor Receptor Monoclonal Antibody Inhibits Constitutive Receptor Phosphorylation, Reduces Autonomous Growth, and Sensitizes Androgen-Independent Prostatic Carcinoma Cells to Tumor Necrosis Factor Alpha," Cancer Research, 1992, vol. 52 (21), pp. 5887-5892.
Foo S.S., et al., "Functional Imaging of Intratumoral Hypoxia," Molecular Imaging and Biology, 2004, vol. 6 (5), pp. 291-305.
Forastiere A., et al., "Head and Neck Cancer," The New England Journal of Medicine, 2001, vol. 345 (26), pp. 1890-1900.
Ford A.C., et al., "Targeting Epidermal Growth Factor Receptor in Head and Neck Cancer," Head & Neck, 2003, vol. 25 (1), pp. 67-73.
Ford, et al., "Pharmacogenomic Approaches for Identifying Markers Predictive of Tumor Response to Cetuximab (Erbitux)," Proceedings of the American Association for Cancer Research, 2004, Abstract 2032, pp. 45.
Fornier M., et al., "Trastuzumab in Combination with Chemotherapy for the Treatment of Metastatic Breast Cancer, Discussion 92-100," Seminars in Oncology, 2000, vol. 27 (6 Suppl. 11), pp. 38-45.
Foulon C.F., et al., "Positively Charged Templates for Labeling Internalizing Antibodies: Comparison of N-Succinimidyl 5-Iodo-3-Pyridinecarboxylate and the D-Amino Acid Peptide KRYRR," Nuclear Medicine and Biology, 2001, vol. 28 (7), pp. 769-777.
Fox S.B., et al., "Tumour Angiogenesis," The Journal of Pathology, 1996, vol. 179 (3), pp. 232-237.
Fraker P.J., et al., "Protein and Cell Membrane Iodinations with a Sparingly Soluble Chloroamide, 1,3,4,6-Tetrachloro-3a,6a-Diphrenylglycoluril," Biochemical and Biophysical Research Communications, 1978, vol. 80 (4), pp. 849-857.
Franklin, et al., "Association Between Activation of Erbb Pathway Genes and Survival Following Gefitinib Treatment in Advanced Bac (Swog 0126)," Proceedings of the Annual Meeting of the American Society of Clinical Oncology, 2004, vol. 620s (Abstract 7015), pp. 22.
Frederick L., et al., "Analysis of Genomic Rearrangements Associated with Egrfviii Expression Suggests Involvement of Alu Repeat Elements," Neuro-Oncology, 2000, vol. 2 (3), pp. 159-163.
Friedman H.S., et al., "Glioblastoma Multiforme and the Epidermal Growth Factor Receptor," The New England Journal of Medicine, 2005, vol. 353 (19), pp. 1997-1999.
Friedman H.S., et al., "Temozolomide and Treatment of Malignant Glioma," Clinical Cancer Research, 2000, vol. 6 (7), pp. 2585-2597.
Friedman L.M., et al., "Synergistic Down-Regulation of Receptor Tyrosine Kinases by Combinations of Mabs: Implications for Cancer Immunotherapy," Proceedings of the National Academy of Sciences, 2005, vol. 102 (6), pp. 1915-1920.
Friess T., et al., "Combination Treatment with Erlotinib and Pertuzumab against Human Tumor Xenografts is Superior to Monotherapy," Clinical Cancer Research, 2005, vol. 11 (14), pp. 5300-5309.
Fry D.W., "Inhibition of the Epidermal Growth Factor Receptor Family of Tyrosine Kinases as an Approach to Cancer Chemotherapy: Progression from Reversible to Irreversible Inhibitors," Pharmacology & Therapeutics, 1999, vol. 82 (2-3), pp. 207-218.
Fry D.W., "Specific, Irreversible Inactivation of the Epidermal Growth Factor Receptor and Erbb2, by a New Class of Tyrosine Kinase Inhibitor," Proceedings of the National Academy of Sciences, 1998, vol. 95 (20), pp. 12022-12027.

(56) References Cited

OTHER PUBLICATIONS

Fry D.W., et al., "A Specific Inhibitor of the Epidermal Growth Factor Receptor Tyrosine Kinase," Science, 1994, vol. 265 (5175), pp. 1093-1095.

Fry D.W., et al., "Biochemical and Antiproliferative Properties of 4-[Ar(Alk)Ylamino]Pyridopyrimidines, a New Chemical Class of Potent and Specific Epidermal Growth Factor Receptor Tyrosine Kinase Inhibitor," Biochemical Pharmacology, 1997, vol. 54 (8), pp. 877-887.

Fry D.W., et al., "Site-Directed Irreversible Inhibitors of the Erbb Family of Receptor Tyrosine Kinases as Novel Chemotherapeutic Agents for Cancer," Anti-Cancer Drug Design, 2000, vol. 15 (1), pp. 3-16.

Fujino S., et al., "A Comparison of Epidermal Growth Factor Receptor Levels and Other Prognostic Parameters in Non-Small Cell Lung Cancer," European Journal of Cancer, 1996, vol. 32A (12), pp. 2070-2074.

Fukai J., et al., "Antitumor Activity of Cetuximab Against Malignant Glioma Cells Overexpressing EGFR Deletion Mutant Variant Iii," Cancer Science, 2008, vol. 99 (10), pp. 2062-2069.

Fukuoka M., et al., "Final Results from a Phase II Trial of Z01839 ('Iressa') for Patients with Advanced Non-small-cell lung Cancer (Ideal 1)," Proceedings of American Society of Clinical Oncology, 2002, vol. 21, pp. 298A.

Fukuoka M., et al., "Multi-Institutional Randomized Phase Ii Trial of Gefitinib for Previously Treated Patients with Advanced Non-Small-Cell Lung Cancer (The Ideal 1 Trial) [Corrected]," Journal of Clinical Oncology, 2003, vol. 21 (12), pp. 2237-2246.

Gamou S., et al., "Glycosylation of the Epidermal Growth Factor Receptor and Its Relationship to Membrane Transport and Ligand Binding," Journal of Biochemistry, 1988, vol. 104 (3), pp. 388-396.

Gan H.K., et al., "Targeting a Unique Egfr Epitope with Monoclonal Antibody 806 Activates Nf-Kappab and Initiates Tumour Vascular Normalization," Journal of Cellular and Molecular Medicine, 2009, vol. 13 (9B), pp. 3993-4001.

Gan H.K., et al., "The EGFR VIII Variant in Glioblastoma Multiforme," Journal of Clinical Neuroscience, 2009, vol. 16 (6), pp. 748-754.

Garinchesa P., et al., "Organ-Specific Expression of the Colon Cancer Antigen A33, a Cell Surface Target for Antibody-Based Therapy," International Journal of Oncology, 1996, vol. 9 (3), pp. 465-471.

George J., et al., "Differential Effects of Anti-Beta2-Glycoprotein I Antibodies on Endothelial Cells and on the Manifestations of Experimental Antiphospholipid Syndrome," Circulation, 1998, vol. 97, pp. 900-906.

Giaccone G., et al., "Combination Therapy With Zd1839 (Iressa),an Orally Active, Selective, Epidermal Growth Factor Receptor Tyrosine Kinase Inhibitor (Egfrtki), Gemcitabine and Cisplatin, in Patients with Advanced Solid Tumors: Promising Preliminary Results on Tolerability, Efficacy, and Pharmacokinetics," Clinical Cancer Research, 2001, vol. 7, pp. 3765S.

Gibson T.B., et al., "Randomized Phase III Trial Results of PanitumumAb, a Fully Human Anti-Epidermal Growth Factor Receptor Monoclonal Antibody, in Metastatic Colorectal Cancer," Clinical Colorectal Cancer, 2006, vol. 6 (1), pp. 29-31.

Gill G.N., et al., "Relationship Between Production of Epidermal Growth Factor Receptors, Gene Amplification, and Chromosome 7 Translocation in Variant A431 Cells," Somatic Cell and Molecular Genetics, 1985, vol. 11 (4), pp. 309-318.

Gill S., et al., "New Targeted Therapies in Gastrointestinal Cancers," Current Treatment Options in Oncology, 2003, vol. 4 (5), pp. 393-403.

Giusti A.M., et al., "Somatic Diversification of S107 from an Antiphosphocholine to an Anti-DNA Autoantibody is due to a Single Base Change in its Heavy Chain Variable Region," Proceedings of the National Academy of Sciences, 1987, vol. 84 (9), pp. 2926-2930.

Glennie M.J., et al., "Clinical Trials of Antibody Therapy," Immunology Today, 2000, vol. 21 (8), pp. 403-410.

Glennie M.J., et al., "Renaissance of Cancer Therapeutic Antibodies," Drug Discovery Today, 2003, vol. 8 (11), pp. 503-510.

Goldberg R.M., "Cetuximab," Nature Reviews Drug Discovery, 2005, Suppl. S10-S11.

Goldenberg A., et al., "Imaging of Human Tumor Xenografts with an Indium-111-Labeled Anti-Epidermal Growth Factor Receptor Monoclonal Antibody," Journal of the National Cancer Institute , 1989, vol. 81 (21), pp. 1616-1625.

Goldenberg D.M., "Advancing Role of Radiolabeled Antibodies in the Therapy of Cancer," Cancer Immunology, Immunotherapy, 2003, vol. 52 (5), pp. 281-296.

Goldenberg D.M., et al., "Targeted Therapy of Cancer with Radiolabeled Antibodies," Journal of nuclear medicine, 2002, vol. 43 (5), pp. 693-713.

Goldman C.K.,et al., "Epidermal Growth Factor Stimulates Vascular Endothelial Growth Factor Production by Human Malignant Glioma Cells: A Model of Glioblastoma Multiforme Pathophysiology; ; ," Molecular Biology of the Cell, 1993, vol. 4 (1), pp. 121-133.

Goldman R., et al., "Heterodimerization of the Erbb-1 and ERRB-2 Receptors in Human Breast Carcinoma Cells: a Mechanism for Receptor Transregulation," Biochemistry, 1990, vol. 29 (50), pp. 11024-11028.

Gonzalez G., et al., "Epidermal Growth Factor-Based Cancer Vaccine for Non-Small-Cell Lung Cancer Therapy," Annals of Oncology, 2003, vol. 14 (3), pp. 461-466.

Gorgoulis V.G., et al., "Molecular and Immunohistochemical Evaluation of Epidermal Growth Factor Receptor and C-Erb-B-2 Gene Product in Transitional Cell Carcinomas of the Urinary Bladder: a Study in Greek Patients," Modern Pathology, 1995, vol. 8 (7), pp. 758-764.

Gorre M.E., et al., "Clinical Resistance to Sti-571 Cancer Therapy Caused by Bcr-Abl Gene Mutation or Amplification," Science , 2001, vol. 293 (5531), pp. 876-880.

Goss G.D., et al., "Final Results of the Dose Escalation Phase of a Phase I Pharmacokinetics (PK), Pharmacodynamic (PD) and Biological Activity Study of ZD1839 NCIC CTG In," Proceedings of American Society of Clinical Oncology, 2001, vol. 20 (Abstract. 335), pp. 85A.

Graeven U., et al., "Phase I Study of the Humanised Anti-EGFR Monoclonal Antibody MatuzumAb (EMD 72000) Combined With Gemcitabine in Advanced Pancreatic Cancer," British Journal of Cancer, 2006, vol. 94 (9), pp. 1293-1299.

Grandal M.V., et al., "EGFR VIIIEscapes Down-Regulation Due to Impaired Internalization and Sorting to Lysosomes," Carcinogenesis, 2007, vol. 28 (7), pp. 1408-1417.

Grandis J.R., et al., "Elevated Levels of Transforming Growth Factor Alpha and Epidermal Growth Factor Receptor Messenger RNA Are Early Markers of Carcinogenesis in Head and Neck Cancer," Cancer Research, 1993, vol. 53 (15), pp. 3579-3584.

Grandis J.R., et al., "Levels of TGP-alpha and EOFR Protein in Head and Neck Squamous Cell Carcinoma and Patient Survival," Journal of the National Cancer Institute, 1998, vol. 90 (11), pp. 824-832.

Graness A., et al., "Protein-tyrosine-phosphatase-mediated Epidermal Growth Factor (Egf) Receptor Transinactivation and EGF Receptor-Independent Stimulation of Mitogen-Activated Protein Kinase by Bradykinin in A431 Cells," Biochemical Journal, 2000, vol. 347 (Pt 2), pp. 441-447.

Graus-Porta D., et al., "Single-Chain Antibody-Mediated Intracellular Retention of Erbb-2 Impairs Neu Differentiation Factor and Epidermal Growth Factor Signaling," Molecular and Cellular Biology, 1995, vol. 15 (3), pp. 1182-1191.

Green M.C. et al., "Monoclonal Antibody Therapy for Solid Tumors," Cancer Treatment Reviews, 2000, vol. 26 (4), pp. 269-286.

Groner B., et al., "Therapeutic Antibodies," Current Molecular Medicine, 2004, vol. 4 (5), pp. 539-547.

Grunwald V., et al., "Development of the Epidermal Growth Factor Receptor Inhibitor Osi-774," Seminars in Oncology , 2003, vol. 30 (3) (Suppl. 6), pp. 23-31.

Gschwind A., et al., "The Discovery of Receptor Tyrosine Kinases: Targets for Cancer Therapy," Nature Reviews Cancer, 2004, vol. 4 (5), pp. 361-370.

Gullick W.J., "Type I Growth Factor Receptors: Current Status and Future Work," Biochemical Society Symposium, 1998, vol. 63, pp. 193-198.

(56) References Cited

OTHER PUBLICATIONS

Gullick W.J., et al., "A New Model for the Interaction of Egf-Like Ligands with their Receptors: the New One-Two," European Journal of cancer, 1994, vol. 30A (14), pp. 2186.

Gullick W.J., et al., "Growth Factors, Growth Factor Receptors and Neoplasia," Human & Experimental Toxicology, 1991, vol. 10 (6), pp. 398-400.

Gullick W.J., et al., "Prevalence of Aberrant Expression of the Epidermal Growth Factor Receptor in Human Cancers," British Medical Bulletin, 1991, vol. 47 (1), pp. 87-98.

Gunnett, et al., "Phase II Study of Antiepidermal Growth Factor Receptor (EGFR) Antibody C225 Alone in Patients (Pts) with Metastatic Renal Carcinoma (RCC)," Annual Meeting of the American Society of Clinical Oncology, 1999, vol. 340a (Abstract 1309), pp. 18.

Gunther N. et al., "The Secreted Form of the Epidermal Growth Factor Receptor. Characterization and Crystallization of the Receptor Ligand Complex," Journal of Biological Chemistry, 1990, vol. 265 (36), pp. 22082-22085.

Gupta, et al., "Development of an EGFR VIIISpecific Recombinant Antibody," BMC Biotechnology, 2010, vol. 72, pp. 10.

Gussow D., et al., "Humanization of Monoclonal Antibodies," Methods in Enzymology, 1991, vol. 203, pp. 99-121.

Haas-Kogan D.A., et al., "Epidermal Growth Factor Receptor, Protein Kinase B/AKT, and Glioma Response to Erlotinib," Journal of the National Cancer Institute, 2005, vol. 97 (12), pp. 880-887.

Haber D.A., et al., "Molecular Targeted Therapy of Lung Cancer: EGFR Mutations and Response to EGFR Inhibitors," Cold Spring Harbor Symposia on Quantitative Biology, 2005, vol. 70, pp. 419-426.

Hackel P.O., et al., "Epidermal Growth Factor Receptors: Critical Mediators of Multiple Receptor Pathways," Current Opinion in Cell Biology, 1999, vol. 11 (2), pp. 184-189.

Haigler H., et al., "Visualization by Fluorescence of the Binding and Internalization of Epidermal Growth Factor in Human Carcinoma Cells A-431," Proceedings of the National Academy of Sciences united states of america, 1978, vol. 75 (7), pp. 3317-3321.

Halaisch M.E., et al., "Marked Inhibition of Glioblastoma Target Cell Tumorigenicity in Vitro by Retrovirus-Mediated Transfer of a Hairpin Ribozyme Against Deletion-Mutant Epidermal Growth Factor Receptor Messenger RNA," Journal of Neurosurgery, 2000, vol. 92 (2), pp. 297-305.

Halatsch M.E., et al., "Epidermal Growth Factor Receptor Inhibition for the Treatment of Glioblastoma Multiforme and other Malignant Brain Tumours," Cancer Treatment Reviews, 2006, vol. 32 (2), pp. 74-89.

Haley J., et al., "The Human Egf Receptor Gene: Structure of the 110 Kb Locus and Identification of Sequences Regulating its Transcription," Oncogene Research, 1987, vol. 1 (4), pp. 375-396.

Haley J.D., "Regulation of Epidermal Growth Factor Receptor Expression and Activation: A Brief Review," Symposia of the Society for Experimental Biology, 1990, vol. 44, pp. 21-37.

Hamblett K.J., et al., "Effects of Drug Loading on the Antitumor Activity a Monoclonal Antibody Drug Conjugate," Clinical Cancer Research, 2004, vol. 10 (20), pp. 7063-7070.

Han S.W., et al., "Predictive and Prognostic Impact of Epidermal Growth Factor Receptor Mutation in Non-Small-Cell Lung Cancer Patients Treated with Gefitinib," Journal of Clinical Oncology, 2005, vol. 23 (11), pp. 2493-2501.

Han Y., et al., "Tyrphostin Ag1478 Preferentially Inhibits Human Glioma Cells Expressing Truncated Rather than Wild-Type Epidermal Growth Factor Receptors," Journal Cancer Research, 1996, vol. 56 (17), pp. 3859-3861.

Hanahan D., et al., "The Hallmarks of Cancer," Cell, 2000, vol. 100 (1), pp. 57-70.

Hanks S.K., et al., "The Protein Kinase Family: Conserved Features and Deduced Phylogeny of the Catalytic Domains," Science, 1988, vol. 241 (4861), pp. 42-52.

Hanna N., et al., "Phase II Trial of Cetuximab in Patients with Previously Treated Non-Small-Cell Lung Cancer," Journal of Clinical Oncology, 2006, vol. 24 (33), pp. 5253-5258.

Harari D., et al., "Molecular Mechanisms Underlying ErbB2/Her2 Action in Breast Cancer," Oncogene, 2000, vol. 19 (53), pp. 6102-6114.

Harari P.M., "Epidermal Growth Factor Receptor Inhibition Strategies in Oncology," Endocrine Related Cancer, 2004, vol. 11 (4), pp. 689-708.

Harari P.M., et al., "Head and Neck Cancer as a Clinical Model for Molecular Targeting of Therapy: Combining Egfr Blockade with Radiation," International Journal of Radiation Oncology, Biology, Physics, 2001, vol. 49 (2), pp. 427-433.

Harari, et al., "Combining Radiation with Molecular Blockade of the EGF Receptor in Cancer Therapy," Proceedings of the American Association for Cancer Research, 1999, 3747s, 5.

Harries M., et al., "The Development and Clinical Use of Trastuzumab (Herceptin)," Endocrine-Related Cancer, 2002, vol. 9 (2), pp. 75-85.

Harris W.J., et al., "Therapeutic antibodies—the Coming of Age," Trends Biotechnol, 1993, vol. 11 (2), pp. 42-44.

Harris, et al., "Epidermal Growth Factor Receptor: A Marker of Early Relapse in Breast Cancer and Tumor Stage Progression in Bladder Cancer; Interactions with Meu" in: The Molecular Diagnostics of Human Cancer, Furth, et al., eds., Cold Spring Harbor Laboratory, New York, 1989, pp. 353-357.

Harris, et al., "The Role of ErbB2 Extracellular Domain in Predicting Response to Chemotherapy in Breast Cancer Patients," Proceedings of the Annual Meeting of the American Society of Clinical Oncology, 1996, vol. 108 (Abstract 96), pp. 15.

Hatanpaa K.J., et al., "Epidermal Growth Factor Receptor in Glioma: Signal Transduction, Neuropathology, Imaging, and Radioresistance," Neoplasia, 2010, vol. 12 (9), pp. 675-684.

Hayman M.J., et al., "Cell Transformation by the Epidermal Growth Factor Receptor and V-Erbb," Cancer Cells, 1991, vol. 3 (8), pp. 302-307.

He Y., et al., "Inhibition of Human Squamous Cell Carcinoma Growth In Vivo by Epidermal Growth Factor Receptor Antisense RNA Transcribed From the U6 Promoter," Journal of the National Cancer Institute, 1998, vol. 90 (14), pp. 1080-1087.

Heath J.K., et al., "The Human A33 Antigen is a Transmembrane Glycoprotein and a Novel Member of the Immunoglobulin Superfamily," Proceedings of the National Academy of Sciences united states of america, 1997, vol. 94 (2), pp. 469-474.

Hecht, et al., "ABX-EGF Monotherapy in Patients (Pts) with Metastatic Colorectal Cancer (mCRC) (An updated analysis)," Proceedings of the American Society of Clinical Oncology, 2004, vol. 247s (Abstract 3511), pp. 23.

Heimberger A.B., et al., "Epidermal Growth Factor Receptor VIII Peptide Vaccination is Efficacious Against Established Intracerebral Tumors," Clinical Cancer Research, 2003, vol. 9 (11), pp. 4247-4254.

Heimberger A.B., et al., "Prognostic Effect of Epidermal Growth Factor Receptor and EGFRVIII in Glioblastoma Multiforme Patients," Clinical Cancer Research, 2005, vol. 11 (4), pp. 1462-1466.

Heimberger A.B., et al., "The Natural History of EGFR and EGFRvIII in Glioblastoma Patients," Journal of translational medicine, 2005, vol. 38, pp. 3.

Helin K., et al., "Internalization and Down-Regulation of the Human Epidermal Growth Factor Receptor are Regulated by the Carboxyl-Terminal Tyrosines," Journal of Biological Chemistry 1991, vol. 266 (13), pp. 8363-8368.

Helin K., et al., "The Biological activity of the Human Epidermal Growth Factor Receptor is Positively Regulated by its C-Terminal Tyrosines," Oncogene, 1991, vol. 6 (5), pp. 825-832.

Hendler F.J., et al., "Human Squamous Cell Lung Cancers Express Increased Epidermal Growth Factor Receptors," Journal of clinical investigation, 1984, vol. 74 (2), pp. 647-651.

Henn W., et al., "Polysomy of Chromosome 7 is Correlated with Overexpression of the Erbb Oncogene in Human Glioblastoma Cell Lines," Human Genetics, 1986, vol. 74 (1), pp. 104-106.

(56) References Cited

OTHER PUBLICATIONS

Henry M.D., et al., "A Prostate-Specific Membrane Antigen-Targeted Monoclonal Antibody-Chemotherapeutic Conjugate Designed for the Treatment of Prostate Cancer," Cancer Research, 2004, vol. 64, pp. 7995-8001.

Hens M., et al., "Anti-EGFRVIII Monoclonal Antibody Armed with 1771.U: In Vivo Comparison of Macrocyclic and Acyclic Ligands," Nuclear Medicine and Biology, 2010, vol. 37 (7), pp. 741-750.

Hens M., et al., "Labeling Internalizing Anti-Epidermal Growth Factor Receptor Variant III Monoclonal Antibody With (177)Lu: in Vitro Comparison of Acyclic and Macrocyclic Ligands," Nuclear Medicine and Biology, 2009, vol. 36 (2), pp. 117-128.

Herbertson R.A., et al., "Phase I Biodistribution and Pharmacokinetic Study of Lewis Y-Targeting Immunoconjugate Cmd-193 in Patients with Advanced Epithelial Cancers," Clinical Cancer Research, 2009, vol. 15 (21), pp. 6709-6715.

Herbst et al., "Regulation of Postendocytic Trafficking of the Epidermal Growth Factor Receptor Through Endosomal Retention," Journal of Biological Chemistry, 1994, 269 (17), pp. 12865-12873.

Herbst R.S., "Targeted Therapy in Non-Small-Cell Lung Cancer," Oncology, 2002, vol. 16 (9), pp. 19-24.

Herbst R.S., et al., "Dose-Comparative Monotherapy Trials of Zd1839 in Previously Treated Non-Small Cell Lung Cancer Patients," Seminars in Oncology, 2003, vol. 30 (1) Suppl. 1), pp. 30-38.

Herbst R.S., et al., "Erlotinib (Tarceva): an Update on the Clinical Trial Program," Seminars in Oncology, 2003, vol. 30 (3) (Suppl. 7), pp. 34-46.

Herbst R.S., et al., "IMC-C225, an Anti-Epidermal Growth Factor Receptor Monoclonal Antibody for Treatment of Head and Neck Cancer," Seminars in Oncology, 2002, vol. 29 (5) (Suppl. 14), pp. 18-30.

Herbst R.S., et al., "Phase I/II Trial Evaluating the Anti-Vascular Endothelial Growth Factor Monoclonal Antibody Bevacizumab in Combination With the Her-1/Epidermal Growth Factor Receptor Tyrosine Kinase Inhibitor Erlotinib for Patients with Recurrent Non-Small-Cell Lung Cancer," Journal of Clinical Oncology, 2005, vol. 23 (11), pp. 2544-2555.

Herbst R.S., et al., "Phase II Multicenter Study of the Epidermal Growth Factor Receptor Antibody Cetuximab and Cisplatin for Recurrent and Refractory Squamous Cell Carcinoma of the Head and Neck.," Journal of Clinical Oncology, 2005, vol. 23 (24), pp. 5578-5587.

Herbst R.S., et al., "Selective Oral Epidermal Growth Factor Receptor Tyrosine Kinase Inhibitor Zd1839 is Generally Well-Tolerated and has Activity in Non-Small-Cell Lung Cancer and Other Solid Tumors: Results of a Phase I Trial," Journal of Clinical Oncology, 2002, vol. 20 (18), pp. 3815-3825.

Hertler A.A., et al., "Immunotoxins: A Clinical Review of their Use in the Treatment of Malignancies," Journal of Clinical Oncology, 1989, vol. 7 (12), pp. 1932-1942.

Hidalgo M., et al., "Phase I and Pharmacologic Study of OSI-774, an Epidermal Growth Factor Receptor Tyrosine Kinase Inhibitor, in Patients With Advanced Solid Malignancies," Journal of Clinical Oncology, 2001, vol. 9 (13), pp. 3267-3279.

Hidalgo, et al., "Phase 1 Trial of EKB-569, an Irreversible Inhibitor of the Epidermal Growth Factor Receptor (EGFR), in Patients with Advanced Solid Tumors," Proceedings of the American Society of Clinical Oncology, 2002, vol. 17a (Abstract 65), pp. 21.

Hirata A., et al., "Zd1839 (Iressa) Induces Antiangiogenic Effects Through Inhibition of Epidermal Growth Factor Receptor Tyrosine Kinase," Cancer research, 2002, vol. 62 (9), pp. 2554-2560.

Hird, et al., "Immunotherapy with Monoclonal Antibodies" In: Genes and Cancer, Chapter 17, Carry, eds., John Wiley & Sons, Ltd., 1990, pp. 183-189.

Hirsch F.R., et al., "Epidermal Growth Factor Receptor in Non-Small-Cell Lung Carcinomas: Correlation Between Gene Copy Number and Protein Expression and Impact on Prognosis," Journal of Clinical Oncology, 2003, vol. 21 (20), pp. 3798-3807.

Hirsch F.R., et al., "Increased Epidermal Growth Factor Receptor Gene Copy Number Detected by Fluorescence In Situ Hybridization Associates With Increased Sensitivity to Gefitinib in Patients With Bronchioloalveolar Carcinoma Subtypes: A Southwest Oncology Group Study," Journal of Clinical Oncology, 2005, vol. 23 (28), pp. 6838-6845.

Hoffman, et al., "Phase I Trials of CDR-Grafted Humanized Monoclonal Antibody Hu3S193 in Patients with Lewis-Y Expressing Solid Tumors," American Society of Clinical Oncology, 2001, Abstract 2634, pp. 20.

Hoffmann T., et al., "Antitumor Activity of Anti-Epidermal Growth Factor Receptor Monoclonal Antibodies and Cisplatin in Ten Human Head and Neck Squamous Cell Carcinoma Lines," Anticancer Research, 1997, vol. 17 (6D), pp. 4419-4425.

Hogg P.J., "Disulfide Bonds as Switches for Protein Function," Trends in biochemical sciences, 2003, vol. 28 (4), pp. 210-214.

Holbro T., et al., "ErbB Receptors: Directing Key Signaling Networks Throughout Life," Annual Review of Pharmacology and Toxicology, 2004, vol. 44, pp. 195-217.

Holbro T., et al., "The Erbb Receptors and their Role in Cancer Progression," Experimental Cell Research, 2003, vol. 284 (1), pp. 99-110.

Holland E.C., et al., "A Constitutively Active Epidermal Growth Factor Receptor Cooperates With Disruption of G1 Cell-Cycle Arrest Pathways to Induce Glioma-Like Lesions in Mice," 1998, vol. 12 (23), pp. 3675-3685.

Holland E.C., et al., "Glioblastoma Multiforme: The Terminator," Proceedings of the National Academy of Sciences united states of america, 2000, vol. 97 (12), pp. 6242-6244.

Hollstein M.C., et al., "Amplification of Epidermal Growth Factor Receptor Gene but no Evidence of Ras Mutations in Primary Human Esophageal Cancers," Cancer research, 1988, vol. 48 (18), pp. 5119-5123.

Holm P., et al., "Functional Mapping and Single Chain Construction of the Anti-Cytokeratin 8 Monoclonal Antibody TS1," Molecular Immunology, 2007, vol. 44, pp. 1075-1084.

Holmes M.A., et al., "Structural Consequences of Humanizing an Antibody1," The Journal of Immunology, 1997, vol. 158 (5), pp. 2192-2201.

Honegger A., et al., "Biological Activities of EGF-Receptor Mutants with Individually Altered Autophosphorylation Site," The EMBO Journal, 1988, vol. 7 (10), pp. 3045-3052.

Hong, et al., "Efficacy and Safety of the Anti-Epidermal Growth Factor Antibody (EGFR) Imc-225, in Combination with Cisplatin in Patients with Recurrent Squamous Cell Carcinoma of the Head and Neck (SCCHN) Refractory to Cisplatin Containing Chemotherapy," Proceedings of the American Society of Clinical Oncology, 2001, vol. 224a (Abstract 895), pp. 20.

Hooft R.W., et al., "Errors in Protein Structures," Nature, 1996, vol. 381 (6580), pp. 272.

Hortobagyi G.N., "Overview of Treatment Results with Trastuzumab (Herceptin) in Metastatic Breast Cancer; ," Seminars in Oncology, 2001, vol. 28 (6 Suppl. 18), pp. 43-47.

Huang P.H., et al., "Phosphotyrosine Signaling Analysis of Site-Specific Mutations on EGFRvIII Identifies Determinants Governing Glioblastoma Cell Growth," Molecular BioSystems, 2010, vol. 6 (7), pp. 1227-1237.

Huang P.H., et al., "Quantitative Analysis of EGFRvIII Cellular Signaling Networks Reveals a Combinatorial Therapeutic Strategy for Glioblastoma," Proceedings of the National Academy of Sciences, 2007, vol. 104 (31), pp. 12867-12872.

Huang P.H., et al., "Uncovering Therapeutic Targets for Glioblastoma: A Systems Biology Approach," Cell Cycle, 2007, vol. 6 (22), pp. 2750-2754.

Huang S., et al. "Dual-Agent Molecular Targeting of the Epidermal Growth Factor Receptor (Egfr) Combining Anti-Egfr Anti Body with Tyrosine Kinase Inhibitor," Cancer Research, 2004, vol. 64, pp. 5355-5362.

Huang S.M., et al., "Epidermal Growth Factor Receptor Blockade with C225 Modulates Proliferation, Apoptosis, and Radiosensitivity in Squamous Cell Carcinomas of the Head and Neck," Cancer research, 1999, vol. 59 (8), pp. 1935-1940.

(56) References Cited

OTHER PUBLICATIONS

Huang S.M., et al., "Epidermal Growth Factor Receptor Inhibition in Cancer Therapy: Biology, Rationale and Preliminary Clinical Results," Investigational New Drugs, 1999, vol. 17 (3), pp. 259-269.
Huang S.M., et al., "Modulation of Radiation Response after Epidermal Growth Factor Receptor Blockade in Squamous Cell Carcinomas: Inhibition of Damage Repair, Cell Cycle Kinetics, and Tumor Angiogenesis," Clinical Cancer Research, 2000, vol. 6 (6), pp. 2166-2174.
Huang S.M., et al., "Modulation of Radiation Response and Tumor-Induced Angiogenesis After Epidermal Growth Factor Receptor Inhibition by ZD1839 (Iressa)," Cancer Research, 2002, vol. 62 (15), pp. 4300-4306.
Hubbard S.R., "EGF Receptor Inhibition: Attacks on Multiple Fronts," Cancer Cell, 2005, vol. 7 (4), pp. 287-288.
Hubbard S.R., et al., "Protein Tyrosine Kinase Structure and Function," Annual Review of Biochemistry, 2000, vol. 69, pp. 373-398.
Huber P.E., et al., "Trimodal Cancer Treatment: Beneficial Effects of Combined Antiangiogenesis, Radiation, and Chemotherapy," Cancer Research, 2005, vol. 65 (9), pp. 3643-3655.
Hudson P.J., et al., "Engineered Antibodies," Nature medicine, 2003, vol. 9 (1), pp. 129-134.
Humphrey P.A., et al., "Amplification and Expression of the Epidermal Growth Factor Receptor Gene in Human Glioma Xenografts," Cancer research , 1988, vol. 48 (8), pp. 2231-2238.
Humphrey P.A., et al., "Deletion-Mutant Epidermal Growth Factor Receptor in Human Gliomas: Effects of Type Ii Mutation on Receptor Function," Biochemical and Biophysical Research Communications , 1991, vol. 178 (3), pp. 1413-1420.
Humphreys D.P., et al., "Therapeutic Antibody Production Technologies: Molecules, Applications, Expression and Purification ," Therapeutic Antibody Production Technologies Humphreys & Glover, 2001, vol. 4 (2), pp. 172-185.
Hunts J., et al., "Hyperproduction and Gene Amplification of the Epidermal Growth Factor Receptor in Squamous Cell Carcinomas," Japanese Journal of Cancer Research 1985, vol. 76 (8), pp. 663-666.
Hurtt M.R., et al., "Amplification of Epidermal Growth Factor Receptor Gene in Gliomas: Histopathology and Prognosis," Journal of Neuropathology & Experimental Neurology, 1992, vol. 51 (1), pp. 84-90.
Hurwitz H., et al., "Bevacizumab Plus Irinotecan, Fluorouracil, and Leucovorin for Metastatic Colorectal Cancer," The New England Journal of Medicine, 2004, vol. 350 (23), pp. 2335-2342.
Hynes N. E., et al., "ERBB Receptors and Cancer: The Complexity of Targeted Inhibitors," Nature Reviews Cancer, 2005, vol. 5 (5), pp. 341-354.
Illidge T.M., et al., "Antibody Therapy of Lymphoma," Expert Opinion on Pharmacotherapy , 2001, vol. 2 (6), pp. 953-961.
Inoue K., et al., "Paclitaxel Enhances the Effects of the Anti-Epidermal Growth Factor Receptor Monoclonal Antibody Imclone C225 in Mice with Metastatic Human Bladder Transitional Cell Carcinoma," Clinical Cancer Research, 2000, vol. 6 (12), pp. 4874-4884.
Ishida T., et al., "The Expression Technology of Chimeric and Humanized Antibodies," Nippon Rinsho, 2002, vol. 60 (3), pp. 439-444.
Ishitoya J., et al., "Gene Amplification and Overexpression of Egf Receptor in Squamous Cell Carcinomas of the Head and Neck," British Journal of Cancer 1989, vol. 59 (4), pp. 559-562.
Italiano A., "Targeting the Epidermal Growth Factor Receptor in Colorectal Cancer: Advances and Controversies," Oncology, 2006, vol. 70 (3), pp. 161-167.
Iznaga-Escobar N., et al. , "Technetium-99m-Antiepidermal Growth Factor-Receptor Antibody in Patients with Tumors of Epithelial Origin: Part ii Pharmacokinetics and Clearances," Journal of Nuclear Medicine, 1998, vol. 39 (11), pp. 1918-1927.
Jamnongjit M., et al., "Epidermal Growth Factor Receptor Signaling is Required for Normal Ovarian Steroidogenesis and Oocyte Maturation," Proceedings of the National Academy of Sciences united states of america , 2005, vol. 102 (45), pp. 16257-16262.

Janne P.A., et al., "Epidermal Growth Factor Receptor Mutations in Non-Small-Cell Lung Cancer: Implications for Treatment and Tumor Biology," Journal of Clinical Oncology, 2005, vol. 23 (14), pp. 3227-3234.
Jaros E., et al., "Prognostic Implications of P53 Protein, Epidermal Growth Factor Receptor, and Ki-67 Labelling in Brain Tumours," British Journal of Cancer, 1992, vol. 66 (2), pp. 373-385.
Jay E.T., et al., "Chemical Synthesis of a Biologically Active Gene for Human Immune Interferon-y, Prospect for Site-Specific Mutagenesis and Structure-Function Studies," Journal of Biological Chemistry, 1984, 259 (10), pp. 6311-6317.
Ji H., et al., "Epidermal Growth Factor Receptor Variant III Mutations in Lung Tumorigenesis and Sensitivity to Tyrosine Kinase Inhibitors," Proceedings of the National Academy of Sciences, 2006, vol. 103 (20), pp. 7817-7822.
Ji H., et al., "The Impact of Human EGFR Kinase Domain Mutations on Lung Tumorigenesis and in Vivo Sensitivity to EGFR-Targeted Therapies," Cancer Cell, 2006, vol. 9 (6), pp. 485-495.
Jiang B., et al., "A Novel Peptide Isolated from a Phage Display Peptide Library with TrastuzumAb can Mimic Antigen Epitope of HER-2," The Journal of Biological Chemistry, 2005, vol. 280 (6), pp. 4656-4662.
Jiang H., et al., "Growth Suppression of Human Hepatocellular Carcinoma Xenografts by a Monoclonal Antibody CH12 Directed to Epidermal Growth Factor Receptor Variant III," Journal of Biological Chemistry, 2011, vol. 286 (7), pp. 5913-5920.
Johns T.G., et al., "MAb 806 Enhances the Efficacy of Ionizing Radiation in Glioma Xenografts Expressing the del-7 Epidermal Growth Factor Receptor," International Journal of Radiation Oncology, Biology, Physics, 2010, vol. 78 (2), pp. 572-578.
Johns, et al., "A Novel Antibody Directed to the Epidermal Growth Factor Receptor (EGFR) Displays Additive and Synergistic Anti-Tumor Activity when used in Combination with Standard EGFR Therapeutics," Proceedings of the International Symposium sponsored by the Cancer Research Institute, 2002, Abstract P-08.
Johns, et al., "A Novel Antibody Directed to the Epidermal Growth Factor Receptor (EGFR) Displays Additive and Synergistic Anti-Tumour Activity When Used in Combination with Standard EGFR Therapeutics," The Proceedings of the 15th Annual Lorne Cancer Conference, 2003, Abstract P212.
Johns, et al., "Biological Properties of the Glioma Associated Delta 2-7 Epidermal Growth Factor Receptor," The 11th International Conference on Second Messengers and Phosphoproteins, 2001, Abstract P183.
Jones R.B., et al., "A Quantitative Protein Interaction Network for the Erbb Receptors Using Protein Microarrays," Nature, 2006, vol. 439 (7073), pp. 168-174.
Jorissen R.N., et al., "Characterization of a Comparative Model of the Extracellular Domain of the Epidermal Growth Factor Receptor," Protein Science, 2000, vol. 9 (2), pp. 310-324.
Jorissen R.N., et al., "Epidermal Growth Factor Receptor: Mechanisms of Activation and Signalling," Experimental Cell Research, 2003, vol. 284 (1), pp. 31-53.
Jost M., et al., "The EGF Receptor—An Essential Regulator of Multiple Epidermal Functions," European Journal of Dermatology, 2000, vol. 10 (7), pp. 505-510.
Jung G., et al., "Local Immunotherapy of Glioma Patients with a Combination of 2 Bispecific Antibody Fragments and Resting Autologous Lymphocytes: Evidence for in Situ T-Cell Activation and Therapeutic Efficacy," International Journal of Cancer , 2001, vol. 91 (2), pp. 225-230.
Jutten B., et al., "Binding of Cetuximab to the EGFRvIII Deletion Mutantand Its Biological Consequences in Malignant Glioma Cells," Radiotherapy and oncology, 2009, vol. 92 (3), pp. 393-398.
Kamat V., et al., "Enhanced Egfr Inhibition and Distinct Epitope Recognition by EGFR Antagonistic.mAbs C225 and 425," Cancer Biology & Therapy, 2008, vol. 7 (5), pp. 726-733.
Kamb A., et al., "A Cell Cycle Regulator Potentially Involved in Genesis of Many Tumor Types," Science, 1994, vol. 264 (5157), pp. 436-440.
Kaminski M.S., et al., "Iodine-131-Anti-B1 Radioimmunotherapy for B-Cell Lymphoma," Journal of Clinical Oncology, 1996, vol. 14 (7), pp. 1974-1981.

(56) References Cited

OTHER PUBLICATIONS

Karnes W.E.Jr., et al., "Autonomous Proliferation of Colon Cancer Cells that Coexpress Transforming Growth Factor Alpha and Its Receptor Variable Effects of Receptor-Blocking Antibody," Gastroenterology, 1992, vol. 102 (2), pp. 474-485.

Karnes W.E.Jr., et al., "Inhibition of Epidermal Growth Factor Receptor Kinase Induces Protease-Dependent Apoptosis in Human Colon Cancer Cells," Gastroenterology, 1998, vol. 114 (5), pp. 930-939.

Karpel-Massler G., et al., "Therapeutic Inhibition of the Epidermal Growth Factor Receptor in High-Grade Gliomas: Where do we Stand," Molecular Cancer Research, 2009, vol. 7 (7), pp. 1000-1012.

Kashmiri S.V., et al., "Development of a Minimally Immunogenic Variant of Humanized Anti-Carcinoma Monoclonal Antibody Cc49," Critical Reviews in Oncology / Hematology , 2001, vol. 38 (1), pp. 3-16.

Kasprzyk P.G., et al., "Therapy of an Animal Model of Human Gastric Cancer using a Combination of Anti-erbB-2 Monoclonal Antibodies," Cancer Research, 1992, vol. 52 (10), pp. 2771-2776.

Katzel J.A., et al., "Recent Advances of Novel Targeted Therapy in Non-Small Cell Lung Cancer," Journal of Hematology & Oncology, 2009, vol. 2, pp. 2.

Kawagoe K., et al., "Immunohistochemical Demonstration of Epidermal Growth Factor (Egf) Receptors in Normal Human Placental Villi," Placenta, 1990, vol. 11 (1), pp. 7-15.

Kawamoto T., et al., "Relation of Epidermal Growth Factor Receptor Concentration to Growth of Human Epidermoid Carcinoma A431 Cells," Journal of Biological Chemistry, 1984, vol. 259 (12), pp. 7761-7766.

Ke L.D., et al., "Differential Expression of Epidermal Growth Factor Receptor in Human Head and Neck Cancers," Head & neck, 1998, vol. 20 (4), pp. 320-327.

Kelly M.P., et al., "Therapeutic Efficacy of 177lu-Chx-A"-Dtpa-Hu3s193 Radioimmunotherapy in Prostate Cancer is Enhanced by Egfr Inhibition or Docetaxel Chemotherapya," Prostate, 2009, vol. 69 (1), pp. 92-104.

Kelly, et al., "ZD1839 (Iressa), An Oral EGFR-TKI (Epidermal Growth Factor Receptor Tyrosine Kinase Inhibitor): Pharmacokinetic Results of a Phase I Study in Patients with Advanced Cancer," Proceedings of the Annual Meeting of the American Association for Cancer Research, 2000, vol. 41 (Abstract 3896), pp. 612-613.

Khazaeli M.B., et al., "Human immune response to monoclonal antibodies," Journal of immunotherapy with emphasis on tumor immunology, 1994, vol. 15 (1), pp. 42-52.

Khazaeli M.B., et al., "Pharmacokinetics and Immune Response of 1311-Chimeric Mouse/Human 872.3 (human γ 4) Monoclonal Antibody in Humans," Cancer Research, 1991, vol. 51 (20), pp. 5461-5466.

Khazaeli, et al., "Low Immunogenicity of a Chimeric Monoclonal Antibody (MoAb), IMC-C225, Used to Treat Epidermal Growth Factor Receptor-Positive Tumors," Proceedings of the American Society of Clinical Oncology, 2000, vol. 207a (Abstract 808), pp. 19.

Khazaie K., et al., "EGF Receptor in Neoplasia and Metastasis," Cancer and Metastasis Reviews, 1993, vol. 12 (3-4), pp. 255-274.

Kies, et al., "Final Report of the Efficacy and Safety of the Anti-Epidermal Growth Factor Antibody Erbitux (Imc-C225), in Combination with Cisplatin in Patients with Recurrent Squamous Cell Carcinoma of the Head and Neck (Scchn) Refractory to Cisplatin Containing Chemotherapy," Proceedings of the American Society of Clinical Oncology, 2002, vol. 232a (Abstract 925), pp. 21.

Kikkawa K., et al., "Immunohistochemical and Histopathological Study of Expression of Epidermal Growth Factor Receptors in Gastric Cancer," Nippon Geka Gakkai Zasshi, 1993, vol. 94 (12), pp. 1231-1238.

Kil S.J., et al., "A Leucine-Based Determinant in the Epidermal Growth Factor Receptor Juxtamembrane Domain is Required for the Efficient Transport of Ligand-Receptor Complexes to Lysosomes," Journal of Biological Chemistry, 1999, vol. 274 (5), pp. 3141-3150.

Kim E.S., et al., A phase II Study of Erhitux (IMC-C225), an Epidermal Growth Factor Receptor(EGFR) Blocking Antibody, in Combination with Docetaxel in Chemotherapy Refractory/resistant Patients with Advanced Non-small Cell, Proceedings of the American Society for Clinical Oncology, 2002, vol. 21, pp. 293A.

Kim E.S., et al., "Epidermal Growth Factor Receptor Biology (Imc-C225)," Current Opinion in Oncology, 2001, vol. 13 (6), pp. 506-513.

Kim J., et al., "Regulation of Epidermal Growth Factor Receptor Internalization by G Protein-Coupled Receptors," Biochemistry, 2003, vol. 42 (10), pp. 2887-2894.

King D.J., et al., "Preparation and Preclinical Evaluation of Humanised A33 Immunoconjugates for Radioimmunotherapy," British Journal of Cancer, 1995, vol. 72 (6), pp. 1364-1372.

Kiyota A., et al., "Anti-Epidermal Growth Factor Receptor Monoclonal Antibody 225 Upregulates P27(Kip1) and P15(Ink4b) and Induces G1 Arrest in Oral Squamous Carcinoma Cell Lines," Oncology, 2002, vol. 63 (1), pp. 92-98.

Kiyota A., et al., "Expression of a Truncated Epidermal Growth Factor Receptor in Oral Squamous Cell Carcinomas," Cancer Letters, 2000, vol. 161 (1), pp. 9-15.

Klapper L.N., et al., "Biochemical and Clinical Implications of the Erbb/Her Signaling Network of Growth Factor Receptors," Advances in Cancer Research 2000, vol. 77, pp. 25-79.

Klapper L.N., et al., "Tumor-Inhibitory Antibodies to Her-2/Erbb-2 May Act by Recruiting C-Cbl and Enhancing Ubiquitination of HER-2," Cancer Research, 2000, vol. 60 (13), pp. 3384-3388.

Klijn J.G., et al., "The Clinical Significance of Epidermal Growth Factor Receptor (Egf-R) in Human Breast Cancer: a Review on 5232 Patients," Endocrine Reviews, 1992, vol. 13 (1), pp. 3-17.

Klijn J.G., et al., "The Prognostic Value of Epidermal Growth Factor Receptor (Egf-R) in Primary Breast Cancer: Results of a 10 Year Follow-up Study," Breast Cancer Research and Treatment, 1994, vol. 29 (1), pp. 73-83.

Klingbeil C.K., et al., "Analysis of Substrate Recognition Determinants in a Synthetic Peptide Containing the Tyr 1173 Autophosphorylation Site of the Epidermal Growth Factor Receptor," Archives of biochemistry and biophysics, 1995, vol. 316 (2), pp. 745.

Klingler-Hoffmann M., et al., "Inhibition of Phosphatidylinositol 3-Kinase Signaling Negates the Growth Advantage Imparted by a Mutant Epidermal Growth Factor Receptor on Human Gliobiastoma Cells," International Journal of Cancer 2003, vol. 105 (3), pp. 331-339.

Klohs W.D., et al., "Inhibitors of Tyrosine Kinase," Current Opinion in Oncology, 1997, vol. 9 (6), pp. 562-568.

Knecht R., et al., "Carcinomas Unresponsive to Either Cisplatinum or Anti-Egfr Therapy can be Growth Inhibited by Combination Therapy of Both Agents," Anticancer Research, 2003, vol. 23 (3B), pp. 2577-2583.

Kobayashi S., et al., "An Alternative Inhibitor Overcomes Resistance Caused by a Mutation of the Epidermal Growth Factor Receptor," Cancer Research, 2005, vol. 65 (16), pp. 7096-70101.

Kobayashi S., et al., "EGFR Mutation and Resistance of Non-Small-Cell Lung Cancer to Gefitinib," The New England Journal of Medicine, 2005, vol. 352 (8), pp. 786-792.

Kondo I., et al., "Mapping of the Human Gene for Epidermal Growth Factor Receptor (Egfr) on the P13 Leads to Q22 Region of Chromosome 7," Cytogenetics and Cell Genetics, 1983, vol. 35 (1), pp. 9-14.

Koprivica V., et al., "EGFR Activation Mediates Inhibition of Axon Regeneration by Myelin and Chondroitin Sulfate Proteoglycans," Science , 2005, vol. 310 (5745), pp. 106-110.

Korshunov A., et al., "Prognostic Value of Tumor Associated Antigen Immunoreactivity and Apoptosis in Cerebral Glioblastomas: An Analysis of 163 Cases," Journal of Clinical Pathology, 1999, vol. 52 (8), pp. 574-580.

Kosaka T., et al., "Mutations of the Epidermal Growth Factor Receptor Gene in Lung Cancer: Biological and Clinical Implications," Cancer Research, 2004, vol. 64 (24), pp. 8919-8923.

Kramer A., et al., "Regulation of Daily Locomotor Activity and Sleep by Hypothalamic Egf Receptor Signaling," Science , 2001, vol. 294 (5551), pp. 2511-2515.

Kris M.G., et al., "Objective regressions in non-small cell lung cancer patients treated in Phase I trials of oral ZD1839 (IressaTM), a selec-

(56) References Cited

OTHER PUBLICATIONS tive tyrosine kinase inhibitor that blocks the epidermal growth factor receptor (EGFR), Abstract 233," Chemotherapy, 2000, pp. 72.
Kris R.B., et al., "A phase II trial of Z01839 ('Iressa') in advanced non-small cell lung cancer (NSCLC) patients who had failed platinum- and docetaxel-based regimens (Ideal 2)," Proceedings of American Society of Clinical Oncology, 2002, vol. 21, pp. 21.
Krug L.M., et al., "Targeting Lewis Y (Le(Y)) in Small Cell Lung Cancer with a Humanized Monoclonal Antibody, Hu3s193: a Pilot Trial Testing Two Dose Levels," Journal of Thoracic Oncology, 2007, vol. 2 (10), pp. 947-952.
Kuan C.T., et al., "125I-Labeled Anti-Epidermal Growth Factor Receptor-Yin Single-Chain Fv Exhibits Specific and High-Level Targeting of Glioma Xenografts," Clinical Cancer Research, 1999, vol. 5 (6), pp. 1539-1549.
Kubo S., et al., "Three-Dimensional Magnetic Resonance Microscopy of Pulmonary Solitary Tumors in Transgenic Mice," Magnetic Resonance in Medicine, 2006, vol. 56 (3), pp. 698-703.
Kumar R., et al., "Regulation of Phosphorylation of the C-Erbb-2/Her2 Gene Product by a Monoclonal Antibody and Serum Growth Factor(S) in Human Mammary Carcinoma Cells," Molecular and Cellular Biology, 1991, vol. 11 (2), pp. 979-986.
Kunkel M.W., et al., "Inhibition of the Epidermal Growth Factor Receptor Tyrosine Kinase by Pd153035 in Human A431 Tumors in Athymic Nude Mice," Investigational New Drugs, 1996, vol. 13 (4), pp. 295-302.
Kurpad S.N., et al., "Tumor Antigens in Astrocytic Gliomas," Glia, 1995, vol. 15 (3), pp. 244-256.
Kwak E.L., et al., "Irreversible Inhibitors of the EGF Receptor May Circumvent Acquired Resistance to Gefitinib," Proceedings of the National Academy of Sciences, 2005, vol. 102 (21), pp. 7665-7670.
Kwok T.T., et al., "Cell Cycle Dependence of Epidermal Growth Factor Induced Radiosensitization," International Journal of Radiation Oncology Biology Physics, 1992, vol. 22 (3), pp. 525-527.
Lackmann M., et al., "Eph, a Protein Family Coming of Age: More Confusion, Insight, or Complexity," Science Signaling, 2008, vol. 1 (15), pp. re2.
Lacouture M.E., "Mechanisms of Cutaneous Toxicities to EGFR Inhibitors," Nature Reviews Cancer, 2006, vol. 6 (10), pp. 803-812.
Laderoute K.R., et al., "Epidermal Growth Factor Modifies Cell Cycle Control in A431 Human Squamous Carcinoma Cells Damaged by Ionizing Radiation," Cancer Research, 1994, vol. 54 (6), pp. 1407-1411.
Lal A., et al., "Mutant Epidermal Growth Factor Receptor Up-Regulates Molecular Effectors of Tumor Invasion," Cancer Research, 2002, vol. 62 (12), pp. 3335-3339.
Lammering G., et al., "EGFRVIII-Mediated Radioresistance Through a Strong Cytoprotective Response," Oncogene, 2003, vol. 22 (36), pp. 5545-5553.
Lammering G., et al., "Inhibition of the Type III Epidermal Growth Factor Receptor Variant Mutant Receptor by Dominant-Negative EGFR-CD533 Enhances Malignant Glioma Cell Radiosensitivity," Clinical Cancer Research, 2004, vol. 10 (19), pp. 6732-6743.
Lammering G., et al., "Radiosensitization of Malignant Glioma Cells through Overexpression of Dominant-Negative Epidermal Growth Factor Receptor," Clinical Cancer Research, 2001, vol. 7 (3), pp. 682-690.
Lammerts Van Bueren J.J., et al., "Effect of Target Dynamics on Pharmacokinetics of a Novel Therapeutic Antibody Against the Epidermal Growth Factor Receptor: Implications for the Mechanisms of Action," Cancer Research, 2006, vol. 66 (15), pp. 7630-7638.
Lammerts Van Bueren J.J., et al., "The Antibody Zalutumumab Inhibits Epidermal Growth Factor Receptor Signaling by Limiting Intra and Intermolecular Flexibility," Proceedings of the National Academy of Sciences of the United States of America, 2008, vol. 105 (16), pp. 6109-6114.
Lango M.N., et al., "Targeting Growth Factor Receptors: Integration of Novel Therapeutics in the Management of Head and Neck Cancer," Current Opinion in Oncology, 2001, vol. 13 (3), pp. 168-175.

Lanzetti L., et al., "The Eps8 Protein Coordinates Egf Receptor Signalling Through Rac and Trafficking through Rab5," Nature, 2000, vol. 408 (6810), pp. 374-377.
Larysz D., et al., "Epidermal Growth Factor Receptor Gene Expression in High Grade Gliomas," Folia Neuropathol 2011, vol. 49 (1), pp. 28-38.
Laskowski R.A., "Procheck: A Program to Check the Sterochemical Quality of Protein Structures," Journal of Applied Crystallography, 1993, vol. 26, pp. 283-291.
Lassman A.B., et al., "Response of Glioblastomas to EGFR Kinase Inhibitors," The New England Journal of Medicine, 2006, vol. 354 (5), pp. 525-526.
Lautrette A., et al., "Angiotensin II and Egf Receptor Cross-Talk in Chronic Kidney Diseases: A New Therapeutic Approach," Nature Medicine, 2005, vol. 11 (8), pp. 867-874.
Lawrentschuk N., et al., "Assessing Regional Hypoxia in Human Renal Tumours using 18f-Fluoromisonidazole Positron Emission Tomography," British Journal of Urology International, 2005, vol. 96 (4), pp. 540-546.
Lee F.T., et al., "Enhanced Efficacy of Radioimmunotherapy with 90Y-CHX-A-DTPA-hu3S193 by Inhibition of Epidermal Growth Factor Receptor (EGFR) Signaling with EGFR Tyrosine Kinase Inhibitor AG1478," Clinical Cancer Research, 2005, vol. 11 (19 pt 2), pp. 7080s-7086s.
Lee F.T., et al., "Immuno-Pet for Tumor Targeting," Journal of Nuclear Medicine, 2003, vol. 44 (8), pp. 1282-1283.
Lee F.T., et al., "Immuno-Pet of Human Colon Xenograft-Bearing Balb/C Nude Mice using 124i-Cdr-Grafted Humanized A33 Monoclonal Antibody," Journal of Nuclear Medicine, 2001, vol. 42 (5), pp. 764-769.
Lee Y.S., et al., "Therapeutic Efficacy of Antiglioma Mesenchymal Extracellular Matrix 131-Radiolabeled Murine Monoclonal Antibody in a Human Glioma Xenograft Model," Cancer Research, 1988, vol. 48 (3), pp. 559-566.
Lei W., et al., "Enhancement of Chemosensitivity and Programmed Cell Death by Tyrosine Kinase Inhibitors Correlates with Egfr Expression in Non-Small Cell Lung Cancer Cells," Anticancer Research, 1999, vol. 19 (1A), pp. 221-228.
Lenferink A.E., et al., "Blockade of the Epidermal Growth Factor Receptor Tyrosine Kinase Suppresses Tumorigenesis in Mmtv/Neu + Mmtv/Tgf-Alpha Bigenic Mice," Proceedings of the National Academy of Sciences, 2000, vol. 97 (17), pp. 9609-9614.
Lenz H.J., et al., "Multicenter Phase II and Translational Study of Cetuximab in Metastatic Colorectal Carcinoma Refractory to Irinotecan, Oxaliplatin, and Fluoropyrimidines," Journal of Clinical Oncology, 2006, vol. 24 (30), pp. 4914-4921.
Lenz, et al., "Consistent Response to Treatment with Cetuximab Monotherapy in Patients with Metastatic Colorectal Cancer," Journal of Clinical Oncology, ASCO Annual Meeting Proceedings, 2005, Abstract 3536, 23 (16S).
Leon S.P., et al., "Genetic Aberrations in Human Brain Tumors," Neurosurgery, 1994, vol. 34 (4), pp. 708-722.
Leu T.H., et al., "Functional Implication of the Interaction Between Egf Receptor and C-Src," Frontiers in Bioscience, 2003, vol. 8, pp. S28-S38.
Levitzki A., et al., "Tyrosine Kinase Inhibition: An Approach to Drug Development," Science 1995, vol. 267 (5205), pp. 1782-1788.
Lewis Phillips G.D., et al., "Targeting HER2-Positive Breast Cancer With Trastuzumab-Dm1, an Antibody-Cytotoxic Drug Conjugate," Cancer Research 2008, vol. 68 (22), pp. 9280-9290.
Li B., et al., "Mutant Epidermal Growth Factor Receptor Displays Increased Signaling Through the Phosphatidylinositol-3 kinase/AKT Pathway and Promotes Radioresistance in Cells of Astrocytic Origin," Oncogene, 2004, vol. 23 (26), pp. 4594-4602.
Li D., et al., "Therapeutic Anti-EGFR Antibody 806 Generates Responses in Murine de Novo EGFR Mutant-Dependent Lung Carcinomas," Journal of Clinical Investigation, 2007, vol. 117 (2), pp. 346-352.
Li G., et al., "EGF Receptor Variant III as a Target Antigen for Tumor Immunotherapy," Expert Review of Vaccines, 2008, vol. 7 (7), pp. 977-985.

(56) References Cited

OTHER PUBLICATIONS

Li S., et al., "Structural Basis for EGF Receptor Inhibition by the Therapeutic Antibody Imc-11F8," Structure, 2008, vol. 16 (2), pp. 216-227.

Libermann T.A., et al., "Expression of Epidermal Growth Factor Receptors in Human Brain Tumors," Cancer Research 1984, vol. 44 (2), pp. 753-760.

Lin C.R., et al., "Expression Cloning of Human Egf Receptor Complementary Dna: Gene Amplification and Three Related Messenger Rna Products in A431 Cells," Science, 1984, vol. 224 (4651), pp. 843-848.

Lindmo T., et al., "Determination of the Immunoreactive Fraction of Radiolabeled Monoclonal Antibodies by Linear Extrapolation to Binding at Infinite Antigen Excess," Journal of Immunological Methods, 1984, vol. 72 (1), pp. 77-89.

Lipton, et al., "Elevated Serum HER-2/neu Level Predicts Decreased Response to Hormone Therapy in Metastatic Breast Cancer," Proceedings of the American Society of Clinical Oncology, 2000, vol. 71a (Abstract 274), pp. 19.

Little M., et al., "Of Mice and Men: Hybridoma and Recombinant Antibodies," Immunology Today, 2000, vol. 21 (8), pp. 364-370.

Liu B., et al., "Epidermal Growth Factor Receptor Activation: An Upstream Signal for Transition of Quiescent Astrocytes into Reactive Astrocytes after Neural Injury," Journal of Neuroscience, 2006, vol. 26 (28), pp. 7532-7540.

Liu L., et al., "Clinical Significance of EGFR Amplification and the Aberrant EgfrvIII Transcript In Conventionally Treated Astrocytic Gliomas," Journal of Molecular Medicine 2005, vol. 83 (11), pp. 917-926.

Liu M., et al., "The Effect of Epidermal Growth Factor Receptor Variant III on Glioma Cell Migration by Stimulating ERK Phosphorylation Through the Focal Adhesion Kinase Signaling Pathway," Archives of Biochemistry and Biophysics, 2010, vol. 502 (2), pp. 89-95.

Livneh E., et al., "Reconstitution of Human Epidermal Growth Factor Receptors and Its Deletion Mutants in Cultured Hamster Cells," Journal of Biological Chemistry, 1986, vol. 261 (27), pp. 12490-12497.

Lo H.W., "EGFR-Targeted Therapy in Malignant Glioma: Novel Aspects and Mechanisms of Drug Resistance," Current Molecular Pharmacology, 2010, vol. 3 (1), pp. 37-52.

Lobuglio A.F., et al., "Mouse/Human Chimeric Monoclonal Antibody in Man: Kinetics and Immune Response," Proceedings of the National Academy of Sciences, 1989, vol. 86 (11), pp. 4220-4224.

Loew S., et al., "The Epidermal Growth Factor Receptor as a Therapeutic Target in Glioblastoma Multiforme and Other Malignant Neoplasms," Anti-Cancer Agents in Medicinal Chemistry, 2009, vol. 9 (6), pp. 703-715.

Lofts F.J., et al., "C-erbB2 Amplification and Overexpression in Human Tumors," Cancer Treatment and Research, 1992, vol. 61, pp. 161-179.

Lorimer I.A., "Mutant Epidermal Growth Factor Receptors as Targets for Cancer Therapy," Current Cancer Drug Targets, 2002, vol. 2 (2), pp. 91-102.

Lorimer I.A., et al., "Activation of Extracellular-Regulated Kinases by Normal and Mutant Egf Receptors," Biochimica et Biophysica Acta, 2001, vol. 1538 (1), pp. 1-9.

Lorusso P.M., et al., "Improvements in Quality of Life and Disease-Related Symptoms in Phase I Trials of the Selective Oral Epidermal Growth Factor Receptor Tyrosine Kinase Inhibitor Zd1839 in Non-Small Cell Lung Cancer and Other Solid Tumors," Clinical Cancer Research, 2003, vol. 9 (6), pp. 2040-2048.

Lu K.V., et al., "Fyn and SRC are Effectors of Oncogenic Epidermal Growth Factor Receptor Signaling in Glioblastoma Patients," Cancer Research, 2009, vol. 69 (17), pp. 6889-6898.

Lui V.W., et al., "EGFR-Mediated Cell Cycle Regulation," Anticancer Research, 2002, 22 (1A), pp. 1-11.

Lund K.A., et al., "Phosphorylation of the Epidermal Growth Factor Receptor at Threonine 654 Inhibits Ligand-Induced Internalization and Down-Regulation," Journal of Biological Chemistry, 1990, vol. 265 (33), pp. 20517-20523.

Luwor R.B., "The monoclonal antibody 806 and tyrosine kinase inhibitor ag1478: novel epidermal growth factor receptor therapeutics (Project Report)," in: Tumour Targeting Program Ludwig Institute for Cancer Research, 2003.

Luwor, et al., "A Soluble Form of the Epidermal Growth Factor Receptor (EGFR) Specific Tyrosine Kinase Inhibitor AG1478 Enhances the Efficacy of Chemotherapy," Proceedings of the American Association for Cancer Research, 2002, vol. 784 (Abstract 3885), pp. 43.

Luwor, et al., "Monoclonal Antibody 806 Inhibits the Growth of Tumor Xenografts Expressing either the de2-7 or Amplified Epidermal Growth Factor Receptor (EGFR) but not Wild-Type EGFR," Austin and Repatriation Medical Centre Research Week, 2000, Abstract 88.

Luwor, et al., "The 806 Antibody Inhibits the Growth of Tumor Xenografts Expressing either the de2-7 or Amplified Epidermal Growth Factor Receptor (EGFR) but not Wild-Type EGFR," Austin and Repatriation Medical Centre Research Week, 2001, Abstract 46.

Luwor, et al., "The 806 Antibody Inhibits the Growth of Tumor Xenografts Expressing either the de2-7 or Amplified Epidermal Growth Factor Receptor (EGFR) but not Wild-Type EGFR," Proceedings of the 13th Annual Lorne Cancer Conference, 2001, Abstract 208.

Lyall, et al., "EGF Induces Receptor Down-regulation with no Receptor Recycling in KB Cells," Chemical Abstracts, 1985, vol. 102 (7), pp. 56832q.

Lydon N.B., et al., "A Potent Protein-Tyrosine Kinase Inhibitor which Selectively Blocks Proliferation of Epidermal Growth Factor Receptor-Expressing Tumor Cells in Vitro and in Vivo," International Journal of Cancer, 1998, vol. 76 (1), pp. 154-163.

Lynch, et al., "A Phase II Trial of Cetuximab as Therapy for Recurrent Non-Small Cell Lung Cancer (NSCLC)," Proceedings of the American Society of Clinical Oncology, 2004, vol. 637s (Abstract 7084), pp. 23.

MacDiarmid J.A., et al., "Sequential Treatment of Drug-Resistant Tumors with Targeted Minicells Containing Sirna or a Cytotoxic Drug," Nature Biotechnology, 2009, vol. 27 (7), pp. 643-651.

MacDonald A., et al., "Production and Response of a Human Prostatic Cancer Line to Transforming growth Factor-like Molecules," British Journal of Cancer, 1990, vol. 62 (4), pp. 579-584.

Mach, "Monoclonal Antibodies" in: Oxford Textbook of Oncology, Chapter 1.8, Peckham, et al., eds., Oxford University Press, 1995, pp. 81-103.

Machiels J.P., et al., "Zalutumumab Plus Best Supportive Care Versus Best Supportive Care Alone in Patients with Recurrent or Metastatic Squamous-Cell Carcinoma of the Head and Neck After Failure of Platinum-Based Chemotherapy: An Open-Label, Randomised Phase 3 Trial," Lancet Oncology, 2011, vol. 12 (4), pp. 333-343.

Maciag T., "The Human Epidermal Growth Factor Receptor-Kinase Complex," Trends in Biochemical Sciences, 1982.

Maeda K., et al., "Ph-Dependent Receptor/Ligand Dissociation as a Determining Factor for Intracellular Sorting of Ligands for Epidermal Growth Factor Receptors in Rat Hepatocytes," Journal of Controlled Release, 2002, vol. 82 (1), pp. 71-82.

Malden L.T., et al., "Selective Amplification of the Cytoplasmic Domain of the Epidermal Growth Factor Receptor Gene in Glioblastoma multiforme," Cancer Research, 1988, vol. 48 (10), pp. 2711-2714.

Malik S.N., et al., "Pharmacodynamic Evaluation of the Epidermal Growth Factor Receptor Inhibitor OSI-774 in Human Epidermis of Cancer Patients," Clinical Cancer Research, 2003, vol. 9 (7), pp. 2478-2486.

Malik, et al., "Safety and Efficacy of Panitumumab Monotherapy in Patients with Metastatic Colorectal Cancer (mCRC)," Journal of Clinical Oncology, ASCO Annual Meeting Proceedings, 2005, Abstract 3520, 23 (16S).

(56) References Cited

OTHER PUBLICATIONS

Maloney D.G., et al., "Idec-C2B8 (RituximAb) Anti-CD20 Monoclonal Antibody Therapy in Patients with Relapsed Low-Grade Non-Hodgkin"s Lymphoma," Blood, 1997, vol. 90 (6), pp. 2188-2195.
Mamot C., et al., "Epidermal Growth Factor Receptor (EGFR)-Targeted Immunoliposomes Mediate Specific and Efficient Drug Delivery to Egfr- and EgfrvIII-Overexpressing Tumor Cells," Cancer Research, 2003, vol. 63 (12), pp. 3154-3161.
Mamot C., et al., "Epidermal Growth Factor Receptor-Targeted Immunoliposomes Significantly Enhance the Efficacy of Multiple Anticancer Drugs in Vivo," Cancer Research, 2005, vol. 65 (24), pp. 11631-11638.
Mano, et al., Phase I Trial of Zalutumumab and Irinotecan in Metastatic Colorectal Cancer Patients Who Have Failed Irinotecan- and Cetuximab-Based Therapy, ASCO Meeting, 2009.
Margolis B.L., et al., "All Autophbsphorylation Sites of Epidermal Growth Factor (EGF) Receptor and HER2/neu are Located in their Carboxyl-Terminal Tails. Identification of a Novel Site in EGF Receptor," Journal of Biological Chemistry, 1989, vol. 264 (18), pp. 10667-10671.
Marie Y., et al., "Egfr Tyrosine Kinase Domain Mutations in Human Gliomas," Neurology, 2005, vol. 64 (8), pp. 1444-1445.
Markowitz S.D., et al., "Growth Stimulation by Coexpression of Transforming Growth Factor-Alpha and Epidermal Growth Factor-Receptor in Normal and Adenomatous Human Colon Epithelium," Journal of Clinical Investigation, 1990, vol. 86 (1), pp. 356-362.
Marks J.D., et al., "By-Passing Immunization: Building High Affinity Human Antibodies by Chain Shuffling," Biotechnology, 1992, vol. 10 (7), pp. 779-783.
Martinazzi M., et al., "Epidermal Growth Factor Receptor Immunohistochemistry in Different Histological Types of Infiltrating Breast Carcinoma," Journal of Clinical Pathology, 1993, vol. 46 (11), pp. 1009-1010.
Maruo T., et al., "Immunohistochemical Demonstration of Elevated Expression of Epidermal Growth Factor Receptor in the Neoplastic Changes of Cervical Squamous Epithelium," Cancer, 1992, vol. 69 (5), pp. 1182-1187.
Masui H., et al., "Cytotoxicity Against Human Tumor Cells Mediated by the Conjugate of Anti-Epidermal Growth Factor Receptor Monoclonal Antibody to Recombinant Ricin a Chain," Cancer Research, 1989, vol. 49 (13), pp. 3482-3488.
Masui H., et al., "Enhanced Tumorigenesis of NR6 Cells which Express Non-Down-Regulating Epidermal Growth Factor Receptors," Cancer Research, 1991, vol. 51 (22), pp. 6170-6175.
Masui, et al., "Treatment with Anti-EGF Receptor Monoclonal Antibody Causes Regression of Difi Human Colorectal Carcinoma Xenografts," Proceedings of the American Association for Cancer Research, 1991, vol. 394 (Abstract 2340), pp. 32.
Matar P., et al. "Combined Epidermal Growth Factor Receptor Targeting with the Tyrosine Kinase Inhibitor Gefitinib (ZD1839) and the Monoclonal Anti Body Cetuximab (IMC-C225) : Superiority Over Single-Agent Receptor Targeting," Clinical Cancer Research, 2004, vol. 10 (19), pp. 6487-6501.
Mateo C., et al., "Humanization of a Mouse Monoclonal Antibody that Blocks the Epidermal Growth Factor Receptor: Recovery of Antagonistic Activity," Immunotechnology, 1997, vol. 3 (1), pp. 71-81.
Matsuo M., et al., "Zd1839, a Selective Epidermal Growth Factor Receptor Tyrosine Kinase Inhibitor, Shows Antimetastatic Activity using a Hepatocellular Carcinoma Model," Molecular Cancer Therapeutics, 2003, vol. 2 (6), pp. 557-561.
Maurizi M., et al., "Prognostic Significance of Epidermal Growth Factor Receptor in Laryngeal Squamous Cell Carcinoma," British Journal of Cancer, 1996, vol. 74 (8), pp. 1253-1257.
Mayes E.L., et al., "Biosynthesis of the Epidermal Growth Factor Receptor in A431 Cells," EMBO Journal, 1984, vol. 3 (3), pp. 531-537.
McCafferty J., et al., "Phage Antibodies: Filamentous Phage Displaying Antibody Variable Domains," Nature, 1990, vol. 348 (6301), pp. 552-554.
McLeod H.L., et al., "In Vivo Pharmacology and Anti-Tumour Evaluation of the Tyrphostin Tyrosine Kinase Inhibitor RG13022," British Journal of Cancer, 1996, vol. 74 (11), pp. 1714-1718.
Meikrantz W., et al., "Apoptosis and the Cell Cycle," Journal of Cellular Biochemistry, 1995, vol. 58 (2), pp. 160-174.
Mellinghoff I.K., et al., "PTEN-Mediated Resistance to Epidermal Growth Factor Receptor Kinase Inhibitors," Clinical Cancer Research, 2007, vol. 13 (2 pt 1), pp. 378-381.
Mellstedt H., "Monoclonal Antibodies in Human Cancer," Drugs Today (Barc), 2003, vol. 39 (Suppl. C), pp. 1-16.
Mendelsoh J., et al., "The EGF Receptor Family as Targets for Cancer Therapy," Oncogene, 2000, vol. 19 (56), pp. 6550-6565.
Mendelsohn J., "Blockade of Receptors for Growth Factors: An Anticancer Therapy the Fourth Annual Joseph H Burchenal American Association of Cancer Research Clinical Research Award Lecture," Clinical Cancer Research, 2000, vol. 6 (3), pp. 747-753.
Mendelsohn J., "Epidermal Growth Factor Receptor Inhibition by a Monoclonal Antibody as Anticancer Therapy," Clincical Cancer Research, 1997, vol. 3 (12 pt 2), pp. 2703-2707.
Mendelsohn J., et al., "Anti-Epidermal Growth Factor Receptor Monoclonal Antibodies May Inhibit A431 Tumor Cell Proliferation by Blocking an Autocrine Pathway," Transactions of the Association of American Physicians, 1987, vol. 100, pp. 173-178.
Mendelsohn J., et al., "Epidermal Growth Factor Receptor Family and Chemosensitization," Journal of the National Cancer Institute, 1997, vol. 89 (5), pp. 341-343.
Mendelsohn J., et al., "Status of Epidermal Growth Factor Receptor Antagonists in the Biology and Treatment of Cancer," Journal of Clinical Oncology, 2003, vol. 21 (14), pp. 2787-2799.
Mendelsohn J., et al., "The Epidermal Growth Factor Receptor as a Target for Cancer Therapy," Endocrine-Related Cancer, 2001, vol. 8 (1), pp. 3-9.
Mendelsohn J., et al.,, "The Willet F. Whitmore, Jr., Lectureship: Blockade of Epidermal Growth Factor Receptors as Anticancer Therapy," Journal of Urology, 2001, vol. 165 (4), pp. 1152-1157.
Mendelsohn, et al., "A Phase I Study of Chimerized Anti-Epidermal Growth Factor Receptor (EGFR) Monoclonal Antibody, C225, in Combination with Cisplatin (CDDP) in Patients (Pts) with Recurrent Head and Neck Squamous Cell Carcinoma (SCC)," Annual Meeting of the American Society of Clinical Oncology, 1999, vol. 389a (Abstract 1502), pp. 18.
Mendelsohn, et al., "Antibodies to Growth Factors and Receptors" in: Biologic Therapy of Cancer, Section 21.6, DeVita, et al., eds., JB Lippincott Co, 1995, pp. 607-623.
Mendelsohn, et al., "Principles of Molecular Cell Biology of Cancer: Growth Factors" in: Cancer: Principles and Practice of Oncology, Chapter 7, DeVita, et al., eds., J.B. Lippincott, Philadelphia, 1993, pp. 114-133.
Merlino G.T., et al., "Structure and Localization of Genes Encoding Aberrant and Normal Epidermal Growth Factor Receptor RNAS from A431 Human Carcinoma Cells," Molecular and Cellular 1985, vol. 5 (7), pp. 1722-1734.
Messa C., et al., "EGF, TGF-Alpha, and EGF-R in Human Colorectal Adenocarcinoma," Methods of Information in Medicine, 1998, vol. 37 (3), pp. 285-289.
Messing E.M., et al., "Epidermal Growth Factor—Interactions with Normal and Malignant Urothelium: In Vivo and in Situ Studies," Journal of Urology, 1987, vol. 138 (5), pp. 1329-1335.
Mickey D.D., et al., "Heterotransplantation of a Human Prostatic Adenocarcinoma Cell Line in Nude Mice," Cancer Research, 1977, vol. 37 (11), pp. 4049-4058.
Milano G., et al., "EGFR-Targeting Drugs in Combination with Cytotoxic Agents: from Bench to Bedside, a Contrasted Reality," British Journal of Cancer, 2008, vol. 99 (1), pp. 1-5.
Milas L., et al., "In Vivo Enhancement of Tumor Radioresponse by C225 Antiepidermal Growth Factor Receptor Antibody," Clinical Cancer Research, 2000, vol. 6, pp. 701-708.
Miller, et al., "A Pilot Trial Demonstrates the Safety of ZD1839 (Iressa), an Oral Epidermal Growth Factor Receptor Tyrosine Kinase Inhibitor (EGFR-TKI), in Combination with Carboplatin (C) and

(56) References Cited

OTHER PUBLICATIONS

Paclitaxel (P) in Previously Untreated Advanced Non-Small Cell Lung Cancer (NSCLC)," 2001, Abstract 1301, pp. 20.
Mills L., et al., "Fully Human Antibodies to MCAM/MUC18 Inhibit Tumor Growth and Metastasis of Human Melanoma1," Cancer Research, 2002, vol. 62 (17), pp. 5106-5114.
Mineo C., et al., "Regulated Migration of Epidermal Growth Factor Receptor from Caveolae," Journal of Biological Chemistry, 1999, vol. 274 43), pp. 30636-30643.
Mischel P.S., et al., "Targeted Molecular Therapy of GBM," Brain Pathology, 2003, vol. 13 (1), pp. 52-61.
Mishima K., et al., "A Peptide Derived from the Non-Receptor-Binding Region of Urokinase Plasminogen Activator Inhibits Glioblastoma Growth and Angiogenesis in Vivo in Combination with Cisplatin," Proceedings of the National Academy of Sciences, 2000, vol. 97 (15), pp. 8484-8489.
Mitra S., et al., "Passive Antibody-Mediated Immunotherapy for the Treatment of Malignant Gliomas," Neurosurgery Clinics of North America 2010, vol. 21 (1), pp. 67-76.
Moasser M.M., et al., "The Tyrosine Kinase Inhibitor ZD1839 ('Iressa') Inhibits Her2-Driven Signaling and Suppresses the Growth of Her2-Overexpressing Tumor Cells," Cancer Research, 2001, vol. 61 (19), pp. 7184-7188.
Modjtahedi H., et al., "Differentiation or Immune Destruction: Two Pathways for Therapy of Squamous Cell Carcinomas With Antibodies to the Epidermal Growth Factor Receptor," Cancer Research, 1994, vol. 54 (7), pp. 1695-1701.
Modjtahedi H., et al., "Egfr Blockade by Tyrosine Kinase Inhibitor or Monoclonal Antibody Inhibits Growth, Directs Terminal Differentiation and Induces Apoptosis in the Human Squamous Cell Carcinoma Hn5," International Journal of Oncology, 1998, vol. 13 (2), pp. 335-342.
Modjtahedi H., et al., "Immunotherapy of Human Tumour Xenografts Overexpressing the Egf Receptor with Rat Antibodies that Block Growth Factor-Receptor Interaction," British Journal of Cancer, 1993, vol. 67 (2), pp. 254-261.
Modjtahedi H., et al., "Phase I Trial and Tumour Localisation of the Anti-EGFR Monoclonal Antibody ICR62 in Head and Neck or Lung Cancer," British Journal of Cancer, 1996, vol. 73 (2), pp. 228-235.
Modjtahedi H., et al., "Targeting of Cells Expressing Wild-type EGFR and Type-III Mutant EGFR (EGFRvIII) by Anti-EGFR MAb ICR62: A Two-pronged Attack for Tumour Therapy," International Journal of Cancer, 2003, vol. 105 (2), pp. 273-280.
Modjtahedi H., et al., "The Human EGF Receptor as a Target for Cancer Therapy: Six New Rat mAbs Against the Receptor on the Breast Carcinoma MDA-MB 468," British Journal of Cancer, 1993, vol. 67 (2), pp. 247-253.
Modjtahedi H., et al., "The Receptor for Egf and Its Ligands—Expression, Prognostic Value and Target for Therapy in Cancer (Review)," International Journal of Oncology, 1994, vol. 4 (2), pp. 277-296.
Moghal N., et al., "Multiple Positive and Negative Regulators of Signaling by the Egf-Receptor," Current Opinion in Cell Biology, 1999, vol. 11 (2), pp. 190-196.
Montgomery R.B., et al., "Expression of Oncogenic Epidermal Growth Factor Receptor Family Kinases Induces Paclitaxel Resistance and Alters Beta-Tubulin Isotype Expression," Journal of Biological chemistry, 2000, vol. 275 (23), pp. 17358-17363.
Morales A.A., et al., "Humanized Versus Murine Anti-Human Epidermal Growth Factor Receptor Monoclonal Antibodies for Immunoscintigraphic Studies," Nuclear Medicine and Biology, 2000, vol. 27 (2), pp. 199-206.
Morea V., et al., "Antibody Structure, Prediction and Redesign," Biophysical Chemistry, 1997, vol. 68 (1-3), pp. 9-16.
Moroni M., et al., "Gene Copy Number for Epidermal Growth Factor Receptor (Egfr) and Clinical Response to Antiegfr Treatment in Colorectal Cancer: A Cohort Study," The Lancet Oncology, 2005, vol. 6 (5), pp. 279-286.
Morrison S.L., et al., "Recombinant Chimeric Monoclonal Antibodies," Important Advances in Oncology, 1990, pp. 3-18.
Moscatello D.K., et al., "A Naturally Occurring Mutant Human Epidermal Growth Factor Receptor as a Target for Peptide Vaccine Immunotherapy of Tumors," Cancer Research, 1997, vol. 57 (8), pp. 1419-1424.
Moscatello D.K., et al., "Constitutive Activation of Phosphatidylinositol 3-Kinase by a Naturally Occurring Mutant Epidermal Growth Factor Receptor," Journal of Biological Chemistry, 1998, vol. 273 (1), pp. 200-206.
Moscatello D.K., et al., "Transformational and Altered Signal Transduction by a Naturally Occurring Mutant Egf Receptor," Oncogene, 1996, vol. 13 (1), pp. 85-96.
Moulder S.L., et al., "Epidermal Growth Factor Receptor (HeR1) Tyrosine Kinase Inhibitor ZD1839 (Iressa) Inhibits HER2/neu (erbB2)-overexpressing Breast Cancer Cells in Vitro and in Vivo," Cancer Research, 2001, vol. 61 (24), pp. 8887-8895.
Moyer J.D., et al., "Induction of Apoptosis and Cell Cycle Arrest by CP-358,774, an Inhibitor of Epidermal Growth Factor Receptor Tyrosine Kinase," 1997, vol. 57 (21), pp. 4838-4848.
Murshudov G.N., et al., "Refinement of Macromolecular Structures by the Maximum-Likelihood Method," Acta Crystallogr D Biol Crystallogr, 1997, vol. 53 (pt 3), pp. 240-255.
Muthuswamy S.K., et al., "Controlled Dimerization of Erbb Receptors Provides Evidence for Differential Signaling by Homo- and Heterodimers," 1999, vol. 19 (10), pp. 6845-6857.
Nagane M., et al., "Drug Resistance of Human Glioblastoma Cells Conferred by a Tumor-Specific Mutant Epidermal Growth Factor Receptor Through Modulation of BCL-XL and Caspase-3-Like Proteases," Proceedings of the National Academy of Sciences, 1998, vol. 95 (10), pp. 5724-5729.
Nagane M., et al., "Human Glioblastoma Xenografts Overexpressing a Tumor-Specific Mutant Epidermal Growth Factor Receptor Sensitized to Cisplatin by the Ag1478 Tyrosine Kinase Inhibitor," Journal of Neurosurgery, 2001, vol. 95 (3), pp. 472-479.
Nair D.T., et al., "Crystal Structure of an Antibody Bound to an Immunodominant Peptide Epitope: Novel Features in Peptide-Antibody Recognition," Journal of Immunology, 2000, vol. 165 (12), pp. 6949-6955.
Nakagawa, et al., "A phase I intermittent Dose-Escalation Trial of ZD1939 (iressa) in Japanese Patients with Solid Malignant Tumours," Proceedings of the American Society of Clinical Oncology, 2000, vol. 183 (Abstract 711), pp. 19.
Naramura M., et al., "Therapeutic Potential of Chimeric and Murine Anti-(Epidermal Growth Factor Receptor) Antibodies in a Metastasis Model for Human Melanoma," Cancer Immunology, Immunotherapy, 1993, vol. 37 (5), pp. 343-349.
Narita Y., et al., "Mutant Epidermal Growth Factor Receptor Signaling Down-Regulates P27 Through Activation of the Phosphatidylinositol 3-Kinase/Akt Pathway in Glioblastomas," Cancer Research, 2002, vol. 62 (22), pp. 6764-6769.
Natale R.B., et al., "Zd1839 (Iressa): What's in it for the Patient," Oncologist, 2002, vol. 7 (Suppl. 4), pp. 25-30.
Neal D.E., et al., "Epidermal-Growth-Factor Receptors in Human Bladder Cancer: Comparison of Invasive and Superficial Tumours," Lancet, 1985, vol. 1 (8425), pp. 366-368.
Neal D.E., et al., "The Epidermal Growth Factor Receptor and the Prognosis of Bladder Cancer," Cancer, 1990, vol. 65 (7), pp. 1619-1625.
Negri D.R., et al., "In Vitro and In Vivo Stability and Anti-Tumour Efficacy of an Anti-EGFR/Anti-CD3 F(Ab')2 Bispecific Monoclonal Antibody," British Journal of Cancer, 1995, vol. 72 (4), pp. 928-933.
Neidhardt F.C., et al., "Culture Medium for Enterobacteria," Journal of bacteriology, 1974, vol. 119, pp. 736-747.
Niikura H., et al., "Expression of Epidermal Growth Factor-Related Proteins and Epidermal Growth Factor Receptor in Common Epithelial Ovarian Tumors," International Journal of Gynecological Pathology, 1997, vol. 16 (1), pp. 60-68.
Nishikawa R., et al., "Immunohistochemical Analysis of the Mutant Epidermal Growth Factor, AEGFR, in Glioblastoma," Brain Tumor Pathology 2004, vol. 21 (2), pp. 53-56.
Noonberg S.B., et al., "Tyrosine Kinase Inhibitors Targeted to the Epidermal Growth Factor Receptor Subfamily: Role as Anticancer Agents," Drugs, 2000, vol. 59 (4), pp. 753-767.

(56) References Cited

OTHER PUBLICATIONS

Normanno N., et al., "Cooperative Inhibitory Effect of ZD1839 (Iressa) in Combination with Trastuzumab (Herceptin) on Human Breast Cancer Cell Growth," Annals of Oncology, 2002, vol. 13 (1), pp. 65-72.
Normanno N., et al., "Growth Inhibition of Human Colon Carcinoma Cells by Combinations of Anti-Epidermal Growth Factor-Related Growth Factor Antisense Oligonucleotides," Clinical Cancer Research, 1996, vol. 2 (3), pp. 601-609.
Norton, et al., "Overall Survival (OS) Advantage to Simultaneous Chemotherapy (CRx) Plus the Humanized Anti-HER2 Monoclonal Antibody Herceptin (H) in HER2-Overexpressing (HER2+) Metastatic Breast Cancer (MBC)," Proceedings of the American Society of Clinical Oncology, 1999, vol. 127a (Abstract 483), pp. 18.
Ochiai H., et al., "EGFRvIII-Targeted Immunotoxin Induces Antitumor Immunity that is Inhibited in the Absence of CD4+ and CD8+ T Cells," Cancer Immunology, Immunotherapy, 2008, vol. 57 (1), pp. 115-121.
Oflazoglu E., et al., "Potent Anticarcinoma Activity of the Humanized Anti-Cd70 Antibody H1 F6 Conjugated to the Tubulin Inhibitor Auristatin via an Uncleavable Linker," Clinical Cancer Research, 2008, vol. 14 (19), pp. 6171-6180.
Okamoto I., et al., "Expression of Constitutively Activated Egfrviii in Non-Small Cell Lung Cancer," Cancer Science, 2003, vol. 94 (1), pp. 50-56.
Olapade-Olaopa E.O., et al., "Evidence for the Differential Expression of a Variant EGF Receptor Protein in Human Prostate Cancer," British Journal of Cancer, 2000, vol. 82 (1), pp. 186-194.
Olayioye M.A., et al., "ErbB-1 and ErbB-2 Acquire Distinct Signaling Properties Dependent Upon their Dimerization Partner," Molecular and Cellular Biology, 1998, vol. 18 (9), pp. 5042-5051.
Omidfar K., et al., "Production of a Novel Camel Single-Domain Antibody Specific for the Type III Mutant EGFR," Tumor Biology, 2004, vol. 25 (5-6), pp. 296-305.
Opresko L.K., et al., "Endocytosis and Lysosomal Targeting of Epidermal Growth Factor Receptors are Mediated by Distinct Sequences Independent of the Tyrosine Kinase Domain," Journal of Biological Chemistry, 1995, vol. 270 (9), pp. 4325-4333.
Orntoft T.F., et al., "Clinical Aspects of Altered Glycosylation of Glycoproteins in Cancer," Electrophoresis, 1999, vol. 20 (2), pp. 362-371.
Osband M.E., et al., "Problems in the Investigational Study and Clinical Use of Cancer Immunotherapy," Immunology Today, 1990, vol. 11 (6), pp. 193-195.
Ostermann E., et al., "Effective Immunoconjugate Therapy in Cancer Models Targeting as Serine Protease of Tumor Fibroblasts," Clinical Cancer Research, 2008, vol. 14 (14), pp. 4584-4592.
Otwinowski Z., et al., "Processing of X-Ray Diffraction Data Collected in Oscillation Mode," Methods in Enzymology, 1997, vol. 276, pp. 307-326.
Overdijk, et al., "Role of ADCC in the in Vivo Antitumor Effects of Zalutumumab, a Human anti-EGF Receptor Antibody," ASCO Meeting, 2010.
Overholser J.P., et al., "Epidermal Growth Factor Receptor Blockade by Antibody Imc-C225 Inhibits Growth of a Human Pancreatic Carcinoma Xenograft in Nude Mice," Cancer, 2000, vol. 89 (1), pp. 74-82.
Owens R.J., et al., "The Genetic Engineering of Monoclonal Antibodies," Journal of Immunological Methods, 1994, vol. 168 (2), pp. 149-165.
Ozanne B., et al., "Over-Expression of the EGF Receptor is a Hallmark of Squamous Cell Carcinomas," The Journal of Pathology, 1986, vol. 149 (1), pp. 9-14.
Ozawa S., et al., "Prognostic Significance of Epidermal Growth Factor Receptor in Esophageal Cell Carcinomas," Cancer, 1989, vol. 63 (11), pp. 2169-2173.
Padlan E.A., "A Possible Procedure for Recucing the Immunogenicity of Antibody Variable Domains While Preserving Their Ligand-Binding Properties," Molecular Immunology, 1991, vol. 28 (4-5), pp. 489-498.
Padlan E.A., et al., "Anatomy of the Antibody Molecule," Molecular Immunology, 1994, vol. 31 (3), pp. 169-217.
Padlan E.A., et al., "Identification of Specificity-determining Residues in Antibodies," FASEB Journal, 1995, vol. 9 (1), pp. 133-139.
Padlan E.A., et al., "On the Nature of Antibody Combining Sites: Unusual Structural Features that may Confer on these Sites an Enhanced Capacity for Binding Ligands," Proteins, 1990, vol. 7 (2), pp. 112-124.
Paganelli G. et al., "Antibody-Guided Three-Step Therapy for High Grade Glioma with Yttrium-90 Biotin," European Association of Nuclear Medicine, 1999, vol. 26 (4), pp. 348-357.
Pai L.H., et al., "The Use of Immunotoxins for Cancer Therapy," European Journal of Cancer, 1993, vol. 29A (11), pp. 1606-1609.
Pai R., et al., "Prostaglandin E2 Transactivates EGF Receptor: a Novel Mechanism for Promoting Colon Cancer Growth and Gastrointestinal Hypertrophy," Nature Medicine, 2002, vol. 8 (3), pp. 289-293.
Palacios R., et al., "Interleukin-3 Supports Growth of Mouse Pre-B-Cell Clones in Vitro," Nature, 1984, vol. 309 (5964), pp. 126-131.
Pao W., et al., "EGF Receptor Gene Mutations are Common in Lung Cancers From 'Never Smokers' and are Associated with Sensitivity of Tumors to Gefitinib and Erlotinib," Proceedings of the National Academy of Sciences, 2004, vol. 101 (36), pp. 13306-13311.
Pao W., et al., "Epidermal Growth Factor Receptor Mutations, Small-Molecule Kinase Inhibitors, and Non-Small-Cell Lung Cancer: Current Knowledge and Future Directions," Journal of Clinical Oncology, 2005, vol. 23 (11), pp. 2556-2568.
Pao W., et al., "KRAS Mutations and Primary Resistance of Lung Adenocarcinomas to Gefitinib or Erlotinib," PLOS Medicine, 2005, vol. 2 (1), pp. e17.
Park K., et al., "A Review of the Benefit-Risk Profile of Gefitinib in Asian Patients with Advanced Non-Small-Cell Lung Cancer," Current Medical Research and Opinion, 2006, vol. 22 (3), pp. 561-573.
Parker C., et al., "Preferential Activation of the Epidermal Growth Factor Receptor in Human Colon Carcinoma Liver Metastases in Nude Mice," Journal of Histochemistry and Cytochemistry, 1998, vol. 46 (5), pp. 595-602.
Pastan I., "Targeted Therapy of Cancer with Recombinant Immunotoxins," Biochimica et Biophysica Acta 1997, vol. 1333 (2), pp. C1-C6.
Patel D., et al., "Monoclonal Antibody Cetuximab Binds to and Down-Regulates Constitutively Activated Epidermal Growth Factor Receptor VIII on the Cell Surface," Anticancer Research, 2007, vol. 27 (5A), pp. 3355-3366.
Pavelic K., et al., "Evidence for a Role of EGF Receptor in the Progression of Human Lung Carcinoma," Anticancer Research, 1993, vol. 13 (4), pp. 1133-1137.
Pawson T., "Protein Modules and Signalling Networks," Nature, 1995, vol. 373 (6515), pp. 573-580.
Pawson T., et al., "SH2 and SH3 Domains," Current Biology, 1993, vol. 3 (7), pp. 434-442.
Pedersen M.W., et al., "Analysis of the Epidermal Growth Factor Receptor Specific Transcriptome: Effect of Receptor Expression Level and an Activating Mutation," Journal of Cellular Biochemistry, 2005, vol. 96 (2), pp. 412-427.
Pedersen M.W., et al., "Mutations in the Epidermal Growth Factor Receptor: Structure and Biological Function in Human Tumors," Ugeskrift for Laeger, 2006, vol. 168 (24), pp. 2354-2361.
Pegram M., et al., "Inhibitory Effects of Combinations of Her-2/Neu Antibody and Chemotherapeutic Agents Used for Treatment of Human Breast Cancers," Oncogene, 1999, vol. 18 (13), pp. 2241-2251.
Pegram M.D, et al., "Phase II Study of Receptor-Enhanced Chemosensitivity Using Recombinant Humanized Anti-P185HER2/Neu Monoclonal Antibody Plus Cisplatin in Patients With HER2/Neu-Overexpressing Metastatic Breast Cancer Refractory to Chemotherapy Treatment," Journal of Clinical Oncology, 1998, vol. 16 (8), pp. 2659-2671.
Pegram M.D, et al., "Rational Combinations of Trastuzumab with Chemotherapeutic Drugs Used in the Treatment of Breast Cancer," Journal of the National Cancer Institute, 2004, vol. 96 (10), pp. 739-749.

(56) References Cited

OTHER PUBLICATIONS

Pegram M.D, et al., "The Effect of HER-2/neu Overexpression on Chemotherapeutic Drug Sensitivity in Human Breast and Ovarian Cancer Cells," Oncogene, 1997, vol. 15 (5), pp. 537-547.

Pegram, et al., "Antibody Dependent Cell-Mediated Cytotoxicity in Breast Cancer Patients in Phase III Clinical Trials of a Humanized Anti-HER2 Antibody," Proceedings of the Annual Meeting of the American Association for Cancer Research, 1997, vol. 602 (Abstract 4044), pp. 39.

Pelloski C.E., et al., "Epidermal Growth Factor Receptor Variant III Status Defines Clinically Distinct Subtypes of Glioblastoma," Journal of Clinical Oncology, 2007, vol. 25 (16), pp. 2288-2294.

Perera R.M., et al., "Internalization, Intracellular Trafficking, and Biodistribution of Monoclonal Antibody 806: A Novel Anti-Epidermal Growth Factor Receptor Antibody," Neoplasia, 2007, vol. 9 (12), pp. 1099-1110.

Perera, et al., "Internalisation and Trafficking of the Monoclonal Antibody 806 Reactive Epidermal Growth Factor Receptor," Austin Health Research Week, 2003, Abstract 112.

Perera, et al., "The Influence of Epidermal Growth Factor Receptor (EGFR) Number and Activation on the Efficacy of Antibodies Directed to the Receptor," Proceedings of the 14th Annual Lorne Cancer Conference, 2002, Abstract 216.

Perez-Soler R., et al., "HER1/EGFR Targeting: Refining the Strategy," Oncologist, 2004, vol. 9 (1), pp. 58-67.

Perez-Soler, et al., "A PhaseII Trial of the Epidermal Growth Factor Receptor (EGFR) Tyrosine Kinase Inhibitor OSI-774, Following Platinum-Based Chemotherapy in Patients (Pts) with Advanced EGFR-Expressing, Non-Small Cell Lung Cancer (NSCLC)," Proceedings of the American Society of Clinical Oncology, 2001, vol. 310a (Abstract 1235), pp. 20.

Perez-Soler, et al., "Tumor Studies in Patients With Head & Neck Cancer Treated With Humanized Anti-Epidermal Growth Factor (Egfr) Monoclonal Antibody C225 in Combination With Cisplatin," Proceedings of the American Society of Clinical Oncology, 1998, vol. 393a (Abstract 1514), pp. 17.

Perl A.K., et al., "Conditional Gene Expression in the Respiratory Epithelium of the Mouse," Transgenic Research, 2002, vol. 11 (1), pp. 21-29.

Perrotte P., et al., "Anti-Epidermal Growth Factor Receptor Antibody C225 Inhibits Angiogenesis in Human Transitional Cell Carcinoma Growing Orthotopically in Nude Mice," Clinical Cancer Research, 1999, vol. 5 (2), pp. 257-265.

Petit A.M., et al., "Neutralizing Antibodies Against Epidermal Growth Factor and ErbB-2/Neu Receptor Tyrosine Kinases Down-Regulate Vascular Endothelial Growth Factor Production by Tumor Cells in Vitro and in Vivo: Angiogenic Implications for Signal Transduction Therapy of Solid Tumors," The American Journal of Pathology, 1997, vol. 151 (6), pp. 1523-1530.

Petrides P.E., et al., "Modulation of Pro-Epidermal Growth Factor, Pro-Transforming Growth Factor Alpha and Epidermal Growth Factor Receptor Gene Expression in Human Renal Carcinomas," Cancer Research, 1990, vol. 50 (13), pp. 3934-3939.

Pfister, et al., "A Phase I trial of the Epidermal Growth Factor Receptor (EGFR)-Directed Bispecific Antibody (BsAB) MDX-447 in Patients with Solid Tumors," Proceedings of the American Society of Clinical Oncology, 1999, vol. 433a (Abstract 1667), pp. 18.

Pfosser A., et al., "Role of Target Antigen in Bispecific-Antibody-Mediated Killing of Human Glioblastoma Cells: A Pre-Clinical Study," International Journal of Cancer, 1999, vol. 80 (4), pp. 612-616.

Pfreundschuh M., et al., "Serological Analysis of Cell Surface Antigens of Malignant Human Brain Tumors," Proceedings of the National Academy of Sciences, 1978, vol. 75 (10), pp. 5122-5126.

Pietras R.J., et al., "Monoclonal Antibody to HER-2/Neureceptor Modulates Repair of Radiation-Induced DNA Damage and Enhances Radiosensitivity of Human Breast Cancer Cells Overexpressing this Oncogene," Cancer Research, 1999, vol. 59 (6), pp. 1347-1355.

Pietras R.J., et al., "Remission of Human Breast Cancer Xenografts on Therapy with Humanized Monoclonal Antibody to her-2 Receptor and DNA-Reactive Drugs," Oncogene, 1998, vol. 17 (17), pp. 2235-2249.

Pillay V., et al., "The Plasticity of Oncogene Addiction: Implications for Targeted Therapies Directed to Receptor Tyrosine Kinases1," Neoplasia, 2009, vol. 11 (5), pp. 448-458.

Politi K., et al., "Lung Adenocarcinomas Induced in Mice by Mutant EGF Receptors Found in Human Lung Cancers Respond to a Tyrosine Kinase Inhibitor or to Down-Regulation of the Receptors," Genes & Development, 2006, vol. 20 (11), pp. 1496-1510.

Ponten J., et al., "Long Term Culture of Normal and Neoplastic Human Glia," Acta Pathologica et Microbiologica Scandinvica, 1968, vol. 74 (4), pp. 465-486.

Power B.E., et al., "Construction, Expression and Characterisation of a Single-Chain Diabody Derived from a Humanised Anti-Lewis Y Cancer Targeting Antibody using a Heat-Inducible Bacterial Secretion Vector," Cancer Immunology, Immunotherapy, 2001, vol. 50 (5), pp. 241-250.

Power B.E., et al., "Noncovalent scFv Multimers of Tumor-Targeting Anti-Lewisy hu3S193 Humanized Antibody," Protein Science, 2003, vol. 12 (4), pp. 734-747.

Prados M.D., et al., "Biology and Treatment of Malignant Glioma," Seminars in Oncology, 2000, vol. 27 (3) (Suppl. 6), pp. 1-10.

Prenzel N., et al., "The Epidermal Growth Factor Receptor Family as a Central Element for Cellular Signal Transduction and Diversification," Endocrine Related Cancer, 2001, vol. 8 (1), pp. 11-31.

Press O.W., et al., "Inhibition of Catabolism of Radiolabeled Antibodies by Tumor Cells Using Lysosomotropic Amines and Carboxylic Ionophores" Cancer Research, 1990, vol. 50 (4), pp. 1243-1250.

Press O.W., et al., "Ricin A-Chain Containing Immunotoxins Directed Against Different Epitopes on the CD2 Molecule Differ in Their Ability to Kill Normal and Malignant T Cells," The Journal of Immunology, 1988, vol. 141, pp. 4410-4417.

Presta L.G., et al., "Humanization of an Anti-Vascular Endothelial Growth Factor Monoclonal Antibody for the Therapy of Solid Tumors and Other Disorders," Cancer Research, 1997, vol. 57 (20), pp. 4593-4599.

Presta L.G., et al., "Humanization of an Antibody Directed Against IgE," Journal of Immunology, 1993, vol. 151 (5), pp. 2623-2632.

Prewett M., et al., "Anti-Tumor and Cell Cycle Responses in KBCells Treated With a Chimeric Anti-Egfr Monoclonal Antibody in Combination with Cisplatin," International Journal of Oncology, 1996, vol. 9 (2), pp. 217-224.

Prewett M., et al., "Mouse-Human Chimeric Anti-Epidermal Growth Factor Receptor Antibody C225 Inhibits the Growth of Human Renal Cell Carcinoma Xenografts in Nude Mice," Clinical Cancer Research, 1998, vol. 4 (12), pp. 2957-2966.

Prewett M., et al., "The Biologic Effects of C225, a Chimeric Monoclonal Antibody to the EGFR, on Human Prostate Carcinoma," Journal of Immunother Emphasis Tumor Immunol, 1996, vol. 19 (6), pp. 419-427.

Prewett M.C., et al., "Enhanced Antitumor Activity of Anti-Epidermal Growth Factor Receptor Monoclonal Antibody IMC-C225 in Combination With Irinotecan (CPT-11) Against Human Colorectal Tumor Xenografts," Clinical Cancer Research, 2002, vol. 8 (5), pp. 994-1003.

Prigent S.A., et al., "Enhanced Tumorigenic Behavior of Glioblastonia Cells Expressing a Truncated Epidermal Growth Factor Receptor is Mediated Through the Ras-Shc-Grb2 Pathway," Journal of Biological Chemistry 1996, vol. 271 (41), pp. 25639-25645.

Prigent S.A., et al., "The Type 1 (EGFR-Related) Family of Growth Factor Receptors and their Ligands," Progress in Growth Factor Research 1992, vol. 4 (1), pp. 1-24.

Privalsky M.L., et al., "The Membrane Glycoprotein Encoded by the Retroviral Oncogene v-erb-B is Structurally Related to Tyrosine-Specific Protein Kinases," Proceedings of the National Academy of Sciences, 1984, vol. 81 (3), pp. 704-707.

Raben D., et al., "ZD1839, a Selective Epidermal Growth Factor Receptor Tyrosine Kinase Inhibitor, Alone and in Combination With

(56) References Cited

OTHER PUBLICATIONS

Radiation and Chemotherapy as a New Therapeutic Strategy in Non-Small Cell Lung Cancer," Seminars in Oncology, 2002, vol. 29 (1) (Suppl. 4), pp. 37-46.
Raben, et al., "C225 Anti-EGFR Antibody Potentiates Radiation (RT) and Chemotherapy (Ct) Cytotoxicity in Human Non-Small Cell Lung Cancer (Nscic) Cells In Vitro and In Vivo," Proceedings of the American Society of Clinical Oncology, 2001, vol. 257a (Abstract 1026), pp. 20.
Raben, et al., "Treatment of Human Intracranial Gliomas with Chimeric Monoclonal Antibody Against the Epidermal Growth Factor Receptor Increases Survival of Nude Mice when Treated Concurrently with Irradiation," Proceedings of the American Association for Cancer Research, 1999, vol. 184 (Abstract 1224), pp. 40.
Radinsky R., et al., "Level and Function of Epidermal Growth Factor Receptor Predict the Metastatic Potential of Human Colon Carcinoma Cells1," Clinical Cancer Research, 1995, vol. 1, pp. 19-31.
Raizer J.J., "HERVEGFR Tyrosine Kinase Inhibitors for the Treatment of Glioblastoma Multiforme," Journal of Neuro-Oncology, 2005, vol. 74 (1), pp. 77-86.
Rakowicz-Szulcznska E.M., et al., "Epidermal Growth Factor (EGF) and Monoclonal Antibody to Cell Surface EGF Receptor Bind to the Same Chromatin Receptor," Archives of Biochemistry and Biophysics, 1989, vol. 268 (2), pp. 456-464.
Ramnarain D.B., et al., "Differential Gene Expression Analysis Reveals Generation of an Autocrine Loop by a Mutant Epidermal Growth Factor Receptor in Glioma Cells," Cancer Research, 2006, vol. 66 (2), pp. 867-874.
Ramos T.C., et al., "Treatment of High-Grade Glioma Patients with the Humanized Anti-Epidermal Growth Factor Receptor (EGFR) Antibody H-R3," Cancer Biology and Therapy, 2006, vol. 5 (4), pp. 375-379.
Ramsland P.A., et al., "Structural Convergence of Antibody Binding of Carbohydrate Determinants in Lewis Y Tumor Antigens," Jouranal of Molecular Biology, 2004, vol. 340 (4), pp. 809-818.
Ranson M., "ZD1839 (IressaT): For More Than Just Non-Small Cell Lung Cancer," Oncologist, 2002, vol. 7 (Suppl. 4), pp. 16-24.
Rao G.S., et al., "Radiosensitization of Human Breast Cancer Cells by a Novel ErbB Family Receptor Tyrosine Kinase Inhibitor," International Journal of Radiation Oncology Biology Physics, 2000, vol. 48 (5), pp. 1519-1528.
Rayzman, et al., "Monoclonal Antibodies for Cancer Therapy," Cancer Forum, 2002, vol. 26 (2), pp. 104-108.
Reardon D.A., et al., "Recent Advances in the Treatment of Malignant Astrocytoma," Journal of Clinical Oncology, 2006, vol. 248 (8), pp. 1253-1265.
Reed J.C., "Dysregulation of Apoptosis in Cancer," Journal of Clinical Oncology, 1999, vol. 17 (9), pp. 2941-2953.
Reese, et al., "Effects of the 4D5 Antibody on HER2/Neu Heterodimerization with other Class I-Receptors in Human Breast Cancer Cells," Proceedings of the Annual Meeting of the American Association for Cancer Research, 1996, vol. 51 (Abstract 353), pp. 37.
Reilly R.M., et al., "A Comparison of EGFand MAb 528 Labeled with 111 In for Imaging Human Breast Cancer," Journal of Nuclear Medicine, 2000, vol. 41 (5), pp. 903-911.
Reiss M., et al., "Activation of the Autocrine Transforming Growth Factor Alpha Pathway in Human Squamous Carcinoma Cells," Cancer Research, 1991, vol. 51 (23 Pt 1), pp. 6254-6262.
Reist C.J., et al., "Astatine-211 Labeling of Internalizing Anti-EGFRvIII Monoclonal Antibody Using N-Succinimidyl 5-[211At]Astato-3-Pyridinecarboxylate," Nuclear Medicine and Biology, 1999, vol. 26 (4), pp. 405-411.
Reist C.J., et al., "Radioiodination of Internalizing Monoclonal Antibodies Using N-Succinimidyl 5-Iodo-3-Pyridinecarboxylate,," Cancer Research, 1996, vol. 56 (21), pp. 4970-4977.
Reiter J.L, et al., "Comparative Genomic Sequence Analysis and Isolation of Human and Mouse Alternative EGFR Transcripts Encoding Truncated Receptor Isoforms," Genomics, 2001, vol. 71, pp. 1-20.

Rettig W.J., et al., "Immunogenetics of Human Cell Surface Differentiation," Annual Review of Immunology, 1989, vol. 7, pp. 481-511.
Reynolds F.H., et al., "Human Transforming Growth Factors Induce Tyrosine Phosphorylation of EGF Receptors," Nature, 1981, vol. 292 (5820), pp. 259-262.
Ribas, et al., "Systemic Delivery of Sirna via Targeted Nanoparticles in Patients with Cancer: Results:from a First-in-Class phase I Clinical Trial," Journal of Clinical Oncology, 2010, vol. 28 (15s) (Abstract 3022).
Riemer A.B., et al., "Mimotope Vaccines: Epitope Mimics Induce Anti-Cancer Antibodies," Immunology Letters, 2007, vol. 113 (1), pp. 1-5.
Riemer A.B., et al., "Vaccination with Cetuximab Mimotopes and Biological Properties of Induced Anti-Epidermal Growth Gactor Receptor Antibodies," Journal of National Cancer Institute, 2005, vol. 97 (22), pp. 1663-1670.
Riese D.J., et al., "Specificity within the EGF Family/ErbB Receptor Family Signaling Network," Bioessays, 1998, vol. 20 (1), pp. 41-48.
Rieske P., et al., "A Comparative Study of Epidermal Growth Factor Receptor (EGFR) and MDM2 Gene Amplification and Protein Immunoreactivity in Human Glioblastomas," Polish Society of Pathologists, 1998, vol. 49 (3), pp. 145-149.
Rinehart, et al.,"A Phase 1 Clinical and Pharmacokinetic Study of Oral CI-1033, a Pan-Erbb Tyrosine Kinase Inhibitor in Patients with Advanced Solid Tumors," Proceedings of the American Society of Clinical Oncology, 2002, vol. 11a (Abstract 41), pp. 21.
Ritter G., et al., "Serological Analysis of Human Anti-Human Antibody Responses in Colon Cancer Patients Treated with Repeated Doses of Humanized Monoclonal Antibody A33," Cancer Research, 2001, vol. 61 (18), pp. 6851-6859.
Riva P., et al., "Role of Nuclear Medicine in the Treatment of Malignant Gliomas: The Locoregional Radioimmunotherapy Approach," European Journal of Nuclear Medicine, 2000, vol. 27 (5), pp. 601-609.
Rivera F., et al., "Current Situation of Panitumumab, Matuzumab, Nimotuzumab and Zalutumumab," Acta Oncoloqica 2008, vol. 47 (1), pp. 9-19.
Ro J., et al., "Amplified and Overexpressed Epidermal Growth Factor Receptor Gene in Uncultured Primary Human Breast Carcinoma," Cancer Research, 1988, vol. 48 (1), pp. 161-164.
Rocha-Lima C.M., et al., "EGFR Targeting of Solid Tumors," Cancer Control, 2007, vol. 14 (3), pp. 295-304.
Rodeck U., et al., "Monoclonal Antibody 425 Inhibits Growth Stimulation of Carcinoma Cells by Exogenous EGF and Tumor-Derived EGF/TGF-c," Journal of Cellular Biochemistry, 1990, vol. 44 (2), pp. 69-79.
Roguska M.A., et al., "A Comparison of Two Murine Monoclonal Antibodies Humanized by Cdr-Grafting and Variable Domain Resurfacing," Protein Engineering, 1996, vol. 9 (10), pp. 895-904.
Roguska M.A., et al., "Humanization of Murine Monoclonal Antibodies through Variable Domain Resurfacing," Proceedings of the National Academy of Sciences, 1994, vol. 91 (3), pp. 969-973.
Rosell, et al., "Randomized phase II study of cetuximab in combination with cisplatin (C) and vinorelbine (V) vs. CV alone in the first-line treatment of patients (pts) with epidermal growth factor receptor (EGFR)-expressing advanced non-small-cell lung cancer (NSCLC)," 2004, Abstract 7012, pp. 22.
Rosell, et al., "Randomized Phase II Study of Cetuximab in Combination with Cisplatin (C) and vinorelbine (V) vs. CV Alone in the First-Line Treatment of Patients (Pts) with Epidermal Growth Factor Receptor (EGFR)-Expressing Advanced Non-Small-Cell Lung Cancer (NSCLC)," Proceedings of the American Society of Clinical Oncology, 2004, vol. 620s (Abstract 7012), pp. 23.
Ross J.S., et al., "Anticancer Antibodies," American Journal of Clinical Pathology, 2003, vol. 119 (4), pp. 472-485.
Rougier, et al., "Cetuximab + FOLFIRI as First-Line Treatment for Metastatic Colorectal CA," Proceedings of the Annual Meeting of the American Society of Clinical Oncology, 2004, vol. 248s (Abstract 3513), pp. 22.
Rowinsky E.K., et al., "Safety, Pharmacokinetics, and Activity of ABX-EGF, a Fully Human Anti-Epidermal Growth Factor Receptor Monoclonal Antibody in Patients with Metastatic Renalcell Cancer," Journal of Clinical Oncology, 2004, vol. 22 (15), pp. 3003-3015.

(56) References Cited

OTHER PUBLICATIONS

Rubin G.J., et al., "Inhibition of Epidermal Growth Factor Receptor Gene Expression and Function Decreases Proliferation of Head and Neck Squamous Carcinoma but not Normal Mucosal Epithelial Cells," Oncogene, 1997, vol. 15 (4), pp. 409-416.

Rubin Grandis J., et al., "Quantitative Immunohistochemical Analysis of Transforming Growth Factor-Alpha and Epidermal Growth Factor Receptor in Patients with Squamous Cell Carcinoma of the Head and Neck," Cancer, 1996, vol. 78 (6), pp. 1284-1292.

Rubin, et al., "Monoclonal Antibody (MoAb) IMC-C225, an Anti-Epidermal Growth Factor Receptor (EGFR), for Patients with EGFR-positive Tumors Refractory to or in Relapse from Previous Therapeutic Regimens," Proceedings of the American Society of Clinical Oncology, 2000, vol. 474a (Abstract 1860), pp. 193.

Rubin, et al., "Monoclonal Antibody (Moab) IMC-C225, an Anti-Epidermal Growth Factor Receptor (EGFR,.for Patients (Pts) with EGFr-Positive Tumors Refractory to or in Relapse from Previous Therapeutic Regimens," American Society of Clinical Oncology, 2000, Abstract 1860, pp. 19.

Rubio, et al., "Cetuximab in Combination with oxaliplatin/5-Fluorouracil (5-FU)/folinic Acid (FA) (FOLFOX-4) in the First-Line Treatment of Patients with Epidermal Growth Factor Receptor (EGFR)-Expressing Metastatic Colorectal Cancer: An International Phase II Study," Journal of Clinical Oncology, 2005 ASCO Annual Meeting Proceedings, 2005, Abstract 3535, pp. 23.

Rusch V., et al., "Overexpression of the Epidermal Growth Factor Receptor and Its Ligand Transforming Growth Factor Alpha is Frequent in Resectable Non-Small Cell Lung Cancer but Does not Predict Tumor Progression," Clinical Cancer Research, 1997, vol. 3 (4), pp. 515-522.

Rusnak D.K., et al., "The Effects of the Novel, Reversible Epidermal Growth Factor Receptor/ErbB-2 Tyrosine Kinase Inhibitor, GW2016, on the Growth of Human Normal and Tumor-Derived Cell Lines in Vitro and in Vivo," Molecular Cancer Therapeutics, 2001, vol. 1 (2), pp. 85-94.

Rusnak, et al., "The Effects of the Novel EGFR/ErbB-2 Tyrosine Kinase Inhibitor, GW2016, on the Growth of Human Normal and Transformed Cell Lines," Proceedings of the American Association for Cancer Research, 2001, vol. 803 (Abstract 4309), pp. 42.

Safa M.M., et al., "Adjuvant Immunotherapy for Melanoma and Colorectal Cancers," Seminars in Oncology, 2001, vol. 28 (1), pp. 68-92.

Saikali S., et al., "Expression of Nine Tumour Antigens in a Series of Human Glioblastoma Multiforme: Interest of EGFRVIII, II-13ralpha2, GP100 and TRP-2 for Immunotherapy," Journal of Neuro-Oncology, 2007, vol. 81 (2), pp. 139-148.

Sainsbury J.R., et al., "Epidermal-Growth-Factor Receptor Status as Predictor of Early Recurrence of and Death from Breast Cancer," Lancet, 1987, vol. 1 (8547), pp. 1398-1402.

Sainsbury J.R., et al., "Presence of Epidermal Growth Factor Receptor as an Indicator of Poor Prognosis in Patients with Breast Cancer," Journal of Clinical Pathology, 1985, vol. 38 (11), pp. 1225-1228.

Sakurada A., et al., "Epidermal Growth Factor Receptor Tyrosine Kinase Inhibitors in Lung Cancer: Impact of Primary or Secondary Mutations," Clinical Lung Cancer, 2006, vol. 7 (Supply 4), pp. S138-S144.

Salazar, et al., "Dose-Dependent Inhibition of the EGFR and Signalling Pathways with the Anti-EGFR Monoclonal Antibody (MAb) EMD 72000 Administered every Three Weeks (q3w). A Phase I Pharmacokinetic/Pharmacodynamic (PK/PD) Study to Define the Optimal Biological Dose (OBD)," 2004, vol. 127s (Abstract 2002), pp. 22.

Saleh M.N., et al., "Combined Modality Therapy of A431 Human Epidermoid Cancer Using Anti-EGFr Antibody C225 and Radiation," Cancer Biother Radiopharm, 1999, vol. 14 (6), pp. 451-463.

Salomon D.S., et al., "Epidermal Growth Factor-Related Peptides and their Receptors in Human Malignancies," Critical Reviews in Oncology/Hematology, 1995, vol. 19 (3), pp. 183-232.

Saltz L.B., et al., "Phase II Trial of Cetuximab in Patients With Refractory Colorectal Cancer that Expresses the Epidermal Growth Factor Receptor," Journal of Clinical Oncology, 2004, vol. 22 (7), pp. 1201-1208.

Saltz, et al., "Cetuximab (IMC-225) Plus Irinotecan (CPT-11) is Active in CPT-11-Refractory Colorectal Cancer (CRC) that Expresses Epidermal Growth Factor Receptor (EGFR)," Proceedings of the American Society of Clinical Oncology, 2001, vol. 3a (Abstract 7), pp. 20.

Saltz, et al., "Interim Report of Randomized Phase II Trial of Cetuximab/Bevacizumab/Irinotecan (CBI) versus Cetuximab/Bevacizumab (CB) in Irinotecan-Refractory Colorectal Cancer," Proceedings of the American Society of Clinical Oncology, 2006, Abstract 169b.

Saltz, et al., "Single Agent IMC-C225 (Erbitux[TM]) has Activity in CPT-11 Refractory Colorectal Cancer that Expresses the Epidermal Growth Factor Receptor (EGFR)," Proceedings of the American Society of Clinical Oncology, 2002, vol. 127a (Abstract 504), pp. 21.

Sampson J.H., et al., "Tumor-Specific Immunotherapy Targeting the EGFRVIII Mutation in Patients with Malignant Glioma," Seminars in immunology, 2008, vol. 20 (5), pp. 267-275.

Sampson, et al., "An EGFRvIII Specific Peptide Vaccine Generates Antitumor Immunity Through a Humoral Pathway," Neuro-Oncology, 1999, vol. S103 (Abstract 135).

Sanderson R.J., et al., "In Vivo Drug-Linker Stability of an Anti-CD30 Dipeptide-Linked Auristatin Immunoconjugate," Clinical Cancer Research, 2005, vol. 11 (2 Pt 1), pp. 843-852.

Sandler A.B., "Nondermatologic Adverse Events Associated with Anti-EGFR Therapy," Oncology, 2006, vol. 20 (5 Suppl. 2), pp. 35-40.

Santon J.B., et al., "Effects of Epidermal Growth Factor Receptor Concentration on Tumorigenicity of A431 Cells in Nude Mice,," Cancer Research, 1986, vol. 46 (9), pp. 4701-4705.

Sartor C.L., "Mechanisms of Disease: Radiosensitization.by Epidermal Growth Factor Receptor Inhibitors," Nature Clinical Practice Oncology, 2004, vol. 1 (2), pp. 80-87.

Sartor, C.L., "Biological Modifiers as Potential Radiosensitizers: Targeting the Epidermal Growth Factor Receptor Family," Seminars in Oncology, 2000, 27 (6 Suppl 11), pp. 15-20.

Sarup J.C., et al., "Characterization of an Anti-P185HER2 Monoclonal Antibody that Stimulates Receptor Function and Inhibits Tumor Cell Growth," Growth Regulation, 1991, vol. 1 (2), pp. 72-82.

Sauter G., et al., "Patterns of Epidermal Growth Factor Receptor Amplification in Malignant Gliomas," 1996, vol. 148 (4), pp. 1047-1053.

Scher H.I., et al., "Changing Pattern of Expression of the Epidermal Growth Factor Receptor and Transforming Growth Factor Alpha in the Progression of Prostatic Neoplasm," Clinical Cancer Research, 1995, vol. 1 (5), pp. 545-550.

Schlegel J., et al., "Amplification of the Epidermal-Growth-Factor-Receptor Gene Correlates with Different Growth Behaviour in Human Glioblastoma," International Journal of Cancer, 1994, vol. 56 (1), pp. 72-77.

Schlessinger J., "Cell Signaling by Receptor Tyrosine Kinases," Cell, 2000, vol. 103 (2), pp. 211-225.

Schlessinger J., "Common and Distinct Elements in Cellular Signaling via EGF and FGF Receptors," 2004, vol. 306 (5701), pp. 1506-1507.

Schmidt M., et al., "Expression of an Oncogenic Mutant Egf Receptor Markedly Increases the Sensitivity of Cells to an EGF-Receptor-Specific Antibody-Toxin," International Journal of Cancer, 1998, vol. 75 (6), pp. 878-884.

Schmidt M., et al., "Suppression of Metastasis Formation by a Recombinant Single Chain Antibody-Toxin Targeted to Full-Length and Oncogenic Variant EGF Receptors," Oncogene, 1999, vol. 18 (9), pp. 1711-1721.

Schmidt-Ullrich R.K., et al., "Radiation-Induced Proliferation of the Human A431 Squamous Carcinoma Cells is Dependent on EGFR Tyrosine Phosphorylation," Oncogene, 1997, vol. 15 (10), pp. 1191-1197.

Schmiedel J. et al., "MatuzumAb Binding to EGFR Prevents the Conformational Rearrangement Required for Dimerization," Cancer Cell, 2008, vol. 13 (4), pp. 365-373.

(56) References Cited

OTHER PUBLICATIONS

Schmitz K.R., et al., "Interaction of Antibodies with ErbB Receptor Extracellular Regions," Experimental Cell Research 2009, vol. 315 (4), pp. 659-670.
Schnurch H.G., et al., "Growth Inhibition of Xenotransplanted Human Carcinomas by a Monoclonal Antibody Directed Against the Epidermal Growth Factor Receptor," European Journal of Cancer, 1994, vol. 30A (4), pp. 491-496.
Schwechheimer K., et al., "EGFR Gene Amplification—Rearrangement in Human Glioblastomas," International Journal of Cancer, 1995, vol. 62 (2), pp. 145-148.
Scott A.M., et al., "A Phase I Biodistribution and Pharmacokinetic Trial of Humanized Monoclonal Antibody Hu3s193 in Patients with Advanced Epithelial Cancers that Express the Lewis-Y Antigen," Clinical Cancer Research, 2007, vol. 13 (11), pp. 3286-3292.
Scott A.M., et al., "A Phase I Dose-Escalation Study of SibrotuzumAb in Patients with Advanced or Metastatic Fibroblast Activation Protein-Positive Cancer," Clinical Cancer Research, 2003, vol. 9 (5), pp. 1639-1647.
Scott A.M., et al., "A Phase I Trial of Humanized Monoclonal Antibody A33 in Patients with Colorectal Carcinoma: Biodistribution, Pharmacokinetics, and Quantitative Tumor Uptake," Clinical Cancer Research, 2005, vol. 11 (13), pp. 4810-4817.
Scott A.M., et al., "Clinical Promise of Tumour Immunology," Lancet, 1997, vol. 349 (Suppl. 2), pp. SII19-SII22.
Scott A.M., et al., "Comparison of Phase I Trials of Anti-epidermal Growth Factor Receptor (egfr) Monoclonal Antibodies (mats) 528 and 225 Labelled with 1-131 and in-111, Abstract 1005," Journal of Nuclear Medicine, 1993, vol. 34 (5), pp. 213P.
Scott A.M., et al., "Construction, Production, and Characterization of Humanized Anti-Lewis Y Monoclonal Antibody 3S193 for Targeted Immunotherapy of Solid Tumors," Cancer Research, 2000, vol. 60 (12), pp. 3254-3261.
Scott A.M., et al., "Specific Targeting, Biodistribution, and Lack of Immunogenicity of Chimeric Anti-GD3 Monoclonal Antibody KM871 in Patients with Metastatic Melanoma: Results of a Phase I Trial," Journal of Clinical Oncology, 2001, vol. 19 (19), pp. 3976-3987.
Scott A.M., et al., "Tumor Imaging and Therapy," Radiologic Clinics of North America, 1993, vol. 31 (4), pp. 859-879.
Scott et al., "Immunological Effects of Chimeric Anti-Gd3 Monoclonal Antibody Km871 in Patients with Metastatic Melanoma," Cancer immunity: a journal of the Academy of Cancer Immunology, 2005, vol. 3, pp. 5.
Scott, "Antibody Therapeutics," Ludwig Institute Colon Cancer Initiative Symposium, Baltimore, MD, United States, 2010.
Scott, "Cell Surface and Intracellular Targets for Antibody Directed Cancer Therapeutics," City of Hope Cancer Center, Los Angeles, CA, United States, 2007.
Scott, "Cell Surface Targets for Therapy," LICR Brain Cancer Initiative Meeting, Rockville, MD, United States, 2009.
Scott, "Development of a Humanised Antibody Against a Novel Epitope of EGFR," Australasian Vaccines & Immunotherapy Development Meeting, Melbourne, Australia, 2010.
Scott, "Development of a Novel Anti-EGFR Humanised Antibody—the Complex Path from Academia to Industry," Lowy Symposium, Sydney, Australia, 2010.
Scott, "Epidermal Growth Factor Receptor Targeting for Cancer Therapy," 3rd Barossa Meeting—Signalling Systems, Barossa Valley, South Australia, 2007.
Scott, "Growth Factors and their implications in head and neck cancer," Garnett Passe Scientific Meeting: Frontiers in Otorhinolarvnqologv, Noosa, Queensland, Australia, 2004.
Scott, "Implications of Antibody:Receptor Binding Structure and Signalling on Tumour Growth," Discovery Science & Biotechnology Conference, Melbourne, Australia, 2006.
Scott, "Implications of Antibody:Receptor Binding Structure and Signalling on Tumour Growth," Monash University—Department of Biochemistry & Molecular Biology, Melbourne, Australia, 2005.
Scott, "Molecular Targets for Cancer Therapeutics," Baker Institute Seminar, Melbourne, Australia, 2002.
Scott, "Molecular Targets for Cancer Therapeutics," Cambridge University Seminar, United Kingdom, 2002.
Scott, "Molecular Targets for Cancer Therapeutics," Monash University Seminar, Melbourne, Australia, 2002.
Scott, "Novel Antibodies that Bind to a Conformational Epitope of EGFR," IBC 20th Annual Antibody Engineering Conference, San Diego, CA, United States, 2009.
Scott, "Novel Antibody that Inhibits EGFR Activation," Fifth International Congress on Monoclonal Antibodies in Cancer, Quebec City, Canada, 2005.
Scott, "Of Mice and Man—The Role of Growth Factor Receptors in Cancer," Austin Hospital Division of Medicine Grand Round, Melbourne, Australia, 2007.
Scott, "Pathway Specific Therapeutics: from Cancer Biology to Targeted Therapy," Garvan Signalling Symposium, Melbourne, Australia, 2010.
Scott, "Receptor Based Targets for Antibody Therapy of Solid Tumours," The Second China International Symposium on Antibody Engineering: Current Status and Future Perspective of Antibody Therapeutics, Belling, China, 2005.
Scott, "Recombinant Antibodies for Immune and Cell Signalling Based Therapeutics," AntibOZ 2 Conference, Heron Island, Queensland, Australia, 2004.
Scott, "Recombinant Antibody Therapy of Cancer—the LICR Antibody Program," A Star Agency for Science, Technology and Research, ICMB, Singapore, 2008, D776.
Scott, "Structural Biology and Molecular Imaging in Cancer Therapeutics," Bosch Institute Annual Scientific Meeting, Sydney, Australia, 2010.
Scott, "Targeted Cancer Therapeutics—the Role of Signalling and Immune Effector Mechanisms," Royal North Shore Hospital Scientific Forum Sydney, NSW, Australia, 2003.
Scott, "Targeted Therapeutics—the Role of Signalling and Immune Effector Mechanism," Centre for Immunology and Cancer Research, University of Queensland, Brisbane, Queensland, Australia, 2003.
Scott, "Targeted Therapeutics—the Role of Signalling and Immune Effector Mechanisms," Peter MacCallum Cancer Immunology Program Seminar, Melbourne, Australia, 2003.
Scott, "Targeting a Novel EGFR Epitope on Cancer Cells," Keystone Symposia: Antibodies as Drugs: Targeted Cancer Therapies, Whistler British Columbia, Canada, 2009.
Scott, "Targeting a Novel EGFR Epitope on Cancer Cells," Ludwig Institute for Cancer Research, 2010, Abstract 014.
Scott, "Targeting a Tumour Specific Epitope of the Epidermal Growth Factor Receptor," Keystone Symposium: Antibodies as Drugs: From Basic Biology to the Clinic, Alberta, Canada, 2007.
Scott, "Targeting the Epiderm'al Growth Factor Receptor for Antibody Therapy of Solid Tumours," 17th Annual IBC Antibody Engineering Conference, San Diego, CA, United States, 2006.
Scott, "Targeting the Epidermal Growth Factor Receptor for Antibody Therapy of Solid Tumours," EGFR Cascade Meeting, San Diego, CA, United States, 2006.
Scott, Targeting the Epidermal Growth Factor Receptor for Antibody Therapy of Solid TuMours.7 Third International AntibOZ Conference, Heron, Island, Queensland, Australia, 2007.
Scott, "The Biology of EGFR in Normal and Diseased Tissues," Australian Lung Cancer Conference, Surfers Paradise, Qlc1, Australia, 2008.
Scott, "Therapy of EGFR Expressing Cancers with a Novel Tumour Specific Antibody," AHMRC Congress, Brisbane, Old Australia, 2008.
Scott, "Understanding the Biology of Targeted Therapies in Cancer," University of Melbburne/Roval Melbourne HospitaVWestern Hospital Consortium Seminar, Melbourne, Australia 2008.
Scott., "Targeting a Novel EGFR Epitope on Cancer Cells" Ludwig Institute for Cancer Research, LICR Translational Oncology Conference, Melbourne (Australia) (Nov. 6-8, 2009) Abstract No. abs#014.
Sellers W.R., et al., "Apoptosis and Cancer Drug Targeting," Journal of Clinical Investigation, 1999, vol. 104 (12), pp. 1655-1661.
Senter P.D., "Potent Antibody Drug Conjugates for Cancer Therapy," Current Opinion in Chemical Biology, 2009, vol. 13 (3), pp. 235-244.

(56) References Cited

OTHER PUBLICATIONS

Senzer, et al., "Phase 2 Evaluation of OSI-774, a Potent Oral Antagonist of the EGFR-Tk in Patients with Advanced Squamous Cell Carcinoma of the Head and Neck," Proceedings of the American Society of Clinical Oncology, 2001, 2a (Abstract 6), 20.

Sepp-Lorenzino, et al., "Farnesyl:Protein Transferase Inhibitors (Ftis) Block Tyrosine Kinase Signal Transduction and Act in Concert With an Anti-EGR Receptor Antibody to Inhibit Cancer Cell Growth," Proceedings of the Annual of the American Association for Cancer Research, 1996, vol. 37 (Abstract 2877), pp. 421-422.

Seymour L., et al., "Novel Anti-Cancer Agents in Development: Exciting Prospects and New Challenges," Cancer Treatment Reviews, 1999, vol. 25, pp. 301-312.

Sharafinski M.E., et al., "Epidermal Growth Factor Receptor Targeted Therapy of Squamous Cell Carcinoma of the Head and Neck," Head Neck, 2010, vol. 32 (10), pp. 1412-1421.

She Q.B., et al., "The BAD Protein Integrates Survival Signaling by EGFR/MAPK and PI3K/Akt Kinase Pathways in PTEN-Deficient Tumor Cells," Cancer Cell, 2005, vol. 8 (4), pp. 287-297.

Shepherd F.A., et al., "Unraveling the Mystery of Prognostic and Predictive Factors in Epidermal Growth Factor Receptor Therapy," Journal of Clinical Oncology, 2006, vol. 24 (7), pp. 1219-1220.

Shibata T., et al., "Enhancing Effects of Epidermal Growth Factor on Human Squamous Cell Carcinoma Motility and Matrix Degradation but Not Growth," Tumor Biology, 1996, vol. 17 (3), pp. 168-175.

Shigematsu H., et al., "Clinical and biological features associated with epidermal growth factor receptor gene mutations in lung cancers," Journal of the National Cancer Institute, 2005, vol. 97 (5), pp. 339-346.

Shigematsu H., et al., "Somatic Mutations of Epidermal Growth Factor Receptor Signaling Pathway in Lung Cancers," International Journal of Cancer, 2006, vol. 118 (2), pp. 257-262.

Shimizu N., et al., "Detection of Epidermal Growth Factor Receptor Gene Amplification in Human Squamous Cell Carcinomas Using Fluorescence in Situ Hybridization," Japanese Journal of Cancer Research, 1994, vol. 85 (6), pp. 567-571.

Shimizu N., et al., "Genetics of Cell Surface Receptors for Bioactive Polypeptides: Binding of Epidermal Growth Factor Is Associated With the Presence of Human Chromosome 7 in Human-Mouse Cell Hybrids," Proceedings of the National Academy of Sciences, 1980, vol. 77 (6), pp. 3600-3604.

Shin D.M., et al., "Dysregulation of Epidermal Growth Factor Receptor Expression in Premalignant Lesions During Head and Neck Tumorigenesis," Cancer Research, 1994, vol. 54 (12), pp. 3153-3159.

Shinkawa T., et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry, 2003, vol. 278 (5), pp. 3466-3473.

Shinojima N., et al., "Prognostic Value of Epidermal Growth Factor Receptor in Patients with Glioblastoma Multiforme," Cancer Research, 2003, vol. 63 (20), pp. 6962-6970.

Shintani S., et al., "Gefitinib ('Iressa', ZD1839), an Epidermal Growth Factor Receptor Tyrosine Kinase Inhibitor, Up-Regulates P27kip1 and Induces G1 Arrest in Oral Squamous Cell Carcinoma Cell Lines," Oral Oncology, 2004, vol. 40 (1), pp. 43-51.

Shintani S., et al., "Intragenic Mutation Analysis of the Human Epidermal Growth Factor Receptor (Egfr) Gene in Malignant Human Oral Keratinocytes," Cancer Research, 1999, vol. 59 (16), pp. 4142-4147.

Sibilia M., et al., "The EGF Receptor Provides an Essential Survival Signal for SOS-Dependent Skin Tumor Development," Cell, 2000, vol. 102 (2), pp. 211-220.

Silver J., et al., "Erbb Is Linked to the Alpha-Globin Locus on Mouse Chromosome 11," Molecular Cell Biology, 1985, vol. 5 (7), pp. 1784-1786.

Sirotnak F.M., et al., "Efficacy of Cytotoxic Agents Against Human Tumor Xenografts is Markedly Enhanced by Coadministration of Zd1839 (Iressa), an Inhibitor of Egfr Tyrosine Kinase," Clinical Cancer Research, 2000, vol. 6 (12), pp. 4885-4892.

Sirotnak, et al., "Potentiation of Cytotoxic Agents Against Human Tumors in Mice by Zd1839 (Iressa), an Inhibitor of Egfr Tyrosine Kinase, Does Not Require High Levels of Expression of EGFR," Proceedings of the Annual Meeting of the American Association for Cancer Research, 2000, vol. 482 (Abstract 3076), pp. 41.

Sizeland A.M., et al., "Anti-Sense Transforming Growth Factor Alpha Oligonucleotides Inhibit Autocrine Stimulated Proliferation of a Colon Carcinoma Cell Line," Molecular Biology of the Cell, 1992, vol. 3 (11), pp. 1235-1243.

Sizeland A.M., et al., "The Proliferative and Morphologic Responses of a Colon Carcinoma Cell Line (LIM 1215) Require the Production of Two Autocrine Factors," Molecular and Cellular Biology, 1991, vol. 11 (8), pp. 4005-4014.

Skov K., et al., "Interaction of Platinum Drugs with Clinically Relevant x-ray doses in Mammalian Cells: A Comparison of Cisplatin, Carboplatin, Iproplatin, and Tetraplatin.," International Journal of Radiation Oncology Biology Physics, 1991, vol. 20 (2), pp. 221-225.

Slamon D.J., et al., "Studies of the Her-2/Neu Proto-Oncogene in Human Breast and Ovarian Cancer," Science, 1989, vol. 244, pp. 707-712.

Slamon D.J., et al., "Use of Chemotherapy Plus a Monoclonal Antibody Against HER2 for Metastatic Breast Cancer that Overexpresses HER2," The New England Journal of Medicine, 2001, vol. 344 (11), pp. 783-792.

Slamon et al., "Addition of Herceptin (Humanized Anti-Her2 Antibody) to First Line Chemotherapy for Her2 Overexpressing Metastatic Breast Cancer (Her2+/Mbc) Markedly Increases Anticancer Activity: A Randomized, Multinational Controlled Phase III Trial," Proceedings of the Annual Meeting of the American Society of Clinical Oncology, 1998, vol. 98a (Abstract 377), pp. 17.

Slichenmyer W.J., et al., "Anticancer Therapy Targeting the ErbB Family of Receptor Tyrosine Kinases," Seminars in Oncology, 2001, vol. 28 (Suppl. 16), pp. 67-79.

Slieker L.J., et al., "Post-Translational Processing of the Epidermal Growth Factor Receptor. Glycosylation-Dependent Acquisition of Ligand-Binding Capacity," Journal of Biological Chemistry, 1985, vol. 260 (2), pp. 687-690.

Slieker L.J., et al., "Synthesis of Epidermal Growth Factor Receptor in Human a431 Cells Glycosylation-Dependent Acquisition of Ligand Binding Activity Occurs Post-Translationally in the Endoplasmic Reticulum," Journal of Biological Chemistry, 1986, vol. 261 (32), pp. 15233-15241.

Sliwkowski M.X., et al., "Nonclinical Studies Addressing the Mechanism of Action of TrastuzumAb (Herceptin)," Seminars in Oncology, 1999, vol. 26 (Suppl. 12), pp. 60-70.

Smith J.S., et al., "PTEN Mutation, EGFR Amplification, and outcome in Patients with Anaplastic Astrocytoma and Glioblastoma Multiforme," Journal of the National Cancer Institute, 2001, vol. 93 (16), pp. 1246-1256.

Snyder L.C., et al., "Overview of Monoclonal Antibodies and Small Molecules Targeting the Epidermal Growth Factor Receptor Pathway in Colorectal Cancer," Clinical Colorectal Cancer, 2005, vol. 5 (Suppl. 2), pp. S71-S80.

Sobol R.E., et al., "Epidermal Growth Factor Receptor Expression in Human Lung Carcinomas Defined by a Monoclonal Antibody," Journal of the National Cancer Institute, 1987, vol. 79 (3), pp. 403-407.

Soderquist A.M., et al., "Glycosylation of the Epidermal Growth Factor Receptor in a-431 Cells. The Contribution of Carbohydrate to Receptor Function," Journal of Biological Chemistry, 1984, vol. 259 (20), pp. 12586-12594.

Solbach C., et al., "Antitumor Effect of MAb EMD 55900 Depends on EGF-R Expression and Histopathology1," Neoplasia, 2002, vol. 4 (3), pp. 237-242.

Solomon B., et al., "EGFR Blockade with ZD1839 (Iressa) Potentiates the Antitumor Effects of Single and Multiple Fractions of Ionizing Radiation in Human A431 Squamous Cell Carcinoma," International Journal of Radiation Oncology Biology Physics, 2003, vol. 55 (3), pp. 713-723.

Solomon B.M., et al., "Rash from EGFR Inhibitors: Opportunities and Challenges for Palliation," Current Oncology Reports, 2008, vol. 10 (4), pp. 304-308.

(56) References Cited

OTHER PUBLICATIONS

Sonabend A.M., et al., "Targeting Epidermal Growth Factor Receptor Variant Iii: A Novel Strategy for the Therapy of Malignant Glioma," Expert Review of Anticancer Therapy, 2007, vol. 7 (12 Suppl), pp. S45-S50.
Sorensen O.E., et al., "Injury-Induced Innate Immune Response in Human Skin Mediated by Transactivation of the Epidermal Growth Factor Receptor," Journal of Clinical Investigation, 2006, vol. 116 (7), pp. 1878-1885.
Sorscher S.M., et al., "EGFR Mutations and Sensitivity to Gefitinib," The New England Journal of Medicine, 2004, vol. 351 (12), pp. 1260-1261.
Soulieres D., et al., "Multicenter Phase II Study of Erlotinib, an Oral Epidermal Growth Factor Receptor Tyrosine Kinase Inhibitor, in Patients With Recurrent or Metastatic Squamous Cell Cancer of the Head and Neck," Journal of Clinical Oncology, 2004, vol. 22 (1), pp. 77-85.
Spurr N.K., et al., "Chromosomal localisation of the Human Homologues to the Oncogenes erb A and B," The EMBO Journal, 1984, vol. 3 (1), pp. 159-169.
Spurr N.K., et al., "Mapping of cellular oncogenes; erb B on chromosome 7," Cytogenet, 1984, vol. 37, pp. 590.
Sridhar S.S., et al., "Inhibitors of Epidermal-Growth-Factor Receptors: A Review of Clinical Research with a Focus on Non-Small-Cell Lung Cancer," Lancet Oncology, 2003, vol. 4 (7), pp. 397-406.
Stabin M.G., et al., "Olinda/Exm: The Second-Generation Personal Computer Software for Internal Dose Assessment in Nuclear Medicine," Journal of Nuclear Medicine, 2005, vol. 46 (6), pp. 1023-1027.
Stamos J., et al., "Structure of the Epidermal Growth Factor Receptor Kinase Domain Alone and in Complex with a 4-Anilinoquinazoline Inhibitor," Journal of Biological Chemistry, 2002, vol. 277 (48), pp. 46265-46272.
Steffens M.G., et al., "Targeting of Renal Cell Carcinoma with Iodine-131-Labeled Chimeric Monoclonal Antibody G250," Journal of Clinical Oncology, 1997, vol. 15 (4), pp. 1529-1537.
Stockhausen M.T., et al., "Maintenance of Egfr and EgfrVIII Expressions in an In Vivo and In Vitro Model of Human Glioblastoma Multiforme," Experimental Cell Research, 2011, vol. 317 (11), pp. 1513-1526.
Studnicka G.M., et al., "Human-Engineered Monoclonal Antibodies Retain Full Specific Binding Activity by Preserving Non-CDR Complementarity-Modulating Residues," Protein Engineering, 1994, vol. 7 (6), pp. 805-814.
Sugawa N., et al., "Function of Aberrant EGFR in Malignant Gliomas," Brain Tumor Pathology, 1998, vol. 15 (1), pp. 53-57.
Sugimura M., et al., "Immunohistochemical study on the expression of epidermal growth factor receptor (EGF-R) in invasive cervical cancer of the uterus," Nippon Sanka Fujinka Gakkai Zasshi, 1992, vol. 44 (6), pp. 689-694.
Sunada H., et al., "Monoclonal Antibody against Epidermal Growth Factor Receptor is Internalized without Stimulating Receptor Phosphorylation," Proceedings of the National Academy of Sciences, 1986, vol. 83 (11), pp. 3825-3829.
Sutherland M.S., et al., "Lysosomal Trafficking and Cysteine Protease Metabolism Confer Target-Specific Cytotoxicity by Peptide-Linked Anti-Cd30-Auristatin Conjugates," Journal of Biological Chemistry, 2006, vol. 281 (15), pp. 10540-10547.
Suwa T., et al., "Epidermal Growth Factor Receptor-Dependent Cytotoxic Effect of Anti-Egfr Antibody-Ribonuclease Conjugate on Human Cancer Cells," Anticancer Research, 1999, vol. 19 (5B), pp. 4161-4165.
Swaisland H., et al., "Pharmacokinetics and Tolerability of the Orally Active Selective Epidermal Growth Factor Receptor Tyrosine Kinase Inhibitor ZD1839 in Healthy Volunteers," Clinical Pharmacokinetics, 2001, vol. 40 (4), pp. 297-306.
Tabernero, et al., "An international phase II study of cetuxirriab in combination with •oxaliplatin/5-fluorouracil (5-FU)/folinic acid (FA) (FOLFOX-4) in the first-line treatment of patients with metastatic colorectal cancer (CRC) expressing epidermal growth factor receptor (EGFR)," Proceedings of the American Society of Clinical Oncology, 2004, vol. 248s (Abstract 3512), pp. 23.
Taetle R., et al., "Effects of Anti-Epidermal Growth Factor (Egf) Receptor Antibodies and an Anti-Egf Receptor Recombinant-Ricin A Chain Immunoconjugate on Growth of Human Cells," National Cancer Institute, 1988, vol. 80 (13), pp. 1053-1059.
Taetle, et al., "Effects of Anti-Epidermal Growth Factor (EGF) Receptor Antibodies and an Anti-Egf Receptor Recombinant-Ricina Chain Immunoconjugate on Growth of Human Cell," Chemical Abstracts, 1988, vol. 109 (21), pp. 184218a.
Tahtis K., et al., "Biodistribution Properties of 111 Indium-labeled C-Functionalized trans-Cyclohexyl Diethylenetriaminepentaacetic Acid Humanized 3S193 Diabody and F(ab ¢)2 Constructs in a Breast Carcinoma Xenograft Model," Clinical Cancer Research, 2001, vol. 7 (4), pp. 1061-1072.
Tai A.L.S., et al., "Co-Overexpression of Fibroblast Growth Factor 3 and Epidermal Growth Factor Receptor Is Correlated with the Development of Nonsmall Cell Lung Carcinoma," Cancer, 2006, vol. 106, pp. 146-155.
Takahashi H., et al., "Radioimmunodetection of Human Glioma Xenografts by Monoclonal Antibody to Epidermal Growth Factor Receptor," Cancer Research, 1987, vol. 47 (14), pp. 3847-3850.
Takasu S., et al., "Antibody-based therapy for brain tumor," Nihon Rinsho, 2005, vol. 63 (Suppl. 9), pp. 563-568.
Takasu S., et al., "Radioimmunoscintigraphy of Intracranial Glioma Xenograft with a Technetium-99m-Labeled Mouse Monoclonal Antibody Specifically Recognizing Type III Mutant Epidermal Growth Factor Receptor," Journal of Neuro-Oncology, 2003, vol. 63 (3), pp. 247-256.
Tan A.R., et al., "Pharmacokinetics of CetuximAb after Administration of Escalating Single Dosing and Weekly Fixed Dosing in Patients with Solid Tumors," Clinical Cancer Research, 2006, vol. 12 (21), pp. 6517-6522.
Tang P., et al., "The Autocrine Loop of Tgf-Alpha/Egfr and Brain Tumors," Journal of Neuro Oncology, 1997, vol. 35 (3), pp. 303-314.
Tang P.A., et al., "Phase II study of Ispinesib in Recurrent or Metastatic Squamous Cell Carcinoma of the Head and Neck," Investigational New Drugs, 2008, vol. 26 (3), pp. 257-264.
Tannock I.F., "Treatment of Cancer with Radiation and Drugs," Journal of Clinical Oncology, 1996, vol. 14 (12), pp. 3156-3174.
Tanswell P., et al., "Population Pharmacokinetics of Antifibroblast activation protein monoclonal antibody F19 in cancer patients," British Journal of Clinical Pharmacology, 2001, vol. 51 (2), pp. 177-180.
Tateishi M., et al., "Prognostic Influence of the Co-Expression of Epidermal Growth Factor Receptor and c-erbB-2 Protein in Human Lung Adenocarcinoma," Surgical Oncology, 1994, vol. 3 (2), pp. 109-113.
Temam, et al., "Epidermal Growth Factor Receptor Copy Number Alterations Correlate with Poor Clinical Outcome in Patients with Head and Neck Squamous Cancer," Journal of Clinical Oncology, 2007, vol. 25 (16), pp. 2164-2170.
Temming K., et al., "Evaluation of RGD-Targeted Albumin Carriers for Specific Delivery of Auristatin E to Tumor Blood Vessels," Bioconjugate Chemistry, 2006, vol. 17 (6), pp. 1385-1394.
Teramoto T., et al., "Inhibitory Effect of Antiepidermal Growth Factor Receptor Antibody on a Human Gastric Cancer," Cancer, 1996, vol. 77 (8), pp. 1639-1645.
Tewes, et al., "Results of a phase I trial of the humanized anti epidermal growth factor receptor (EGFR) monoclonal antibody EMD 72000 in patients with EGFR expressing solid tumors," Proceedings of the American Society of Clinical Oncology, 2002, vol. 95a (Abstract 378), pp. 21.
Thaung C., et al., "Novel ENU-Induced Eye Mutations in the Mouse: Models for Human Eye Disease," Human Molecular Genetics, 2002, vol. 11 (7), pp. 755-767.
Thomas S.M., et al., "Pharmacokinetic and Pharmacodynamic Properties of EGFR Inhibitors Under Clinical Investigation," Cancer Treatment Reviews, 2004, vol. 30 (3), pp. 255-268.
Thompson D.M., et al., "The EGF receptor: Structure, Regulation and Potential Role in Malignancy," 1985, vol. 4 (4), pp. 767-788.
Tice D.A., et al., "Mechanism of Biological Synergy Between Cellular Src and Epidermal Growth Factor Receptor," Proceedings of the National Academy of Sciences, 1999, vol. 96 (4), pp. 1415-1420.

(56) References Cited

OTHER PUBLICATIONS

Tietze L.F., et al., "Novel Analogues of cc-1065 and the Duocarmycins for the use in Targeted Tumour Therapies," Anti-Cancer Agents in Medicinal Chemistry, 2009, vol. 9 (3), pp. 304-325.
Tochon-Danguy H.J., et al., "Imaging and Quantitation of the Hypoxic Cell Fraction of Viable Tumor in an Animal Model of Intracerebral High Grade Glioma Using [18F]Fluoromisonidazole (FMISO)," Nuclear Medicine and Biology, 2002, vol. 29 (2), pp. 191-197.
Todd R., et al., "Epidermal Growth Factor Receptor (EGFR) Biology and Human Oral Cancer," Histol Histopathol, 1999, vol. 14 (2), pp. 491-500.
Toi M., et al., "Epidermal Growth Factor Receptor Expression as a Prognostic Indicator in Breast Cancer," European Journal of Cancer, 1991, vol. 27 (8), pp. 977-980.
Tokuda Y., et al., "In Vitro and in Vivo Anti-Tumour Effects of a Humanised Monoclonal Antibody Against C-Erbb-2 Product," British Journal of Cancer, 1996, vol. 73 (11), pp. 1362-1365.
Tokumo M., et al., "The Relationship Between Epidermal Growth Factor Receptor Mutations and Clinicopathologic Features in Non-Small Cell Lung Cancers," Clinical Cancer Research, 2005, vol. 11 (3), pp. 1167-1173.
Torres L.A., et al., "Phase I/II Clinical Trial of the Humanized Anti-Egf-R Monoclonal Antibody H-R3 Labelled With 99mtc in Patients with Tumour of Epithelial Origin," Nuclear medicine communications, 2005, vol. 26 (12), pp. 1049-1057.
Toth J., et al., "Analysis of EGFR Gene Amplification, Protein Over-Expression and Tyrosine Kinase Domain Mutation in Recurrent Glioblastoma," Pathology & Oncology Research, 2009, vol. 15 (2), pp. 225-229.
Toyooka, et al., "EGFR Mutation and Response of Lung Cancer to Gefitinib," The New England Journal of Medicine, 2005, vol. 352 (20), pp. 2136.
Trail P.A., et al., "Monoclonal Antibody Drug Conjugates in the Treatment of Cancer," Current Opinion in Immunology, 1999, vol. 11, pp. 584-588.
Tran D.D., et al., "CAML Is Required for Efficient EGF Receptor Recycling," Developmental Cell, 2003, vol. 5 (2), pp. 245-256.
Traxler P., et al., "AEE788: A Dual Family Epidermal Growth Factor Receptor/Erbb2 and Vascular Endothelial Growth Factor Receptor Tyrosine Kinase Inhibitor With Antitumor and Antiangiogenic Activity," Cancer Research, 2004, vol. 64 (14), pp. 4931-4941.
Trigo, et al., "Cetuximab Monotherapy is Active in Patients (Pts) with Platinum-Refractory Recurrent/Metastatic Squamous Cell Carcinoma of the Head and Neck (Scchn) (Results of a Phase II Study)," Proceedings of the American Society of Clinical Oncology, 2004, vol. 488s (Abstract 5502), pp. 22.
Trummell, et al., "The Biological Effects of Anti-Epidermal Growth Factor Receptor and Ionizing Radiation in Human Head and Neck Tumor Cell Lines," Proceedings of the American Association for Cancer Research, 1999, vol. 144 (Abstract 958), pp. 40.
Tsao M.S., et al., "Erlotinib in Lung Cancer—Molecular and Clinical Predictors of Outcome," The New England Journal of Medicine, 2005, vol. 352 (2), pp. 133-144.
Tsuchihashi Z., et al., "Responsiveness to Cetuximab without Mutations in EGFR," The New England Journal of Medicine, 2005, vol. 353 (2), pp. 208-209.
Tsugu, et al., "Localization of Aberrant Messenger RNA of Epidermal Growth Factor Receptor (EGFR) in Malignant Glioma," Anticancer research , 1997, vol. 17 (3C), pp. 2225-2232.
Turkeri L.N., et al., "Impact of the Expression of Epidermal Growth Factor, Transforming Growth Factor Alpha, and Epidermal Growth Factor Receptor on the Prognosis of Superficial Bladder Cancer," Urology, 1998, vol. 51 (4), pp. 645-649.
Turner T., et al., "EGF Receptor Signaling Enhances in Vivo Invasiveness of Du-145 Human Prostate Carcinoma Cells," Clinical and Experimental Metastasis, 1996, vol. 14 (4), pp. 409-418.
Tzahar E., et al., "Bivalence of EGF-like Ligands Drives the ERBP Signaling Network," The EMBO Journal, 1997, vol. 16 (16), pp. 4938-4950.
Uegaki K., et al., "Clinicopathological Significance of Epidermal Growth Factor and its Receptor in Human Pancreatic Cancer," Anticancer research, 1997, vol. 17 (5B), pp. 3841-3847.
Uemura H.E., et al., "Internal Image Anti-Idiotype Antibodies Related to Renal-Cell Carcinoma-Associated Antigen G250.Int. J. Cancer," International Journal of Cancer, 1994, vol. 56 (4), pp. 609-614.
Vagin A.A., et al., "Spherically Averaged Phased Translation Function and its Application to the Search for Molecules and Fragments in Electron-Density Maps," Acta Crystallographica, 2001, vol. 57 (10), pp. 1451-1456.
Vaidyanathan G., et al., "Improved Xenograft Targeting of Tumor-Specific Anti-Epidermal Growth Factor Receptor Variant III Antibody Labeled Using N-Succinimidyl 4-Guanidinomethyl-3-Iodobenzoate," Nuclear Medicine and Biology, 2002, vol. 29, pp. 1-11.
Van De Loosdrecht A.A., et al., "A Tetrazolium-Based Colorimetric MTT Assay to Quantitate Human Monocyte Mediated Cytotoxicity against Leukemic Cells from Cell Lines and Patients with Acute Myeloid Leukemia," Journal of Immunological Methods, 1994, vol. 174 (1-2), pp. 311-320.
Van Den Eynde B.J., et al., "Tumor Antigens" in: Encyclopedia of Immunology, 2nd Edition, Academic Press Limited, 1998, pp. 2424-2431.
Van Dijk M.A., et al., "Human Antibodies as Next Generation Therapeutics," Current Opinion in Chemical Biology, 2001, vol. 5 (4), pp. 368-374.
Van Doorn R., et al., "Follicular and Epidermal Alterations in Patients Treated with Zd1839 (Iressa), an Inhibitor of the Epidermal Growth Factor Receptor," British Journal of Dermatology, 2002, vol. 147 (3), pp. 598-601.
Vanhoefer U., et al., "Phase I Study of the Humanized Antiepidermal Growth Factor Receptor Monoclonal Antibody EMD72000 in Patients with Advanced Solid Tumors that Express the Epidermal Growth Factor Receptor," Journal of Clinical Oncology, 2004, vol. 22 (1), pp. 175-184.
Veale D., et al., "Epidermal Growth Factor Receptors in Non-Small Cell Lung Cancer," British Journal of Cancer, 1987, vol. 55, pp. 513-516.
Veale D., et al., "The Relationship of Quantitative Epidermal Growth Factor Receptor Expression in Non-Small Cell Lung Cancer to Long Term Survival," British Journal of Cancer, 1993, vol. 68 (1), pp. 162-165.
Velu T.J., et al., "Epidermal Growth-Factor-Dependent Transformation by a Human Egf Receptor Proto-Oncogene," Science, 1987, vol. 238 (4832), pp. 1408-1410.
Venter D.J., et al., "Overexpression of the C-Erbb-2 Oncoprotein in Human Breast Carcinomas: Immunohistological Assessment Correlates With Gene Amplification," Lancet, 1987, vol. 2 (8550), pp. 69-72.
Verbeek B.S., et al., "Overexpression of EGFR and c-erbB2 Causes Enhanced Cell Migration in Human Breast Cancer Cells and NIH3T3 Fibroblasts," FEBS Letters, 1998, vol. 425 (1), pp. 145-150.
Vermorken J.B., et al., "Platinum-Based Chemotherapy Plus Cetuximab in Head and Neck Cancer," The New England Journal of Medicine, 2008, vol. 359 (11), pp. 1116-1127.
Vermorken, et al., "Cett.Iximab (Erbitux®) in Recurrent/Metastatic (R&M) Squamous Cell Carcinoma of the Head and Neck (SCCHN) Refractory to First-Line Platinum-Based Therapies," Journal of Clinical Oncology, 2005, Abstract 5505, pp. 23.
Verveer P.J., et al., "Quantitative Imaging of Lateral ErbB1 Receptor Signal Propagation in the Plasma Membrane," Science, 2000, vol. 290 (5496), pp. 1567-1570.
Viana-Pereira M., et al., "Analysis of EGFR Overexpression, EGFR Gene Amplification and the EEGFRvIII Mutation in Portuguese High-Grade Gliomas," Anticancer Research, 2008, vol. 28 (2A), pp. 913-920.
Vincent P.W., et al., "Anticancer Efficacy of the Irreversible EGFR Tyrosine Kinase Inhibitor PD 0169414 Against Human Tumor Xenografts," Cancer Chemother Pharmacol, 2000, vol. 45 (3), pp. 231-238.

(56) References Cited

OTHER PUBLICATIONS

Voelzke W.R., et al., "Targeting the Epidermal Growth Factor Receptor in High-Grade Astrocytomas," Current Treatment Options in Oncology, 2008, vol. 9 (1), pp. 23-31.
Vogel C.L., et al., "Efficacy and Safety of Trastuzumab as a Single Agent in First-Line Treatment of HER2-Overexpressing Metastatic Breast Cancer," Journal of Clinical Oncology, 2002, vol. 20 (3), pp. 719-726.
Vogel C.L., et al., "First-Line Herceptin Monotherapy in Metastatic Breast Cancer," Oncology, 2001, vol. 61 (Suppl. 2), pp. 37-42.
Vogt N., et al., "Relationships Linking Amplification Level to Gene Over-Expression in Gliomas," PLoS One, 2010, vol. 5 (12), pp. e14249.
Volm M., et al., "Prognostic Value of ERBB-1, VEGF, cyclin A, FOS, JUN and MYC in Patients with Squamous Cell Lung Carcinomas," British Journal of Cancer, 1998, vol. 77 (4), pp. 663-669.
Wade J.D., et al., "An Automated Peptide and Protein Thiazolidine Coupling Chemistry for Biosensor Immobilization giving a Unique N-Terminal Orientation," Analytical Biochemistry, 2006, vol. 348 (2), pp. 315-317.
Wakeling A.E., et al., "Specific Inhibition of Epidermal Growth Factor Receptor Tyrosine Kinase by 4-Anilinoquinazolines," Breast Cancer Research and Treatment, 1996, vol. 38 (1), pp. 67-73.
Wakeling E.L., et al., "Human EGFR, a Candidate Gene for the Silver-Russell Syndrome, Is Biallelically Expressed in a Wide Range of Fetal Tissues," European Journal of Human Genetics, 1998, vol. 6 (2), pp. 158-164.
Waldmann, et al.,"Monoclonal antibodies in diagnosis and therapy," Science, 1991, 252 (5013), 1657-1662.
Walewski J., et al., "Rituximab (Mabthera, Rituxan) in Patients with Recurrent Indolent Lymphoma: Evaluation of Safety and Efficacy in a Multicenter Study," Medical Oncology, 2001, vol. 18 (2), pp. 141-148.
Walker F., et al., "CR1/CR2 Interactions Modulate the Functions of the Cell Surface Epidermal Growth Factor Receptor," Journal of Biological Chemistry, 2004, vol. 279 (21), pp. 22387-22398.
Walker R.A., et al., "Expression of Epidermal Growth Factor Receptor mRNA and Protein in Primary Breast Carcinomas," Breast Cancer Research and Treatment, 1999, vol. 53 (2), pp. 167-176.
Walton G.M., et al., "Analysis of Deletions of the Carboxyl Terminus of the Epidermal Growth Factor Receptor Reveals Self-Phosphorylation at Tyrosine 992 and Enhanced in Vivo Tyrosine Phosphorylation of Cell Substrates," Journal of Biological Chemistry, 1990, vol. 265 (3), pp. 1750-1754.
Wang D.P., et al., "Immunohistochemical Localization of C-Erbb-2 Protein and Epidermal Growth Factor Receptor in Normal Surface Epithelium, Surface Inclusion Cysts, and Common Epithelial Tumours of the Ovary," Virchows Arch A Pathol Anat Histopathol, 1992, vol. 421 (5), pp. 393-400.
Wang H., et al., "Epidermal Growth Factor Receptor VIII Enhances Tumorigenicity and Resistance to 5-Fluorouracil in Human Hepatocellular Carcinoma," Cancer Letters, 2009, vol. 279 (1), pp. 30-38.
Wang X., et al., "Epidermal Growth Factor Receptor is a Cellular Receptor for Human Cytomegalovirus," Nature, 2003, vol. 424 (6947), pp. 456-461.
Wang Z., et al., "Endocytosis Deficiency of Epidermal Growth Factor (EGF) Receptor-ERBB2 Heterodimers in Response to EGF Stimulation," Molecular Biology of the Cell, 1999, vol. 10 (5), pp. 1621-1636.
Wargalla, et al., "Rate of Internalization of an Immunotoxin Correlates With Cytotoxic Activity Against Human Tumor Cells," Proceedings of the National Academy of Sciences, 1989, vol. 86 (13), pp. 5146-5150.
Waterman H., et al., "Alternative Intracellular Routing of ERBB Receptors May Determine Signaling Potency," Journal of Biological Chemistry, 1998, vol. 273 (22), pp. 13819-13827.
Waterman H., et al., "Molecular Mechanisms Underlying Endocytosis and Sorting of ErbB Receptor Tyrosine Kinases," FEBS Letters, 2001, vol. 490 (3), pp. 142-152.
Waugh M.G., et al., "Epidermal Growth Factor Receptor Activation Is Localized Within Low-Buoyant Density, Non-Caveolar Membrane Domains," Biochemical Journal, 1999, vol. 337 (pt 3), pp. 591-597.
Webster W.M., et al., "Engineering Antibody Affinity and Specificity," International Journal of Cancer—Supplement, 1988, vol. 3, pp. 13-16.
Wedegaertner P.B., et al., "Activation of the Purified Protein Tyrosine Kinase Domain of the Epidermal Growth Factor Receptor," Journal of Biological Chemistry, 1989, vol. 264 (19), pp. 11346-11353.
Wedegaertner P.B., et al., "Effect of Carboxyl Terminal Truncation on the Tyrosine Kinase Activity of the Epidermal Growth Factor Receptor," Archives of Biochemistry and Biophysics, 1992, vol. 292 (1), pp. 273-280.
Wells A., et al., "Ligand-Induced Transformation by a Noninternalizing Epidermal Growth Factor Receptor," Science, 1990, vol. 247 (4945), pp. 962-964.
Welt S., et al., "Antibody Targeting in Metastatic Colon Cancer: A Phase I Study of Monoclonal Antibody F19 Against a Cell-Surface Protein of Reactive Tumor Stromal Fibroblasts," Journal of Clinical Oncology, 1994, vol. 12 (6), pp. 1193-1203.
Welt S., et al., "Phase I Study of Anticolon Cancer Humanized Antibody A33," Clinical Cancer Research, 2003, vol. 9, pp. 1338-1346.
Welt S., et al., "Phase I/II Study of Iodine 125-Labeled Monoclonal Antibody A33 in Patients with Advanced Colon Cancer," Journal of Clinical Oncology, 1996, vol. 14 (6), pp. 1787-1797.
Welt S., et al., "Phase I/II Study of Iodine 131-Labeled Monoclonal Antibody A33 in Patients with Advanced Colon Cancer," Journal of Clinical Oncology, 1994, vol. 12 (8), pp. 1561-1571.
Welt S., et al., "Preliminary Report of a Phase I Study of Combination Chemotherapy and Humanized A33 Antibody Immunotherapy in Patients with Advanced Colorectal Cancer," Clinical Cancer Research, 2003, vol. 9 (4), pp. 1347-1353.
Welt S., et al., "Quantitative Analysis of Antibody Localization in Human Metastatic Colon Cancer: A Phase I Study of Monoclonal Antibody A33," Journal of Clinical Oncology, 1990, vol. 8 (11), pp. 1894-1906.
Welt, et al., "Phase I Study of Humanized A33 (huA33) Antibody in Patients with Advanced Colorectal Cancer," Proceedings of the Annual Meeting of the American Society of Clinical Oncology, 1977, vol. 436a (Abstract 1563), pp. 16.
Wen, et al., "Potentiation of Antitumor Activity of PG-TXL with Anti-EGFR Monoclonal Antibody C225 in MDA-MB-468 Human Breast Cancer Xenograft," Proceedings of the American Association for Cancer Research, 2000, vol. 323 (Abstract 2052), pp. 51.
Weppler S.A., et al., "Expression of EGFR Variant vIII promotes Both Radiation Resistance and Hypoxia Tolerance," Radiotherapy and Oncology, 2007, vol. 83 (3), pp. 333-339.
Wersall P., et al., "Intratumoral Infusion of the Monoclonal Antibody, mAb 425, against the Epidermal-Growth-Factor Receptor in Patients with Advanced Malignant Glioma," Cancer Immunology Immunotherapy, 1997, vol. 44 (3), pp. 157-164.
Westwood J.A., et al., "Adoptive transfer of T cells modified with a humanized chimeric receptor gene inhibits growth of Lewis-Y-expressing tumors in mice," Proceedings of the National Academy of Sciences, 2005, vol. 102 (52), pp. 19051-19056.
Wheeler D.L., et al., "Mechanisms of Acquired Resistance to Cetuximab: Role of HER (ErbB) Family Members," Oncogene, 2008, vol. 27 (28), pp. 3944-3956.
Wheeler S.E., et al., "Epidermal Growth Factor Receptor Variant III Mediates Head and Neck Cancer Cell Invasion, via STAT3 Activation," Oncogene, 2010, vol. 29 (37), pp. 5135-5145.
Whitson K.B., et al., "Functional Effects of Selective Glycosylation at Asn-579 of the Epidermal Growth Factor Receptor," Biochemistry, 2005, vol. 44 (45), pp. 14920-14931.
Wikstrand C.J., et al., "Cell Surface Localization and Density of the Tumor-Associated Variant of the Epidermal Growth Factor Receptor, EGFRvIII," Cancer Research, 1997, vol. 57, pp. 4130-4140.
Wikstrand C.J., et al., "Comparative Localization of Glioma-Reactive Monoclonal Antibodies in Vivo in an Athymic Mouse Human Glioma Xenograft Model," Journal of Neuroimmunology, 1987, vol. 15 (1), pp. 37-56.

(56) References Cited

OTHER PUBLICATIONS

Wikstrand C.J., et al., "Investigation of a Synthetic Peptide as Immunogen for a Variant Epidermal Growth Factor Receptor Associated with Gliomas," Journal of Neuroimmunology, 1993, vol. 46 (1-2), pp. 165-173.

Wikstrand C.J., et al., "Production and Characterization of Two Human Glioma Xenograft-Localizing Monoclonal Antibodies," Cancer Research, 1986, vol. 46 (11), pp. 5933-5940.

Wikstrand, et al., "Antibodies and molecular immunology: immunohistochemistry and antigens of diagnostic significance" in: Russell and Rubinsteins Pathology of Tumors of the Nervous System, Chapter 8, Bigner, et al., eds., Arnold and Oxford University Press, Inc, 1998, pp. 251-304.

Wiley H.S., et al., "The Role of Tyrosine Kinase Activity in Endocytosis, Compartmentation, and Down-Regulation of the Epidermal Growth Factor Receptor," Journal of Biological Chemistry, 1991, vol. 266 (17), pp. 11083-11094.

Wiley H.S., et al., "Trafficking of the ErbB Receptors and its Influence on Signaling," Experimental Cell Research, 2003, vol. 284 (1), pp. 78-88.

Willett C.J., et al., "Direct evidence that the VEGF-specific antibody bevacizumab has antivascular effects in human rectal cancer," Nature Medicine, 2004, vol. 10, pp. 145-147.

Williams K.J., et al., "ZD1839 ('Iressa'), a Specific Oral Epidermal Growth Factor Receptor-Tyrosine Kinase Inhibitor, Potentiates Radiotherapy in a Human Colorectal Cancer Xenograft Model," British Journal of Cancer, 2002, vol. 86 (7), pp. 1157-1161.

Williams, et al., "Combination of ZD1839 (Iressa), an EGFR Tyrosine Kinase Inhibitor, and Radiotherapy Increases Antitumour Efficacy in a Human Colon Cancer Xenograft Model," Proceedings of the American Association for Cancer Research, 2001, vol. 715 (Abstract 3840), pp. 42.

Winer E.P., et al., "New Combinations with Herceptin in Metastatic Breast Cancer," Oncology, 2001, vol. 61 (Suppl. 2), pp. 50-57.

Winter G., et al., "Man-Made Antibodies," Nature, 1991, vol. 349 (6307), pp. 293-299.

Wollman R., et al., "Effect of Epidermal Growth Factor on the Growth and Radiation Sensitivity of Human Breast Cancer Cells In Vitro," International Journal of Radiation Oncology, 1994, vol. 30 (1), pp. 91-98.

Woltjer R.L., et al., "Direct Identification of Residues of the Epidermal Growth Factor Receptor in Close Proximity to the Amino Terminus of Bound Epidermal Growth Factor," Proceedings of the National Academy of Sciences, 1992, vol. 89 (16), pp. 7801-7805.

Wood E.R., et al., "A Unique Structure for Epidermal Growth Factor Receptor Bound to GW572016 (Lapatinib): Relationships among Protein Conformation, Inhibitor off-rate, and Receptor Activity in Tumor Cells," Cancer Research, 2004, vol. 64 (18), pp. 6652-6659.

Woodburn J.R., et al., "The Epidermal Growth Factor Receptor and Its Inhibition in Cancer Therapy," Pharmacology and Therapeutics, 1999, vol. 82 (2-3), pp. 241-250.

Woodburn, et al., "ZD1839 (Iressa) a Selective Epidermal Growth Factor Receptor Tyrosine Kinase Inhibitor (Egfr-Tki): Inhibition of CFOS MRNA, an Intermediate Marker of EGFR Activation,Corre-Lates with Tumor Growth Inhibition," Proceedings of the Annual Meeting of the American Association for Cancer Research, 2000, vol. 402 (Abstract 2552), pp. 41.

Woodburn, et al., "ZD1839, an Epidermal Growth Factor Tyrosine Kinase Inhibitor Selected for Clinical Development," Proceedings of the Annual Meeting of the American Association for Cancer Research, 1997, vol. 633 (Abstract 4251), pp. 38.

Wu G., et al., "Targeted Delivery of Methotrexate to Epidermal Growth Factor Receptor-Positive Brain Tumors by means of Cetuximab (IMC-C225) Dendrimer Bioconjugates," Molecular cancer therapeutic, 2006, vol. 5 (1), pp. 52-59.

Wu H., et al., "Humanization of a Murine Monoclonal Antibody by Simultaneous Optimization of Framework and CDR Residues," Journal of Molecular Biology, 1999, vol. 294 (1), pp. 151-162.

Wu X., et al., "Apoptosis Induced by an Anti-Epidermal Growth Factor Receptor Monoclonal Antibody in a Human Colorectal Carcinoma Cell Line and its Delay by Insulin," The Journal of Clinical Investigation, 1995, vol. 95 (4), pp. 1897-1905.

Xie H., et al., "In Vitro Invasiveness of Du-145 Human Prostate Carcinoma Cells is Modulated by EGF Receptor-Mediated Signals," Clinical & experimental metastasis, 1995, vol. 13 (6), pp. 407-419.

Xiong H.Q., et al., "Cetuximab, a Monoclonal Antibody Targeting the Epidermal Growth Factor Receptor, in Combination With Gemcitabine for Advanced Pancreatic Cancer: A Multicenter Phase II Trial," Journal of Clinical Oncology, 2004, vol. 22 (13), pp. 2610.

Xu F., et al., "Antibody-Induced Growth Inhibition is Mediated through Immunochemically and Functionally Distinct Epitopes on the Extracellular Domain of the c-ErbB-2 (HER-2/neu) Gene Product p185," International Journal of Cancer, 1993, vol. 53, pp. 401-408.

Xu Y.H., et al., "Characterization of Epidermal Growth Factor Receptor Gene Expression in Malignant and Normal Human Cell Lines," Proceedings of the National Academy of Sciences, 1984, vol. 81 (23), pp. 7308-7312.

Xu Y.H., et al., "Human Epidermal Growth Factor Receptor CDNAIs Homologous to a Variety of RNAs Overproduced in A431 Carcinoma Cells," Nature, 1984, vol. 309 (5971), pp. 806-810.

Yamanaka Y., et al., "Coexpression of Epidermal Growth Factor Receptor and Ligands in Human Pancreatic Cancer is Associated with Enhanced Tumor Aggressiveness," Anticancer Research, 1993, vol. 13 (3), pp. 565-569.

Yamazaki H., et al., "Amplification of the Structurally and Functionally Altered Epidermal Growth Factor Receptor Gene (c-erbB) in Human Brain Tumors," Molecular and Cellular Biology, 1988, vol. 8 (4), pp. 1816-1820.

Yamazaki H., et al., "Inhibition of Tumor Growth by Ribozyme-Mediated Suppression of Aberrant Epidermal Growth Factor Receptor Gene Expression," Journal of the National Cancer Institute, 1998, vol. 90 (8), pp. 581-587.

Yang E.B., et al., "Genistein, a Tyrosine Kinase Inhibitor, Reduces EGF-Induced EGF Receptor Internalization and Degradation in Human Hepatoma HepG2 Cells," Biochimica et Biophysica Acta, 1996, vol. 224, pp. 309-317.

Yang et al., "Potent Anti-tumor Activity of ABX-EGF, a Fully Human Monoclonal Antibody to Epidermal Growth Factor Receptor," Proceedings of the American Society of Clinical Oncology, 1999, vol. 18 (Abstract 1765), pp. 457a.

Yang W., et al., "Development of a Syngeneic Rat Brain Tumor Model Expressing EGFRvIII and its Use for Molecular Targeting Studies with Monoclonal Antibody L8A4," Clinical Cancer Research, 2005, vol. 11 (1), pp. 341-350.

Yang W., et al., "Molecular Targeting and Treatment of EGFRvIII-Positive Gliomas Using Boronated Monoclonal Antibody L8A4," Clinical Cancer Research, 2006, vol. 12 (12), pp. 3792-3802.

Yang, et al., "Therapeutic Potential of ABX-EGF, a Fully Human Anti-EGF Receptor Monoclonal Antibody, for Cancer Treatment," Proceedings of the American Society of Clinical Oncology, 2000, vol. 48a (Abstract 183), pp. 19.

Yao M., et al., "Enhanced Expression of C-Myc and Epidermal Growth Factor Receptor (C-Erbb-1) Genes in Primary Human Renal Cancer," Cancer Research, 1988, vol. 48 (23), pp. 6753-6757.

Yarden Y., et al., "Self-Phosphorylation of Epidermal Growth Factor Receptor: Evidence for a Model of Intermolecular Allosteric Activation," Biochemistry, 1987, vol. 26 (5), pp. 1434-1442.

Ye D., et al., "Augmentation of a Humanized Anti-HER2 MAB 4D5 Induced Growth Inhibition by a Human-Mouse Chimeric Anti-EGF Receptor Mab C225," Oncogene, 1999, vol. 18 (3), pp. 731-738.

Yen L., et al., "Differential Regulation of Tumor Angiogenesis by Distinct ErbB Homo- and Heterodimers," Molecular Biology of the Cell, 2002, vol. 13, pp. 4029-4044.

Ymer S., et al., "Constitutive Synthesis of Interleukin-3 by Leukaemia Cell Line Wehi-3B is due to Retroviral Insertion near the Gene," Nature, 1985, vol. 317 (6034), pp. 255-258.

Ymer, et al., "Glioma Specific Extracellular Missense Mutations in the First Cysteine Rich Region f Epidermal Growth Factor Receptor (EGFR) Initiate Ligand Independent Activation," Cancers, 2011, vol. 3, pp. 2032-2049.

(56) References Cited

OTHER PUBLICATIONS

Yoshida K., et al., "Egf and Tgf-A, the Ligands of Hyperproduced Egfr in Human Esophageal Carcinoma Cells, act as Autocrine Growth Factors," International Journal of Cancer, 1990, vol. 45 (1), pp. 131-135.

Yoshida K., et al., "Studies of the Expression of Epidermal Growth Factor Receptor in Human Renal Cell Carcinoma: A Comparison of Immunohistochemical Method Versus Ligand Binding Assay," Oncology, 1997, vol. 54 (3), pp. 220-225.

Yoshimoto K., et al., "Development of a Real-Time RT-PCR Assay for Detecting EGFRvIII in Glioblastoma Samples," Clinical Cancer Research, 2008, vol. 14 (2), pp. 488-493.

Yoshitake S., et al., "Conjugation of Glucose Oxidase from *Aspergillus niger* and Rabbit Antibodies Using N-Hydroxysuccinimide Ester of N-(4-Carboxycyclohexylmethyl)-Maleimide," European Journal of Biochemistry, 1979, vol. 101 (2), pp. 395-399.

Yu H., et al., "Co-Expression of EGFRvIII with ErbB-2 Enhances Tumorigenesis: EGFRvIII Mediated Constitutively Activated and Sustained Signaling Pathways, whereas EGF-Induced a Transient Effect on EGFR-Mediated Signaling Pathways," Cancer Biology & Therapy, 2008, vol. 7 (11), pp. 1818-1828.

Yu T.W., et al., "The Biosynthetic Gene Cluster of the Maytansinoid Antitumor Agent Ansamitocin from *Actinosynnema pretiosum*," Proceedings of the National Academy of Sciences, 2002, vol. 99 (12), pp. 7968-7973.

Zarcone R., et al., "Epidermal Growth Factor Receptor Expression: is it the Same in Normal and Malignant Endometria," Clinical & Experimental Obstetrics & Gynecology, 1995, vol. 22 (4), pp. 298-300.

Zhang H., et al., "Therapeutic Monoclonal Antibodies for the ERBB Family of Receptor Tyrosine Kinases," Cancer Biology & Therapy, 2003, vol. 2 (4 Suppl. 1), pp. S122-S126.

Zhang W., et al., "Novel Approaches to Treatment of Advanced Colorectal Cancer with Anti-EGFR Monoclonal Antibodies," Annals of Medicine, 2006, vol. 38 (8), pp. 545-551.

Zhu H.J., et al., "Epidermal Growth Factor Receptor: Association of Extracellular Domain Negatively Regulates Intracellular Kinase Activation in the Absence of Ligand," Growth Factors, 2003, vol. 21 (1), pp. 15-30.

Zhu X.F., et al., "Egfr Tyrosine Kinase Inhibitor Ag1478 Inhibits Cell Proliferation and Arrests Cell Cycle in Nasopharyngeal Carcinoma Cells," Cancer Letters, 2001, vol. 169 (1), pp. 27-32.

Zinner, et al., "A Phase 1 Clinical and Biomarker Study of the Novel Pan-ERBB Tyrosine Kinase Inhibitor, CI-1033, in Patients with Solid Tumors," Clinical Cancer Research, 2001, vol. 3767s (Abstract 566), pp. 7.

\* cited by examiner

FIGURE 3
A
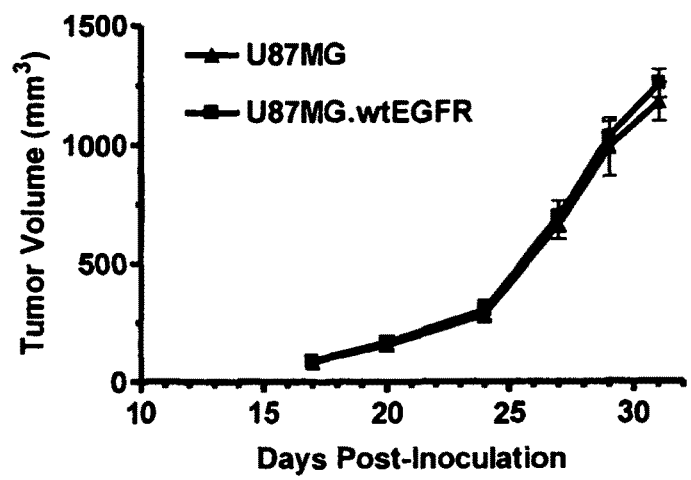
B
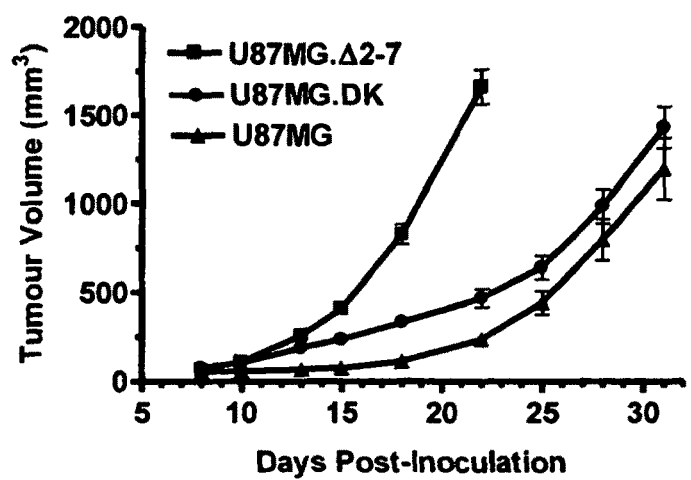

FIGURE 4
A
B
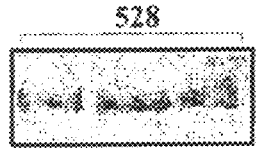

FIGURE 5
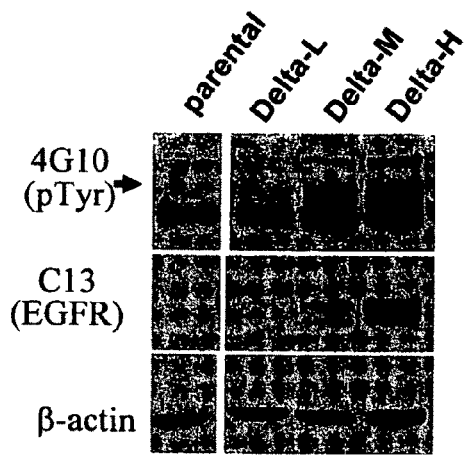
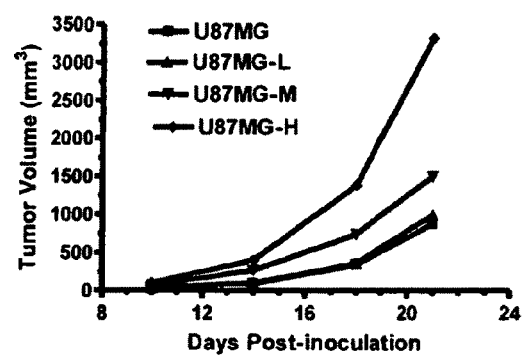
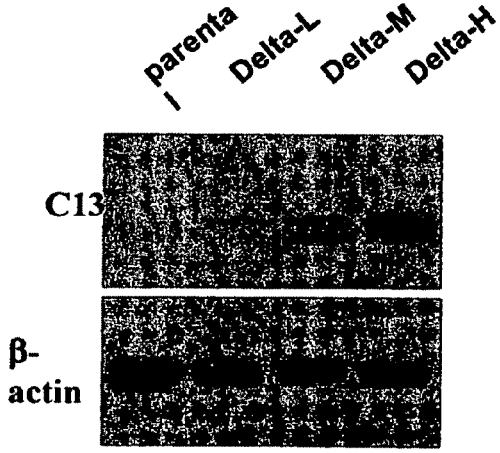
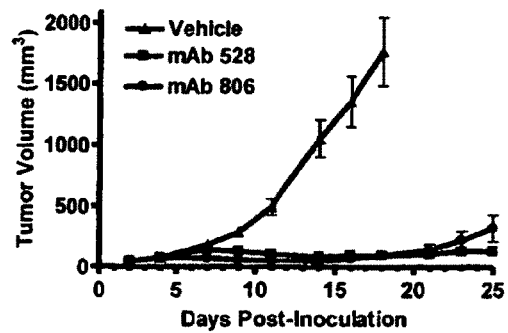

FIGURE 7
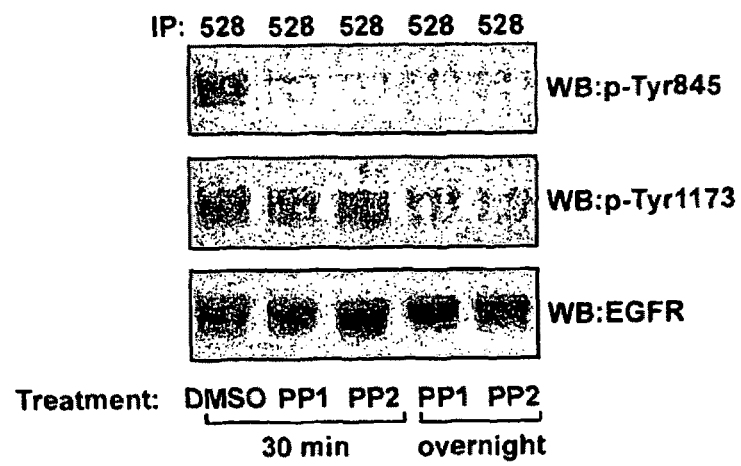
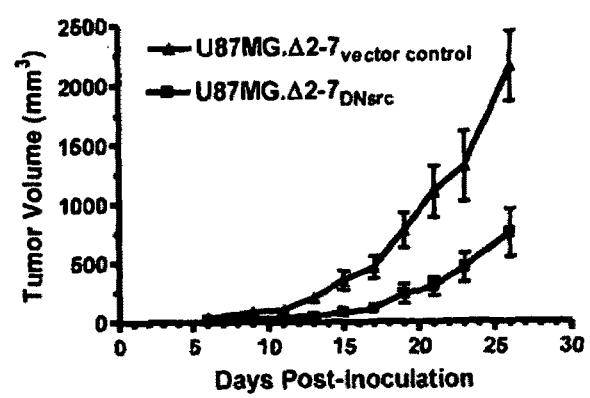
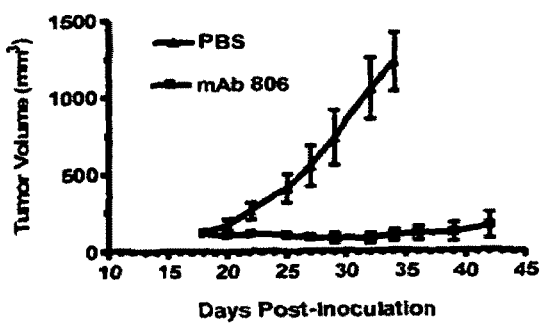

FIGURE 10
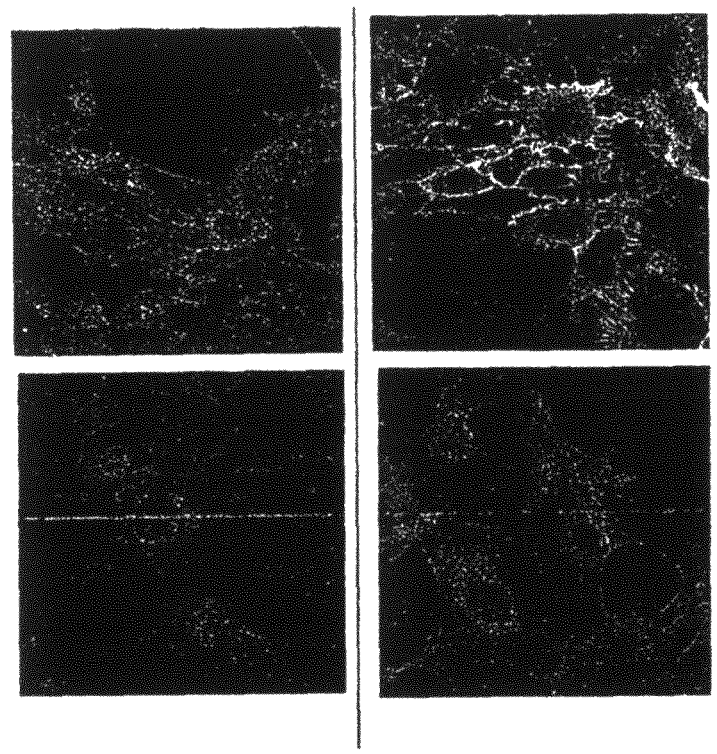
mAb 806
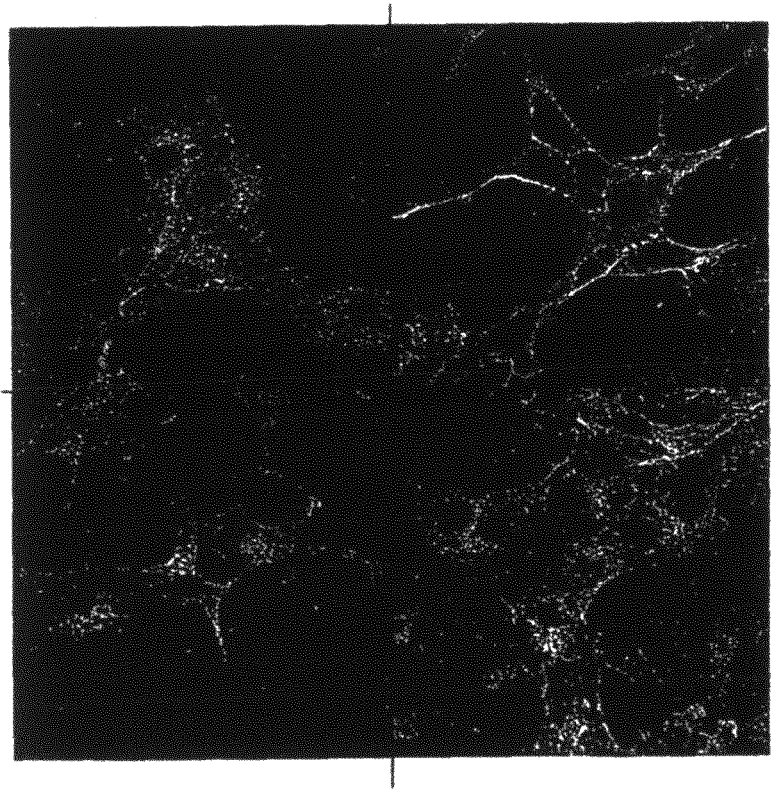
mAb 528

TREATMENT METHOD USING EGFR ANTIBODIES AND SRC INHIBITORS AND RELATED FORMULATIONS

CROSS-REFERENCE TO RELATED APPLICATIONS

The present application claims priority pursuant to 35 U.S.C. §119 to U.S. Provisional Patent Application Ser. No. 60/918,084, filed Mar. 15, 2007, which is incorporated herein by reference in its entirety.

FIELD OF THE INVENTION

The present invention relates to the treatment of EGFR-mediated disease, particularly cancer. Methods for treatment of cancer using combinations of EGFR modulators, particularly EGFR antibody(ies), and src inhibitors are provided. Methods and combinations of MAb806 antibody and src inhibitors are provided.

BACKGROUND OF THE INVENTION

Targeted cancer therapy is designed to disrupt the function of specific molecules needed for carcinogenesis and tumor growth and thus either kills or prevents the growth of cancer cells (Ji H et al (2006) Cell Cycle 5(18):2072-2076 Epub 2006 Sep. 15). In contrast to conventional cytotoxic chemotherapy, such targeted cancer therapies may be more effective and less harmful to normal cells. A main effort in the targeted cancer therapy field has been the development of agents that target the epidermal growth factor receptor (EGFR). EGFR is a member of the ErbB family of closely related receptors including EGFR (ErbB-1), Her2/neu (ErbB-2), Her3 (ErbB-3) and Her4 (ErbB-4). Activation of EGFR leads to receptor tyrosine kinase activation and a series of downstream signaling events that mediate cellular proliferation, motility, adhesion, invasion, and resistance to chemotherapy as well as inhibition of apoptosis, processes that are crucial to the continual proliferation and survival of cancer cells.

As expression of the EGFR vIII mutant receptor is restricted to tumor cells, it represents a highly specific target for antibody therapy. Accordingly, both polyclonal and monoclonal antibodies specific to the unique peptide of de2-7 EGFR have been generated. A series of mouse mAbs, isolated following immunization with the unique de2-7 peptide, all showed selectivity and specificity for the truncated receptor and targeted de2-7 EGFR positive xenografts grown in nude mice (Wikstrand C J et al (1995) Cancer Res 55:3140-3148; Okamoto, S et al (1996) Br J Cancer 73:1366-1372; Hills D et al (1995) Int J Cancer 63:537-543; Reist C J et al (1997) Cancer Res 57:1510-1515; Reist C J et al (1995) Cancer Res 55:4375-4382; U.S. Pat. No. 5,401,828). Examples of anti-EGFR vIII antibodies include ABX-EGF (panitumumab), DH8.3, L8A.4, and Y10.

MAb806 is a novel murine antibody, originally raised to recognize the unique truncation mutant, EGFRvIII using whole cells expressing EGFR vIII mutant as immunogen. Importantly, the epitope recognized by mAb806 is not accessible in inactive wild-type (wt) EGFR, but is exposed in a transitional form of wt EGFR in cells with overexpression of EGFR, and expression of EGFRvIII. MAb806 binds to an epitope present or available in the EGFRvIII/Δ2-7 EGFR mutant, but recognizes an epitope distinct from the mutant's junctional peptide LEEKKGNYVVTDH. The epitope studies are supported by immunohistochemical studies demonstrating that the 806 antibody binds to epitopes present in gliomas, as well as a broad range of epithelial cancers, but not to normal human tissues. These and other preclinical data suggest that mAb806 might have a different spectrum of clinical activity and side effect profile distinct from cetuximab and other anti-EGFR antibodies. In xenograft models, mAb806 has exhibited a potent anti-tumor activity with no targeting of normal tissues. Thus, the unique targeting capabilities of mAb806 represent a new paradigm for cancer-specific molecularly targeted therapy.

The non-receptor protein tyrosine, Src, is a 60-kDa protein that is a member of a nine-gene family, including Src, Yes, Fyn, Lyn, Lck, Hck, Fgr, Blk, and Yrk, that plays a critical role in the regulation of many cellular processes, such as proliferation, differentiation, migration, adhesion, invasion, angiogenesis, and immune function (Yeatman T J. (2004) Nat Rev Cancer 4(6):470-80; Frame M C. (2004) J Cell Sci 117:989-98). The Src family kinase contains a poorly conserved domain and three conserved Src homology domains: SH2, SH3, and SH1 or protein tyrosine kinase domain. Critical to the regulation of Src is a COOH-terminal tyrosine (Y530) that, when phosphorylated by C-terminal Src kinase (Csk), leads to a more inactive Src conformation. Src interacts with many proteins, depending on the input signal. It further assumes its active conformation through dephosphorylation of Y530 and autophosphorylation of Y418. Src also associates with structural and signaling proteins, and the resulting complexes are critical to Src's role in diverse cellular processes. Src has been reported to be overexpressed or aberrantly activated in a number of cancers, such as colon, breast, melanomas, ovarian cancer, gastric cancer, head and neck cancers, pancreatic cancer, lung cancer, brain cancers, and blood cancers (Dehm S M and Bonham K (2004) Biochem Cell Biol 2004; 82:263-74). There are several known small molecule inhibitors of src and some have entered clinical trials, for example dasatinib (BMS354825), AZD-0530, SKI-606, PP1 (4-Amino-5-(4-methylphenyl)-7-(t-butyl)pyrazolo[3,4-d]-pyrimidine), PP2 (4-chlorophenyl)-7-O-butyl)pyrazolo[3,4-d]-pyrimidine), PD166326.

There is a clinical need for enhanced, more efficacious and more broadly effective treatment protocols for EGFR-mediated disease including cancer.

The citation of references herein shall not be construed as an admission that such is prior art to the present invention.

SUMMARY OF THE INVENTION

The invention relates to the discovery that alteration of src expression or activity enhances the efficacy of anti-EGFR therapies. In particular alteration of src expression or activity dramatically enhances anti-EGFR antibody efficacy, particularly the activity of mAb806 antibody.

The invention relates to the combination of EGFR and src inhibitors for treatment of cancer or other EGFR-mediated disease.

The invention further provides a method of treating EGFR-mediated cancer in a mammal comprising administering to said mammal a src inhibitor and anti-EGFR antibody, either in combination, simultaneously, or in series, one after the other. In one aspect, the src inhibitor is a tyrosine kinase inhibitor. In one aspect, the anti-EGFR antibody is MAb806.

In a particular embodiment of the method the anti-EGFR antibody is mAb806 antibody or an active fragment thereof. MAb806 includes murine antibody, recombinant antibody or a humanized antibody.

The EGFR-mediated cancer may be selected from glioblastoma, head and neck cancer, pancreatic cancer, lung cancer, cancer of the nervous system, gastrointestinal cancer, prostate cancer, ovarian cancer, breast cancer, kidney cancer, retina cancer, skin cancer, liver cancer, genital-urinary cancer, and bladder cancer. The cancer may further be selected from colon, breast, melanomas, ovarian cancer, gastric cancer, pancreatic cancer, brain cancers, and blood cancers. In particular, the cancer may be glioma.

The invention provides a method of treating cancer in a mammal comprising administering to said mammal a src inhibitor and anti-EGFR antibody, wherein said src inhibitor and anti-EGFR antibody are administered simultaneously, in combination, or one after another series. In an aspect of the method, the anti-EGFR antibody is an antibody which recognizes an EGFR epitope which is found in tumorigenic, hyperproliferative or abnormal cells and not detectable in normal cells. In a particular such aspect, the anti-EGFR antibody is mAb806 or an active fragment thereof.

In the method(s), the src inhibitor may be selected from dasatinib (BMS354825), AZD-0530, SKI-606, PP1 (4-Amino-5-(4-methylphenyl)-7-(t-butyl)pyrazolo[3,4-d]-pyrimidine), PP2 (4-chlorophenyl)-7-(t-butyl)pyrazolo[3,4-d]-pyrimidine), and PD166326. In the method(s), the src inhibitor is particularly a tyrosine kinase inhibitor. In a particular embodiment of the method, the src inhibitor is dasatinib and the anti-EGFR antibody is mAb806.

The cancer may be selected from glioblastoma, head and neck cancer, pancreatic cancer, lung cancer, cancer of the nervous system, gastrointestinal cancer, prostate cancer, ovarian cancer, breast cancer, kidney cancer, retina cancer, skin cancer, liver cancer, genital-urinary cancer, bladder cancer, colon cancer, melanomas, gastric cancer, pancreatic cancer, brain cancers, and blood cancers.

The invention provides a method for blocking or reducing tumor growth of an EGFR-mediated cancer in a mammal comprising administering to said mammal a src inhibitor and anti-EGFR antibody, wherein said src inhibitor and anti-EGFR antibody are administered simultaneously, in combination, or one after another in series. In a particular such method, the anti-EGFR antibody is an antibody which recognizes an EGFR epitope which is found in tumorigenic, hyperproliferative or abnormal cells and not detectable in normal cells. The anti-EGFR antibody is particularly mAb806 or an active fragment(s) thereof.

The invention provides a method for blocking or reducing tumor growth of an EGFR-mediated cancer in a mammal comprising administering to said mammal a src inhibitor and anti-EGFR antibody, wherein the src inhibitor is dasatinib and the anti-EGFR antibody is mAb806.

The EGFR-mediated cancer may be selected from glioblastoma, head and neck cancer, pancreatic cancer, lung cancer, cancer of the nervous system, gastrointestinal cancer, prostate cancer, ovarian cancer, breast cancer, kidney cancer, retina cancer, skin cancer, liver cancer, genital-urinary cancer, and bladder cancer.

The invention further provides a method of enhancing the effectiveness or activity of an anti-EGFR antibody in a mammal comprising administering to said mammal a combination of the anti-EGFR antibody and a src inhibitor. The src inhibitor may be selected from dasatinib (BMS354825), AZD-0530, SKI-606, PP1 (4-Amino-5-(4-methylphenyl)-7-(t-butyl)pyrazolo[3,4-d]-pyrimidine), PP2 (4-chlorophenyl)-7-(t-butyl)pyrazolo[3,4-d]-pyrimidine), and PD166326. The anti-EGFR antibody is particularly an antibody which recognizes an EGFR epitope which is found in tumorigenic, hyperproliferative or abnormal cells and not detectable in normal cells. In a particular such aspect, the anti-EGFR antibody is mAb806.

The invention further relates to pharmaceutical composition(s) comprising an anti-EGFR antibody and one or more src inhibitor in a pharmaceutically acceptable carrier or diluent. The compositions included are compositions wherein the anti-EGFR antibody is an antibody which recognizes an EGFR epitope which is found in tumorigenic, hyperproliferative or abnormal cells and not detectable in normal cells. In a particular such composition, the anti-EGFR antibody is mAb806.

Other objects and advantages will become apparent to those skilled in the art from a review of the following description which proceeds with reference to the following illustrative drawings.

BRIEF DESCRIPTION OF THE DRAWINGS

FIG. 3. Xenograft growth curves for U87MG based cell lines. Xenografts were established by injection of $1 \times 10^6$ cells in both flanks of nude BALB/c mice in order to determine growth curves. Data are expressed as mean tumor volume±SE.

FIGS. 4A and 4B. In Vitro Phosphorylation of de2-7 EGFR Variants in U87MG.Δ2-7, U87MG.DK and U87MG.DY5 cells. A, the de2-7 EGFR protein was immunoprecipitated with mAb 806, mAb 528 or an irrelevant isotype matched control antibody and resulting samples immunoblotted. All de2-7 EGFR variants were positive for phosphorylation at Y1045, the major site associated with ubiquitination and degradation (top panel). While the de2-7 EGFR was constitutively phosphorylated at position Y1173, both the DK and DY5 variants were negative for phosphorylation at this site as expected (middle panel). The presence of EGFR was confirmed using the rabbit c-terminal polyclonal antibody to the EGFR (lower panel). This c-terminal antibody did not recognize the DY5 variant because it contains a Y1068F mutation, which turns out to be a critical residue for antibody binding. Thus, the presence of total DY5 protein was confirmed in (B) by immunoblotting with mAb 806.

FIG. 5A-5D. U87MG cells expressing high levels of de2-7 EGFR. U87MG.Δ2-7 cells were FACS sorted into low (L), medium (M) and high (H) expressing populations. A, Cells were lysed following 36 h of serum starvation and analyzed by immunoblotting for de2-7 expression (C13) and tyrosine phosphorylation (4G10) of the de2-7 EGFR. Levels of phosphorylation correlated with de2-7 EGFR. B, Parental U87MG, U87MG-L, U87MG-M and U87MG-H xenografts were established by injection of $1 \times 10^6$ cells in both flanks of nude BALB/c mice in order to determine growth curves. Data are expressed as mean tumor volume±SE. C, Tumors from (B) were analyzed by immunoblotting for expression of de2-7 EGFR(C13). D, Mice with U87MG-H xenografts were treated with 1 mg of mAb 528 or mAb 806 three times per week for two weeks (days 4, 6, 8, 11, 13 and 15). Data are expressed as mean tumor volume±SE.

FIG. 7A-7C. Interaction between de2-7 EGFR and Src. (A) Cells were serum starved overnight prior to treatment with 10 μM PP1 or PP2 or vehicle (DMSO) for 30 minutes or 24 h prior to immunoprecipitation with mAb528, mAb806 or an irrelevant isotype control. Immunoblotting was performed with an antibody specific for Y845 of the EGFR, while total de2-7 EGFR was visualized with the rabbit c-terminal polyclonal antibody. Results shown are representative of four independent experiments. (B) U87MG.Δ2-7$_{vector\ control}$ and U87MG.Δ2-7$_{DNSrc}$ xenografts were established by injection of 1×10⁶ cells in both flanks of nude BALB/c mice in order to determine growth curves. Data are expressed as mean tumor volume±SE. (C) U87MG.Δ2-7$_{DNSrc}$ xenografts were established by injection of 3×10⁶ cells in both flanks of nude BALB/c mice. Antibody therapy commenced when xenografts reached an approximate mean volume of 100 mm³. Mice were treated with 1 mg mAb 806 three times per week for two weeks (days 18, 20, 22, 25, 27 and 29). Data are expressed as mean tumor volume±SE.

FIG. 10. Internalization of mAb 806 and mAb 528 in NR6.Δ2-7 Cells. Cells were pre-incubated with mAb 806-Cy3 (left panel) or mAb 528-Cy3 (right panel) at 4° C. (0 min), prior to incubation at 37° C. for varying periods of time to induce internalization. Images representing 15, 30 and 60 mins incubation at 37° C. are shown. Staining with both antibodies prior to internalization was associated with membrane junctions between cells (blue arrowhead) and focal adhesions (red arrowhead), while some cells showed very little membrane staining (yellow arrowhead). Internalized antibody at later time points is indicated by white arrows. Scale bar=20 μm.

DETAILED DESCRIPTION

Figure 1:
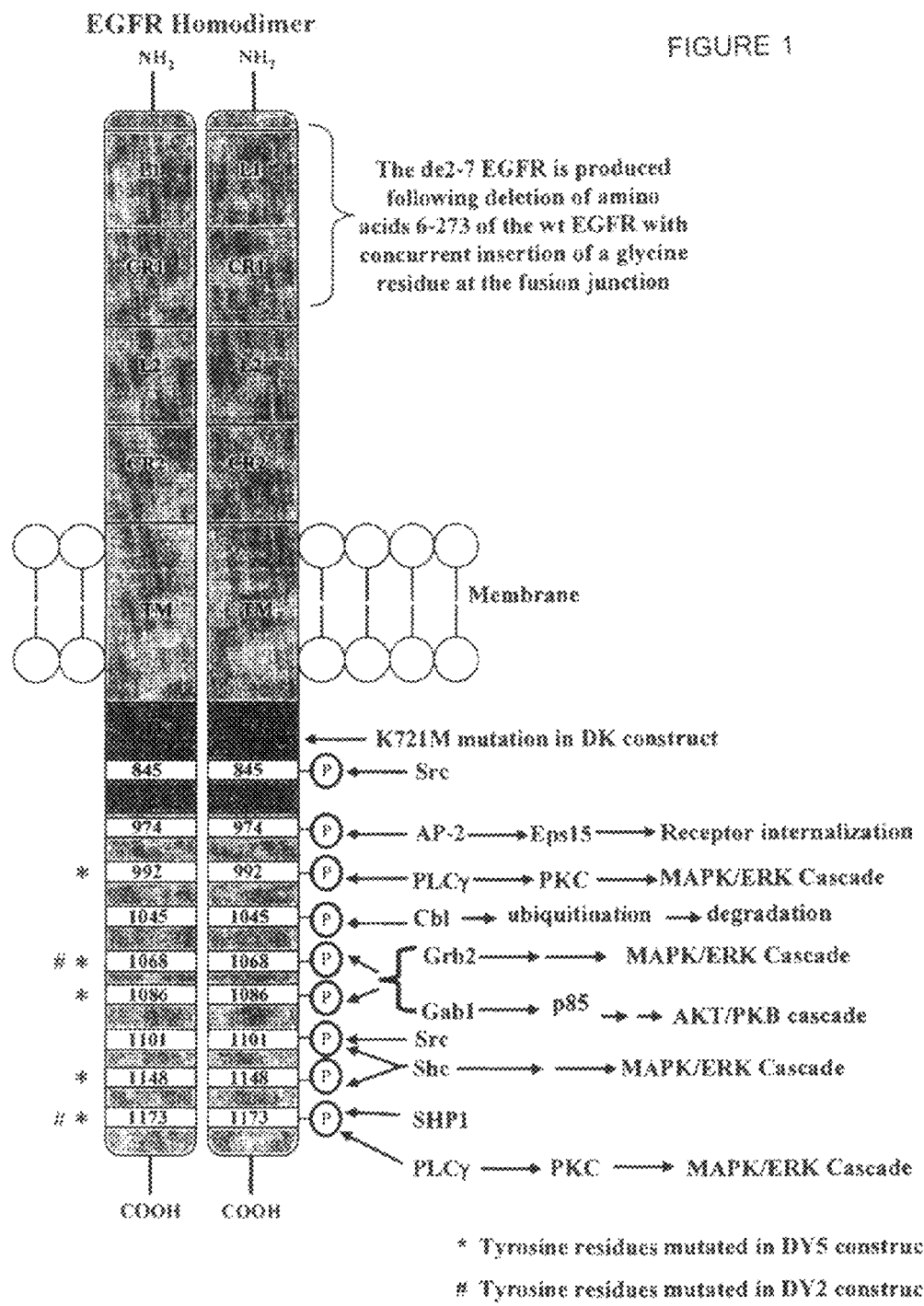
FIG. 1. Schematic representation of the EGFR. The extracellular region deleted in the de2-7 EGFR is identified by parenthesis. The dead kinase version of the de2-7 EGFR contains a single point mutation (K→M) at position 721. The DY2 version of the de2-7 EGFR has Y→F mutations at residues 1068 and 1173, while the DY5 variant also has these substitutions plus 992, 1086 and 1148.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The term "antibody" describes an immunoglobulin whether natural or partly or wholly synthetically produced. Antibody includes any immunoglobulin, including antibodies and fragments thereof, that binds a specific epitope. The term encompasses polyclonal, monoclonal, recombinant, humanized, and chimeric antibodies. The term also covers any polypeptide or protein having a binding domain which is, or is homologous to, an antibody binding domain. CDR grafted antibodies are also contemplated by this term.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) multivalent antibody fragments (scFv dimers, trimers and/or tetramers (Power and Hudson, J. Immunol. Methods 242: 193-204 9 (2000)) (ix) bispecific single chain Fv dimers (PCT/US92/09965) and (x) "diabodies", multivalent or multispecific fragments constructed by gene fusion (WO94/13804; P. Holliger et al Proc. Natl. Acad. Sci. USA 90 6444-6448, (1993)).

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-EGFR antibody, for instance antibody 528 (U.S. Pat. No. 4,943,533), the chimeric and humanized 225 antibody (U.S. Pat. No. 4,943,533 and WO/9640210), an anti-de2-7 antibody such as DH8.3 (Hills, D. et al (1995) Int. J. Cancer 63(4):537-543), antibody L8A4 and Y10 (Reist, C J et al (1995) Cancer Res. 55(19):4375-4382; Foulon C F et al. (2000) Cancer Res. 60(16):4453-4460), ICR62 (Modjtahedi H et al (1993) Cell Biophys. January-June; 22(1-3):129-46; Modjtahedi et al (2002) P.A.A.C.R. 55(14):3140-3148, or the antibody of Wikstrand et al (Wikstrand C. et al (1995) Cancer Res. 55(14):3140-3148). The other binding domain may be an antibody that recognizes or targets a particular cell type, as in a neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine (e.g. tumor necrosis factor (TNF), and particularly, the TNF bispecific modality demonstrated in U.S. Ser. No. 60/355,838 filed Feb. 13, 2002 incorporated herein in its entirety) or a toxin (e.g., ricin) or anti-mitotic or apoptotic agent or factor.

Fab and F(ab')$_2$ portions of antibody molecules may be prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptans with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

The terms "mAb806", "806 antibody", "monoclonal antibody 806", "ch806", "humanized 806" and any variants not specifically listed, may be used herein interchangeably, and as used throughout the present application and claims refer to Accordingly, antibodies, including recombinant, chimeric, genetically modified, or alternative antibodies, displaying substantially equivalent or altered activity are likewise contemplated. These modifications may be deliberate, for example, such as modifications obtained through site-directed mutagenesis, or may be accidental, such as those obtained through mutations in hosts that are producers of the antibody or its fragments. Also, the terms "mAb806", "806 antibody", "monoclonal antibody 806", "ch806", "humanized 806" are intended to include within their scope proteins and immunoglobulins specifically recited herein and known to the skilled artisan, publicly disclosed, as well as all substantially homologous analogs and allelic variations. The mAb806 antibody, including its generation, particular activities, amino acid and nucleic acid sequence, antigen binding domains, variable region sequences, are disclosed and known to the skilled artisan, including as provided in WO 02/092771; Luwor R B et al (2001) Cancer Res 61:5355-5361; Mishima K et al (2001) Cancer Res 61:5349-5354; Johns T G et al (2002) Int J Cancer 98:398-408; Jungbluth A A et al (2003) Proc Natl Acad Sci 100(2):639-644, each of which is incorporated by reference herein in its entirety.

It should be appreciated that also within the scope of compositions for use in the methods of the present invention are DNA sequences encoding and/or expressing effective anti-EGFR antibodies, particularly including mAb806 and ch806, which code for anti-EGFR antibodies, antigen binding domains thereof, or active fragments thereof having the same amino acid sequence as the mAb806 antibody as publicly disclosed and known to the skilled artisan, but which are degenerate to the known mAb806 sequence(s). By "degenerate to" is meant that a different three-letter codon is used to specify a particular amino acid.

The phrase "src inhibitor" contemplates and includes any modulator which reduces the expression or activity of src, reduces the phosphorylation of the src phosphorylated site, particularly on EGFR, or reduces the signal of the src kinase cascade. A modulator may include a chemical entity, peptide, antibody or other such agent, etc. A modulator may include a kinase inhibitor, phosphatase, etc.

There are several known small molecule inhibitors of src and some have entered clinical trials, for example dasatinib (BMS354825), AZD-0530, SKI-606, PP1 (4-Amino-5-(4-methylphenyl)-7-(t-butyl)pyrazolo[3,4-d]-pyrimidine), PP2 (4-chlorophenyl)-7-(t-butyl)pyrazolo[3,4-d]-pyrimidine), PD166326.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 20 percent, more preferably by at least 30 percent, still more preferably by at least 50 percent, more preferably by at least 70 percent, more preferably by at least 90 percent, a clinically significant change in the S phase activity of a target cellular mass, or a significant change in the size or dimensions of a target cellular mass or tumor, or other feature of pathology as may attend its presence and activity.

The antibody or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic antibody or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition desired or extent of tumor mass being targeted. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

As used herein, "pg" means picogram, "ng" means nanogram, "ug" or "µg" mean microgram, "mg" means milligram, "ul" or "µl" mean microliter, "ml" means milliliter, "l" means liter.

Thus, both therapeutic and diagnostic applications and methods are provided and raised by the demonstration of the anti tumor activity of anti-EGFR antibody, particularly of mAb806. As suggested earlier and elaborated further on herein, the present invention contemplates pharmaceutical intervention in the cascade of reactions and signaling in which EGFR is implicated, to modulate the tumorigenic capacity associated with EGFR mutations, including kinase domain mutations, both primary and secondary resistant mutations.

The invention further provides a method of treating EGFR-mediated cancer in a mammal comprising administering to said mammal a src inhibitor and anti-EGFR antibody. In one aspect, the src inhibitor and anti-EGFR antibody are administered simultaneously. In one aspect, the src inhibitor and anti-EGFR antibody are administered simultaneously or serially and repeatedly, before or after traditional chemotherapy.

The anti-EGFR antibody, particularly mAb806 may be administered in the methods alone or in combination with other anti-EGFR antibodies. MAb806 may also be administered serially or in combination with other anti-EGFR vIII antibodies, including cetuximab, ABX-EGF (panitumumab), DH8.3, L8A4, and or active fragments thereof. The src inhibitor may be administered in the methods alone or in combination with one or more anti-EGFR antibody(ies) and optionally one or more src inhibitor may be administered.

The anti-EGFR antibody(ies) may be prepared in pharmaceutical compositions, with a suitable carrier and at a strength effective for administration by various means to a patient. A variety of administrative techniques may be utilized, among them parenteral techniques such as subcutaneous, intravenous and intraperitoneal injections, catheterizations and the like. Quantities of the antibody or their active fragments may vary and in particular should be based upon the recommendations and prescription of a qualified physician or veterinarian, including upon consideration of the results and data provided herein.

The src inhibitor(s) may be prepared in pharmaceutical compositions, with a suitable carrier and at a strength effective for administration by various means to a patient. A variety of administrative techniques may be utilized, among them parenteral techniques such as subcutaneous, intramuscular, intravenous and intraperitoneal injections, catheterizations and the like and/or oral administration or transdermal administration or application. Quantities of the src inhibitor(s) may vary and in particular should be based upon the recommendations and prescription of a qualified physician or veterinarian, including upon consideration of the results and data provided herein. Pharmaceutical compositions which are combinations of one or more anti-EGFR antibody(ies) and one or more src inhibitor(s) may also be prepared suitably for administration.

Antibodies of the invention may be labeled with a detectable or functional label. Detectable labels include, but are not limited to, radiolabels such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{121}I$, $^{124}I$, $^{125}I$, $^{131}I$, $^{111}In$, $^{211}At$, $^{198}Au$, $^{67}Cu$, $^{225}Ac$, $^{213}Bi$, $^{99}Tc$ and $^{186}Re$, which may be attached to antibodies of the invention using conventional chemistry known in the art of antibody imaging. Labels also include fluorescent labels and labels used conventionally in the art for MRI-CT imagine. They also include enzyme labels such as horseradish peroxidase. Labels further include chemical moieties such as biotin which may be detected via binding to a specific cognate detectable moiety, e.g. labeled avidin.

Functional labels include substances which are designed to be targeted to the site of a tumor to cause destruction of tumor tissue. Such functional labels include cytotoxic drugs such as 5-fluorouracil or ricin and enzymes such as bacterial carboxypeptidase or nitroreductase, which are capable of converting prodrugs into active drugs at the site of a tumor.

The radiolabeled anti-EGFR antibodies and fragments thereof, are useful in in vitro diagnostics techniques and in in vivo radioimaging techniques and in radioimmunotherapy. In the instance of in vivo imaging, the specific binding members of the present invention may be conjugated to an imaging agent rather than a radioisotope(s), including but not limited to a magnetic resonance image enhancing agent, wherein for instance an antibody molecule is loaded with a large number of paramagnetic ions through chelating groups. Examples of chelating groups include EDTA, porphyrins, polyamines crown ethers and polyoximes. Examples of paramagnetic ions include gadolinium, iron, manganese, rhenium, europium, lanthanum, holmium and ferbium. In a further aspect of the invention, radiolabelled specific binding members, particularly antibodies and fragments thereof, particularly radioimmunoconjugates, are useful in radioimmunotherapy, particularly as radiolabelled antibodies for cancer therapy. In a still further aspect, the radiolabelled specific binding members, particularly antibodies and fragments thereof, are useful in radioimmunoguided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the specific binding members, particularly antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

Radioimmunotherapy (RAIT) has entered the clinic and demonstrated efficacy using various antibody immunoconjugates. $^{131}I$ labeled humanized anti-carcinoembryonic antigen (anti-CEA) antibody hMN-14 has been evaluated in colorectal cancer (Behr T M et al (2002) Cancer 94(4Suppl):1373-81) and the same antibody with $^{90}Y$ label has been assessed in medullary thyroid carcinoma (Stein R et al (2002) Cancer 94(1):51-61). Radioimmunotherapy using monoclonal antibodies has also been assessed and reported for non-Hodgkin's lymphoma and pancreatic cancer (Goldenberg D M (2001) Crit Rev Oncol Hematol 39(1-2):195-201; Gold D V et al (2001) Crit Rev Oncol Hematol 39 (1-2) 147-54). Radioimmunotherapy methods with particular antibodies are also described in U.S. Pat. Nos. 6,306,393 and 6,331,175. Radioimmunoguided surgery (RIGS) has also entered the clinic and demonstrated efficacy and usefulness, including using anti-CEA antibodies and antibodies directed against tumor-associated antigens (Kim J C et al (2002) Int J Cancer 97(4):542-7; Schneebaum S et al (2001) World J Surg 25(12): 1495-8; Avital S et al (2000) Cancer 89(8):1692-8; McIntosh D G et al (1997) Cancer Biother Radiopharm 12 (4):287-94).

Antibodies of the present invention may be administered to a patient in need of treatment via any suitable route, usually by injection into the bloodstream or CSF, or directly into the site of the tumor. The precise dose will depend upon a number of factors, including whether the antibody is for diagnosis or for treatment, the size and location of the tumor, the precise nature of the antibody (whether whole antibody, fragment, diabody, etc), and the nature of the detectable or functional label attached to the antibody. Where a radionuclide is used for therapy, a suitable maximum single dose is about 45 $mCi/m^2$, to a maximum of about 250 $mCi/m^2$. Preferable dosage is in the range of 15 to 40 mCi, with a further preferred dosage range of 20 to 30 mCi, or 10 to 30 mCi. Such therapy may require bone marrow or stem cell replacement. A typical antibody dose for either tumor imaging or tumor treatment will be in the range of from 0.5 to 40 mg, preferably from 1 to 4 mg of antibody in F(ab')2 form. Naked antibodies are preferable administered in doses of 20 to 1000 mg protein per dose, or 20 to 500 mg protein per dose, or 20 to 100 mg protein per dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. The dosage and administration of the src inhibitor(s) may be determined and varied by a physician or other individual skilled in the art.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

The Efficacy of EGFR-Specific Antibodies is Enhanced Upon SRC Inactivation or Inhibition Factors affecting the efficacy of therapeutic monoclonal antibodies (mAbs) directed to the EGFR remain relatively unknown, especially in glioma. The efficacy of two EGFR-specific mAbs was examined (mAb 806 and 528) against U87MG derived glioma xenografts expressing EGFR variants. Using this approach permitted the change of the form of the EGFR while keeping the genetic background constant. These variants included the de2-7 EGFR (or EGFRvIII), a constitutively active mutation of the EGFR expressed in glioma.

The efficacy of the mAbs correlated with EGFR number, however the most important factor was receptor activation. While U87MG xenografts expressing the de2-7 EGFR responded to therapy, those exhibiting a dead kinase de2-7 EGFR were refractory. A modified de2-7 EGFR that was kinase active but autophosphorylation deficient also responded, suggesting that these mAbs function in de2-7 EGFR expressing xenografts by blocking trans-phosphorylation. Since de2-7 EGFR expressing U87MG xenografts co-express the wt EGFR, efficacy of the mAbs was also tested against NR6 xenografts that expressed the de2-7 EGFR in isolation. While mAb 806 displayed anti-tumor activity against NR6 xenografts, mAb 528 therapy was ineffective, suggesting that mAb 528 mediates its anti-tumor activity by disrupting interactions between the de2-7 and wt EGFR.

Finally, genetic disruption of Src in U87MG xenografts expressing the de2-7 EGFR dramatically enhanced mAb 806 efficacy. The effective use of EGFR-specific antibodies in glioma will depend on identifying tumors with activated EGFR. The combination of EGFR and Src inhibitors provides a new and effective strategy for the treatment of glioma.

Background

The epidermal growth factor receptor (EGFR) is a transmembrane glycoprotein with intrinsic tyrosine kinase activity. Over-expression of the EGFR is observed in numerous epithelial tumors and is often associated with a poorer clinical prognosis (1-3). Over-expression of the EGFR can result from EGFR gene amplification, particularly in glioma (4). In glioma, gene amplification is associated with EGFR rearrangements with the most common mutation, the de2-7 EGFR (or EGFRvIII), characterized by an in-frame deletion of 801 base pairs spanning exons 2 to 7 of the coding sequence (4-6). This rearrangement results in the deletion of 267 amino acids from the extracellular domain and the insertion of a novel glycine at the fusion site, all of which produces a unique junctional peptide. While the de2-7 EGFR is unable to bind any known ligand, the receptor displays a low level of constitutive activation and is able to enhance the growth of glioma and breast cancer xenografts (7, 8).

Inhibition of the EGFR is a rational strategy for the development of new cancer therapeutics. Potential therapeutics include monoclonal antibodies (mAbs) directed to the EGFR (e.g. C225, ABX-EGF, EMD 55900) (9-11) and small molecular weight tyrosine kinase inhibitors (TKI's) of the EGFR (e.g. ZD1839, OSI 774) (12). Indeed, some of these therapeutics have been approved for limited clinical use in lung cancer (ZD1839, Iressa) and colon cancer (C225, Erbitux). From these clinical trials it is abundantly clear that not all patients positive for the EGFR respond to these targeted therapeutics (Table 1). Determining factors that cause patients to be susceptible to EGFR therapeutics is an important goal from a patient welfare and economic point of view. Likewise, understanding the nature of resistance to EGFR therapeutics may help identify approaches for overcoming it.

TABLE 1

Cellular aspects associated with susceptibility to EGFR therapeutics.

| EGFR Inhibitor | Experimental System | Observation | Comment | Ref(s) |
|---|---|---|---|---|
| PD153035 | Multiple cell lines in vitro | Sensitivity correlated with wt EGFR number | no in vivo data | (32) |
| C225 | Renal cell carcinomas in vitro | Only cells containing the VHL gene were sensitive | no in vivo data | (33) |
| EMD55900 and EMD72000 | Multiple cell lines in vitro and xenografts | Sensitivity correlated with wt EGFR number | | (34) |
| SU1195 and ZD1839 | Multiple cell lines in vitro and xenografts | More difficult to inhibit the phosphorylation of EGFR in the presence of ErbB2 | | (35) |
| mAbR3 and C225 | A431 xenografts | Recurrent xenografts following complete regression were often resistant to further therapy | Over-expression of VEGF was a common observation in resistant cell lines | (36) |
| ZD1839 | A431 and NR6M (express the de2-7 EGFR) xenografts | Xenografts expressing the de2-7 EGFR were resistant | NR6M express the de2-7 EGFR in the absence of the wt EGFR, clinically both are co-expressed | (37) |
| AG1478 | Glioma cell lines in vitro | Resistant glioma expresses IGFR-1 which is further up-regulated by AG1478. IGFR-1 effect appears mediated through P13-K/Akt | Observation restricted to a single cell line in vitro | (38) |
| CGP59326 | BT474 breast and MKN7 gastric cancer cells in vitro | Activation of erbB2/3 heterodimers by heregulin generated resistance | no in vivo data | (39) |
| ZD1839 | Multiple cell lines in vitro | Sensitivity correlated with wt EGFR number. Constitutive active MAPK increased resistance. | no in vivo data | (40) |
| AG1478 | Large cell panel in vitro | Two requirements for sensitivity: high wt EGFR and ability to respond to EGF by entering cell cycle. | no in vivo data | (41) |
| ZD1839 and PD153035 | Multiple cell lines in vitro | Sustained signaling through Akt or Erk may cause resistance. | no in vivo data | (42) |

TABLE 1-continued

Cellular aspects associated with susceptibility to EGFR therapeutics.

| EGFR Inhibitor | Experimental System | Observation | Comment | Ref(s) |
| --- | --- | --- | --- | --- |
| ZD1839 | A431 and MDA-468 breast cancer cells in vitro | Sustained signaling through Akt causes resistance. Presence of PTEN increases effectiveness of EGFR therapeutics. | no in vivo data | (43) |
| ZD1839 and C225 | A431 and multiple NSCLC in vitro | No correlation with EGFR number. | no in vivo data | (44) |
| ZD1839 | Patients with NSCLC | Patients with activating mutations in the EGFR kinase domain more likely to respond. | Subsequent data suggests that not all patients with mutations respond | (28, 45) |
| ZD1839 | NR6 fibroblasts and U87MG glioma cells | Cells expressing the de2-7 EGFR were resistant, possibly related to an inability to fully inhibit de2-7 EGFR phosphorylation. | no in vivo data | (46) |
| OSI-774 | Panel of glioma cell lines | Cells capable of increasing the mRNA for EGFR in response to therapy are more resistant. | | (47) |
| ZD1839 and OSI-774 | Patients with NSCLC | A secondary mutation in EGFR kinase causes resistance | | (48) |
| C225 and ABX | Patients with colorectal cancer | Response correlated with increase in EGFR copy number | Small sample numbers | (26) |
| OSI-774 and ZD1839 | Patients with glioma | Co-expression of EGFRvIII and PTEN is associated with responsiveness | | (49) |

Mechanisms causing resistance/susceptibility to EGFR targeted TKI's have been studied extensively, whereas factors affecting the efficacy anti-EGFR antibodies remains relatively unknown (see Table 1). A few generalizations can be drawn from these studies with respect to TKI's. Firstly, the sensitivity of cell lines to inhibition by TKI's correlates with increasing cell surface EGFR (Table 1), suggesting that there is some intrinsic level of EGFR expression required for these inhibitors to function. Secondly, the ability to sustain signalling through the PI3-kinase/Akt pathway following EGFR inactivation reduces the efficacy of TKI's (Table 1). The overwhelming number of these studies has been done in vitro, thus it is not known if these observations hold true in the in vivo setting. Recently a number of studies have analysed the status of the EGFR gene in lung cancer patients treated with Iressa (ZD1839) and found that patients who responded to therapy often had gain of function mutations in the kinase domain (Table 1). Furthermore a secondary kinase mutation that leads to Iressa resistance has also been described (Table 1). Initial studies suggest however that these observations are not general and that the mutations described in lung patients are not observed in other tumor types.

The limited number of studies using anti-EGFR antibodies makes it difficult to derive any generalizations regarding susceptibility to these agents (Table 1). Apart from the lack of in vivo studies, many of these susceptibility studies have been done using cell panels which, given the variation in signalling pathways between cells lines and the presence or absence of other ErbB family members, makes it difficult to identify single factors associated with EGFR sensitivity or resistance. In order to address some of these issues we tested the in vivo susceptibility of the U87MG glioma cell line, which expresses modest levels of the wild type (wt) EGFR, to two EGFR-specific antibodies. We then transfected U87MG cells with a variety of wt and de2-7 EGFR constructs to determine what effect receptor number and activation has on susceptibility to antibody therapy.

The two antibodies used in this study are mAb 806 and 528. MAb 806 is a novel anti-EGFR specific antibody that was raised against cells expressing the de2-7 EGFR (13). Interestingly, while mAb 806 clearly binds the de2-7 EGFR, it also binds to a subset of the wt EGFR (~10%) expressed on the surface of cells over-expressing the receptor (13). Recent analysis showed that the mAb 806 epitope is only exposed in a conformational form of the EGFR that exists transiently as the receptor moves from its inactive to active state (14). Unlike the wt EGFR, the de2-7 EGFR is constitutively in this transitional conformation and thus available for mAb 806 binding. Our previous studies have shown that treatment of xenografts which express the de2-7 or over-express the wt EGFR with mAb 806 causes significant inhibition of tumor growth (15-17). The 528 antibody was produced and isolated at the same time as the murine version of the C225 antibody (Erbitux) and displays very similar properties (18). MAb 528 acts as a ligand antagonist and inhibits the growth of EGFR expressing cells both in vitro and in vivo when grown as xenografts (18).

Materials And Methods

Cell Lines and Monoclonal Antibodies.

The U87MG transfected cell lines U87MG.Δ2-7, U87MG.DK, U87MG.wt, U87MG.DY5 and U87MG.DY2 have been described in detail elsewhere (16, 19). The A431 cell line has also been described previously (20). All cell lines were maintained in either DMEM (DMEM/F12; Life Technologies, Inc, Grand Island, N.Y.) or RPMI containing 10% FCS (CSL, Melbourne, Victoria, Australia), 2 mM glutamine (Sigma Chemical Co, St. Louis, Mo.), and penicillin/streptomycin (Life Technologies, Inc, Grand Island, N.Y.). In addition, transfected cell lines were maintained in 400 mg/ml of Geneticin (Life Technologies, Inc, Melbourne, Victoria, Australia).

The mAb 806 and 528 were produced and purified in the Biological Production Facility (Ludwig Institute for Cancer Research, Melbourne, Australia). Antibodies to the specific tyrosine phosphorylation sites of the EGFR and a rabbit polyclonal anti-EGFR antibody were obtained from Cell Signaling Technology (Danvers, Mass.). Src was detected using the mouse monoclonal antibodies v-Src 327 (Oncogene Research Products, CA, USA) or c-Src H-12 (Santa Cruz Biotechnology, Inc, CA, USA). The rabbit polyclonal antibody PY418 (BioSource International, Inc., CA, USA) was used for the detection of phospho-Src. The anti-phosphotyrosine antibody 4G10 was purchased from Upstate Biotechnology, (Lake Placid, N.Y.). The C13 used for detection of both wild-type and truncated EGFR was obtained from BD Transduction Laboratory (San Diego, Calif.).

Generation of U87MG.$\Delta$2-7$_{DNSrc}$ Cell Line.

A dominant negative (DN), kinase dead Src construct (K296R/Y528F) was obtained from Upstate Biotechnology (Lake Placid, N.Y., USA). A Hind III fragment containing the DNSrc was sub-cloned into the pcDNA3.1/Hygro(+) vector obtained from Invitrogen Life Technologies (Carlsbad, Calif.) and the resulting construct transfected into U87MG.$\Delta$2-7 cells b electroporation. A second cell line transfected with the pcDNA3.1/Hygro vector alone was also generated. Cells were plated out in 1 ml aliquots into 96 well plates, at a density of approximately $2 \times 10^4$ cells per well, and incubated at 37° C. for 48 hours after which 100 µg/ml hygromycin (Roche Diagnostics, Mannheim, Germany) was added. Once clones were obtained (approximately two weeks) cells were placed back in 400 µg/ml Geneticin as well as the hygromycin.

Transfected cells were initially screened by FACS analysis to confirm that expression of the de2-7 EGFR had been retained. Clones were then subjected to either whole cell lysis or immunoprecipitation prior to western blotting using Src specific antibodies (v-Src 327, c-Src H-12). Several clones showing dramatically increased levels of total Src (Src levels are very low in the original cell line) were identified and expanded. The increased Src levels were further confirmed by immunoprecipitating $^{35}$S-labelled cell lysates with the v-Src 327 antibody and subjecting the resulting precipitates to SDS-PAGE and quantitative autoradiography. The clone expressing the highest levels of DNSrc was selected and the DNSrc was shown to be phosphorylated at position Y418 suggesting that it is correctly folded.

In Vitro Growth Assays.

The anti-proliferative effect of mAb 806 and 528 in vitro was examined as described in detail previously (18). Briefly, cells were seeded at $1 \times 10^4$ cells per well in 24 well plates in media containing 0.5% FCS. After 4 days cells were removed with trypsin and counted using a haemocytometer. Antibodies were used at a final concentration of 100 µg/ml, a concentration consistent with that obtained within xenografts.

Xenograft Models.

Tumor cells ($3 \times 10^6$) in 100 µl of PBS were inoculated s.c. into both flanks of 4-6 week old, female nude mice (Animal Research Centre, Perth, Australia). All studies were conducted using established tumor models as previously reported (15, 16). Treatment commenced once tumors had reached a mean volume a mean volume of approximately 100 mm$^3$.

Tumor volume in mm$^3$ was determined using the formula (length×width$^2$)/2, where length was the longest axis and width being the measurement at right angles to the length. Data are expressed as mean tumor volume±SE for each treatment group. All data was analyzed for significance by Student's t test. A minimum of 10 xenografts per group were used in each study.

Immunoblotting.

Cells were lysed in cold lysis buffer (30 mM HEPES, 150 mM NaCl, 10 mM NaF, 1% Triton X-100, 200 µM NaO$_3$V, 0.4% H$_2$O$_2$ and the protease inhibitor cocktail set 1 (Calbiochem, San Diego, Calif.) containing 500 µM AEBSF, 150 nM Aprotinin, 1 µM E-64 protease inhibitor, 0.5 mM EDTA and 1 µM Leupeptin, pH 7.4). Lysates were immunoprecipitated with the mAb 806 or 528 and the resultant precipitates analyzed by immunoblotting as described by us in detail (21).

Immunofluorescence Microscopy.

MAbs 806 and 528 were directly labelled with Cyanine 3 (Cy3) dye using the Cy3 Monoclonal Antibody Labeling kit (Amersham Pharmacia Biotech UK Ltd, Buckinghamshire, England) according to the manufacturer's instructions. Successful labeling of antibody was determined via flow cytometry analysis of binding to U87MG.$\Delta$2-7 cells. The early endosome specific, anti-mouse Early Endosome Autoantigen 1 (EEA1) monoclonal antibody was purchased from Transduction Laboratories (San Diego, Calif., U.S.A.). Cyt conjugated AffiniPure F(ab')$_2$ fragment donkey anti-mouse IgG secondary antibody and unlabeled AffiniPure Fab fragment goat anti-mouse IgG blocking antibody were purchased from Jackson ImmunoResearch Laboratories (West Grove, Pa., U.S.A.). U87MG.$\beta$2-7 or NR6.$\Delta$2-7 cells were grown on 12 mm glass coverslips or 12 mm Biocoat Cell Environments Poly-D-Lysine coverslips (Becton Dickinson labware, Bedford, Mass., U.S.A.) in MEM (GibcoBRL Grand Island, N.Y., U.S.A.) supplemented with 10% FBS, penicillin/streptomycin, and glutamate at 37° C. Antibody binding to cells was carried out in the presence of 0.25% bovine serum albumin (BSA) (Sigma Chemical Co., St Louis, Mo., U.S.A.). Cy3-conjugated mAb 806 and 528 were used at concentrations of 5 µg/ml and 2 µg/ml respectively and surface labeling was carried out at 4° C. for 20 mM under humidified conditions. Cells were washed in ice cold 0.25% Bovine Serum Albumin (BSA)/PBS three times. Internalization of surface bound antibody was initiated by incubation of individual coverslips at 37° C. Following internalization for varying periods of time, individual coverslips were removed from 37° C., washed three times in ice cold BSA/PBS to stop internalization and fixed in 4% PFA for 20 mins at RT. Coverslips were then washed in BSA/PBS prior to washing in double distilled water (DDW) and mounted onto glass slides with fluoromount G mounting medium (Southern Biotechnology, Birmingham, Ala., U.S.A.). Samples were analyzed with confocal microscope (Nikon Instech Co., Ltd., Kanagawa, Japan) using appropriate wavelength settings. For co-localization studies, cells were permeabilized with 0.1% triton X-100 for 1 min. Samples were then washed and incubated with unlabelled goat anti-mouse Fab fragment to block all existing mouse binding sites (i.e. internalized mAb 806 or 528) for 20 min at RT. Samples were then washed in BSA/PBS prior to incubation with anti-EEA1 for 20 min at RT. Cells were finally washed and incubated with Cy2-conjugated secondary donkey anti-mouse F(ab')$_2$ antibody fragment. DNA vectors for green fluorescence protein (GFP)-tagged Lysosomal Glycoprotein 120 (lgp-120-GFP) was kindly provided by Professor Ira Mellman and Professor from the Department of Cell Biology, Yale University School of Medicine, New Haven, Conn., U.S.A. Cells grown in mat-tek glass bottom microwell dishes containing an embedded 14 mm glass coverslip (Mat-Tek Corp. Ashland, Mass., U.S.A.), were transfected overnight using LipofectAMINE reagent (Invitrogen™ Life Technologies, Mulgrave, Vic, Australia) following the manufacturer's instructions. Confocal imaging of positively transfected cells, which fluoresced green when excited with 488 nm wavelength light, was undertaken 24 hrs after transfection.

Results

Correlation Between In Vitro and In Vivo Sensitivity.

Many of the studies described in Table 1 have been conducted in vitro. Our experience both with mAb and TKI targeted EGFR therapy clearly demonstrates that in vitro sensitivity and in vivo response do not reliably correlate. Indeed, we recently published an example where two cell lines showing similar sensitivity to the EGFR-specific TKI AG1478 in vitro, differed notably in their in vivo response to the same agent (22). Using a standard in vitro growth inhibition assay previously described for C225, and an antibody concentration consistent with that achieved at the xenograft site, we saw little correlation between antibody inhibition in vitro and in vivo anti-tumor activity (Table 2). Neither mAb 528 or 806 inhibited the growth of U87MG.Δ2-7 cells in vitro, but both antibodies display robust anti-tumor activity in vivo that was independent of immune effector function (see FIG. 2). Also, even if one EGFR-targeted antibody showed correlation in vitro and in vivo in a particular cell line (e.g. mAb 528 in A431 cells and xenografts, Table 2), this did not necessarily imply another EGFR-specific antibody will correlate in the same cell line (e.g. mAb 806 in A431 cells and xenografts, Table 2). This simple analysis along with our previous observations, clearly demonstrate the limited value of in vitro assays in determining sensitivity to EGFR therapeutics.

TABLE 2

In vitro and in vivo comparison of sensitivity to EGFR therapeutics

| | CELL LINE | | | |
|---|---|---|---|---|
| | U87MG.Δ2-7 | | A431 | |
| | mAb 528 | mAb 806 | mAb 528 | mAb 806 |
| In Vitro | − | − | + | − |
| In Vivo* | + | + | ++ | ++ |

*In vivo data for A431 xenografts is from our recent paper (16)

Antibody Therapy of U87MG Glioma Xenografts Expressing Different Forms of the EGFR.

Figure 2A:
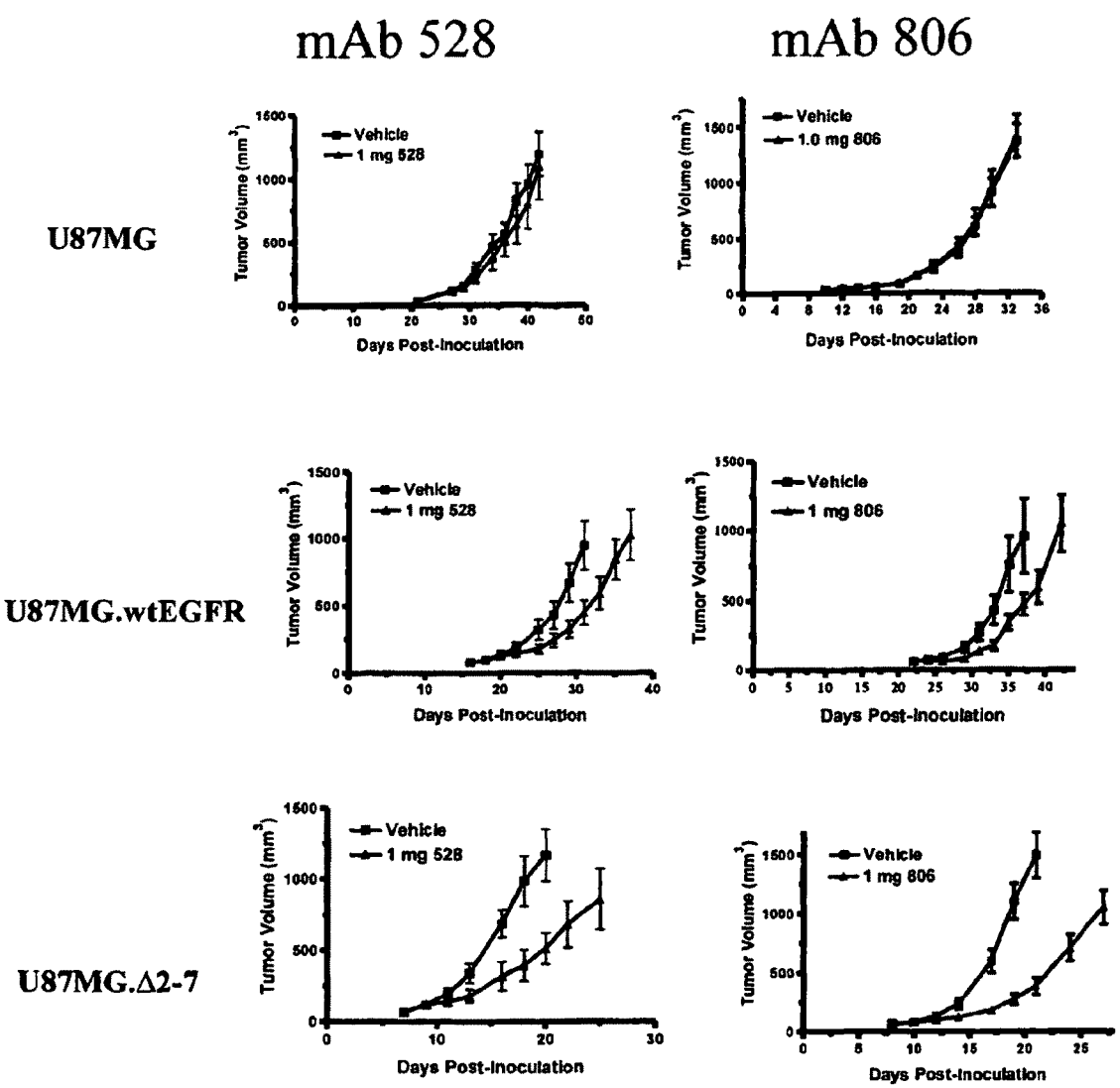
FIG. 2. Sensitivity of different xenografts to EGFR-specific antibodies. Xenografts were established by injection of $3 \times 10^6$ cells in both flanks of nude BALB/c mice. Antibody therapy commenced when xenografts reached an approximate mean volume of 100 mm$^3$. Mice were treated with 1 mg of mAb 528 (left panel) or mAb 806 (right panel) three times per week for two weeks (i.e. a total of 6 injections). Data are expressed as mean tumor volume±SE.
Figure 2B:
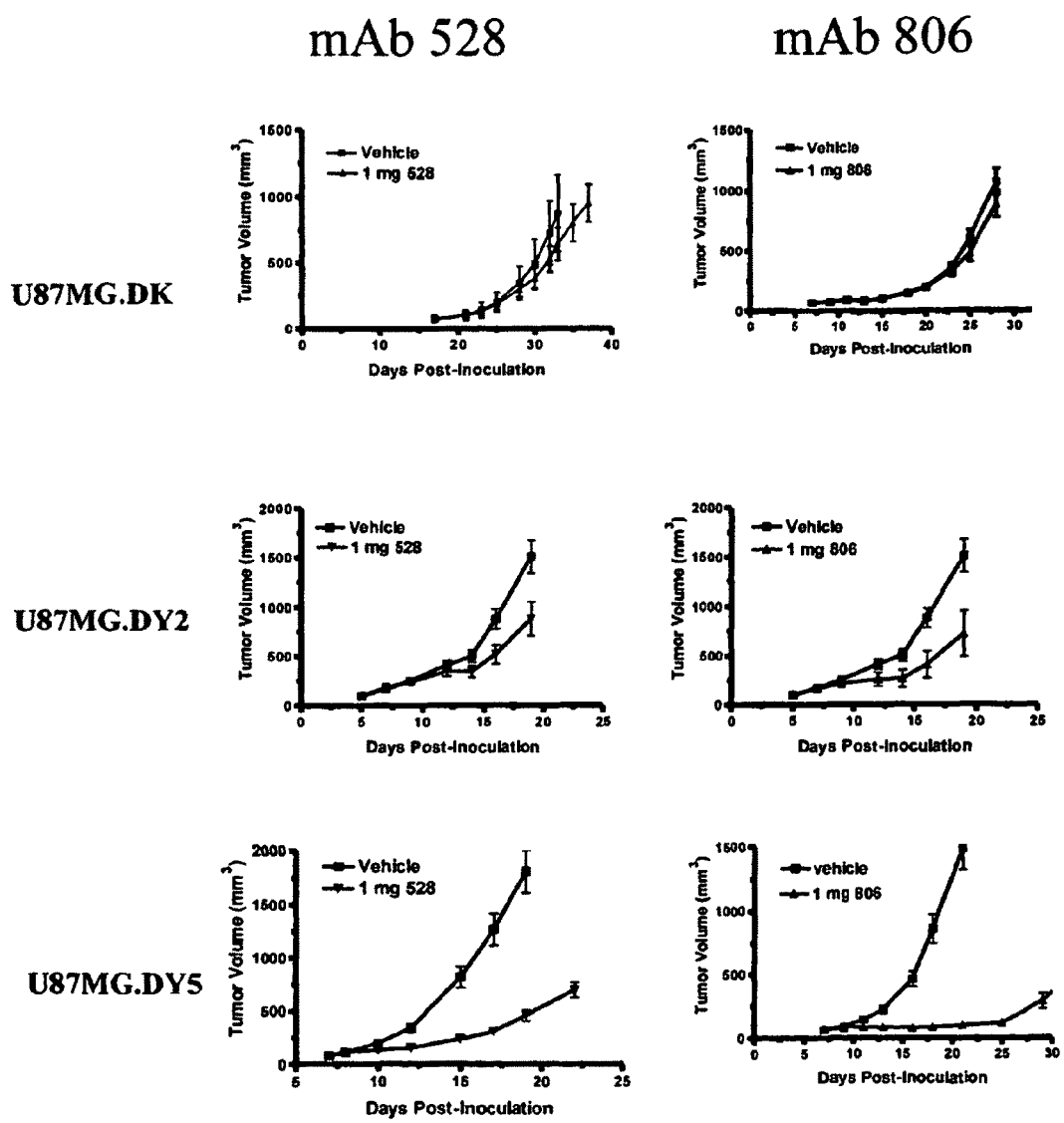

The parental U87MG cells, which express moderate levels of the wt EGFR, or the same cell line transfected with additional wt EGFR, the de2-7 EGFR or various modified forms of the de2-7 EGFR (FIG. 1) were injected s.c. into nude mice and allowed to establish as tumor xenografts. Treatment with antibody commenced once xenografts had reached approximately 100 mm$^3$. All tumors were treated with 1 mg of mAb 528 or 806 three times per week for 2 weeks. This dose and schedule of antibody treatment was chosen as it elicits a strong anti-tumor response in our standard U87MG.Δ2-7 xenograft model, but is not so efficacious that it would obscure any increased anti-tumor activity that might be seen in other U87MG-derived cell lines containing different variants of the EGFR. As discussed in detail below, the anti-tumor efficacy of mAb 806 and 528 was similar in all the U87MG derived glioma xenografts (FIG. 2).

1. Parental Cells (U87MG):

Neither antibody inhibited the growth of the U87MG xenografts despite the fact it expresses the EGFR at moderate levels (~5×10$^4$ receptors per cell) (13).

2. Cells Over-Expressing the Wt EGFR (U87MG.wt):

Transfection of U87MG cells with the wt EGFR to increase expression (approximately 1×10$^6$ receptors per cell) did not change the in vivo growth rate of the xenografts (FIG. 3A) but did cause the tumors to become sensitive to both antibodies. While this is not surprising for mAb 806, as it preferentially binds to cells over-expressing the wt EGFR, it was somewhat unexpected for mAb 528, as it suggests that even an increase in receptor number in the absence of a phenotypic change can induce a response to antibody therapy. On day 31, when the control group was sacrificed, the inhibition induced by mAb 528 was significant (p<0.01), with xenografts in the vehicle group having a mean tumor volume of 950 mm$^3$ compared with 450 mm$^3$ in the mAb 528 treatment group. Analysis of the mAb 806 experiment on day 39 showed that antibody treatment significantly inhibited xenograft growth (p<0.001) with tumors volumes being 960 mm$^3$ and 470 mm$^3$ for the PBS and mAb 806 groups respectively.

3. Cells Expressing the de2-7 EGFR (U87MG.Δ2-7):

The growth of U87MG xenografts transfected with the constitutively active, but ligand independent, de2-7 EGFR was also inhibited by both antibodies (FIG. 2). Unlike over-expression of the wt EGFR, co-expression of the de2-7 EGFR in the presence of endogenous wt EGFR, generates a significant growth advantage to U87MG xenografts (FIG. 3B). The constitutive phosphorylation of this receptor was confirmed by immunoblotting (FIG. 4). Treatment with mAb 528 significantly inhibited tumor growth (p<0.005) with the vehicle group having an average tumor volume of 1170 mm$^3$ compared to 510 mm$^3$ for the mAb 528 group at day 20 post-inoculation. Given that the primary function of mAb 528 has been presumed to be ligand antagonism, its anti-tumor activity against a xenograft expressing the ligand independent de2-7 EGFR was unexpected. Thus, mAb 528 probably disrupts EGFR signalling by other mechanisms apart from its ability to block ligand. Likewise, mAb 806, which only binds the de2-7 EGFR and not the wt EGFR in these cells, must mediate its anti-tumor activity independent of any effect on ligand interaction as it inhibited the growth of de2-7 EGFR expressing xenografts to a similar level as mAb 528. At day 21, when the vehicle group was culled, the control xenografts had a mean tumor volume of 1500 mm$^3$ compared to a significantly lower 390 mm$^2$ in the mAb 806 treated group (p<0.0001). Thus, both antibodies can inhibit glioma xenografts expressing a ligand-independent but constitutively active form of the EGFR.

4. Cells Expressing a Dead Kinase Version of the de2-7 EGFR (U87MG.DK):

U87MG cells transfected with a dead kinase (DK) version of the de2-7 EGFR grew as xenografts at a rate similar to parental cells (FIG. 3B) and were not significantly inhibited by either antibody (FIG. 2). This receptor lacks phosphorylation at the major sites associated with signalling but remains phosphorylated at sites associated with receptor internalization and degradation (FIG. 4). Binding of both antibodies to these cells is similar to that seen in de2-7 EGFR expressing cells both in vitro and in vivo (16). Furthermore, since the DK variant of the de2-7 EGFR only contains a single intracellular point mutation, the affinity of mAb 806 and 528, which bind the extracellular domain, should not be altered. This result demonstrates that any immune effector function mediated by these antibodies in vivo is insufficient to initiate an anti-tumor response. Furthermore, it shows that the anti-tumor activity of anti-EGFR antibodies require a receptor with a functional kinase domain.

5. Cells Expressing a Version of the de2-7 EGFR with Deletion of 2 Major Sites for Autophosphorylation (U87MG.DY2):

U87MG xenografts expressing a de2-7 EGFR construct unable to autophosphorylate at two major autophosphorylation sites (tyrosine 1068 and 1173 changed to phenylalanine) were significantly inhibited by both antibodies when grown as tumor xenografts (p<0.01 and 0.006 for mAb 528 and 806 respectively) (FIG. 2). This observation, combined with the lack of activity seen against the U87MG.DK xenografts, suggests that the kinase activity, as opposed to autophosphorylation, correlates with responsiveness to antibody therapy.

6. Cells Expressing a Version of the de2-7 EGFR Incapable of Autophosphorylation (U87MG.DY5):

U87MG cells expressing a de2-7 EGFR construct unable to autophosphorylate at all 5 major autophosphorylation sites associated with signaling (tyrosine 1173, 1148, 1086, 1068 and 992 changed to phenylalanine) were grown as tumor xenografts. This receptor lacks phosphorylation at the major sites associated with signaling but remains phosphorylated at sites associated with receptor internalization and degradation (FIG. 4). Consistent with the result obtained with DY2 xenografts, both antibodies significantly inhibited the growth of xenografts expressing the DY5 de2-7 EGFR construct (p<0.0001 for both antibodies) (FIG. 2). Given this somewhat unexpected result, we repeated this experiment with both antibodies, at a lower dose (0.5 versus 1 mg per injection), and once again obtained significant inhibition of tumor growth in both cases (data not shown). Since the DY5 form of the de2-7 EGFR is incapable of directly binding adapter molecules critical for downstream signaling, it suggests that an active kinase domain rather than the interaction with these molecules, is a critical feature that leads to responsiveness to EGFR-specific antibodies.

Treatment of U87MG Xenografts Expressing High Levels of the de2-7 EGFR.

The data in FIG. 2 suggests that the more dependent a xenograft becomes to EGFR signaling the more likely it is to respond to EGFR-specific antibody therapy. Therefore, using FACS sorting we isolated the cells expressing very high levels of the de2-7 EGFR (U87MG.Δ2-7$_{high}$) (FIG. 5A). U87MG.Δ2-7$_{high}$ xenografts grew faster than the original U87MG.Δ2-7 xenografts (FIG. 5B), suggesting that the rapid growth of these xenografts is reliant on the high levels of the de2-7 EGFR. The levels of de2-7 EGFR expression were retained in vivo as determined by immunoblotting of xenograft lysates (FIG. 5C). Treatment with mAb 806 or mAb 528 caused significant inhibition of U87MG.Δ2-7$_{high}$ xenografts that was greater than that observed for any other of the U87MG derived cell lines (FIG. 5D). On day 18, when the control group was sacrificed for ethical reasons, the mean tumor volume was 1760, 90 and 90 mm$^3$ for the vehicle, mAb 806 and mAb 528 groups respectively (p<0.001). Significantly, while there were no complete regressions in any of the previous U87MG-derived therapy studies (FIG. 2), 40% of the mAb 806 and 20% mAb 528 treated U87MG.Δ2-7$_{high}$ xenografts completely regressed. One of the mAb 806 tumors recurred at day 46 post-inoculation while other tumors had not recurred by day 126 when the mice were sacrificed. Thus, xenografts driven by the over-expression of a constitutively active form of the EGFR are more sensitive to EGFR-specific antibodies.

mAb 806 and 528 Therapy of Established NR6 Derived Xenografts.

Figure 6:
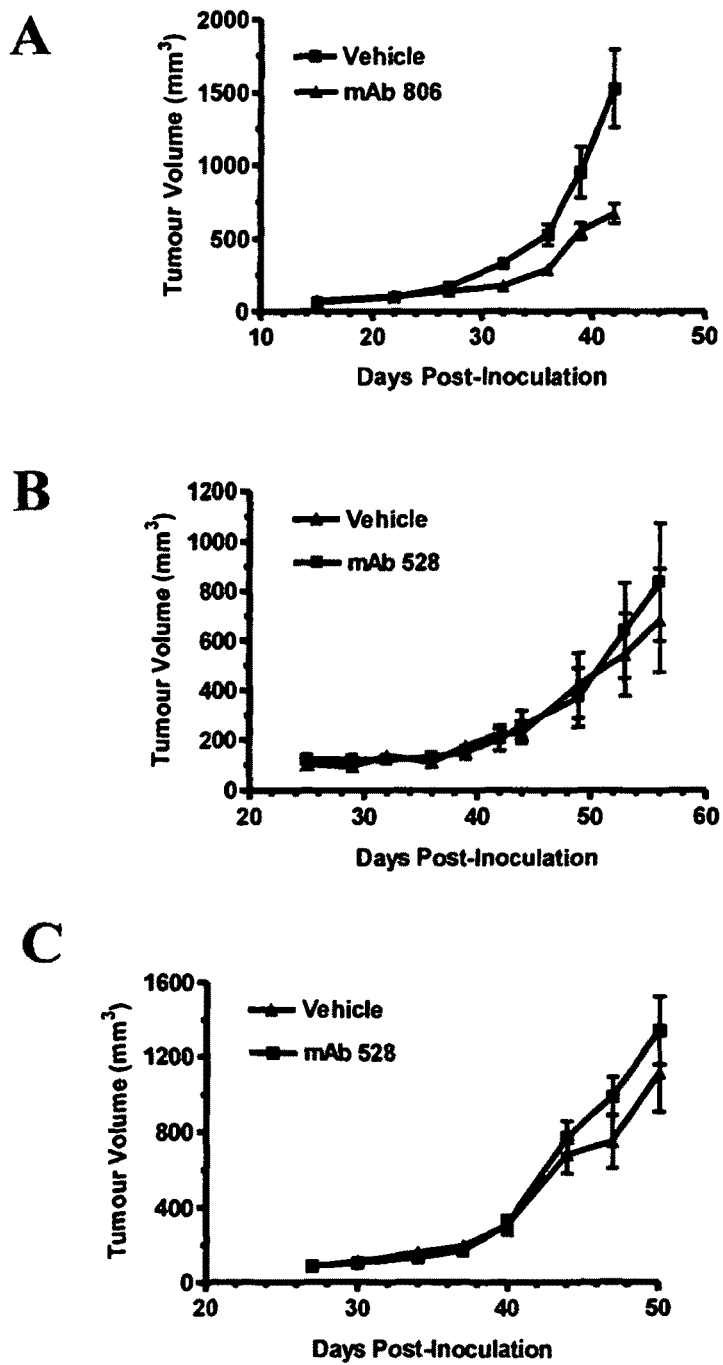
FIG. 6A-6C. Treatment of NR6.Δ2-7 xenografts with EGFR-specific antibodies. Xenografts were established by injection of 3×10⁶ cells in both flanks of nude BALB/c mice. Antibody therapy commenced when xenografts reached an approximate mean volume of 100 mm³. Mice were treated with 1 mg of mAb 806 (A) or mAb 528 (B) three times per week for two weeks (days 22, 25, 29, 32, 36 and 39) or with mAb 528 (C) two times per week for three weeks (days 27, 30, 34, 37, 41 and 44). Data are expressed as mean tumor volume±SE.

The NR6 murine fibroblastic cell line does not endogenously express any members of the ErbB family (23), an observation we confirmed by FACS for EGFR, ErbB2 and ErbB3 (data not shown). These cells were then stably transfected with human de2-7 EGFR(NR6.Δ2-7). Since all the U87MG derived cell lines used to test the efficacy of mAb 806 and 528 against the de2-7 EGFR also co-express the wt EGFR we assessed their therapeutic efficacy in mice with established NR6.Δ2-7 xenografts. mAb 806 treatment resulted in a reduction in overall tumor growth rate compared to treatment with vehicle that was highly significant at day 42 post-inoculation (P<0.003) (FIG. 6). The average tumor volume on the final day of therapy (day 39) was 1520 and 670 mm$^3$ for the vehicle and mAb 806 treatment groups respectively (FIG. 6A).

Mice bearing established NR6.Δ2-7 xenografts were also treated with mAb 528. On day 56 post-inoculation, when animals were killed for ethical reasons, the size of tumors treated with mAb 528 did not differ from that of vehicle treated xenografts (FIG. 6B). We conducted a second therapy experiment with mAb 528 using a slightly varied protocol whereby mice received antibody twice per week for three weeks. Once again mAb 528 failed to inhibit the growth of established NR6.Δ2-7 xenografts under these conditions (FIG. 6C). Thus, unlike mAb 806, mAb 528 is unable to inhibit xenografts expressing the de2-7 EGFR in the absence of the wt EGFR.

Src Activity Modulates the Responsiveness of de2-7 EGFR Expressing Xenografts to Antibody Therapy.

Since mAb 806 and 528 inhibit xenografts expressing the DY5 version of the de2-7 EGFR and because neither antibody decreases de2-7 EGFR phosphorylation as a single agent in vivo (16), it is likely that these antibodies mediate their anti-tumor activity by disrupting the trans-phosphorylation of a target downstream of the de2-7 EGFR. Our observations with the NR6.Δ2-7 xenografts suggest that the anti-tumor activity of mAb 528 is dependent on the co-expression of the de2-7 EGFR with another member of the ErbB family, whereas mAb 806 activity is independent of this interaction. Therefore, we examined if the de2-7 EGFR could interact with Src, as is the case for the wt EGFR, and if this potential interaction is related to mAb 806 efficacy.

Activation of the wt EGFR leads to the transient activation of Src kinase. In a synergistic manner, activation of Src leads to phosphorylation tyrosine 845 (Y845) on the EGFR, which is not an auto-phosphorylation site rather a target for Src phosphorylation (24). Using an antibody specific to Y845 we examined the phosphorylation of Y845 in the de2-7 EGFR. When expressed in U87MG glioma cells the de2-7 EGFR showed robust phosphorylation of Y845 (FIG. 7A). Phosphorylation at Y845 was rapidly blocked by incubating cells with PP1 and PP2, inhibitors of the Src-family kinases, while the autophosphorylation site at Y1173 was relatively unaffected (FIG. 7A).

Given that the de2-7 EGFR appears to be a target for Src kinase phosphorylation in a manner analogous to that of the wt EGFR, we sought to determine if this interaction was critical to mAb 806 activity. Initially we constructed a de2-7 EGFR containing a Y845F substitution, however this protein showed reduced phosphorylation at multiple sites (Johns, unpublished observations) and was therefore considered unsuitable for these studies. Thus, as described in the materials and methods, we developed a U87MG cell line co-expressing the de2-7 EGFR and a DNSrc (U87MG.Δ2-7$_{DNSrc}$). U87MG.Δ2-7$_{DNSrc}$ xenografts grew as tumor xenografts in nude mice but at a rate slower than U87MG.Δ2-7 transfected with a vector control (FIG. 7B). Treatment of U87MG.Δ2-7$_{DNSrc}$ with mAb 806 resulted in robust inhibition of tumor growth (FIG. 7C). At day 34 post-inoculation, the average xenograft volume was 1220 mm$^3$ in the vehicle group compared with 100 mm$^3$ in the mAb 806 treated group (p<0.001) (FIG. 7C). Furthermore, 60% of all U87MG.Δ2-7$_{DNSrc}$ xenografts in the mAb 806 treated group completely regressed and had not recurred by day 50 post-inoculation. Thus, inhibition of Src signaling increases the efficacy of mAb 806 therapy (FIG. 7C cf FIG. 2).

Internalization of mAb 806 in U87MG.Δ2-7 Cells.

Figure 8:
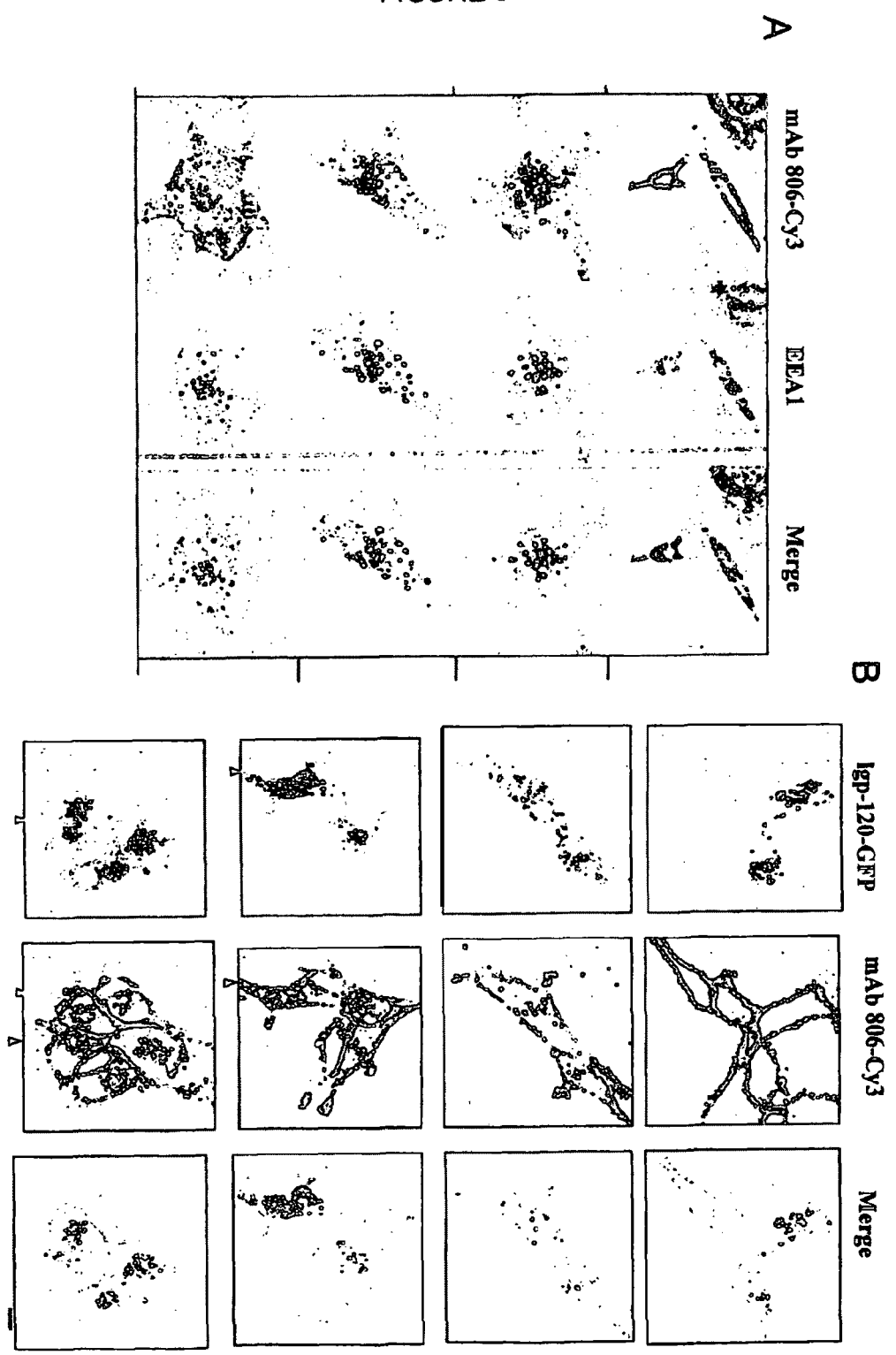
FIGS. 8A and 8B. Co-localization of internalized mAb 806-Cy3 and EEA1 or lgp-120 in U87MG.β2-7 Cells. (A) Cells seeded on glass coverslips were pre-incubated with mAb 806-Cy3 (red) at 4° C. (0 min). Internalization was stimulated by incubation at 37° C. for 10, 20 and 30 mins. Cells were fixed and permeabilized, then stained with anti-EEA1 followed by Cy2-conjugated donkey anti-mouse antibody (green). Co-localization is indicated by yellow in the merged images (arrows). Scale bar=20 μm. (B) Cells were transiently transfected with lgp-120 tagged with GFP (lgp-120-GFP; green). Positively transfected cells are shown in the lgp-120-GFP panel and by green arrowheads. Following transfection, cells were incubated with mAb 806-cy3 at 4° C. (red; 0 min), prior to induction of internalization by incubating at 37° C. for 30, 60 and 120 min. Samples were subsequently fixed and co-localization of mAb 806-Cy3 and lgp-120-GFP are indicated by the presence of yellow in the merged images (white arrows). Scale bar=10 μm.

The intracellular trafficking of mAb 806 following binding to de2-7 EGFR expressed in U87MG.Δ2-7 cells, was investigated by confocal microscopy. Following incubation of mAb 806-Cy3 at 4° C. and prior to chase at 37° C., mAb 806 bound to de2-7 EGFR was located along the plasma membrane (FIG. 8A; 0 min, mAb 806-Cy3). Following incubation at 37° C., mAb 806 (FIG. 8A; mAb 806-Cy3) was observed to translocate to small, punctate, cytoplasmic vesicles. Subsequent immunostaining with anti-early endosome autoantigen 1 (EEA1), which identifies early endosomes (FIG. 8A; EEA1), showed partial co-localization with mAb 806 as visualized by the presence of yellow fluorescence (FIG. 8A; Merge). Following 60 mins chase at 37° C., the co-localization was minimal (FIG. 8A; Merge, 60 min), suggesting that the majority of antibody has moved out of early endocytic compartments. These observations indicate that mAb 806 localizes to early endocytic compartments immediately following internalization before moving to an alternative location later in its intracellular trafficking cycle.

Lysosomal localization of mAb 806 following binding and internalization of de2-7 EGFR in U87MG.Δ2-7 cells was accomplished via co-localization analysis in cells transiently transfected with lgp-120-GFP (FIG. 8B). Cells positively transfected for lgp-120-GFP displayed cytoplasmic peri-nuclear green fluorescence consistent with localization to lysosomal compartments as expected (FIG. 8B; lgp-120-GFP). Prior to induction of internalization, mAb 806-Cy3 was only detected on the cell surface (FIG. 8B; 0 min, mAb 806-Cy3), and did not co-localized with lgp-120-GFP (FIG. 8B; 0 min, merge). Following warming to 37° C. for 30 min, small intracellular vesicular structures corresponding to internalized mAb 806 were observed (FIG. 8B; 30 min, mAb 806-Cy3). Some of these structures co-localized with lgp-120-GFP, however the majority of red and green signal remained segregated (FIG. 8B; 30 min, merge). Longer incubation at 37° C. for 60 and 120 mins resulted in increased co-localization of internalized mAb 806-Cy3 and lgp-120-GFP (FIG. 8B; 60-120 min, merge). These observations are consistent with the hypothesis that mAb 806 initially traverses through early endocytic compartment, but after longer periods moves into lysosomal compartments where it accumulates.

Figure 9:
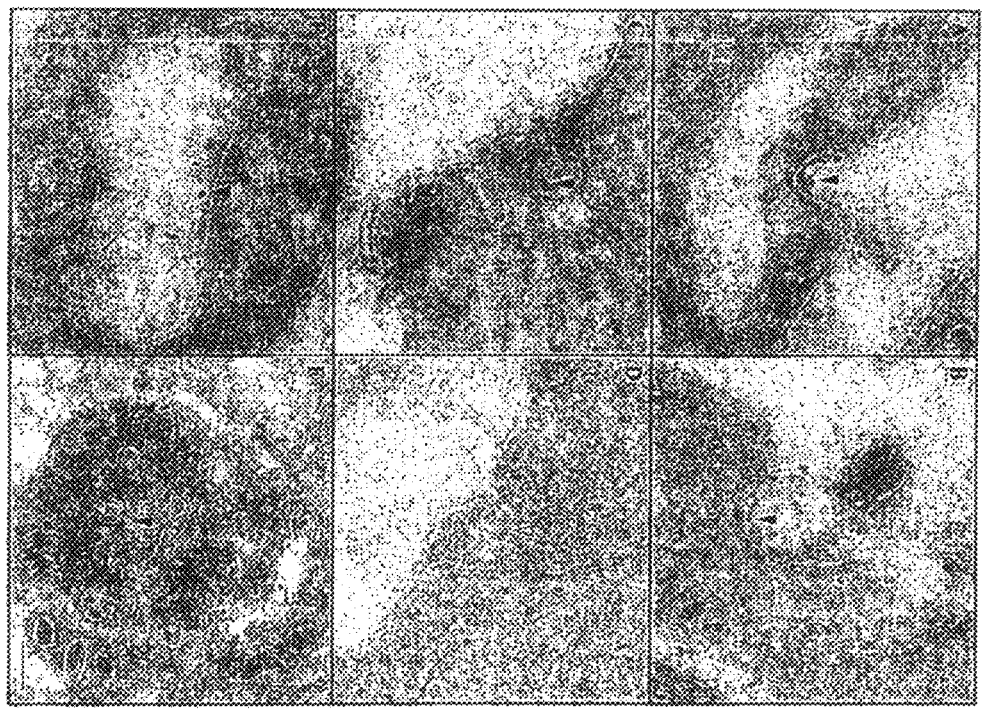
FIG. 9A-9F. Electron microscopic analysis of clathrin mediated endocytosis and intracellular trafficking of mAb 806 following binding to de2-7 EGFR in U87MG.Δ2-7 cells. Gold particles (mAb 806-Au; arrowheads) were readily detected in clathrin coated pits (A-B) and vesicles (C) following induction of internalization for 5 mins. No gold particles were present in structures resembling caveolae (open arrowheads) (D). After 10-15 mins of internalization, gold particles were detected in tubular vesicular structures resembling early endosomes (E). After longer periods of internalization, gold particles were seen in multivesicular bodies (F). Scale bar=100 nm.

The internalization of mAb 806 following binding to the de2-7 EGFR expressed on U87MG.Δ2-7 cells was also analyzed by electron microscopy. Following 5 mins incubation at 37° C., gold particles, corresponding to mAb 806, were observed in structures resembling clathrin-coated pits (FIGS. 9A and B). Gold particles were also detected in free clathrin-coated vesicles located within the cytoplasm (FIG. 9C). No gold particles were observed in structures resembling caveolae (FIG. 9D). Following 10 min of chase at 37° C., mAb 806 localized to large tubular-vesicular structures resembling early endocytic compartments (FIG. 9E). Longer chase periods of 30 mins resulted in antibody localization in structures resembling multivesicular bodies (FIG. 9F). These observations are consistent with the immuno-fluorescence microscopy data that indicated co-localization of mAb 806 with lgp-120 between 30 and 60 mins.

Internalization of MAb 806 and 528 in NR6.Δ2-7 Cells.

Given the differences in therapeutic efficacy of mAbs 806 and 528 against NR6.Δ2-7 xenografts, the internalization characteristics of each antibody was investigated in this cell line. Furthermore, since NR6.Δ2-7 cells do not express any endogenous members of the ErbB family, this cell line can determine if the presence of wt EGFR is required for internalization of these antibodies. Cells incubated with mAb 806-Cy3 at 4° C. showed membrane staining with no intracellular fluorescence as expected (FIG. 10; mAb 806, 0 min). In contrast to U87MG.Δ2-7 cells (FIG. 8), membrane staining was not uniform. More intense staining was associated with membrane junctions between cells (FIG. 10; mAb 806, 0 min) and focal adhesions (FIG. 10; mAb 806, 0 min). Some cells showed very little membrane staining (FIG. 10; mAb 806, 0 min). Following induction of internalization by raising the temperature to 37° C., characteristic intracellular punctate vesicular structures were observed. These accumulated in a peri-nuclear pattern (FIG. 10; mAb 528 15-60 min) consistent with rapid lysosomal localization. Initial localization (FIG. 10; mAb 528, 0 min) and subsequent internalization (FIG. 10; mAb 528, 1-60 min) of mAb 528 was identical to that of mAb 806. Thus both antibodies were rapidly internalized to the lysosomal compartment following binding to the de2-7 EGFR even in the absence of the wt EGFR.

Discussion mAb 528.

Many, but not all, previous studies have suggested that EGFR number on the cell surface is one factor that influences the efficacy of EGFR targeted therapeutics, especially TKI's (Table 1). However, these experiments have always compared anti-tumor activity using different cell lines and thus are not controlled with respect to genetic background, the presence of other ErbB family members and the occurrence of other functional receptors/kinases capable of modulating the EGFR signaling pathway. Furthermore, many of these studies have been conducted in vitro, which we have shown does not correlate with in vivo activity. Increasing the wt EGFR number 10-fold converts U87MG glioma xenografts from mAb 528 resistant to antibody responsive. Since the increase in wt EGFR number did not alter the growth rate of the U87MG xenografts, the advent of anti-tumor activity was not simply the result of mAb 528 inhibiting an induced growth advantage. The presence of more wt EGFR within U87MG.wtEGFR xenografts would almost certainly lead to increased antibody localization at the tumor site. Given that mAb 528 possess low, but measurable, immune effector function (25), the increased level of antibody at the tumor site may result in increased complement deposition and recruitment of immune cells that contribute to inhibition of tumor growth. However, a role for immune effector function in initiating the anti-tumor activity of mAb 528 seems unlikely given our data with the U87MG.DK xenografts. These xenografts have as many mAb 528 binding sites as the U87MG.wtEGFR xenografts but are not inhibited by the antibody. One intriguing possibility is that over-expression of the wt EGFR leads to ligand independent EGFR signaling (the parental U87MG appear not to have a strong autocrine-ligand loop), which in turn causes the cells to become more dependent on the EGFR signaling system. Thus, U87MG.wtEGFR xenografts respond to mAb 528 therapy because, unlike the parental cell line, the EGFR signaling pathway is active and functional. Therefore, over-expression of the wt EGFR is a surrogate marker of cells dependence on EGFR signaling and therefore such cells are more likely, but not guaranteed, to respond to EGFR therapeutics (26).

It has been presumed that the anti-tumor activity of antibodies such as mAb 528 is predominantly mediated by their ability to antagonize ligand activation of the EGFR. Given that mAb 528 inhibited the growth U87MG.wtEGFR xenografts in the absence of significant ligand expression suggests that other mechanisms may contribute to the anti-tumor effect. Furthermore, mAb 528 displayed significant efficacy against xenografts expressing the ligand independent de2-7 EGFR. This anti-tumor activity could not directly result from mAb 528 binding the endogenous wt EGFR co-expressed in these xenografts, as it did not inhibit the growth of parental U87MG or U87MG.DK xenografts, both of which express identical levels of the wt EGFR. Excluding immune effector function, alternate anti-tumor mechanisms could include receptor down-regulation, induction of inappropriate signaling, translocation of the receptor to unsuitable membrane domains and interference with receptor dimerization and/or oligomerization. Indeed, some TKI's directed to the EGFR not only function by inhibiting kinase activity but induce inactive dimers capable of "mopping" up excess ligand, an unanticipated anti-tumor mechanism (27).

Interestingly, a recent immunohistochemistry study analyzing EGFR expression in colon patients showing differential response to C225, reported that several patients "negative" for EGFR had clinical responses to this EGFR-specific antibody (26). Presumably these patients have levels of EGFR below the detection sensitivity of immunohistochemistry yet the EGFR present is activated and contributes to tumor growth/survival. This observation suggests that EGFR activation is at least as important, if not more so, than simply the level of EGFR expression. Our data showing that mAb 528 did not inhibit the growth of U87MG xenografts expressing a dead kinase version of this truncated receptor (U87MG.DK) supports the view that the efficacy of EGFR-specific antibodies is intimately associated with kinase active receptors. As suggested above, EGFR over-expression represents one mechanism by which this activation can occur; the expression of a constitutively active mutant such as the de2-7 EGFR denotes another. This continuous activation of the EGFR causes cells to become "addicted" to EGFR signaling, which in turn makes them susceptible to anti-EGFR therapy. This concept is analogous to the situation in lung cancer patients, where most patients who respond to EGFR-specific TKI's carry activating mutations in the EGFR kinase domain (28).

Figure 11:
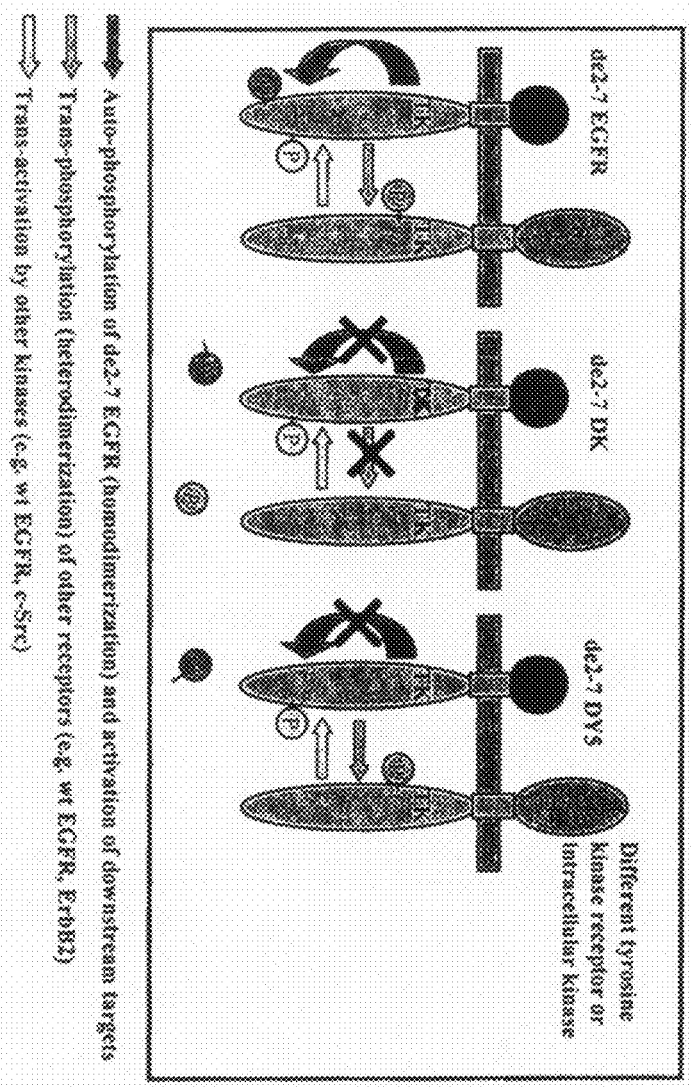
FIG. 11. Schematic representation of the interaction of the de2-7 EGFR variants with other cellular components. The de2-7 EGFR has an active kinase and therefore can autophosphorylate, transphosphorylate or be the target of phosphorylation by other kinases. In contrast, the dead kinase de2-7 EGFR can only be the target of phosphorylation. Finally, the DY5 construct can be the target of phosphorylation and transphosphorylate other cell targets such as the wt EGFR. Given that both mAb 528 and 806 can inhibit U87MG.DY5 xenografts but not U87MG.DK xenografts, it suggests that the ability of these antibodies to prevent the phosphorylation of other cellular components is critical to their anti-tumor activity.

The ability of mAb 528 to inhibit the growth of U87MG.DY2 or DY5 xenografts highlights the significance of an active kinase domain as opposed to autophosphorylation as a determinant of efficacy. Thus, it is an active kinase that determines the response to antibody therapy, not the direct interaction of phosphorylated tyrosine's with adapter or signaling molecules. One corollary to this result is that mAb 528 seemingly inhibits the growth of U87MG.Δ2-7/DY2/DY5 xenografts by preventing the trans-phosphorylation of a downstream target (FIG. 11). Since all these U87MG-derived cell lines co-express the wt EGFR, and given that we recently demonstrated that the de2-7 EGFR can form dimers and phosphorylate the wt EGFR (29), the wt EGFR is a likely candidate for this secondary target. This proposition is supported by the fact that NR6 cells expressing the de2-7 EGFR in the absence of the wt EGFR were completely refractory to the anti-tumor effects of mAb 528. Taken together these studies suggest that, along with its ligand blocking properties, mAb 528 functions in part by preventing the homo-dimerization of the over-expressed wt EGFR and hetero-dimerization between the wt and de2-7 EGFR. Interestingly, the structure of C225 (an antibody very similar to mAb 528) in complex with the EGFR suggests that apart from ligand blockade, this antibody may prevent EGFR dimerization by partially inhibiting EGFR untethering (30).

mAb 806.

Responsiveness of U87MG-derived cell lines in vivo to mAb 806 completely mirrored that observed with mAb 528, indicating that many of the above principles apply although there are some important differences. This study confirms and extends our previous studies demonstrating that mAb 806 reactivity is associated with EGFR activation (16). Unlike mAb 528, and all current antibodies in clinical evaluation, mAb 806 does not target normal tissue such as the liver, as EGFR activation is extremely low or non-detectable in organs such as the liver. A myriad of factors can stimulate EGFR activation within tumors (see (31) for a review). We have confirmed that at least three of these, EGFR over-expression (15), mutation (17) and presence of an autocrine loop (Johns et al, in preparation) can lead to mAb 806 reactivity. The association of wt EGFR over-expression for mAb 806 anti-tumor activity is intimately related to its unique specificity as over-expression increases the transient, untethered form of the EGFR recognized by mAb 806, through multiple mechanisms such as ligand independent activation and alterations in EGFR glycosylation (21). Given that the work described here, along with the clinical data obtained with EGFR-specific TKI's, suggests that EGFR inhibitors are most effective against tumors with an activated EGFR, the unique ability of mAb 806 to specifically recognize activated forms of the EGFR makes it an advantageous therapeutic.

Molecular modeling suggests that mAb 806 binding would prevent the formation of active wt EGFR dimers (14), a hypothesis we have confirmed by solving the crystal structure of mAb 806 in complex with its epitope (Johns et al. in preparation). Despite this mAb 806 does not significantly inhibit the phosphorylation of the de2-7 or wt EGFR in xenograft models (16), strongly suggesting that any proposed mechanism of action for mAb 806 includes more than blockade of auto-phosphorylation. Furthermore, known downstream targets of EGFR signaling such as Akt and MAPK, are also not inhibited by mAb 806 (T. G. Johns, unpublished observations). Consistent with this hypothesis, mAb 806 displayed robust anti-tumor activity against U87MG.DY2/DY5 xenografts, two models where autophosphorylation is not pertinent. The lack of mAb 806 efficacy against U87MG.DK xenografts, emphasizes that the presence of an active kinase and trans-phosphorylation events (FIG. 11) are critical factors leading to sensitivity. In contrast to mAb 528, mAb 806 was able to inhibit the growth of NR6 cells expressing the de2-7 EGFR in the absence of other ErbB family members. This result indicates that mAb 806 potentially disrupts other targets of de2-7 EGFR trans-phosphorylation, distinct from the wt EGFR. Interestingly, there was no obvious difference in the internalization and intracellular tracking of mAb 806 and 528 following binding of either antibody to surface de2-7 EGFR in NR6 cells, suggesting antibody trafficking did not contribute to the difference in efficacy in this xenograft model.

We report here for the first time that Y845 is phosphorylated on the de2-7 EGFR in a Src-dependent manner. Thus, we examined whether the interaction between the de2-7 EGFR and Src was a potential target of mAb 806 activity. If mAb 806 mediated part of its anti-tumor activity by inhibiting this interaction, then genetically disrupting this interaction using a DNSrc should have reduced the efficacy of mAb 806.

In contrast to this possibility, the presence of a DNSrc dramatically enhanced the anti-tumor activity of mAb 806. This suggests that Src has a role in limiting the efficacy of EGFR therapeutics and provides a rationale for using Src and EGFR inhibitors in combination.

Conclusion

These studies demonstrate the relevance of in vivo studies for analyzing the sensitivity of cell lines to EGFR therapeutics. Unlike previous studies we were able to conduct most of our analysis in the same genetic background, making the predominant variable the nature of the EGFR. Using this approach we conclusively showed the significance of receptor number to efficacy. While EGFR number is related to EGFR therapeutic susceptibility, this factor alone is not enough as the receptor also needs to contain a functional kinase. Indeed, while somewhat intuitive, this work shows formally that "forcing" a cell line to use EGFR signaling, either by over-expression of the wt EGFR or expression of a constitutive active mutant, can switch it from non-responsive to responsive. Thus, the EGFR must not only be present at the cell surface, it must be significantly contributing the growth and survival of the cell. Therefore, strategies for selecting patients who will respond to EGFR therapeutics should be directed to identifying tumors highly dependent on the EGFR, not merely the presence or absence of receptor protein. This task may be relatively straight forward in some cases such as when the de2-7 EGFR, EGFR gene amplification or kinase activating mutants are present, but is clearly more difficult in cases where the wt EGFR is genetically normal. In these cases the complex interplay of multiple receptor kinases makes it difficult to identify those tumors truly dependent on EGFR signaling. Long term, detailed expression profiling of yet to be identified target genes unique to each receptor kinase may be the only viable approach to addressing this problem.

REFERENCES

1. Arteaga C L. Overview of epidermal growth factor receptor biology and its role as a therapeutic target in human neoplasia. Seminars in Oncology 2002; 29: 3-9.
2. Baselga J. Why the epidermal growth factor receptor? The rationale for cancer therapy. Oncologist 2002; 4: 2-8.
3. Mendelsohn J. Targeting the epidermal growth factor receptor for cancer therapy. Journal of Clinical Oncology 2002; 20:1 S-13S.
4. Frederick L, Wang X Y, Eley G, James C D. Diversity and frequency of epidermal growth factor receptor mutations in human glioblastomas. Cancer Res 2000; 60: 1383-7.
5. Wong A J, Ruppert J M, Bigner S H, et al. Structural alterations of the epidermal growth factor receptor gene in human gliomas. Proc Natl Acad Sci USA 1992; 89: 2965-9.
6. Sugawa N, Ekstrand A J, James C D, Collins V P. Identical splicing of aberrant epidermal growth factor receptor transcripts from amplified rearranged genes in human glioblastomas. Proc Natl Acad Sci USA 1990; 87: 8602-6.
7. Tang C K, Gong X Q, Moscatello D K, Wong A J, Lippman M E. Epidermal growth factor receptor vIII enhances tumorigenicity in human breast cancer. Cancer Res 2000; 60: 3081-7.
8. Nishikawa R, Ji X D, Harmon R C, et al. A mutant epidermal growth factor receptor common in human glioma confers enhanced tumorigenicity. Proc Natl Acad Sci USA 1994; 91: 7727-31.
9. Baselga J, Pfister D, Cooper M R, et al. Phase I studies of anti-epidermal growth factor receptor chimeric antibody C225 alone and in combination with cisplatin. J Clin Oncol 2000; 18: 904-14.
10. Stragliotto G, Vega F, Stasiecki P, Gropp P, Poisson M, Delattre J Y. Multiple infusions of anti-epidermal growth factor receptor (EGFR) monoclonal antibody (EMD 55,900) in patients with recurrent malignant gliomas. Eur J Cancer 1996; 32A: 636-40.
11. Lynch D H, Yang X D. Therapeutic potential of ABX-EGF: a fully human anti-epidermal growth factor receptor monoclonal antibody for cancer treatment. Semin Oncol 2002; 29: 47-50.
12. Siegel-Lakhai W S, Beijnen J H, Schellens J H. Current knowledge and future directions of the selective epidermal growth factor receptor inhibitors erlotinib (Tarceva) and gefitinib (Iressa). Oncologist 2005; 10: 579-89.
13. Johns T G, Stockert E, Ritter G, et al. Novel monoclonal antibody specific for the de2-7 epidermal growth factor receptor (EGFR) that also recognizes the EGFR expressed in cells containing amplification of the EGFR gene. Int J Cancer 2002; 98: 398-408.
14. Johns T G, Adams T E, Cochran J R, et al. Identification of the Epitope for the Epidermal Growth Factor Receptor-specific Monoclonal Antibody 806 Reveals That It Preferentially Recognizes an Untethered Form of the Receptor. J Biol Chem 2004; 279: 30375-84.
15. Luwor R B, Johns T G, Murone C, et al. Monoclonal antibody 806 inhibits the growth of tumor xenografts expressing either the de2-7 or amplified epidermal growth factor receptor (EGFR) but not wild-type EGFR. Cancer Res 2001; 61: 5355-61.
16. Perera R M, Narita Y, Furnari F B, et al. Treatment of human tumor xenografts with monoclonal antibody 806 in combination with a prototypical epidermal growth factor receptor-specific antibody generates enhanced antitumor activity. Clinical Cancer Research 2005; 11: 6390-9.
17. Mishima K, Johns T G, Luwor R B, et al. Growth suppression of intracranial xenografted glioblastomas overexpressing mutant epidermal growth factor receptors by systemic administration of monoclonal antibody (mAb) 806, a novel monoclonal antibody directed to the receptor. [erratum appears in Cancer Res 2001 Oct. 15; 61(20):7703-5]. Cancer Research 2001; 61: 5349-54.
18. Kawamoto T, Sato J D, Le A, Polikoff J, Sato G H, Mendelsohn J. Growth stimulation of A431 cells by epidermal growth factor: identification of high-affinity receptors for epidermal growth factor by an anti-receptor monoclonal antibody. Proc Natl Acad Sci USA 1983; 80: 1337-41.
19. Huang H S, Nagane M, Klingbeil C K, et al. The enhanced tumorigenic activity of a mutant epidermal growth factor receptor common in human cancers is mediated by threshold levels of constitutive tyrosine phosphorylation and unattenuated signaling. J Biol Chem 1997; 272: 2927-35.
20. Kwok T T, Sutherland R M. Differences in EGF related radiosensitisation of human squamous carcinoma cells with high and low numbers of EGF receptors. British Journal of Cancer 1991; 64: 251-4.
21. Johns T G, Melhnan I, Cartwright G A, et al. The antitumor monoclonal antibody 806 recognizes a high-mannose form of the EGF receptor that reaches the cell surface when cells over-express the receptor. Faseb J 2005; 19: 780-2.
22. Johns T G, Luwor R B, Murone C, et al. Antitumor efficacy of cytotoxic drugs and the monoclonal antibody 806 is enhanced by the EGF receptor inhibitor AG 1478. Proc Natl Acad Sci USA 2003; 100: 15871-6.

23. Pruss R M, Herschman H R. Variants of 3T3 cells lacking mitogenic response to epidermal growth factor. Proc Natl Acad Sci USA 1977; 74: 3918-21.
24. Ishizawar R, Parsons S J. c-Src and cooperating partners in human cancer. Cancer Cell 2004; 6: 209-14.
25. Masui H, Moroyama T, Mendelsohn J. Mechanism of antitumor activity in mice for anti-epidermal growth factor receptor monoclonal antibodies with different isotypes. Cancer Res 1986; 46: 5592-8.
26. Chung K Y, Shia J, Kemeny N E, et al. Cetuximab shows activity in colorectal cancer patients with tumors that do not express the epidermal growth factor receptor by immunohistochemistry. J Clin Oncol 2005; 23: 1803-10.
27. Lichtner R B, Menrad A, Sommer A, Klar U, Schneider M R. Signaling-inactive Epidermal Growth Factor Receptor/Ligand Complexes in Intact Carcinoma Cells by Quinazoline Tyrosine Kinase Inhibitors. Cancer Res 2001; 61: 5790-5.
28. Lynch T J, Bell D W, Sordella R, et al. Activating mutations in the epidermal growth factor receptor underlying responsiveness of non-small-cell lung cancer to gefitinib. N Engl J Med 2004; 350: 2129-39.
29. Luwor R B, Zhu H J, Walker F, et al. The tumor-specific de2-7 epidermal growth factor receptor (EGFR) promotes cells survival and heterodimerizes with the wild-type EGFR. Oncogene 2004; 23: 6095-104.
30. Li S, Schmitz K R, Jeffrey P D, Wiltzius J J, Kussie P, Ferguson K M. Structural basis for inhibition of the epidermal growth factor receptor by cetuximab. Cancer Cell 2005; 7: 301-11.
31. Normanno N, De Luca A, Bianco C, et al. Epidermal growth factor receptor (EGFR) signaling in cancer. Gene 2006; 366: 2-16.
32. Bos M, Mendelsohn J, Kim Y M, Albanell J, Fry D W, Baselga J. PD153035, a tyrosine kinase inhibitor, prevents epidermal growth factor receptor activation and inhibits growth of cancer cells in a receptor number-dependent manner. Clin Cancer Res 1997; 3: 2099-106.
33. Perera A D, Kleymenova E V, Walker C L. Requirement for the von Hippel-Lindau tumor suppressor gene for functional epidermal growth factor receptor blockade by monoclonal antibody C225 in renal cell carcinoma. Clin Cancer Res 2000; 6: 1518-23.
34. Hambek M, Solbach C, Schnuerch H G, et al., Tumor necrosis factor alpha sensitizes low epidermal growth factor receptor (EGFR)-expressing carcinomas for anti-EGFR therapy. Cancer Res 2001; 61: 1045-9.
35. Christensen J G, Schreck R E, Chan E, et al. High levels of HER-2 expression alter the ability of epidermal growth factor receptor (EGFR) family tyrosine kinase inhibitors to inhibit EGFR phosphorylation in vivo. Clin Cancer Res 2001; 7: 4230-8.
36. Viloria-Petit A, Crombet T, Jothy S, et al., Acquired resistance to the antitumor effect of epidermal growth factor receptor-blocking antibodies in vivo: a role for altered tumor angiogenesis. Cancer Res 2001; 61: 5090-101.
37. Heimberger A B, Learn C A, Archer G E, et al. Brain tumors in mice are susceptible to blockade of epidermal growth factor receptor (EGFR) with the oral, specific, EGFR-tyrosine kinase inhibitor ZD1839 (iressa). Clin Cancer Res 2002; 8: 3496-502.
38. Chakravarti A, Loeffler J S, Dyson N J. Insulin-like growth factor receptor I mediates resistance to anti-epidermal growth factor receptor therapy in primary human glioblastoma cells through continued activation of phosphoinositide 3-kinase signaling. Cancer Res 2002; 62: 200-7.
39. Motoyama A B, Hynes N E, Lane H A. The efficacy of ErbB receptor-targeted anticancer therapeutics is influenced by the availability of epidermal growth factor-related peptides. Cancer Res 2002; 62: 3151-8.
40. Magne N, Fischel J L, Dubreuil A, et al., Influence of epidermal growth factor receptor (EGFR), p53 and intrinsic MAP kinase pathway status of tumor cells on the antiproliferative effect of ZD1839 ("Iressa"). Br J Cancer 2002; 86: 1518-23.
41. Bishop P C, Myers T, Robey R, et al. Differential sensitivity of cancer cells to inhibitors of the epidermal growth factor receptor family. Oncogene 2002; 21: 119-27.
42. Li B, Chang C M, Yuan M, McKenna W G, Shu H K. Resistance to small molecule inhibitors of epidermal growth factor receptor in malignant gliomas. Cancer Res 2003; 63: 7443-50.
43. Bianco R, Shin I, Ritter C A, et al. Loss of PTEN/MMAC1/TEP in EGF receptor-expressing tumor cells counteracts the antitumor action of EGFR tyrosine kinase inhibitors. Oncogene 2003; 22: 2812-22.
44. Janmaat M L, Kruyt F A, Rodriguez J A, Giaccone G. Response to epidermal growth factor receptor inhibitors in non-small cell lung cancer cells: limited antiproliferative effects and absence of apoptosis associated with persistent activity of extracellular signal-regulated kinase or Akt kinase pathways. Clin Cancer Res 2003; 9: 2316-26.
45. Paez J G, Janne P A, Lee J C, et al., EGFR Mutations in Lung Cancer: Correlation with Clinical Response to Gefitinib Therapy. Science 2004.
46. Learn C A, Hartzell T L, Wikstrand C J, et al. Resistance to tyrosine kinase inhibition by mutant epidermal growth factor receptor variant III contributes to the neoplastic phenotype of glioblastoma multiforme. Clin Cancer Res 2004; 10: 3216-24.
47. Halatsch M E, Gehrke E E, Vougioukas V I, et al. Inverse correlation of epidermal growth factor receptor messenger RNA induction and suppression of anchorage-independent growth by OSI-774, an epidermal growth factor receptor tyrosine kinase inhibitor, in glioblastoma multiforme cell lines. J Neurosurg 2004; 100: 523-33.
48. Pao W, Miller V A, Politi K A, et al. Acquired resistance of lung adenocarcinomas to gefitinib or erlotinib is associated with a second mutation in the EGFR kinase domain. PLoS Med 2005; 2: e73.
49. Mellinghoff I K, Wang M Y, Vivanco I, et al. Molecular determinants of the response of glioblastomas to EGFR kinase inhibitors. N Engl J Med 2005; 353: 2012-24.

EXAMPLE 2

Animal Therapy Study of Src Inhibitor Dasatinib and mAb806 Therapy

Animal therapy studies were performed to assess in vivo effects of the anti-EGFR antibody mAb806 alone or in combination with the src inhibitor dasatinib. Eight week old female Balb/C nu nu mice were injected with $1 \times 10^6$ U87MG.Δ2-7$_{SRC}$ cells (per tumour site) subcutaneously. The U87MG.Δ2-7$_{SRC}$ cells express an activated Src (Y529F mutation) and the Δ2-7 mutant EGFR. Two tumours were generated per mouse by injection of these cells to each of the right and left flanks. Treatment was commenced when mean tumour size reached approximately 80 mm$^3$. Mice were treated three times per week for two weeks in four treatment groups, consisting of 4-5 mice per group. Treatment groups were as follows: (1) control—100 μl of diluents 4% DMSO/ dH$_2$O; (2) dasatinib—10 mg/kg of drug dissolved in diluents; (3) mAb806—1 mg; (4) mAb806 1 mg and dasatinib 10 mg/kg.

Antibodies. Src was detected using the mouse monoclonal antibodies v-Src 327 (Oncogene Research Products, CA, USA) or c-Src H-12 (Santa Cruz Biotechnology, Inc, CA, USA). The rabbit polyclonal antibody PY418 (BioSource International, Inc., CA, USA) was used for the detection of phospho-Src.

Construction of U87MG.Δ2-7$_{scr}$ cell line. An activated Src construct (Y529F mutation) was obtained from Upstate Technologies (Lake Placid, N.Y., USA). A PmeI fragment containing the activated Src c-DNA was subcloned into the pcDNA3.1/Hygro(+) vector obtained from Invitrogen Life Technologies (Carlsbad, Calif.), prior to the transfection of U87MG.Δ2-7 by electroporation. Cells were plated out in 1 ml aliquots into 96 well plates, at a density of approximately 2×10$^4$ cells per well, and incubated at 37° C. for 48 hours after which 100 μg/ml hygromycin (Roche Diagnostics, Mannheim, Germany) and 400 μg/ml geneticin (Invitrogen Life Technologies, Carlsbad, Calif.) was added.

Transfected cells were initially screened by FACS analysis to confirm that expression of the de2-7 EGFR had been retained. Clones were then subjected to either whole cell lysis or immunoprecipitation prior to western blotting using Src specific antibodies (v-Src 327, PY418). Several clones showing dramatically increased levels of both total and phosphorylated Src (Src levels are very low in the original cell line) were identified and expanded.

Xenograft Models.

Figure 12:
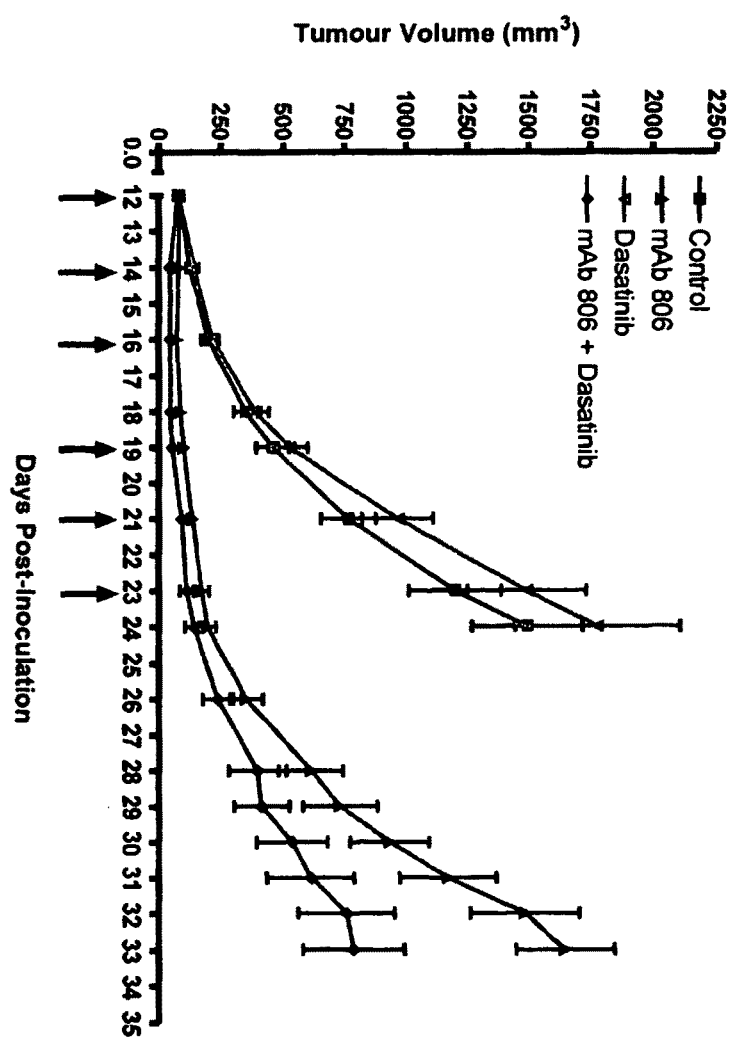
FIG. 12. Therapy of U87MG.Δ2-7$_{scr}$ xenografts with mAb 806 and Dasatinib alone or in combination. U87MG.Δ2-7$_{src}$ xenografts were established by injection of 1×10⁶ cells in both flanks of nude BALB/c mice in Therapy commenced when xenografts reached an approximate mean volume of 80 mm³. Mice were treated with vehicle (4% DMSO in dH₂O), 1 mg of mAb 806 in PBS, 10 mg/kg⁻¹ Dasatinib in 4% DMSO in dH₂O or a combination of both, three times per week for two weeks on the days indicated. Data are expressed as mean tumor volume±SE. At day 33 the combination treated group was significantly smaller than the group treated with mAb 806 alone (p<0.0076).
Figure 13:
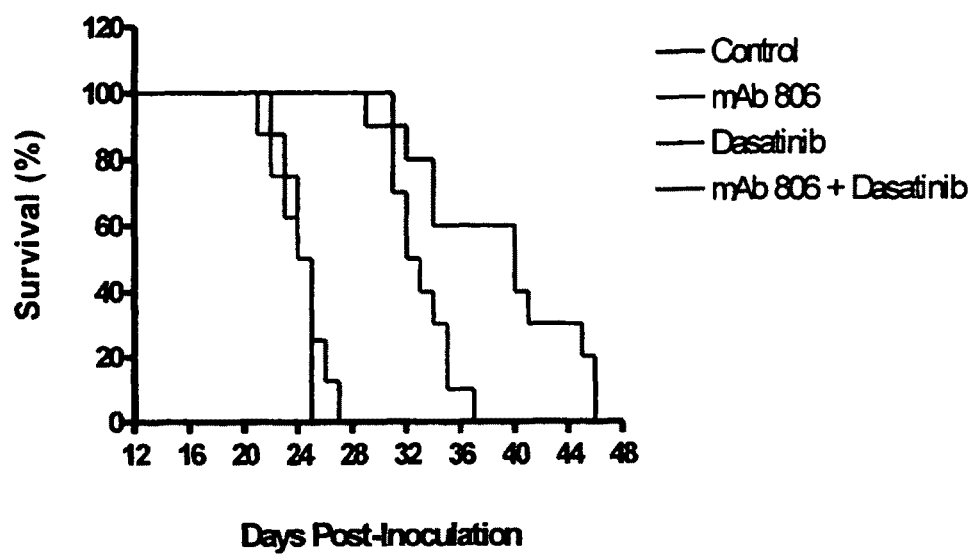
FIG. 13. Therapy of U87MG.Δ2-7$_{scr}$ xenografts with mAb 806 and Dasatinib alone or in combination. Data from the above experiment were transformed into Kaplan-Meier survival curves and analyzed by Wilcoxon analysis using dual endpoints of moribund or tumor volume>1500 mm³. The combination group survived longer than other groups Log Rank p<0.0001.

Tumor cells (1×10$^6$) in 100 μl of PBS were inoculated s.c. into both flanks of 8 week old, female nude mice (Animal Research Centre, Perth, Australia). All studies were conducted using established tumor models as previously. Treatment commenced once tumors had reached a mean volume a mean volume of approximately 80 mm$^3$. Tumor volume in mm$^3$ was determined using the formula (length×width$^2$)/2, where length was the longest axis and width being the measurement at right angles to the length. Data are expressed as mean tumor volume±SE for each treatment group (FIG. 12). All data was analyzed for significance by Student's t test. Data was also transformed into Kaplan-Meier survival curves and analyzed by Wilcoxon analysis using dual endpoints of moribund or tumor volume>1500 mm$^3$ (FIG. 13).

At day 33 the combination mAb806 and dasatinib treated group tumour growth was significantly smaller than the group treated with mAb 806 alone (p<0.0076) (FIG. 12). Data from the tumour growth experiment were transformed into Kaplan-Meier survival curves and analyzed by Wilcoxon analysis using dual endpoints of moribund or tumor volume>1500 mm$^3$ (FIG. 13). The combination mAb806 and dasatinib treated group survived longer than all other groups (Log Rank p<0.0001).

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

The invention claimed is:

1. A method of treating glioblastoma in a human, comprising administering to said human the src inhibitor dasatinib (BMS354825) and the anti-EGFR antibody mAb806 or an antigen-binding fragment thereof, wherein said src inhibitor dasatinib (BMS354825) and said anti-EGFR antibody mAb806 or antigen-binding fragment thereof are administered to said human simultaneously, in combination, or one after another in series, and wherein the glioblastoma is characterized by EGFR over-expression or an EGFR mutation.

2. A method for blocking or reducing tumor growth of glioblastoma in a human, comprising administering to said human the src inhibitor dasatinib (BMS354825) and the anti-EGFR antibody mAb806 or an antigen-binding fragment thereof, wherein said src inhibitor dasatinib (BMS354825) and said anti-EGFR antibody mAb806 or antigen-binding fragment thereof are administered to said human simultaneously, in combination, or one after another series, and wherein the glioblastoma is characterized by EGFR over-expression or an EGFR mutation.

3. A method of enhancing the effectiveness or activity of the anti-EGFR antibody mAb806 or an antigen-binding fragment thereof in a human with glioblastoma, comprising administering to said human a combination of the anti-EGFR antibody mAb806 or an antigen-binding fragment thereof and the src inhibitor dasatinib (BMS354825), and wherein the glioblastoma is characterized by EGFR over-expression or an EGFR mutation.

4. A method of treating glioblastoma in a human according to claim 1, wherein said antigen-binding fragment is Fab or F(ab')$_2$.

5. A method for blocking or reducing tumor growth of glioblastoma in a human according to claim 2, wherein said antigen-binding fragment is Fab or F(ab')$_2$.

6. A method of enhancing the effectiveness or activity of the anti-EGFR antibody mAb806 or an antigen-binding fragment thereof in a human according to claim 3, wherein said antigen-binding fragment is Fab or F(ab')$_2$.

7. The method of any one of claim 1, 2 or 3 wherein the EGFR mutation is a de2-7 EGFR mutation.

8. The method of any one of claim 1, 2 or 3, wherein mAb806 is a chimeric or humanized antibody.

9. The method of any one of claim 1, 2 or 3, wherein mAb806 is labeled with a detectable or functional label.

10. The method of claim 9, wherein the detectable or functional label is covalently attached.

11. The method of claim 9, wherein the functional label is selected from the group consisting of a chemical ablation agent, toxin, immunomodulator, cytokine, cytotoxic agent, chemotherapeutic agent and drug.

12. The method of claim 9, wherein the functional label is a toxin.

13. The method of claim 9, wherein the functional label is a cytotoxic agent.

14. The method of claim 9, wherein the detectable label is a radiolabel.

* * * * *